(12) United States Patent
Wong et al.

(10) Patent No.: US 11,155,615 B2
(45) Date of Patent: Oct. 26, 2021

(54) ANTI-ROR1 ANTIBODIES

(71) Applicants: FIVE PRIME THERAPEUTICS, INC., South San Francisco, CA (US); EUREKA THERAPEUTICS, INC., Emeryville, CA (US)

(72) Inventors: Brian Wong, South San Francisco, CA (US); Emma Masteller, South San Francisco, CA (US); Cheng Liu, Emeryville, CA (US); Yiyang Xu, Emeryville, CA (US); Hong Liu, Emeryville, CA (US); Su Yan, Emeryville, CA (US); Jingyi Xiang, Emeryville, CA (US); Pei Wang, Emeryville, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 457 days.

(21) Appl. No.: 15/574,810

(22) PCT Filed: May 17, 2016

(86) PCT No.: PCT/US2016/032911
§ 371 (c)(1),
(2) Date: Nov. 16, 2017

(87) PCT Pub. No.: WO2016/187220
PCT Pub. Date: Nov. 24, 2016

(65) Prior Publication Data
US 2018/0142016 A1 May 24, 2018

Related U.S. Application Data

(60) Provisional application No. 62/193,237, filed on Jul. 16, 2015, provisional application No. 62/163,241, filed on May 18, 2015.

(51) Int. Cl.
| | | |
|---|---|---|
| *A61K 39/00* | (2006.01) | |
| *C07K 16/28* | (2006.01) | |
| *A61K 51/10* | (2006.01) | |
| *A61K 47/68* | (2017.01) | |
| *A61P 35/02* | (2006.01) | |
| *A61P 35/00* | (2006.01) | |
| *A61K 38/05* | (2006.01) | |
| *C07K 16/00* | (2006.01) | |
| *G01N 33/574* | (2006.01) | |
| *C07K 16/30* | (2006.01) | |

(52) U.S. Cl.
CPC .......... *C07K 16/2803* (2013.01); *A61K 38/05* (2013.01); *A61K 47/6817* (2017.08); *A61K 47/6851* (2017.08); *A61K 47/6881* (2017.08); *A61K 51/1027* (2013.01); *A61K 51/1042* (2013.01); *A61K 51/1096* (2013.01); *A61P 35/00* (2018.01); *A61P 35/02* (2018.01); *C07K 16/005* (2013.01); *C07K 16/2809* (2013.01); *C07K 16/30* (2013.01); *G01N 33/57492* (2013.01); *A61K 2039/505* (2013.01); *C07K 2317/14* (2013.01); *C07K 2317/21* (2013.01); *C07K 2317/31* (2013.01); *C07K 2317/34* (2013.01); *C07K 2317/52* (2013.01); *C07K 2317/55* (2013.01); *C07K 2317/56* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2317/77* (2013.01); *C07K 2317/92* (2013.01); *C07K 2319/00* (2013.01); *G01N 2333/912* (2013.01)

(58) Field of Classification Search
CPC ................................................ A61K 2039/505
See application file for complete search history.

(56) References Cited

U.S. PATENT DOCUMENTS

| | | | | |
|---|---|---|---|---|
| 5,068,177 | A | * | 11/1991 | Carson ................... C07K 16/18 424/130.1 |
| 2003/0232009 | A1 | | 12/2003 | Babcook et al. |
| 2004/0110930 | A1 | | 6/2004 | Reinl et al. |
| 2006/0093599 | A1 | | 5/2006 | Gazit-Bornstein et al. |
| 2009/0232804 | A1 | | 9/2009 | Lazarides et al. |
| 2010/0062005 | A1 | | 3/2010 | Kipps et al. |
| 2012/0282177 | A1 | | 11/2012 | Rohlff et al. |
| 2013/0251723 | A1 | | 9/2013 | Rohlff et al. |

(Continued)

FOREIGN PATENT DOCUMENTS

| | | |
|---|---|---|
| CN | 102712695 B | 1/2015 |
| WO | WO 2008/076868 A2 | 6/2008 |
| WO | WO 2010/124188 A1 | 10/2010 |

(Continued)

OTHER PUBLICATIONS

Wang et al. (Proc. Natl. Acad. Sci. USA. 1999; 96 (4): 1627-32).*

(Continued)

*Primary Examiner* — Stephen L Rawlings
(74) *Attorney, Agent, or Firm* — Cooley LLP

(57) ABSTRACT

The invention relates to antibodies, and in particular, to antibodies exhibiting specificity for Receptor tyrosine kinase-like Orphan Receptors (ROR), and to uses thereof, for example in the treatment of cancer. The invention extends to polynucleotide and polypeptide sequences encoding the antibodies, and therapeutic uses thereof, and to diagnostic kits comprising these molecules. The invention also extends to antibody-drug conjugates and to uses thereof in therapy.

13 Claims, 32 Drawing Sheets
Specification includes a Sequence Listing.

(56) References Cited

U.S. PATENT DOCUMENTS

| | | | |
|---|---|---|---|
| 2013/0295113 A1 | 11/2013 | Mytych et al. | |
| 2018/0348232 A1* | 12/2018 | Kipps | C07K 16/40 |

FOREIGN PATENT DOCUMENTS

| | | |
|---|---|---|
| WO | WO 2011/079902 A2 | 7/2011 |
| WO | WO 2012/076066 A1 | 6/2012 |
| WO | WO 2013/079973 A1 | 6/2013 |
| WO | WO 2014/031174 A1 | 2/2014 |
| WO | WO 2014/105849 A1 | 7/2014 |
| WO | WO 2016/187220 A2 | 11/2016 |

OTHER PUBLICATIONS

Shimizu et al. (Mol. Immunol. 1983; 20 (2): 141-148).*
Daneshmanesh et al. (Leukemia. Jun. 26, 2012 (6): 1348-55).*
Yang et al. (PLoS One. 2011; 6 (6): e21018; pp. 1-15).*
George et al. (Circulation. 1998; 97: 900-906).*
Rudikoffetal. (Proc. Natl. Acad. Sci. USA. 1982; 79: 1979-1983).*
Mariuzza et al. (Annu. Rev. Biophys. Biophys. Chem. 1987; 16: 139-159).*
Gussowetal. (Methods in Enzymology. 1991; 203: 99-121).*
Giusti et al. (Proc. Natl. Acad. Sci. USA. May 1987 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Gassetetal. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Yamaguchi et al. (Biochem. Biophys. Res. Commun. Nov. 1, 2014; 454 (4): 600-603).*
Sano et al. (J. Biochem. Jan. 2007; 141 (1): 127-36).*
Stancovski et al. (Proceedings of the National Academy of Science USA. 1991; 88: 8691-8695).*
Press et al. (J. Immunol. Dec. 15, 1988; 141 (12): 4410-4417).*
Jiang et al. (J. Biol. Chem. Feb. 11, 2005; 280 (6): 4656-4662).*
Riemer et al. (Mol. Immunol. 2005; 42: 1121-1124).*
Pettersen et al. (J. Immunol. Jun. 15, 1999; 162 (12): 7031-7040).*
Takeshita et al. (Leukemia. Jul. 23, 2009; (7): 1329-36).*
Henry et al. (Cancer Res. Nov. 1, 2004; 64: 7995-8001).*
Yip et al. (J. Immunol. Apr. 15, 2001; 166 (8): 5271-8).*
Borcherding, N., et al., "ROR1, an embryonic protein with an emerging role in cancer biology." Protein Cell (Jul. 2014); 5(7): 496-502. Epub Apr. 22, 2014.
Carlsson and Söderlind, "n-CoDeR concept: unique types of antibodies for diagnostic use and therapy." Expert Review of Molecular Diagnostics (2001); 1(1): 102-108.
Extended European Search Report for European Patent Application No. EP 16797161.3, dated Jan. 9, 2019, 9 pages.
Invitation to pay additional search fees, for International Application No. PCT/US2016/032911, dated Aug. 12, 2016, 3 pages.
Steinitz, M., (ed.), "Human Monoclonal Antibodies: The Residual Challenge of Antibody Immunogenicity". Methods and Protocols" In: " Human Monoclonal Antibodies Methods and Protocols, Humana Press, Springer Science+Business Media, LLC (2014); vol. 1060, pp. 1-137, pp. 139-243, pp. 245-295, pp. 297-307, pp. 309-351, pp. 353-361, 368 pages.
Asano et al., "Cytotoxic Enhancement of a Bispecific Diabody by Format Conversion to Tandem Single-chain Variable Fragment (taFv)." Journal of Biological Chemistry (2011); 286(3): 1812-1818.
Baskar et al., "Unique Cell Surface Expression of Receptor Tyrosine Kinase ROR1 in Human B-Cell Chronic Lymphocytic Leukemia." Clinical Cancer Research (2008); 14(2): 396-404.
Choudhury et al., "Silencing of ROR1 and FMOD with siRNA results in apoptosis of CLL cells." British Journal of Haematology (2010); 151(4): 327-335.
Fukuda et al., "Antisera induced by infusions of autologous Ad-CD154-leukemia B cells identify ROR1 as an oncofetal antigen and receptor for Wnt5a." Proceedings of the National Academy of Sciences (2008); 105(8): 3047-3052.
Gunasekaran et al., "Enhancing Antibody Fc Heterodimer Formation Through Electrostatic Steering Effects: Applications to Bispecific Molecules and Monovalent IgG." Journal of Biological Chemistry (2010); jbc-M110.
International Preliminary Report on Patentability for International Application No. PCT/US2016/032911, dated Nov. 21, 2017, 13 pages.
International Search Report and Written Opinion, dated Nov. 8, 2016, for International Application No. PCT/US2016/032911, 20 pages.
Jaggi et al., "Selective Alpha-Particle Mediated Depletion of Tumor Vasculature with Vascular Normalization." PLoS One (2007); 2(3): e267.
Loffler et al., "A recombinant bispecific single-chain antibody, CD19 X CD3, induces rapid and high lymphoma-directed cytotoxicity by unstimulated T lymphocytes." Blood (2000); 95(6): 2098-2103.
McDevitt et al., "Tumor Therapy with Targeted Atomic Nanogenerators." Science (2001); 294(5546): 1537-1540.
Muller et al., "Improved Pharmacokinetics of Recombinant Bispecific Antibody Molecules by Fusion to Human Serum Albumin." The Journal of Biological Chemistry (2007); 282 (17): 12650-12660.
Nishita et al., "Cell/tissue-tropic functions of Wnt5a signaling in normal and cancer cells." Trends in Cell Biology (2010); 20(6): 346-354.
Rossi et al., "Stably tethered multifunctional structures of defined composition made by the dock and lock method for use in cancer targeting." Proceedings of the National Academy of Sciences (2006); 103(18): 6481-6486.
Thompson et al., "CLUSTAL W: improving the sensitivity of progressive multiple sequence alignment through sequence weighting, position-specific gap penalties and weight matrix choice." Nucleic Acids Research (1994); 22(22): 4673-4680.
Thompson et al., "The CLUSTAL_X windows interface: flexible strategies for multiple sequence alignment aided by quality analysis tools." Nucleic Acids Research (1997); 25(24): 4876-4882.
Tomimatsu et al., "Production of human monoclonal antibodies against FcεRIα by a method combining in vitro immunization with phage display." Bioscience, biotechnology and biochemistry (2009); 73(7): 1465-1469.
Weiner et al., "The role of T cell activation in anti-CD3 x antitumor bispecific antibody therapy." The Journal of Immunology (1994); 152(5): 2385-2392.
Zhang et al., "ROR1 Is Expressed in Human Breast Cancer and Associated with Enhanced Tumor-Cell Growth," PloS one (2012); 7(3): e31127, pp. 1-12.
Reddy, et al., "Human neural tissues express a truncated Ror1 receptor tyrosine kinase, lacking both extracellular and transmembrane domains." Oncogene (Oct. 3, 1996); 13(7): 1555-1559.
Bernard, et al., "A unique epitope on the CD2 molecule defined by the monoclonal antibody 9-1: epitope-specific modulation of the E-rosette receptor and effects on T-cell functions." Human Immunology (Dec. 1986); 17(4): 388-405.
Wang, Lingfei, et al., "The research progress of receptor tyrosine kinase-like orphan receptor in tumor immunotherapy", Modern Immunology (Mar. 31, 2015); 35(2): 167-171 (and English Abstract).
Berger, et al., "Safety of Targeting ROR1 in Primates with Chimeric Antigen Receptor—Modified T Cells", Cancer Immunol Res. (Feb. 2015); 3(2): 206-216. Epub Oct. 29, 2014.

* cited by examiner

Human heavy chain constant region and IgG1 Fc domain sequence:

ASTKGPSVFPLAPSSKSTSGGTAALGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

Human light chain constant region (kappa):

TVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

FIG. 15

| Samples | $K_d$ [1/s] | Error in $k_d$ | $k_a$ [1/Ms] | $K_D$ [M] |
|---|---|---|---|---|
| Positive control Ab | 1.76E-3 | 4.03E-5 | 3.70E5 | 4.76E-9 |
| Antibody 601-3-2 | 2.06E-5 | 1.41E-6 | 1.21E6 | 1.70E-11 |
| Antibody 601-3-12 | 1.58E-5 | 1.44E-6 | 1.07E6 | 1.48E-11 |
| Antibody 601-3-16 | 5.26E-6 | 2.22E-6 | 6.11E5 | 8.61E-12 |

FIG. 17B

| Antibody | Pesudo $k_d$[1/Ms] | Percentage Blocking* |
|---|---|---|
| 601-3-2 | 1.3E4 | 38% |
| 601-3-12 | 5.3E3 | 75% |
| 601-3-16 | 6.7E3 | 68% |
| mAb Control | 2.1E4 | 0% |

ANTI-ROR1 ANTIBODIES

CROSS REFERENCE TO RELATED APPLICATIONS

This application is a 371 of International Application No. PCT/US2016/032911, filed May 17, 2016, which claims the benefit under 35 U.S.C. § 119(e) of U.S. Provisional Application No. 62/193,237, filed Jul. 16, 2015, and U.S. Provisional Application No. 62/163,241, filed May 18, 2015, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FIVE_004_02WO_ST25.txt. The text file is 185 KB, was created on May 17, 2016, and is being submitted electronically via EFS-Web, concurrent with the filing of the specification.

FIELD OF THE INVENTION

The present invention relates to antibodies, and in particular, to antibodies exhibiting specificity for Receptor tyrosine kinase-like Orphan Receptors (ROR), and to use thereof, for example in the treatment of cancer. The invention extends to polynucleotide and polypeptide sequences encoding the antibodies, and compositions comprising these molecules and therapeutic uses thereof. Diagnostic kits and methods comprising these molecules are also described. The invention also extends to antibody-drug conjugates and to uses thereof in therapy.

BACKGROUND OF THE INVENTION

Receptor tyrosine kinase-like orphan receptors (ROR) belong to a conserved family of receptor tyrosine kinases, which consists of two family members, ROR1 and ROR2, which are type-I transmembrane receptor tyrosine kinases. The extracellular region of ROR1 and ROR2 contains an immunoglobulin (Ig) domain, a cysteine-rich domain (CRD), also called a Frizzled (Fz) domain, and a Kringle (Kr) domain. All three domains are involved in protein-protein interactions. Intracellularly, ROR1 and ROR2 possess a tyrosine kinase (TK) domain and a proline-rich domain (PRD) straddled by two serine/threonine-rich domains 1.

The cellular function of this family is to regulate cell migration, planar cell polarity (PCP) and apical-basal cell polarity, and axon outgrowth in developmental processes, including skeletal and neuronal development. Wnt5a, a glycoprotein critical in carcinogenesis, has been identified as regulating these functions by binding and activating ROR1 and ROR2 (Nishita et al., 2010, Trends Cell Biol. 20(6): 346-54). Wnt5a binding to ROR2 and its co-receptor, Frizzled domain, can activate the JNK pathway and filamin A to regulate cell migration and invasion, cause Rac1 and Rho A to regulate cell polarity, and induce Src family members to modulate the expression of matrix metalloproteases, such as MMP 1, 2, 13, and inhibit the canonical Wnt pathways. Unlike ROR2, the molecular mechanism behind the regulation of ROR1 cellular function is still not clear. A recent study showed that ROR1 could promote cell proliferation through NF-B when co-expressed with Wnt5a (Fukuda et al., 2008, Proc Natl. Acad Sci USA. 105(8):3047-52). ROR proteins are embryonic proteins. In mice, they are expressed only during the developmental stage. ROR expression is quickly silenced after birth, and is undetectable in adult tissues. ROR1 or ROR2 knockout mice exhibit neonatal lethality and die shortly after birth. Mice with ROR1 knockout develop normally and show no visible phenotype. Mice with ROR2 knockout express skeletal defects such as shortened snouts, limbs, tails and a cleft palate, and a defect in the membranous part of ventricular septum.

ROR1 is aberrantly expressed in B-cell chronic lymphocytic leukemia (CLL) and mantle cell lymphoma (MCL). Like its mouse counterpart, human ROR1 expression cannot be detected in normal blood cells and other adult tissues, apart from low levels in adipose tissue. Studies have demonstrated that knockdown of ROR1 and fibromodulin results in significantly increased apoptosis of CLL cells (Choudhury et al., 2010, Br J Haematol. 151(4):327-35).

CLL is the most common form of human leukemia in the Western hemisphere. According to the Leukemia and Lymphoma Society, approximately 16,000 new cases of CLL are diagnosed in the U.S. each year, and 4,400 people die from the disease annually. CLL is characterized by the accumulation of functionally immature cells in the bone marrow, blood, lymph tissue and other organs. It is a malignancy of mature B-cells, and most often affects adults over the age of 55, of which two-thirds are men, though sometimes occurs in young adults. There is a significant unmet medical need for new and improved therapeutic options for CLL. Despite treatment using chemotherapy and stem cell transplantation, CLL is an incurable disease with average five year survival of only 50%.

It has been reported, with statistical significance, that a high level of ROR1 and ROR2 expression is correlated with a lower survival rate in neuroblastoma patients (FIGS. 1 and 2). Gene expression profiling data from pre-B ALL patients also suggest a correlation between ROR1 upregulation and t(1; 19) translocation, which generates the E2A-PBX1 fusion protein and serves as a biomarker of a subtype of pre-B-ALL (FIG. 3).

Recent advances in monoclonal antibodies (mAbs) for oncology indications have yielded new options for the treatment of CLL, either as stand-alone therapies or in combination with chemotherapy regimens. In 2007, CAMPATH® (anti-CD52 humanized antibody) received FDA approval as a first-line treatment for CLL. Previously, CAMPATH® was approved as a second-line treatment for CLL patients that stopped responding to alkylating agents and Fludara. CAMPATH® treatment showed significantly superior patient response compared to using chlorambucil as an initial treatment. CAMPATH® also exhibited a favorable toxicity profile. RITUXAN®, an anti-CD20 antibody drug, was approved by the FDA for treatment of patients with CLL in combination with two other chemotherapy drugs, fludarabine and cyclophosphamide. With all of these advances, approximately 20% of patients still do not achieve complete disease control, and most patients eventually developed resistance to the available therapies. Therefore, there is still a great need for more effective and innovative CLL therapies.

BRIEF DESCRIPTION OF THE DRAWINGS

For a better understanding of the invention, and to show how embodiments of the same may be carried into effect, reference will now be made, by way of example, to the accompanying diagrammatic drawings.

FIG. 15 shows protein sequences of human antibody constant domains of an embodiment of the anti-ROR1 full-length IgG1 antibody of the invention.

FIGS. 17a and 17b show Kd binding affinity analysis of anti-ROR1 full-length IgG1 antibodies by bio-layer interferometry.

DETAILED DESCRIPTION OF THE INVENTION

Figure 1:
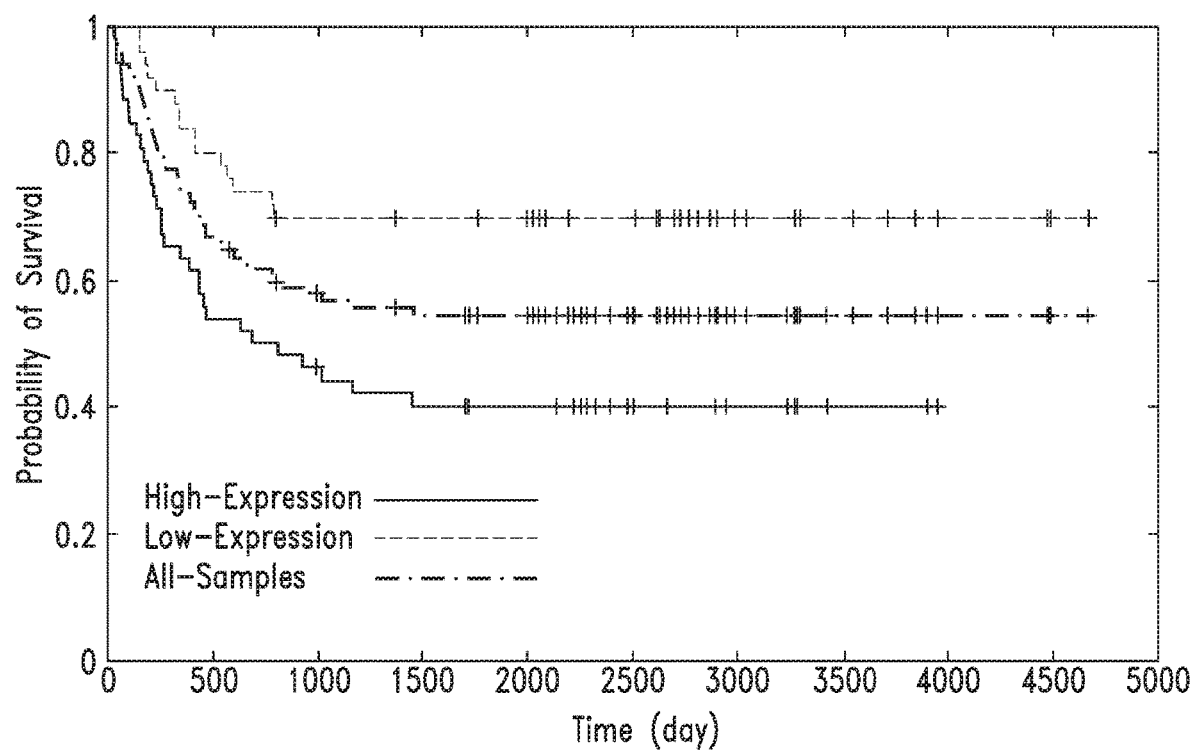
FIG. 1 is a graph showing statistically significant lower survival of neuroblastoma patients with high levels of ROR1 gene expression.
Figure 2:
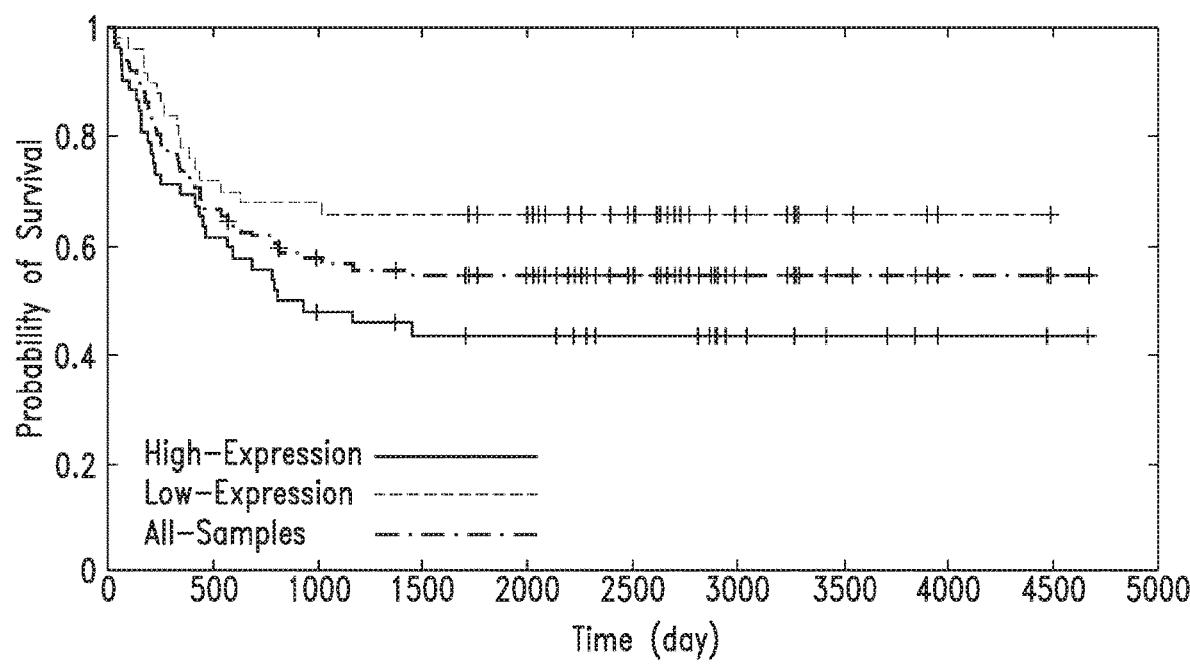
FIG. 2 is a graph showing statistically significant lower survival of neuroblastoma patients with high levels of ROR2 gene expression.
Figure 3A:
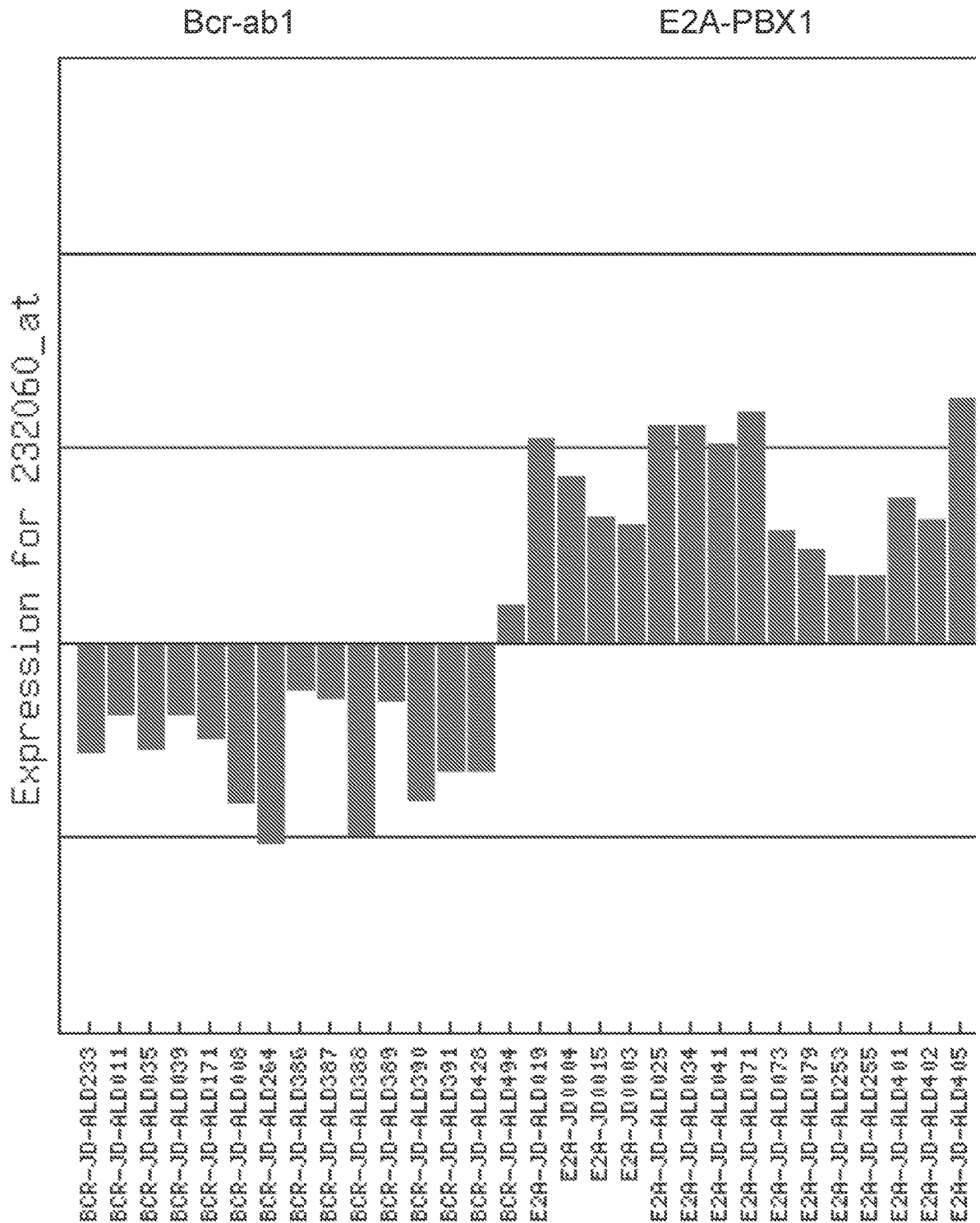
FIGS. 3A-3E show ROR1 mRNA expression in pre-B ALL patients.
Figure 3B:
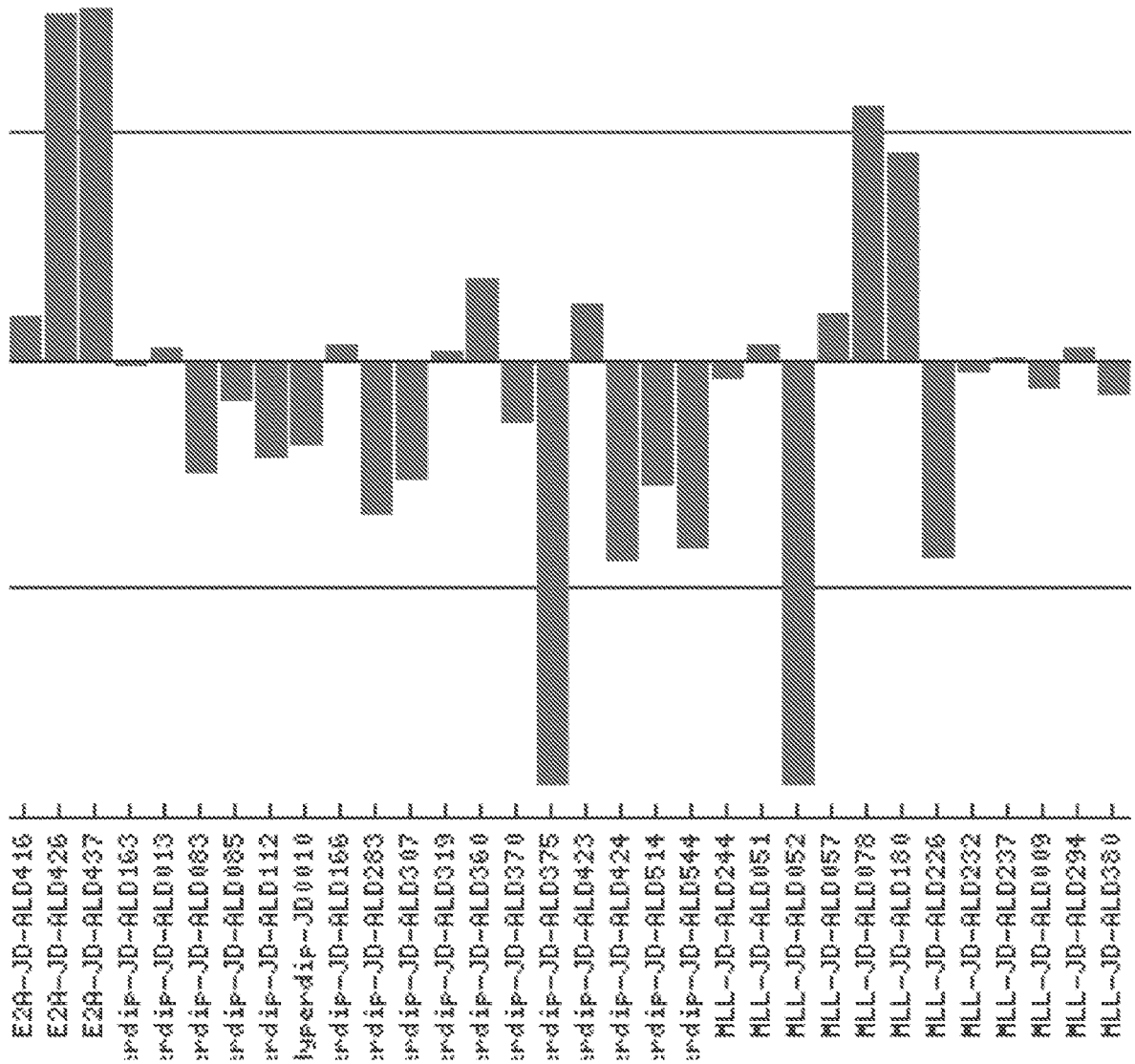
Figure 3C:
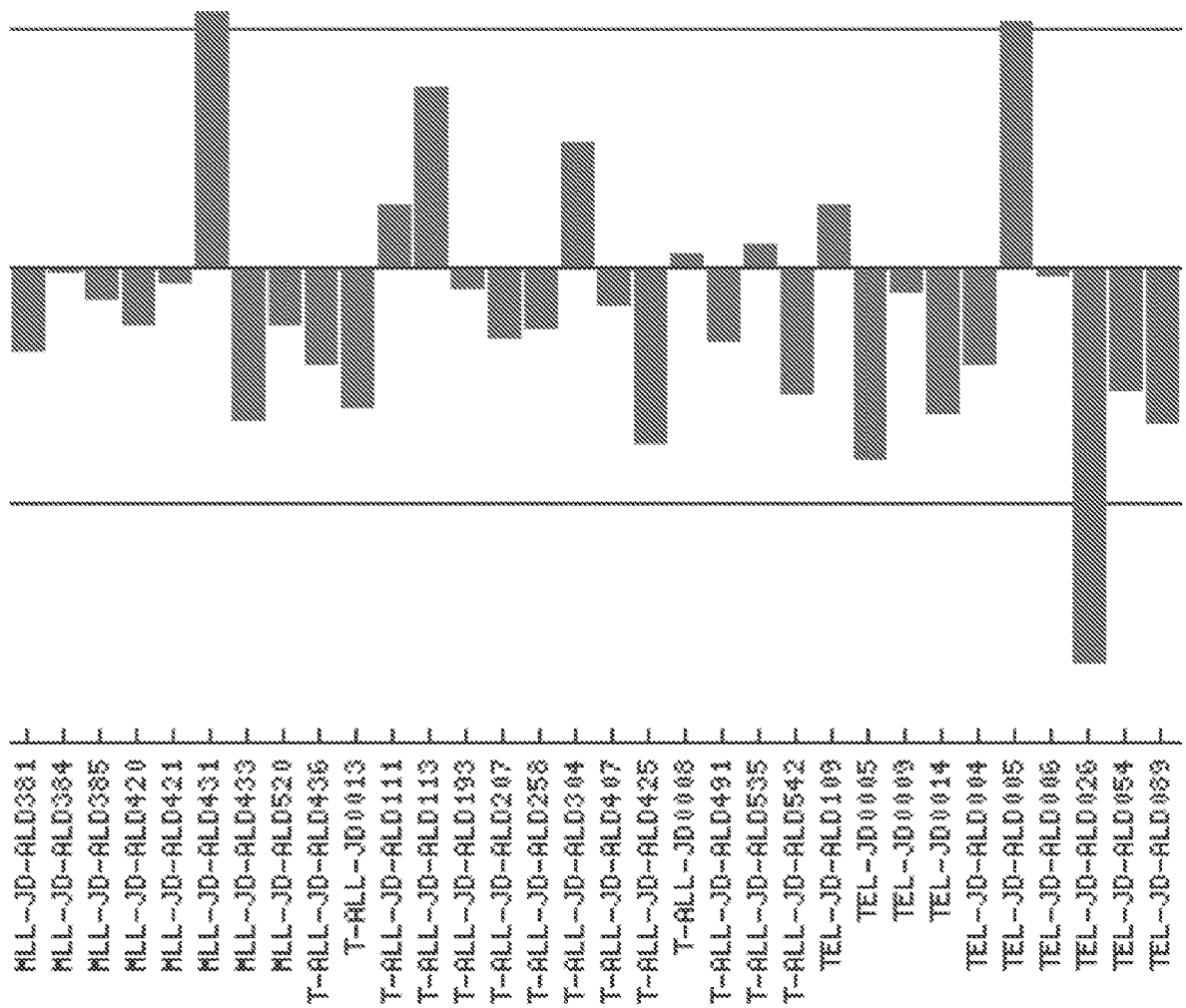
Figure 3D:
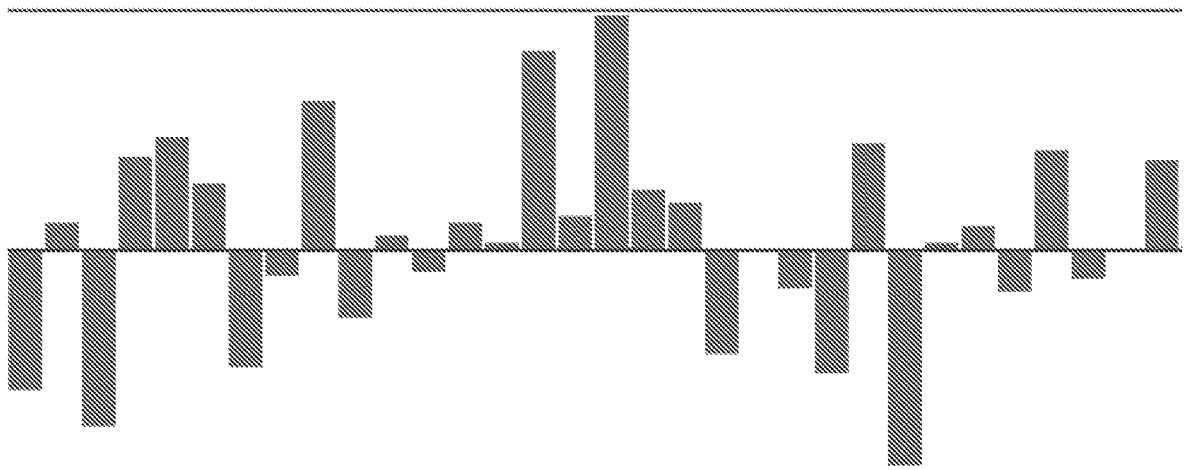
Figure 3E:
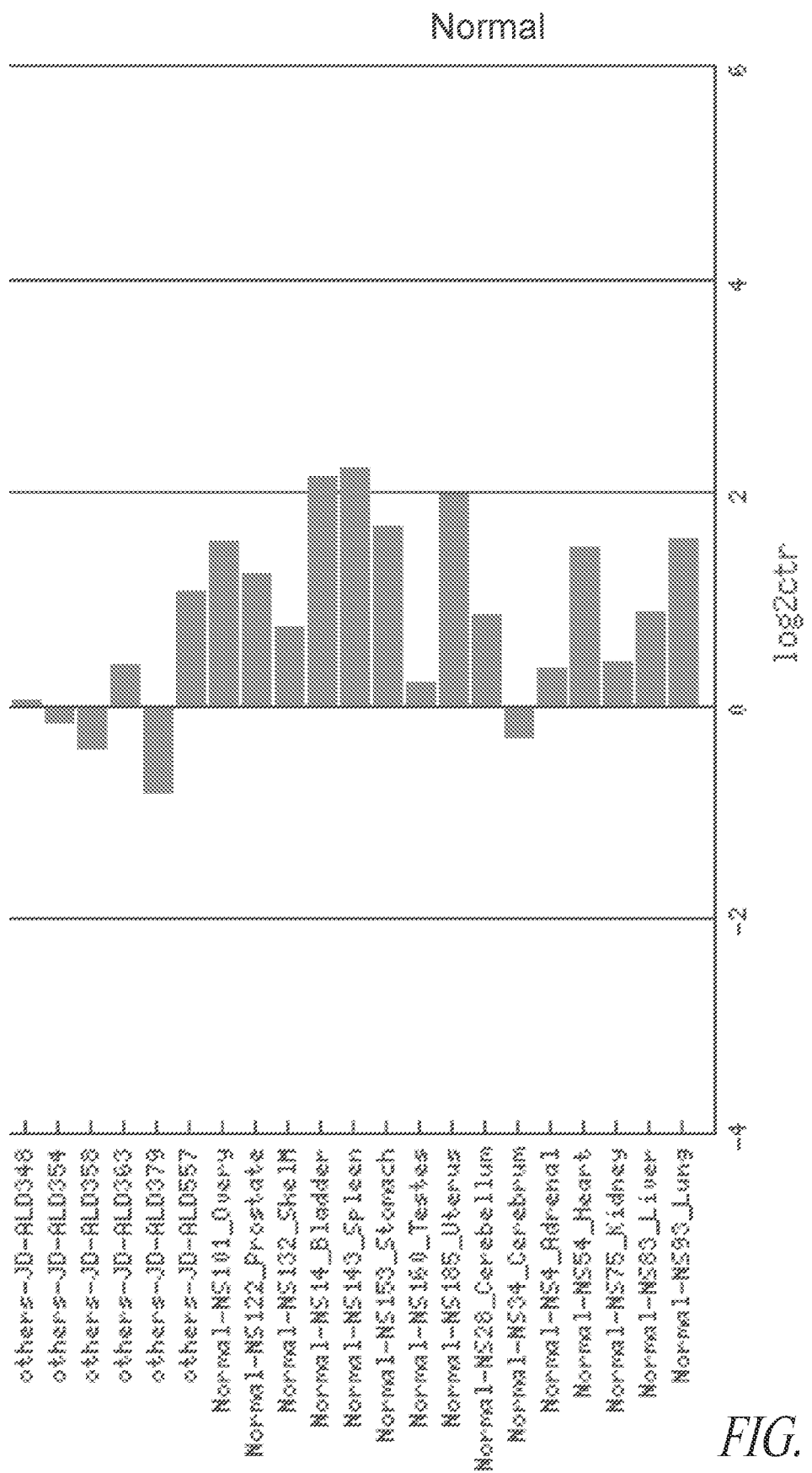

The inventors focused their investigations on Receptor Tyrosine Kinase-Like Orphan Receptor 1 (ROR1), as they considered it to be a promising novel cancer target for CLL, as well as other cancers. However, the inventors found that a significant problem involved in the development of effective ROR1-targeting monoclonal antibody diagnostics and therapies is that ROR1 has very low expression levels on the surface of CLL cancer cells. Indeed, studies have shown that ROR1 expression on CLL cancer cells is estimated to be only few thousand molecules per cell (Baskar et al., 2008, Clin Cancer Res. Jan 15; 14(2):396-404. In contrast, most antibody therapies target molecules that are highly-expressed on cancer cell surfaces. For example, Roche's antibody breast cancer drug HERCEPTIN® targets the Her2 antigen, which has an expression level estimated at >50,000 copies per cell. Accordingly, an effective antibody treatment for CLL must be able to identify CLL cancer cells despite the incredibly low ROR1 copy number. One way to overcome the challenge of low copy number of ROR1 on cancer cell surface is to identify a high affinity antibody that can bind to ROR1 positive cancer cells efficiently despite the low density of ROR1.

The objective of the present invention therefore is to develop highly-specific and high-affinity anti-ROR1 monoclonal antibodies that will target and kill cancerous cells with minimal side effects to normal tissues. By laborious panning against the human ROR1 extracellular domain (ECD) protein using a fully-human antibody phage library, the inventors have been able to isolate a highly specific human ROR1 specific antibody.

Therefore, according to a first aspect of the invention, there is provided a human anti-Receptor Tyrosine Kinase-Like Orphan Receptor 1 (ROR1) antibody, or a functional fragment thereof.

Advantageously, the inventors have isolated the first human ROR1-immunospecific antibody, and developed a ROR1-targeting antibody therapy for ROR1-positive cancer types, such as B-cell Chronic Lymphocytic Leukemia (CLL), the most common form of human leukemia in the Western hemisphere, thereby addressing an unmet medical need. Targeting ROR1 by the antibody according to the invention for cancer therapy is based on the important scientific finding that ROR1 is aberrantly expressed in cancer cells, but absent in normal blood cells and normal adult tissues, and therefore provides a highly specific therapy targeting only cancerous cells and tumors.

As described in the Examples, several different embodiments of the fully human and unique anti-ROR1 antibody of the invention have been isolated, each of these antibodies being capable of recognizing distinct binding epitopes on ROR1 protein with surprisingly high affinity. Advantageously, as described in the Examples the antibody of the invention can: (i) mediate complement-dependent cytotoxicity (CDC), (ii) mediate antibody-dependent cellular cytotoxicity (ADCC) against various ROR1-positive cancer cell lines, (iii) block Wnt5a binding to ROR1, and/or (iv) inhibit Wnt5a induced ROR1 phosphorylation. The inventors believe that this is first time that a fully human anti-ROR1 antibody has been isolated, identified and sequenced. The antibody of the invention therefore presents a highly effective therapeutic agent when used alone, or as a vehicle that is capable of delivering potent anti-cancer reagents, or as an engineered antibody exhibiting enhanced immune functions. Additionally, the antibody of the invention may also be used as a diagnostic or prognostic tool. Advantageously, based on its unique expression profile as a foetal antigen expressed only during embryonic development, and preferential expression profiling in multiple cancers, an effective antibody therapy targeting ROR1 will improve and lengthen life for a broad cancer patient population, and reduce long-term healthcare costs.

The invention extends to both whole antibodies (i.e., immunoglobulins) with immunospecificity for a ROR1 protein, preferably an extracellular domain thereof, as well as to functional fragments thereof. Such fragments retain at least one antigen binding region of a corresponding full-length antibody. The antibody or functional fragment thereof may comprise a monoclonal or polyclonal antibody or functional fragment thereof.

The antibody or functional fragment may be monovalent, divalent or polyvalent. Monovalent antibodies are dimers (HL) comprising a heavy (H) chain associated by a disulphide bridge with a light chain (L). Divalent antibodies are tetramer (H2L2) comprising two dimers associated by at least one disulphide bridge. Polyvalent antibodies may also be produced, for example by linking multiple dimers. A ROR1 antibody of the present invention can be a chimeric antibody, bi-specific antibody, multi-specific antibody, humanized antibody and/or human antibody. The basic structure of an antibody molecule consists of two identical light chains and two identical heavy chains which associate non-covalently and can be linked by disulphide bonds. Each heavy and light chain contains an amino-terminal variable region of about 110 amino acids, and constant sequences in the remainder of the chain. The variable region includes several hypervariable regions, or Complementarity Determining Regions (CDRs), that form the antigen-binding site of the antibody molecule and determine its specificity for the antigen, e.g., ROR1 or an epitope thereof. On either side of the CDRs of the heavy and light chains is a framework region, a relatively conserved sequence of amino acids that anchors and orients the CDRs.

The constant region consists of one of five heavy chain sequences ($\mu$, $\gamma$, $\zeta$, $\alpha$ or $\epsilon$) and one of two light chain sequences ($\kappa$ or $\lambda$). The heavy chain constant region sequences determine the isotype of the antibody and the effector functions of the molecule.

As used herein, the term "human antibody" can mean an antibody, such as a monoclonal antibody, which comprises substantially the same heavy and light chain CDR amino acid sequences as found in a particular human antibody exhibiting immunospecificity for ROR1 protein. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids. Such a human antibody maintains its function of selectively binding to ROR1 protein. Human antibodies include, but are not limited to, antibodies produced in non-human animals that comprise human immunoglobulin genes, such as XENOMOUSE®, and antibodies selected using in vitro methods, such as phage display, wherein the antibody repertoire is based on human immunoglobulin sequences.

The term "human monoclonal antibody" can include a monoclonal antibody with substantially human CDR amino acid sequences produced, for example by recombinant methods such as production by a phage library, by lymphocytes or by hybridoma cells.

The term "humanized antibody" can mean an antibody from a non-human species (e.g., mouse) whose protein sequences have been modified to increase their similarity to antibodies produced naturally in humans The term "humanized antibody" refers to an antibody in which at least one amino acid in a framework region of a non-human variable region (such as mouse, rat, cynomolgus monkey, chicken, etc.) has been replaced with the corresponding amino acid from a human variable region. In some embodiments, a humanized antibody comprises at least one human constant region or fragment thereof. In some embodiments, a humanized antibody is an Fab, an scFv, a (Fab')$_2$, etc.

A "chimeric antibody" as used herein refers to an antibody comprising at least one variable region from a first species (such as mouse, rat, cynomolgus monkey, etc.) and at least one constant region from a second species (such as human, cynomolgus monkey, chicken, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "bispecific antibody" as used herein refers to an antibody comprising a first arm comprising a heavy chain/light chain combination that binds a first antigen and a second arm comprising a heavy chain/light chain combination that binds a second antigen. In some embodiments, one of the arms of a bispecific antibody comprises a heavy chain/light chain combination that binds ROR1.

The antibody may be a recombinant antibody. The term "recombinant human antibody" can include a human antibody produced using recombinant DNA technology.

The term "antigen binding region" can mean a region of the antibody having specific binding affinity for its target antigen, e.g., the ROR1 protein. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to ROR1 protein.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e., the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR, or a functional portion thereof, will vary depending on the sequence and size of the CDR. Those skilled in the art can routinely determine which residues comprise a particular CDR given the variable region amino acid sequence of the antibody.

The term "functional fragment" of an antibody can mean a portion of the antibody which retains a functional activity. A functional activity can be, for example antigen binding activity or specificity (e.g., an antigen-binding fragment). A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH, and Fd; monovalent fragments, such as Fv, Fab, and Fab'; bivalent fragments such as F(ab')2; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the light chain variable and constant regions coupled to the heavy chain variable and constant regions, i.e., VL CL and VH CH-1.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" means a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can means a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')2 fragment" can mean a bivalent antigen-binding fragment of a human monoclonal antibody. An F(ab')2 fragment includes, for example, all or part of the variable regions of two heavy chains-and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

One skilled in the art knows that the exact boundaries of a fragment of a human monoclonal antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise fragments with substantially the same heavy and light chain variable regions as the human antibody. Preferably, the functional fragment is ROR1-specific.

The functional fragment may include fragments wherein at least one of the binding region sequences has substantially the same amino acid sequence as the binding region sequences of the antibody, more preferably the ROR1-specific human antibody. The functional fragment may comprise any of the fragments selected from a group consisting of VH, VL, Fd, Fv, Fab, Fab', scFv, F (ab')$_2$ and Fc fragment.

The functional fragment may comprise any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the functional fragment. Functional fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F(ab') fragment. An F(ab')2 fragment of the invention may be further reduced using, for example, DTT or 2-mercaptoethanol to produce two monovalent Fab' fragments.

Functional fragments produced by proteolysis may be purified by affinity and column chromatographic procedures. For example, undigested antibodies and Fc fragments may be removed by binding to protein A. Additionally, functional fragments may be purified by virtue of their charge and size, using, for example, ion exchange and gel filtration chromatography. Such methods are well known to those skilled in the art.

The human antibody or functional fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably, the CDRs.

The polynucleotide encoding the human antibody or functional fragment of the invention may be produced using methods known to those skilled in the art. The polynucleotide encoding the antibody or a functional fragment thereof may be directly synthesized by methods of oligonucleotide synthesis known in the art. Alternatively, smaller fragments may be synthesized and joined to form a larger functional fragment using recombinant methods known in the art.

As used herein, the term "immunospecificity" can mean the binding region is capable of immunoreacting with a ROR1 protein, by specifically binding therewith. The antibody or functional fragment thereof can selectively interact with an antigen (e.g., ROR1 peptide) with an affinity constant of approximately $10^{-5}$ to $10^{-13}$ M$^{-1}$, preferably $10^{-6}$ to $10^{-9}$ M$^{-1}$, even more preferably, $10^{-10}$ to $10^{-2}$ M$^{-1}$.

A "subject" may be a vertebrate, mammal, or domestic animal. Hence, medicaments according to the invention may be used to treat any mammal, for example livestock (e.g., a horse), pets, or may be used in other veterinary applications. Most preferably, the subject is a human being.

A "therapeutically effective amount" of the antibody or fragment thereof is any amount which, when administered to a subject, is the amount of agent that is needed to treat the cancer, or produce the desired effect.

The term "anti-cancer composition" can mean a pharmaceutical formulation used in the therapeutic amelioration, prevention or treatment of cancer in a subject.

A "pharmaceutically acceptable vehicle" as referred to herein, is any known compound or combination of known compounds that are known to those skilled in the art to be useful in formulating pharmaceutical compositions.

Figure 17A:
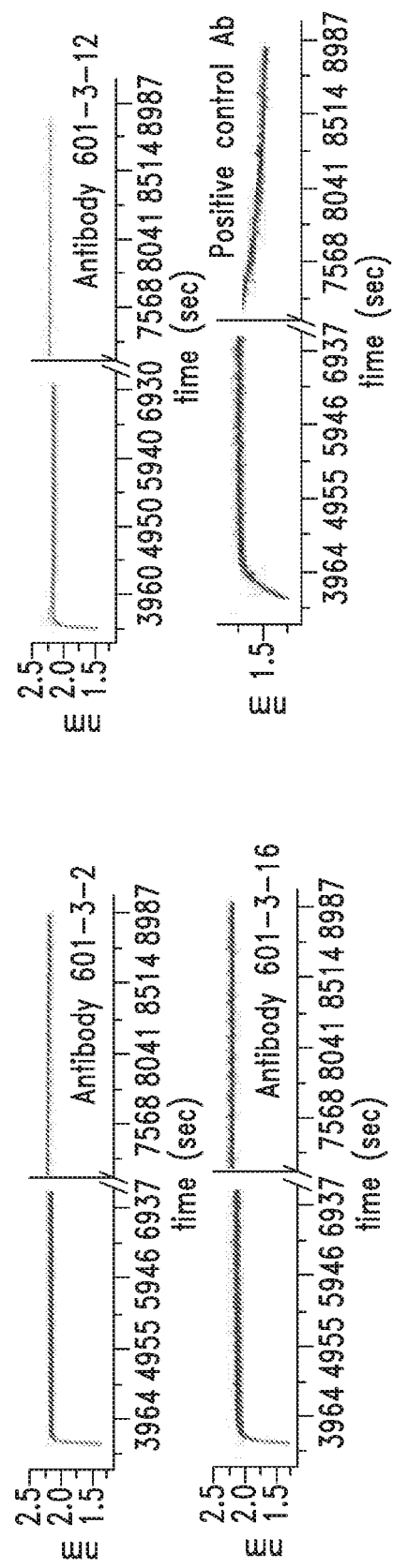

As shown in FIG. 17, kinetic binding analysis confirmed specific binding of the full length IgG1 antibodies to hROR1-ECD, with a Kd in picomolar range. Thus, preferably the KD of the antibody or fragment thereof for ROR1 may be less than $1\times10^{-10}$, preferably less than $1\times10^{-11}$, more preferably less than $1\times10^{-12}$. The antibody or fragment thereof may exhibit an IC50 for ROR1 of about $10^{-7}$ to $10^{-10}$ M$^{-1}$.

The term "immunoreact" can mean the binding region is capable of eliciting an immune response upon binding with an ROR1 protein, or an epitope thereof.

The term "epitope" can mean any region of an antigen with ability to elicit, and combine with, a binding region of the antibody or fragment thereof.

Figure 23:
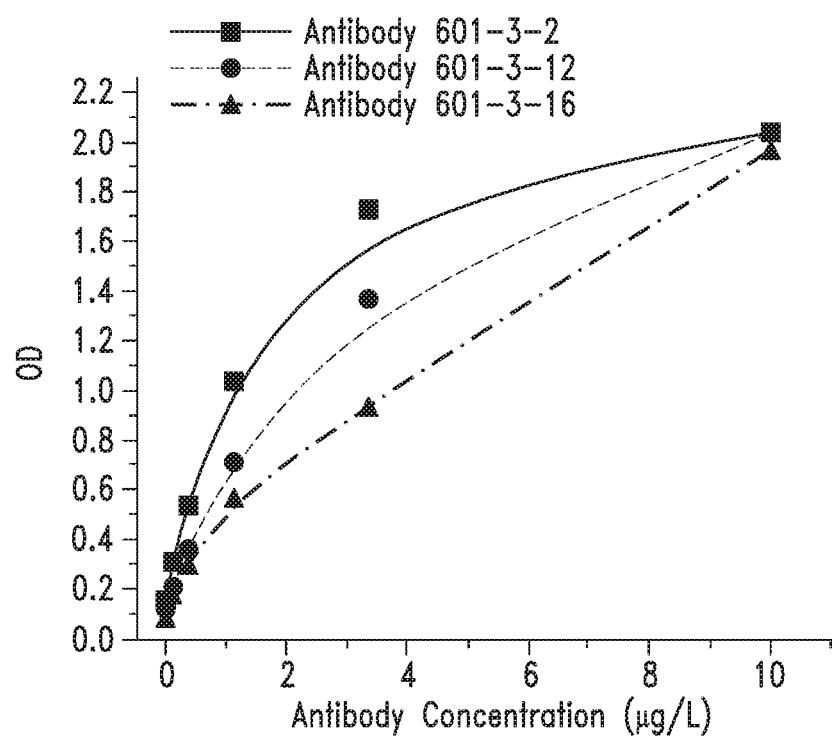
FIG. 23 is a graph showing C1q binding of anti-ROR1 full-length IgG1 antibodies.
Figure 24A:
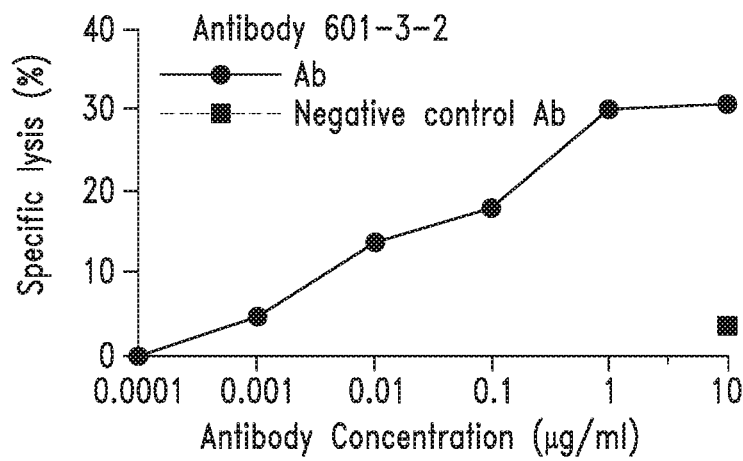
FIG. 24a-24c are graphs showing ADCC activity of anti-ROR1 full-length IgG1 antibodies against MDA-MB-231.
Figure 24B:
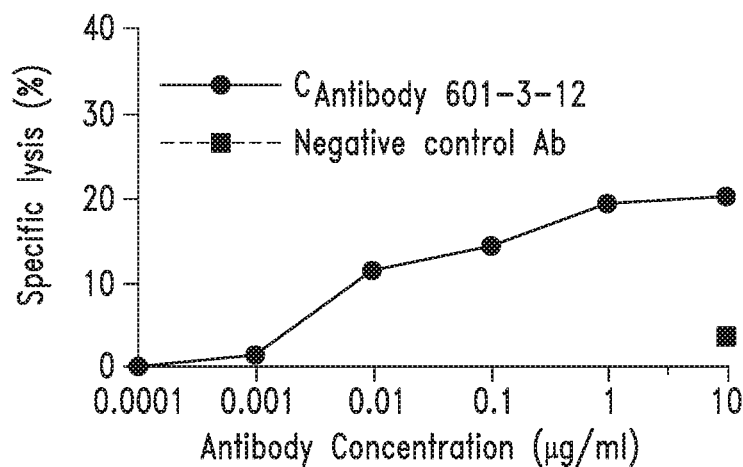
Figure 24C:
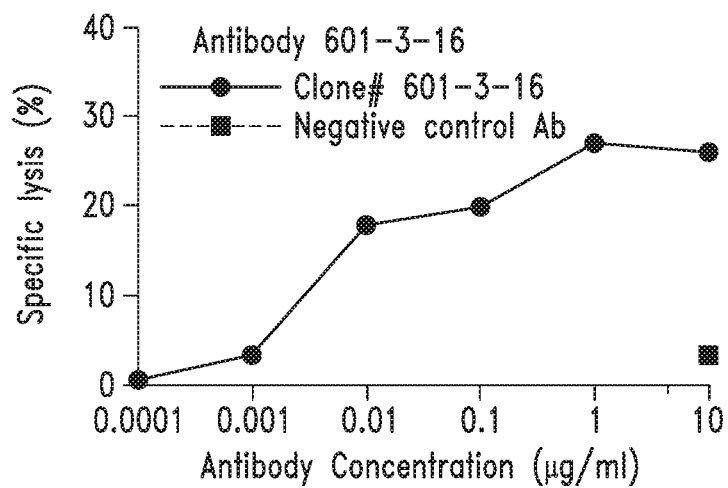

As shown in FIGS. 23 and 24, the antibody or fragment thereof may be capable of mediating killing of ROR1-expressing tumor cells. Killing may be via Complement-Dependent-Cytotoxicity (CDC) and/or via Antibody-Dependent Cellular Cytotoxicity (ADCC).

Figure 25:
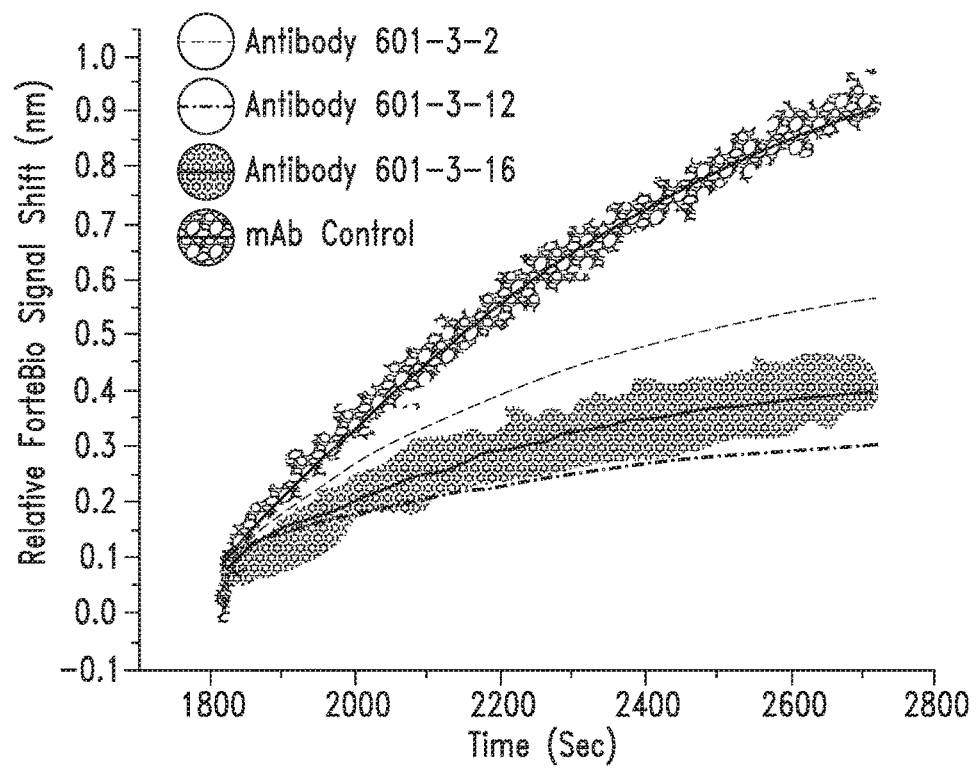
FIG. 25 show blocking of Wnt5a ligand binding by anti-ROR1 full-length IgG1 antibodies.

As illustrated in FIG. 25, the antibody or fragment thereof may be capable of blocking binding of Wnt5a to ROR1 protein.

Figure 26:
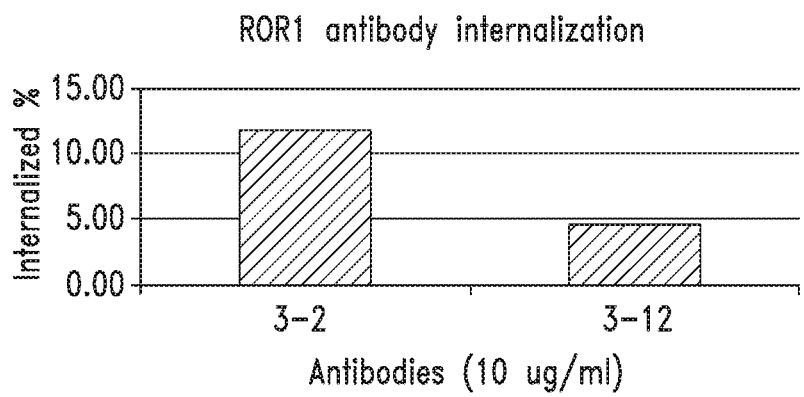
FIG. 26 is a graph showing ROR1 antibody internalization.

As shown in FIG. 26, the antibody of fragment thereof may be capable of being endocytosed upon binding to ROR1.

The antibody or fragment thereof may be capable of blocking Wnt5a ROR1 phosphorylation. The antibody or fragment thereof may be capable of inhibiting cancer cell proliferation.

The term "ROR1" can refer to family 1 of the receptor tyrosine kinase-like orphan receptors (mRNA: NM_005012.2, protein: NP_005003.2). The DNA sequence encoding one embodiment of human ROR1 is provided herein as SEQ ID NO:1.

The polypeptide sequence of one embodiment of human ROR1 is provided herein as SEQ ID NO:2.

As described in the Examples, the inventors have isolated 45 different embodiments of the antibody or functional fragment according to the first aspect of the invention. The inventors have carried out epitope mapping, and found that embodiments of the antibody or fragment thereof are capable of binding to various different epitopes on the ROR1 protein, these epitopes being designated herein as epitope class I-IV. Epitope I may be defined as being residues KNDAPVVQEPRRLSFRSTIYGSR (SEQ ID NO:237; i.e., amino acids 93-115 of SEQ ID NO:2) and AANCIRIGIPMADPI (SEQ ID NO:238; i.e., amino acids 293-307 of SEQ ID NO:2), epitope II may be defined as being residues SSTGVLFVKFGPPPTASPG (SEQ ID NO:239; i.e., amino acids 141-159 of SEQ ID NO:2) and SNPMILMRLKLPNCE (SEQ ID NO:240; i.e., amino acids 269-283 of SEQ ID NO:2), and epitope III and epitope IV may be defined as being the rest of the extracellular sequence of SEQ ID NO:2. Thus, the antibody or fragment thereof is preferably capable of binding to one or more of epitopes I to IV on ROR1 protein, or a functional fragment or variant of any one of these epitopes. It will be appreciated that knowledge of these various epitopes can be used to generate a novel ROR1-specific antibody.

Hence, in a second aspect, there is provided use of an epitope for generating an anti-Receptor Tyrosine Kinase-Like Orphan Receptor 1 (ROR1) antibody, or a functional fragment thereof, wherein the epitope is selected from a group of epitopes consisting of KNDAPVVQEPRRLSFRSTIYGSR (SEQ ID NO:237; i.e., amino acids 93-115 of SEQ ID NO:2); AANCIRIGIPMADPI (SEQ ID NO:238; i.e., amino acids 293-307 of SEQ ID NO:2); SSTGVLFVKFGPPPTASPG (SEQ ID NO:239; i.e., amino acids 141-159 of SEQ ID NO:2); SNPMILMRLKLPNCE (SEQ ID NO:240; i.e., amino acids 269-283 of SEQ ID NO:2); and the rest of the extracellular sequence of SEQ ID NO:2; or a functional fragment or variant of any of these epitopes.

In some embodiments, an anti-ROR1 antibody is provided that binds to a peptide having the sequence KNDAPVVQEPRRLSFRSTIYGSR (SEQ ID NO:237; i.e., amino acids 93-115 of SEQ ID NO:2). In some embodiments, an anti-ROR1 antibody is provided that binds to a peptide having the sequence AANCIRIGIPMADPI (SEQ ID NO:238; i.e., amino acids 293-307 of SEQ ID NO:2). In some embodiments, an anti-ROR1 antibody is provided that binds to a peptide having the sequence SSTGVLFVKFGPPPTASPG (SEQ ID NO:239; i.e., amino acids 141-159 of SEQ ID NO:2). In some embodiments, an anti-ROR1 antibody is provided that binds to a peptide having the sequence SNPMILMRLKLPNCE (SEQ ID NO:240; i.e., amino acids 269-283 of SEQ ID NO:2).

In some embodiments, an anti-ROR1 antibody is provided that competes for binding to ROR1 with antibody 601-3-2. In some embodiments, an anti-ROR1 antibody is provided that competes for binding to ROR1 with antibody 601-3-12. In some embodiments, an anti-ROR1 antibody is provided that competes for binding to ROR1 with antibody 601-3-16.

The inventors have also determined the Complementarity Determining Regions (CDRs) of both the heavy and light chains of the ROR1-specific antibodies of the invention, and have found highly conserved motifs within each of these four epitope classes. Surprisingly, as illustrated in FIGS. 8-11, they found that there are three sub-groups in epitope class I (i.e., sub-groups Ia, Ib and Ic), five sub-groups in epitope class II (i.e., sub-groups IIa, IIb, IIc and IId), and two sub-groups in each of epitope classes III (i.e., sub-groups IIIa and IIIb) and IV (i.e., sub-groups IVa and IVb) to which embodiments of the antibody can bind. In some embodiments, an antibody is provided that competes for ROR1 binding with an antibody in epitope class I (e.g., competes with an antibody in sub-group Ia, Ib or Ic). In some embodiments, an antibody is provided that competes for ROR1 binding with an antibody in epitope class II (e.g., competes with an antibody in sub-group IIa, IIb, IIc or IId.

In some embodiments, an antibody is provided that competes for ROR1 binding with an antibody in epitope class III (e.g., competes with an antibody in sub-group IIIa or IIIb). In some embodiments, an antibody is provided that competes for ROR1 binding with an antibody in epitope class IV (e.g., competes with an antibody in sub-group IVa or IVb).

As described in Example 2, the inventors have isolated a total of 45 antibodies, which are immunospecific for ROR1, 14 of which are preferred. These 14 preferred antibodies: (i) represent all of the above-mentioned epitope classes and their sub-groups, (ii) have high ROR1-binding affinity; and (iii) form a pool that can be converted into full IgG molecules. All of the antibodies described herein can be developed for therapeutic and diagnostic use and so are clearly valuable.

In some embodiments, and anti-ROR1 antibody is provided, wherein the antibody comprises the heavy chain variable region and the light chain variable region of an anti-ROR1 antibody selected from Antibody 601-1; Antibody 601-2 (3-12); Antibody 601-3 (3-16); Antibody 601-4; Antibody 601-5 (3-2); Antibody 601-6; Antibody 601-9; Antibody 601-13; Antibody 601-14; Antibody 601-17; Antibody 601-18 Antibody 601-28; Antibody 601-37; Antibody 601-40; Antibody 601-43; Antibody 601-50; Antibody 601-51; Antibody 601-56; Antibody 601-57; Antibody 601-65; Antibody 601-66; Antibody 601-69; Antibody 601-70; Antibody 601-81; Antibody 601-86; Antibody 601-87; Antibody 601-100; Antibody 601-101; Antibody 601-102; Antibody 601-103; Antibody 601-108; Antibody 601-109; Antibody 601-110; Antibody 601-112; Antibody 601-119; Antibody 601-120; Antibody 601-128; Antibody 601-130; Antibody 601-134; Antibody 601-136; Antibody 601-137; Antibody 601-141; Antibody 601-147; Antibody 601-149; or Antibody 601-153. The heavy chain and light chain variable regions of those antibodies are shown, for example, in the tables herein titled "Table of Certain Light Chain Variable Region Sequences" and "Table of Certain Heavy Chain Variable Region Sequences."

In some embodiments, and anti-ROR1 antibody is provided, wherein the antibody comprises the heavy chain variable region that is at least 90%, at least 91%, at least 92%, at least 93%, at least 94%, at least 95%, at least 96%, at least 97%, at least 98%, or at least 99% identical to a heavy chain variable region of anti-ROR1 antibody selected from Antibody 601-1; Antibody 601-2 (3-12); Antibody 601-3 (3-16); Antibody 601-4; Antibody 601-5 (3-2); Antibody 601-6; Antibody 601-9; Antibody 601-13; Antibody 601-14; Antibody 601-17; Antibody 601-18; Antibody 601-28; Antibody 601-37; Antibody 601-40; Antibody 601-43; Antibody 601-50; Antibody 601-51; Antibody 601-56; Antibody 601-57; Antibody 601-65; Antibody 601-66; Antibody 601-69; Antibody 601-70; Antibody 601-81; Antibody 601-86; Antibody 601-87; Antibody 601-100; Antibody 601-101; Antibody 601-102; Antibody 601-103; Antibody 601-108; Antibody 601-109; Antibody 601-110; Antibody 601-112; Antibody 601-119; Antibody 601-120; Antibody 601-128; Antibody 601-130; Antibody 601-134; Antibody 601-136; Antibody 601-137; Antibody 601-141; Antibody 601-147; Antibody 601-149; or Antibody 601-153. In some such embodiments, the antibody comprises the heavy chain CDRs of the reference antibody. The heavy chain CDRs of each of those antibodies are shown, for example, in the table herein titled "Table of Certain Heavy Chain CDR Sequences."

In some embodiments, and anti-ROR1 antibody is provided, wherein the antibody comprises the light chain variable region that is at least 90%, at least 91%, at least 92%, at least 93%, at least 94%, at least 95%, at least 96%, at least 97%, at least 98%, or at least 99% identical to a light chain variable region of anti-ROR1 antibody selected from Antibody 601-1; Antibody 601-2 (3-12); Antibody 601-3 (3-16); Antibody 601-4; Antibody 601-5 (3-2); Antibody 601-6; Antibody 601-9; Antibody 601-13; Antibody 601-14; Antibody 601-17; Antibody 601-18 Antibody 601-28; Antibody 601-37; Antibody 601-40; Antibody 601-43; Antibody 601-50; Antibody 601-51; Antibody 601-56; Antibody 601-57; Antibody 601-65; Antibody 601-66; Antibody 601-69; Antibody 601-70; Antibody 601-81; Antibody 601-86; Antibody 601-87; Antibody 601-100; Antibody 601-101; Antibody 601-102; Antibody 601-103; Antibody 601-108; Antibody 601-109; Antibody 601-110; Antibody 601-112; Antibody 601-119; Antibody 601-120; Antibody 601-128; Antibody 601-130; Antibody 601-134; Antibody 601-136; Antibody 601-137; Antibody 601-141; Antibody 601-147; Antibody 601-149; or Antibody 601-153. In some such embodiments, the antibody comprises the light chain CDRs of the reference antibody. The light chain CDRs of each of those antibodies are shown, for example, in the table herein titled "Table of Certain Light Chain CDR Sequences."

FIGS. 8-11 show that the inventors have determined consensus sequences for the variable regions of the heavy and light chains of the isolated antibodies, which form the CDRs (L1, L2 and L3 being the three CDRs of the light chain, and H1, H2 and H3 being the three CDRs of the heavy chain). Clearly, these conserved residues are important for defining the antibodies' binding specificity and affinity for the ROR1 protein, preferably the extracellular domain (ECD) thereof, and hence provide useful information for antibody engineering in order to modify and improve the binding profile of the antibody. The inventors have determined the amino acid and DNA sequences of each of the preferred 14 antibodies, as described in Example 2.

Thus, in one embodiment, the antibody or functional fragment thereof may comprise at least one antigen binding region comprising an amino acid sequence selected from a group consisting of: (i) SEQ ID NO: 8; (ii) SEQ ID NO:9; (iii) SEQ ID NO:10; (iv) SEQ ID NO:16; (v) SEQ ID NO: 17; and (vi) SEQ ID NO: 18.

In another embodiment, the antibody or functional fragment thereof may comprise at least one antigen binding region comprising an amino acid sequence selected from a group consisting of: (i) SEQ ID NO:24; (ii) SEQ ID NO:25; (iii) SEQ ID NO:26; (iv) SEQ ID NO:32; (v) SEQ ID NO:33; and (vi) SEQ ID NO:34.

In another embodiment, the antibody or functional fragment thereof may comprise at least one antigen binding region comprising an amino acid sequence selected from a group consisting of: (i) SEQ ID NO:40; (ii) SEQ ID NO:41; (iii) SEQ ID NO:42; (iv) SEQ ID NO:48; (v) SEQ ID NO:49; and (vi) SEQ ID NO:50.

In another embodiment, the antibody or functional fragment thereof may comprise at least one antigen binding region comprising an amino acid sequence selected from a group consisting of: (i) SEQ ID NO:56; (ii) SEQ ID NO:57; (iii) SEQ ID NO:58; (iv) SEQ ID NO:64; (v) SEQ ID NO: 65; and (vi) SEQ ID NO: 66.

In another embodiment, the antibody or functional fragment thereof may comprise at least one antigen binding region comprising an amino acid sequence selected from a group consisting of (i) SEQ ID NO:72; (ii) SEQ ID NO:73; (iii) SEQ ID NO:74; (iv) SEQ ID NO:80; (v) SEQ ID NO:81; and (vi) SEQ ID NO: 82.

In another embodiment, the antibody or functional fragment thereof may comprise at least one antigen binding region comprising an amino acid sequence selected from a group consisting of (i) SEQ ID NO:88; (ii) SEQ ID NO:89; (iii) SEQ ID NO:90; (iv) SEQ ID NO:96; (v) SEQ ID NO: 97; and (vi) SEQ ID NO: 98.

In another embodiment, the antibody or functional fragment thereof may comprise at least one antigen binding region comprising an amino acid sequence selected from a group consisting of (i) SEQ ID NO:104; (ii) SEQ ID NO: 105; (iii) SEQ ID NO:106; (iv) SEQ ID NO:112; (v) SEQ ID NO:113; and (vi) SEQ ID NO: 114.

In another embodiment, the antibody or functional fragment thereof may comprise at least one antigen binding region comprising an amino acid sequence selected from a group consisting of (i) SEQ ID NO:120; (ii) SEQ ID NO:121; (iii) SEQ ID NO:122; (iv) SEQ ID NO:128; (v) SEQ ID NO:129; and (vi) SEQ ID NO:130.

In another embodiment, the antibody or functional fragment thereof may comprise at least one antigen binding region comprising an amino acid sequence selected from a group consisting of (i) SEQ ID NO:136; (ii) SEQ ID NO: 137; (iii) SEQ ID NO:138; (iv) SEQ ID NO:144; (v) SEQ ID NO:145; and (vi) SEQ ID NO: 146.

In another embodiment, the antibody or functional fragment thereof may comprise at least one antigen binding region comprising an amino acid sequence selected from a group consisting of (i) SEQ ID NO:152; (ii) SEQ ID NO: 153; (iii) SEQ ID NO:154; (iv) SEQ ID NO:160; (v) SEQ ID NO:161; and (vi) SEQ ID NO: 162.

In another embodiment, the antibody or functional fragment thereof may comprise at least one antigen binding region comprising an amino acid sequence selected from a group consisting of (i) SEQ ID NO:168; (ii) SEQ ID NO: 169; (iii) SEQ ID NO:170; (iv) SEQ ID NO:176; (v) SEQ ID NO:177; and (vi) SEQ ID NO: 178.

In another embodiment, the antibody or functional fragment thereof may comprise at least one antigen binding region comprising an amino acid sequence selected from a group consisting of: (i) SEQ ID NO:184; (ii) SEQ ID NO:185; (iii) SEQ ID NO:186; (iv) SEQ ID NO:192; (v) SEQ ID NO:193; and (vi) SEQ ID NO:194.

In another embodiment, the antibody or functional fragment thereof may comprise at least one antigen binding region comprising an amino acid sequence selected from a group consisting of: (i) SEQ ID NO:200; (ii) SEQ ID NO:201; (iii) SEQ ID NO:202; (iv) SEQ ID NO:208; (v) SEQ ID NO:209; and (vi) SEQ ID NO:210.

In another embodiment, the antibody or functional fragment thereof may comprise at least one antigen binding region comprising an amino acid sequence selected from a group consisting of: (i) SEQ ID NO:216; (ii) SEQ ID NO:217; (iii) SEQ ID NO:218; (iv) SEQ ID NO:224; (v) SEQ ID NO:225; and (vi) SEQ ID NO:226.

In one embodiment, the antibody or functional fragment thereof may comprise at least one antigen binding region encoded by a nucleic acid comprising a nucleotide sequence selected from a group consisting of: (i) SEQ ID NO: 5; (ii) SEQ ID NO:6; (iii) SEQ ID NO:7; (iv) SEQ ID NO:13; (v) SEQ ID NO: 14; and (vi) SEQ ID NO:15.

In another embodiment, the antibody or functional fragment thereof may comprise at least one antigen binding region encoded by a nucleic acid comprising a nucleotide sequence selected from a group consisting of: (i) SEQ ID NO:21; (ii) SEQ ID NO:22; (iii) SEQ ID NO:23; (iv) SEQ ID NO:29; (v) SEQ ID NO:30; and (vi) SEQ ID NO:31.

In one embodiment, the antibody or functional fragment thereof may comprise at least one antigen binding region encoded by a nucleic acid comprising a nucleotide sequence selected from a group consisting of: (i) SEQ ID NO:37; (ii) SEQ ID NO:38; (iii) SEQ ID NO:39; (iv) SEQ ID NO:45; (v) SEQ ID NO:46; and (vi) SEQ ID NO:47.

In one embodiment, the antibody or functional fragment thereof may comprise at least one antigen binding region encoded by a nucleic acid comprising a nucleotide sequence selected from a group consisting of: (i) SEQ ID NO:53; (ii) SEQ ID NO:54; (iii) SEQ ID NO:55; (iv) SEQ ID NO:61; (v) SEQ ID NO:62; and (vi) SEQ ID NO:63.

In one embodiment, the antibody or functional fragment thereof may comprise at least one antigen binding region encoded by a nucleic acid comprising a nucleotide sequence selected from a group consisting of: (i) SEQ ID NO:69; (ii) SEQ ID NO:70; (iii) SEQ ID NO:71; (iv) SEQ ID NO:77; (v) SEQ ID NO:78; and (vi) SEQ ID NO:79.

In one embodiment, the antibody or functional fragment thereof may comprise at least one antigen binding region encoded by a nucleic acid comprising a nucleotide sequence selected from a group consisting of: (i) SEQ ID NO:85; (ii) SEQ ID NO:86; (iii) SEQ ID NO:87; (iv) SEQ ID NO:93; (v) SEQ ID NO:94; and (vi) SEQ ID NO:95.

In one embodiment, the antibody or functional fragment thereof may comprise at least one antigen binding region encoded by a nucleic acid comprising a nucleotide sequence selected from a group consisting of: (i) SEQ ID NO:101; (ii) SEQ ID NO:102; (iii) SEQ ID NO:103; (iv) SEQ ID NO:109; (v) SEQ ID NO:110; and (vi) SEQ ID NO:111.

In one embodiment, the antibody or functional fragment thereof may comprise at least one antigen binding region encoded by a nucleic acid comprising a nucleotide sequence selected from a group consisting of: (i) SEQ ID NO:117; (ii) SEQ ID NO:118; (iii) SEQ ID NO:119; (iv) SEQ ID NO:125; (v) SEQ ID NO:126; and (vi) SEQ ID NO:127.

In one embodiment, the antibody or functional fragment thereof may comprise at least one antigen binding region encoded by a nucleic acid comprising a nucleotide sequence selected from a group consisting of: (i) SEQ ID NO:133; (ii) SEQ ID NO:134; (iii) SEQ ID NO:135; (iv) SEQ ID NO:141; (v) SEQ ID NO:142; and (vi) SEQ ID NO:143.

In one embodiment, the antibody or functional fragment thereof may comprise at least one antigen binding region encoded by a nucleic acid comprising a nucleotide sequence selected from a group consisting of: (i) SEQ ID NO:149; (ii) SEQ ID NO:150; (iii) SEQ ID NO:151; (iv) SEQ ID NO:157; (v) SEQ ID NO: 158; and (vi) SEQ ID NO:159.

In one embodiment, the antibody or functional fragment thereof may comprise at least one antigen binding region encoded by a nucleic acid comprising a nucleotide sequence selected from a group consisting of: (i) SEQ ID NO:165; (ii) SEQ ID NO:166; (iii) SEQ ID NO:167; (iv) SEQ ID NO:173; (v) SEQ ID NO:174; and (vi) SEQ ID NO:175.

In one embodiment, the antibody or functional fragment thereof may comprise at least one antigen binding region encoded by a nucleic acid comprising a nucleotide sequence selected from a group consisting of: (i) SEQ ID NO:181; (ii) SEQ ID NO:182; (iii) SEQ ID NO:183; (iv) SEQ ID NO:189; (v) SEQ ID NO:190; and (vi) SEQ ID NO:191.

In one embodiment, the antibody or functional fragment thereof may comprise at least one antigen binding region encoded by a nucleic acid comprising a nucleotide sequence selected from a group consisting of: (i) SEQ ID NO:197; (ii) SEQ ID NO:198; (iii) SEQ ID NO:199; (iv) SEQ ID NO:205; (v) SEQ ID NO:206; and (vi) SEQ ID NO:207.

In one embodiment, the antibody or functional fragment thereof may comprise at least one antigen binding region encoded by a nucleic acid comprising a nucleotide sequence selected from a group consisting of: (i) SEQ ID NO:213; (ii) SEQ ID NO:214; (iii) SEQ ID NO:215; (iv) SEQ ID NO:221; (v) SEQ ID NO:222; and (vi) SEQ ID NO:223.

It will be appreciated that the antigen binding region may comprises a Complementarily Determining Region (CDR) of the antibody, or functional fragment thereof, and that mutations may reside in framework regions between the CDRs of the antibody or functional fragment thereof. The recombinant immunoglobulin may comprise any, or all, of the antigen binding regions described herein. The recombinant immunoglobulin may comprise an antigen binding site with which the antigen binds, preferably eliciting an immunological response. Preferably, the at least one antigen binding region forms at least part of the antigen binding site. The antibody or functional fragment thereof may comprise at least two, suitably at least three, more suitably at least four antigen binding regions defined in the first aspect. The antibody or functional fragment may comprise at least five, more preferably at least six antigen binding regions. The antibody or fragment thereof may therefore comprise at least one, two, three, four, five or six amino acid sequences defined in (i) to (vi) in any embodiment of antibody described herein. Preferably, the antibody or fragment thereof comprises all of (i) to (vi) in any embodiment.

In one embodiment of the antibody or a functional fragment thereof, the polypeptide sequence of the variable region of the light chain may comprise an amino acid sequence substantially as set out in SEQ ID NO: 4, 20, 36, 52, 68, 84, 100, 116, 132, 148, 164, 180, 196 or 212, or a functional variant or fragment thereof.

The polypeptide sequence of the variable region of the heavy chain of the antibody or functional fragment thereof may comprise an amino acid sequence substantially as set out in SEQ ID NO: 12, 28, 44, 60, 76, 92, 108, 124, 140, 156, 172, 188, 204 or 220, or a functional variant or fragment thereof.

The antibody or functional fragment thereof may comprise a light chain variable region (VL) and/or a heavy chain variable region (VH), the light chain variable region comprising an amino acid sequence which is substantially as set out in SEQ ID NO: 4, 20, 36, 52, 68, 84, 100, 116, 132, 148, 164, 180, 196 or 212, or a functional fragment or variant thereof, the heavy chain variable region comprising the amino acid sequence which is substantially as set out in SEQ ID NO: 12, 28, 44, 60, 76, 92, 108, 124, 140, 156, 172, 188, 204 or 220, or a functional fragment or variant thereof.

In one embodiment of the antibody or a functional fragment thereof, the DNA sequence of the variable region of the light chain may comprise a nucleotide sequence substantially as set out in SEQ ID NO: 3, 19, 35, 51, 67, 83, 99, 115, 131, 147, 163, 179, 195 or 211, or a functional variant or fragment thereof. In one embodiment of the antibody or a functional fragment thereof, the DNA sequence of the variable region of the heavy chain may comprise a nucleotide sequence substantially as set out in SEQ ID NO: 11, 27, 43, 59, 75, 91, 107, 123, 139, 155, 171, 187, 203 or 219, or a functional variant or fragment thereof.

The antibody or functional fragment thereof may comprise a light chain variable region (VL) and/or a heavy chain variable region (VH), the light chain variable region being encoded by a polynucleotide comprising a nucleotide sequence which is substantially as set out in SEQ ID NO: 3, 19, 35, 51, 67, 83, 99, 115, 131, 147, 163, 179, 195 or 211, or a functional fragment or variant thereof, the heavy chain variable region being encoded by a polynucleotide comprising a nucleotide sequence which is substantially as set out in SEQ ID NO: 11, 27, 43, 59, 75, 91, 107, 123, 139, 155, 171, 187, 203 or 219, or a functional fragment or variant thereof.

The polypeptide sequence of the constant region of the light chain of one embodiment of the antibody of the invention may comprise an amino acid sequence which is substantially as set out in SEQ ID NO: 227, or a functional fragment or variant thereof. The polypeptide sequence of the constant region of the heavy chain of one embodiment of the antibody of the invention may comprise an amino acid sequence which is substantially as set out in SEQ ID NO: 228, or a functional fragment or variant thereof.

The DNA sequence encoding the constant region of the light chain of one embodiment of the antibody of the invention may comprise a nucleotide sequence which is substantially as set out in SEQ ID NO: 229, or a functional fragment or variant thereof. The DNA sequence encoding the constant region of the heavy chain of one embodiment of the antibody of the invention may comprise a nucleotide sequence which is substantially as set out in SEQ ID NO: 230, or a functional fragment or variant thereof.

According to a third aspect, there is provided an isolated peptide capable of binding to Receptor Tyrosine Kinase-Like Orphan Receptor 1 (ROR1) protein, the peptide comprising an amino acid sequence selected from a group consisting of:
(i) SEQ ID NO:8, 9, 10, 16, 17 and/or 18;
(ii) SEQ ID NO:24, 25, 26, 32, 33 and/or 34;
(iii) SEQ ID NO:40, 41, 42, 48, 49 and/or 50;
(iv) SEQ ID NO:56, 57, 58, 64, 65 and/or 66;
(v) SEQ ID NO:72, 73, 74, 80, 81 and/or 82;
(vi) SEQ ID NO:88, 89, 90, 96, 97 and/or 98;
(vii) SEQ ID NO:104, 105, 106, 112, 113 and/or 114;
(viii) SEQ ID NO:120, 121, 122, 128, 129 and/or 130;
(ix) SEQ ID NO:136, 137, 138, 144, 145 and/or 146;
(x) SEQ ID NO:152, 153, 154, 160, 161 and/or 162;
(xi) SEQ ID NO:168, 169, 170, 176, 177 and/or 178;
(xii) SEQ ID NO:184, 185, 186, 192, 193 and/or 194;
(xiii) SEQ ID NO:200, 201, 202, 208, 209 and/or 210; and/or
(xiv) SEQ ID NO:216, 217, 218, 224, 225 and/or 226.

The peptide of the third aspect is preferably capable of binding to an extracellular domain of ROR1 protein. Thus, the isolated peptide of the third aspect may be an anti-Receptor Tyrosine Kinase-Like Orphan Receptor 1 (ROR1) antibody, or a functional fragment thereof. The antibody may or may not be human. For example, the antibody or fragment thereof may be murine. It may also be recombinant. It will be appreciated that the amino acid sequences defined in each of (i) to (xiv) of the third aspect are the CDRs of the antibody or a functional fragment thereof of the first aspect. The isolated peptide may therefore comprise at least two, three, four, five or six amino acid sequences defined in any of (i) to (xiv). Preferably, the peptide comprises all of the amino acid sequences defined in any of (i) to (xiv).

The peptide may comprise an amino acid sequence substantially as set out in SEQ ID NO: 4, 20, 36, 52, 68, 84, 100, 116, 132, 148, 164, 180, 196 or 212, or a functional variant or fragment thereof. The peptide may comprise an amino acid sequence substantially as set out in SEQ ID NO: 12, 28, 44, 60, 76, 92, 108, 124, 140, 156, 172, 188, 204 or 220, or a functional variant or fragment thereof. The peptide may comprise an amino acid sequence which is substantially as set out in SEQ ID NO: 227 or 228, or a functional fragment or variant thereof.

According to a fourth aspect, there is provided an isolated nucleic acid encoding a peptide capable of binding to Receptor Tyrosine Kinase-Like Orphan Receptor 1 (ROR1)

protein, the nucleic acid comprising a nucleotide sequence selected from a group consisting of:

(i) SEQ ID NO:5, 6, 7, 13, 14 and/or 15;
(ii) SEQ ID NO:21, 22, 23, 29, 30 and/or 31;
(iii) SEQ ID NO:37, 38, 39, 45, 46 and/or 47;
(iv) SEQ ID NO:53, 54, 55, 61, 62 and/or 63;
(v) SEQ ID NO:69, 70, 71, 77, 78 and/or 79;
(vi) SEQ ID NO:85, 86, 87, 93, 94 and/or 95;
(vii) SEQ ID NO:101, 102, 103, 109, 110 and/or 111;
(viii) SEQ ID NO:117, 118, 119, 125, 126 and/or 127;
(ix) SEQ ID NO:133, 134, 135, 141, 142 and/or 143;
(x) SEQ ID NO:149, 150, 151, 157, 158 and/or 159;
(xi) SEQ ID NO:165, 166, 167, 173, 174 and/or 175;
(xii) SEQ ID NO:181, 182, 183, 189, 190 and/or 191;
(xiii) SEQ ID NO:197, 198, 199, 205, 206 and/or 207; and/or
(xiv) SEQ ID NO:213, 214, 215, 221, 222 and/or 223.

Preferably, the nucleic acid may encode an anti-Receptor Tyrosine Kinase-Like Orphan Receptor 1 (ROR1) antibody, or a functional fragment thereof. The antibody may or may not be human. For example, the antibody may be murine. It may also be recombinant. It will be appreciated that the nucleotide sequences defined in each of (i) to (xiv) of the fourth aspect encode the CDRs of the antibody or a functional fragment thereof of the first aspect. Thus, the nucleic acid may comprise at least two, three, four, five or six nucleotide sequences defined in any of (i) to (xiv). Preferably, the nucleic acid comprises all of the nucleotide sequences defined in any of (i) to (vi). Preferably, the nucleic acid comprises a nucleotide sequence substantially encoding an amino acid sequence of at least one antigen binding region of the human antibody, or functional fragment thereof.

The nucleic acid may comprise a nucleotide sequence substantially as set out in SEQ ID NO: 3, 19, 35, 51, 67, 83, 99, 115, 131, 147, 163, 179, 195 or 211, or a functional variant or fragment thereof. The nucleic acid may comprise a nucleotide sequence substantially as set out in SEQ ID NO: 11, 27, 43, 59, 75, 91, 107, 123, 139, 155, 171, 187, 203 or 219, or a functional variant or fragment thereof. The nucleic acid may comprise a nucleotide sequence which is substantially as set out in SEQ ID NO: 229 or 230, or a functional fragment or variant thereof.

Advantageously, the antibody or functional fragment thereof has utility of a therapeutic agent in its own right, and is a significant improvement on therapies which use antibodies comprising a non-human region (e.g., murine), such as a Fc fragment or framework regions, or at least one murine antigen binding region or Complementarity Determining Region (CDR). However, in addition, technologies to maximize drug efficacy have been evaluated, including glycosylation engineering to enhance the ADCC (Antibody-Dependent Cell-Mediated Cytotoxicity) and/or CDC (Complement-Dependent Cytotoxicity) activity of the antibody or functional fragment thereof, conjugation to a cytotoxic moiety, such as radiation, a cytotoxic drug or toxin, and generation of a bispecific antibody with one arm targeting a tumor cell, and the other arm attracting cytotoxic T cells.

Thus, in a fifth aspect, there is provided an antibody-drug conjugate (ADC) comprising the antibody or a functional fragment thereof of the first aspect, and a cytotoxic moiety.

Antibody-drug conjugates (ADCs) can be used to deliver a potent cytotoxic drug selectively to a target cell via an antibody. Such methods, when applied to a tumor antigen target, can enhance the antitumor activity of antibodies and improve the tumor-to-normal tissue selectivity of chemotherapy. One key parameter for ADC development is that the antibody can be endocytosed once bound to target antigen, and therefore, deliver the conjugated drug into target cancer cells. FIG. 26 shows that the antibody of the invention is effectively endocytosed.

The cytotoxic moiety may be a toxin, such as monomethyl auristatin E (MMAE), monomethyl auristatin F (MMAF) or maytansine. The drug moiety may be an alpha-emitting radionucleotide, such as a 225Ac label. These toxins can be linked to the antibody or functional fragment thereof (i.e., an antigen-binding fragment thereof) via a cleavable linker, such as a disulfide bond, a hydrazone linker or a peptide linker, or via a non-cleavable linkers, such as a thioether bond using a SMCC (N-succinimidyl-4-(N-maleimidomethyl)-cyclohexane-1-carboxylate) linker.

According to a sixth aspect, there is provided an antibody or a functional fragment thereof as defined in the first aspect, a peptide as defined in the third aspect, a nucleic acid as defined in the fourth aspect, or an antibody-drug conjugate as defined in the fifth aspect, each being optionally derivatized, for use in therapy or in diagnosis.

The antibody or functional fragment thereof as defined in the first aspect, the peptide as defined in the third aspect, the nucleic acid as defined in the fourth aspect, or the antibody-drug conjugate as defined in the fifth aspect, may be used as a medicament, which is preferably adapted for use in the treatment, amelioration or prevention of cancer.

Therefore, according to a seventh aspect, there is provided an antibody or a functional fragment thereof as defined in the first aspect, a peptide as defined in the third aspect, a nucleic acid as defined in the fourth aspect, or an antibody-drug conjugate as defined in the fifth aspect, each being optionally derivatized, for use in treating, preventing or ameliorating cancer.

The term "derivatized" can mean that the antibody or functional fragment thereof, peptide, nucleic acid or conjugate may be modified prior to use, preferably to produce a derivative or variant thereof. Examples of derivatization may include PEGylated antibodies or PEGylated antibody fragments, or antibody-cytokine fusion proteins. However, in some embodiments, the antibody or functional fragment thereof, peptide, nucleic acid or conjugate may not be derivatized.

ROR1 is expressed in a wide range of human cancer types, and so the antibody or functional fragment thereof, peptide, a nucleic acid or conjugate may be used in the treatment, prevention, amelioration or diagnosis of a ROR1-positive cancer type.

Non-limiting exemplary cancers that may be treated with an anti-ROR1 antibody include carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, neuroblastoma, endometrial cancer, testis cancer, cholangiocarcinoma, gallbladder carcinoma, gastric cancer, melanoma, and various types of head and neck cancer. In some embodiments, lung cancer is non-small cell lung cancer or lung squamous cell carcinoma. In some embodiments, leukemia is acute myeloid leukemia, B-cell acute lymphoblastic leukemia (B-ALL); or chronic lymphocytic leukemia (CLL). In some embodiments, lymphoma is mantle cell lymphoma (MCL) or marginal zone lymphoma (MZL). In some embodiments, breast cancer is breast invasive carcinoma. In some embodiments, ovarian cancer is ovarian serous cystadenocarcinoma. In some embodiments, kidney cancer is kidney renal clear cell carcinoma. In some embodiments, colon cancer is colon adenocarcinoma. In some embodiments, bladder cancer is bladder urothelial carcinoma. In any of the cancers described above, the cancer may be an ROR1-positive cancer.

According to an eighth aspect, there is provided a method of treating, preventing or ameliorating cancer in a subject, the method comprising administering, to a patient in need of such treatment, a therapeutically effective amount of an antibody or a functional fragment thereof as defined in the first aspect, a peptide as defined in the third aspect, a nucleic acid as defined in the fourth aspect, or an antibody-drug conjugate as defined in the fifth aspect, each being optionally derivatized.

It will be appreciated that antibodies, fragments, peptides, nucleic acids and conjugates according to the invention (collectively referred to herein as "agents") may be used in a monotherapy (e.g., the use of an antibody or fragment thereof alone, or the use of the antibody-drug conjugate alone), for treating, ameliorating or preventing cancer. Alternatively, agents according to the invention may be used as an adjunct to, or in combination with, known therapies for treating, ameliorating, or preventing cancer. Such therapies include, but are not limited to, chemotherapy, anti-angiogenesis agents, growth inhibitory agents, immunotherapy, radiation therapy, etc.

Nonlimiting exemplary chemotherapeutic agents that may be combined with the anti-ROR1 antibodies described herein include, but are not limited to, alkylating agents such as thiotepa and CYTOCAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal I and calicheamicin omegaII (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycins, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Non-limiting exemplary an anti-angiogenesis agents include antibodies or other antagonists to an angiogenic agent, e.g., antibodies to VEGF-A (e.g., bevacizumab (Avastin)) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D' Amore (1991) Annu. Rev. Physiol. 53:217-39; Streit and Detmar (2003) Oncogene 22:3172-3179 (e.g., Table 3 listing anti-angiogenic therapy in malignant melanoma); Ferrara & Alitalo (1999) Nature Medicine 5(12):1359-1364; Tonini et al. (2003) Oncogene 22:6549-6556 (e.g., Table 2 listing known anti-angiogenic factors); and, Sato (2003) Int. J. Clin. Oncol. 8:200-206 (e.g., Table 1 listing anti-angiogenic agents used in clinical trials).

Examples of growth inhibitory agents include, but are not limited to, agents that block cell cycle progression (at a place other than S phase), such as agents that induce Gi arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest Gi also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

Exemplary therapeutic agents that may be combined with the anti-ROR1 antibodies described herein include chemotherapeutic agents, growth inhibitory agents, cytotoxic agents, agents used in radiation therapy, anti-angiogenesis agents, cancer immunotherapeutic agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, TIM3, or VEGF receptor(s), TRAIL/Apo2, and other bioactive and organic chemical agents, etc. Combinations thereof are also included in the invention.

The agents according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents across the blood-brain barrier.

Medicaments comprising agents of the invention may be used in a number of ways. For instance, oral administration may be required, in which case the agents may be contained within a composition that may, for example, be ingested orally in the form of a tablet, capsule or liquid. Compositions comprising agents and medicaments of the invention may be administered by inhalation (e.g., intranasally). Compositions may also be formulated for topical use. For instance, creams or ointments may be applied to the skin. Agents and medicaments according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g., at least daily injection).

In a preferred embodiment, agents and medicaments according to the invention may be administered to a subject by injection into the blood stream or directly into a site requiring treatment. Injections may be intravenous (bolus or infusion) or subcutaneous (bolus or infusion), or intradermal (bolus or infusion). It will be appreciated that the amount of the antibodies, fragments, peptides and nucleic acids (i.e., agent) that is required is determined by its biological activity and bioavailability, which in turn depends on the mode of administration, the physiochemical properties of the agent, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of agent according to the invention may be used for treating, ameliorating, or preventing cancer, depending upon which agent. More preferably, the daily dose of agent is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The agent may be administered before, during or after onset of cancer. Daily doses may be given as a single administration (e.g., a single daily injection). Alternatively, the agent may require administration twice or more times during a day. As an example, agents may be administered as two (or more depending upon the severity of the cancer infection being treated) daily doses of between 0.07 g and 700 mg (i.e., assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses. Known procedures, such as those conventionally employed by the pharmaceutical industry (e.g., in vivo experimentation, clinical trials, etc.), may be used to form specific formulations of the agents according to the invention and precise therapeutic regimes (such as daily doses of the agents and the frequency of administration).

In a ninth aspect of the invention, there is provided a pharmaceutical composition comprising an antibody or a functional fragment thereof as defined in the first aspect, a peptide as defined in the third aspect, a nucleic acid as defined in the fourth aspect, or an antibody-drug conjugate as defined in the fifth aspect, each being optionally derivatized; and optionally a pharmaceutically acceptable vehicle.

The composition may be an anti-cancer composition.

The antibody or a functional fragment thereof, peptide or a nucleic acid may not be derivatized.

The invention also provides in a tenth aspect, a process for making the composition according to the ninth aspect, the process comprising combining a therapeutically effective amount of an antibody or a functional fragment thereof as defined in the first aspect, a peptide as defined in the third aspect, a nucleic acid as defined in the fourth aspect, or an antibody-drug conjugate as defined in the fifth aspect, each being optionally derivatized, with a pharmaceutically acceptable vehicle.

The antibody or fragment thereof may be as defined with respect to the first aspect.

In some embodiments, a therapeutically effective amount of antibody or fragment thereof used may be from about 0.001 ng to about 1 mg, and preferably from about 0.01 ng to about 100 ng. It is preferred that the amount of antibody or fragment is an amount from about 0.1 ng to about 10 ng, and most preferably from about 0.5 ng to about 5 ng.

In one embodiment, the pharmaceutically acceptable vehicle may be a solid, and the composition may be in the form of a powder or tablet. A solid pharmaceutically acceptable vehicle may include one or more substances which may also act as flavoring agents, lubricants, solubilizers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The invention also provides a kit for diagnosing patients suffering from cancer. Hence, according to an eleventh aspect of the invention, there is provided a kit for diagnosing a subject suffering from cancer, or a pre-disposition thereto, or for providing a prognosis of the subject's condition, the kit comprising detection means for detecting the concentration of antigen present in a sample from a test subject, wherein the detection means comprising an antibody or functional fragment thereof as defined by the first aspect, a peptide as defined by the third aspect, or a nucleic acid as defined by the fourth aspect, each being optionally derivatized, wherein presence of antigen in the sample suggests that the subject suffers from cancer.

According to a twelfth aspect, there is provided a method for diagnosing a subject suffering from cancer, or a pre-disposition thereto, or for providing a prognosis of the subject's condition, the method comprising detecting the concentration of antigen present in a sample obtained from a subject, wherein the detection is achieved using an antibody or functional fragment thereof as defined by the first aspect, a peptide as defined by the third aspect, or a nucleic acid as defined by the fourth aspect, each being optionally derivatized, and wherein presence of antigen in the sample suggests that the subject suffers from cancer.

In some embodiments, methods of selecting a patient for treatment with the anti-ROR1 antibodies described herein comprise determining whether the subject has an ROR1-expressing cancer. Such methods may comprise detecting the presence of ROR1 on cancer cells from the patient, for example, using an anti-ROR1 antibody described herein.

Preferably, the antigen comprises ROR1 protein, more preferably an extracellular domain thereof. The sample may comprise blood, urine, tissue etc.

Preferably, the kit or method is used to identify the presence or absence of ROR1-positive cells in the sample, or determine the concentration thereof in the sample. The term "ROR1-positive cells" can mean a cell expressing ROR1 on its surface. The detection means may comprise an assay adapted to detect the presence and/or absence of ROR1-positive cells in the sample. The kit or method may comprise the use of a positive control and/or a negative control against which the assay may be compared. For example, the kit may comprise a reference for the concentration of ROR1-positive cells in a sample from an individual who does (i.e., positive control) or does not (i.e., a negative control) suffer from cancer. The kit may further comprise a label which may be detected. The term "label" can mean a moiety that can be attached to the antibody, fragment, peptide or nucleic acid. Moieties can be used, for example, for therapeutic or diagnostic procedures. Therapeutic labels include, for example, moieties that can be attached to an antibody or fragment thereof of the invention and used to monitor the binding of the antibody to an ROR1 protein. Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or FACS analysis. Analytical methods also include both in vitro and in vivo imaging procedures. Specific examples of diagnostic labels that can be detected by analytical means include enzymes, radioisotopes, fluorochromes, chemiluminescent markers, and biotin. A label can be attached directly to an antibody of the invention, fragment thereof, peptide or nucleic acid, or be attached to a secondary binding agent that specifically binds a molecule of the invention. Such a secondary binding agent can be, for example, a secondary antibody. A secondary antibody can be either polyclonal or monoclonal, and of human, rodent or chimeric origin.

As described in Example 3, the inventors have demonstrated how a recombinant full length IgG1 human monoclonal antibody of the invention may be made. For example, the antibody or functional fragment thereof may be produced by a bacteriophage expression system. Preferably, the bacteriophage expression system comprises a phage display library.

A useful procedure for isolating the polynucleotide which encodes the antibody or functional fragment thereof begins with isolation of cDNA which can be reverse-transcribed from RNA isolated from an individual suffering from cancer, such as CLL. This disease state is characterized by the presence of antibodies with immunospecificity against ROR1. Methods for cDNA synthesis are well known in the art. A cDNA encoding an antibody or functional fragment thereof including a heavy or light chain can be amplified using, for example, the polymerase chain reaction (PCR), preferably reverse transcription PCR (RT-PCR).

Suitable primers for PCR may be determined by those skilled in the art using conserved sequences which flank the particular functional fragment of a heavy or light chain. Suitable PCR conditions may be determined by those skilled in the art.

Preferably, the PCR is adapted to amplify the heavy chain, more preferably the VH CHI fragment, and even more preferably, the heavy chain variable fragment (VH).

Figure 14A:
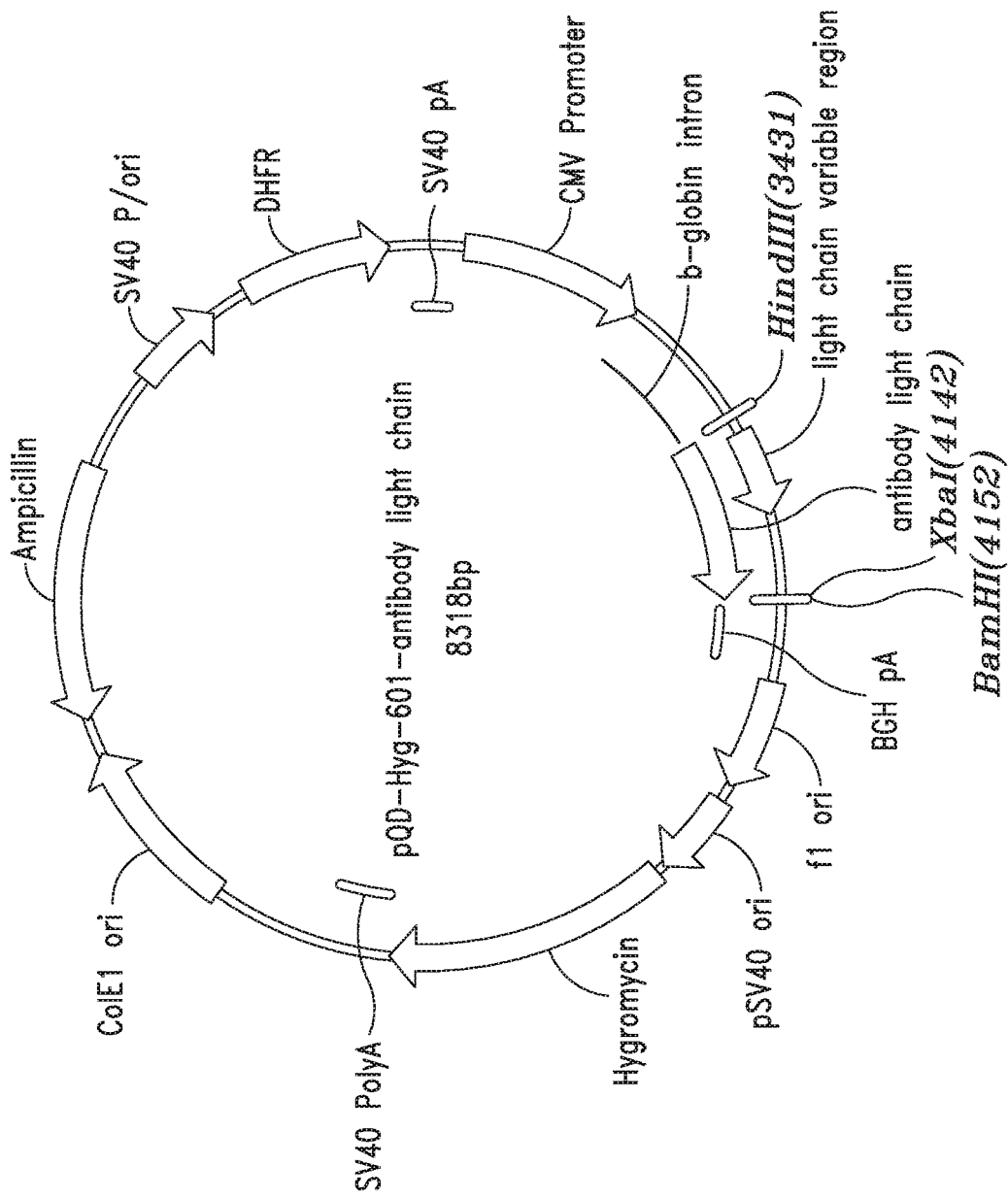
FIGS. 14a and 14b are plasmid maps of human anti-ROR1 full-length IgG1 antibody expression vectors.
Figure 14B:
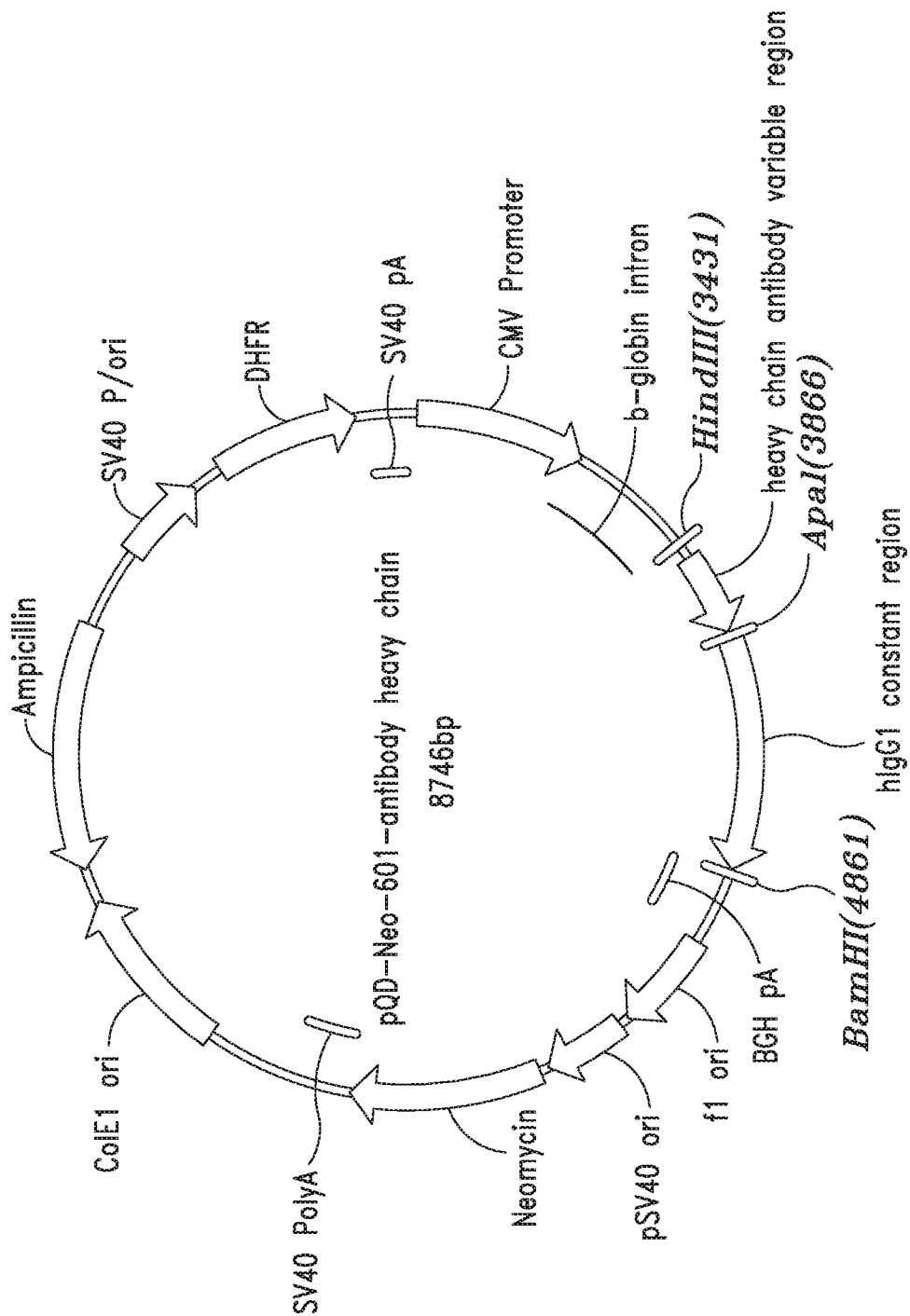

Alternatively, or additionally, the PCR may be adapted to amplify the light chain, more preferably the VL CL fragment, and even more preferably, the light chain variable fragment (VL). Preferably, the PCR products are cloned into a suitable expression vector, more preferably a phage expression vector, one embodiment of which is illustrated in FIGS. 14a and 14b. Preferably, the vector is introduced into a suitable host, for example, Chinese hamster ovary (CHO) cells, for expression of the heavy and preferably, the light fragment, to occur. A suitable vector and host cell system can allow, for example, co-expression and assembly of functional fragments of the heavy and light chains. Preferably, the vector is introduced into the host by electroporation. Other suitable systems for the expression of antibody fragments can be determined by those skilled in the art and include, for example, M13 phage expression vectors. Recombinant monoclonal antibodies or functional fragments thereof can be substantially purified using methods known in the art, and which depend on the particular vector and host expression system used.

In a thirteenth aspect, there is provided a genetic construct comprising the nucleic acid of the fourth aspect. Genetic constructs of the invention may be in the form of an expression cassette, which may be suitable for expression of the encoded polypeptide in a host cell. The genetic construct may be introduced in to a host cell without it being incorporated in a vector. For instance, the genetic construct, which may be a nucleic acid molecule, may be incorporated within a liposome or a virus particle. Alternatively, a purified nucleic acid molecule (e.g., histone-free DNA, or naked DNA) may be inserted directly into a host cell by suitable means, e.g., direct endocytotic uptake. The genetic construct may be introduced directly in to cells of a host subject (e.g., a bacterial cell) by transfection, infection, electroporation, microinjection, cell fusion, protoplast fusion or ballistic bombardment. Alternatively, genetic constructs of the invention may be introduced directly into a host cell using a particle gun. Alternatively, the genetic construct may be harbored within a recombinant vector, for expression in a suitable host cell.

Therefore, in a fourteenth aspect, there is provided a recombinant vector comprising the genetic construct according to the thirteenth aspect.

The recombinant vector may be a plasmid, cosmid or phage. Such recombinant vectors are useful for transforming host cells with the genetic construct of the thirteenth aspect, and for replicating the expression cassette therein. The skilled technician will appreciate that genetic constructs of the invention may be combined with many types of backbone vector for expression purposes. Examples of suitable backbone vectors include those shown in FIGS. 14a and 14b. Recombinant vectors may include a variety of other functional elements including a suitable promoter to initiate gene expression. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favor targeted integration (e.g., by homologous recombination) are envisaged.

The recombinant vector may also comprise DNA coding for a gene that may be used as a selectable marker in the cloning process, i.e., to enable selection of cells that have been transfected or transformed, and to enable the selection of cells harboring vectors incorporating heterologous DNA. Alternatively, the selectable marker gene may be in a different vector to be used simultaneously with vector containing the gene of interest. The vector may also comprise DNA involved with regulating expression of the coding sequence, or for targeting the expressed polypeptide to a certain part of the host cell.

In a fifteenth aspect, there is provided a host cell comprising the genetic construct according to the thirteenth aspect, or the recombinant vector according to the fourteenth aspect.

The host cell may be a bacterial cell. The host cell may be an animal cell, for example a mouse or rat cell. It is preferred that the host cell is not a human cell. The host cell may be transformed with genetic constructs or vectors according to the invention, using known techniques. Suitable means for introducing the genetic construct into the host cell will depend on the type of cell. According to a sixteenth aspect, there is provided a method of preparing a recombinant antibody or functional fragment thereof, the method comprising (i) culturing at least one cell defined in the fifteenth aspect capable of expressing the required antibody or functional fragment thereof, and (ii) isolating the antibody or functional fragment thereof.

As described herein, antibodies according to the invention can bind to ROR1. However, the inventors realize that the antibody or functional fragment thereof of the invention may be used to act as a framework for the development of antibodies showing immunospecificity against other members of the ROR family. For example, through introducing mutations into the CDRs of the ROR1-specific antibodies described herein, it is possible to isolate antibodies that can recognize ROR2 in one embodiment, or both ROR 1 and ROR2 in another embodiment.

Hence, according to a seventeenth aspect, there is provided a method of isolating an antibody or a functional fragment thereof having ability to bind to Receptor Tyrosine Kinase-Like Orphan Receptor 2 (ROR2), the method comprising:
  (i) mutating an antibody or functional fragment thereof as defined in the first aspect to produce a mutant, and
  (ii) selecting the mutant for immunospecificity against ROR2.

The mutant may be specific for ROR2, or for both ROR1 and ROR2.

In a first embodiment, said mutating step may comprise random mutagenesis, for example using degenerative PCR. For example, cDNA for the antibody is used as a template in a PCR reaction which may be doped with a mutagen, such as a mutagenic nucleoside triphosphate, for example dP and 8oxo-2'deoxyguanosine. Advantageously, this allows the introduction of mutations in a highly controlled manner throughout the cDNA to produce a mutant library. The resultant library of mutants may be displayed on the surface of a phage, and antibodies may then be selected against ROR2.

The resultant library of mutant antibodies may be selected against ROR2 using biopanning. For example, an ELISA plate may be coated with ROR2, such as with 100 µl of a 1 pg/ml$^{-1}$ solution of ROR2 in bicarbonate buffer pH 8.6, and incubated overnight at 4° C.

The plate may then be washed with buffer, such as TBS. The plate may then be blocked, for example with 5% BSA in PBS and incubated for one hour at 37° C. After two further washes, 100 µl phage suspension may be added to each well and the plate may be incubated for two hours at 37° C.

The phage may be removed and the wells filled with TBS 0.05% Tween 20 (TBST) and pipetted vigorously. After 5 minutes, the TBST may be removed, and for a first round of panning, the plate may be washed by this method once. In a second round of panning, 5 washes may be used, and in a third and subsequent rounds 10 washes may be used. The phage may then be eluted with 50 µl of elution buffer per well and incubated at room temperature for 10 minutes. After vigorous pipetting, eluted phage may be removed and neutralized with 3 µl of 2M Tris base.

In a second embodiment, said mutating may comprise introducing at least one ligand having immunospecificity against ROR2 into at least one antigen binding region of the antibody of the first aspect. The at least one ligand may comprise at least one of the six CDRs of a ROR2-specific antibody, which may include:

```
Light Chain CDR1:
                                    (SEQ ID NO: 231)
RSSQSLVHSDGNTYLN;

Light Chain CDR2:
                                    (SEQ ID NO: 232)
KVSNRDS;

Light Chain CDR3:
                                    (SEQ ID NO: 233)
MQGTQWPIT;

Heavy Chain CDR1:
                                    (SEQ ID NO: 234)
SYSMN;

Heavy Chain CDR2:
                                    (SEQ ID NO: 235)
YISSSSSTIYYADSVKG;
and Heavy Chain CDR3:
                                    (SEQ ID NO: 236)
DYGGNSGYYYYYMDV.
```

The at least one antigen binding region may be in the heavy and/or light chain variable fragment. Preferably, the at least one ligand is introduced into any of the antigen binding regions in the heavy chain of the immunoglobulin or functional fragment thereof.

The ligand may be inserted by restriction enzyme digestion at an appropriate site determined by a variety of techniques including molecular modelling. A polynucleotide sequence encoding the ligand peptide sequence may be ligated into the cut restriction site, the exact details of this depending on the nature of ligand and the CDR being used.

According to an eighteenth aspect, there is provided a library or panel of recombinant antibodies or functional fragments thereof, generated using the method defined in the seventeenth aspect.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID NO:2 (i.e., the polypeptide sequence of one embodiment of human ROR1) or the nucleotide identified as SEQ ID NO:1 (i.e., the DNA sequence encoding one embodiment of human ROR1), and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g., blosum62, pam250, gonnet etc.), and gap-penalty, e.g., functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. hence, a most preferred method for calculating percentage identity between two sequences comprises (i) preparing a sequence alignment using the clustalw program using a suitable set of parameters, for example, as set out above; and (ii) inserting the values of n and t into the following formula: sequence identity=(N/T)*100.

Alternative methods for identifying similar sequences will be known to those skilled in the art. For example, a substantially similar nucleotide sequence will be encoded by a sequence which hybridizes to any of the nucleic acid sequences shown herein, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×ssc/0.1% SDS at approximately 20-65° c. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

Example 1—Generation of Candidates of Therapeutic Human mAbs Immunospecific for Human ROR1 Extracellular Domain (ECD)

Through panning against the human ROR1 extracellular domain (ECD) protein using a fully-human antibody phage library, multiple ROR1-specific antibodies were identified that exhibited a wide range of affinity (IC50=0.11-263 nM on phage level; see Table 1).

TABLE 1

Affinity ranking of ROR1-positive phage clones by IC50

| Clone No. | IC50 (nM) |
|---|---|
| P601-1 | 0.11 |
| P601-40 | 0.20 |
| P601-109 | 0.22 |
| P601-43 | 0.23 |
| P601-3(601-3-16)* | 0.27 |
| P601-17 | 0.62 |
| P601-51 | 0.62 |
| P601-108 | 0.76 |
| P601-4 | 0.93 |
| P601-13 | 1.21 |
| P601-101 | 1.50 |
| P601-153 | 1.53 |
| P601-2 (601-3-12)* | 1.75 |
| P601-137 | 1.82 |
| P601-86 | 1.84 |
| P601-56 | 1.85 |
| P601-120 | 1.92 |
| P601-6 | 2.12 |
| P601-18 | 2.44 |
| P601-134 | 2.68 |
| P601-81 | 2.76 |
| P601-149 | 2.76 |
| P601-112 | 2.89 |
| P601-136 | 3.02 |
| P601-130 | 3.08 |
| P601-14 | 3.22 |
| P601-87 | 3.86 |
| P601-66 | 4.05 |
| P601-147 | 4.05 |
| P601-57 | 4.08 |
| P601-65 | 4.23 |
| P601-110 | 4.57 |
| P601-141 | 5.68 |
| P601-100 | 5.80 |
| P601-5 (601-3-2)* | 7.99 |
| P601-28 | 8.05 |
| P601-103 | 8.72 |
| P601-69 | 9.81 |
| P601-102 | 10.21 |
| P601-9 | 14.62 |
| P601-119 | 17.70 |
| P601-50 | 24.06 |
| P601-37 | 27.93 |
| P601-70 | 74.00 |
| P601-128 | 263.18 |

*Clones selected to convert into full-length human IgG1 antibodies

Figure 4:
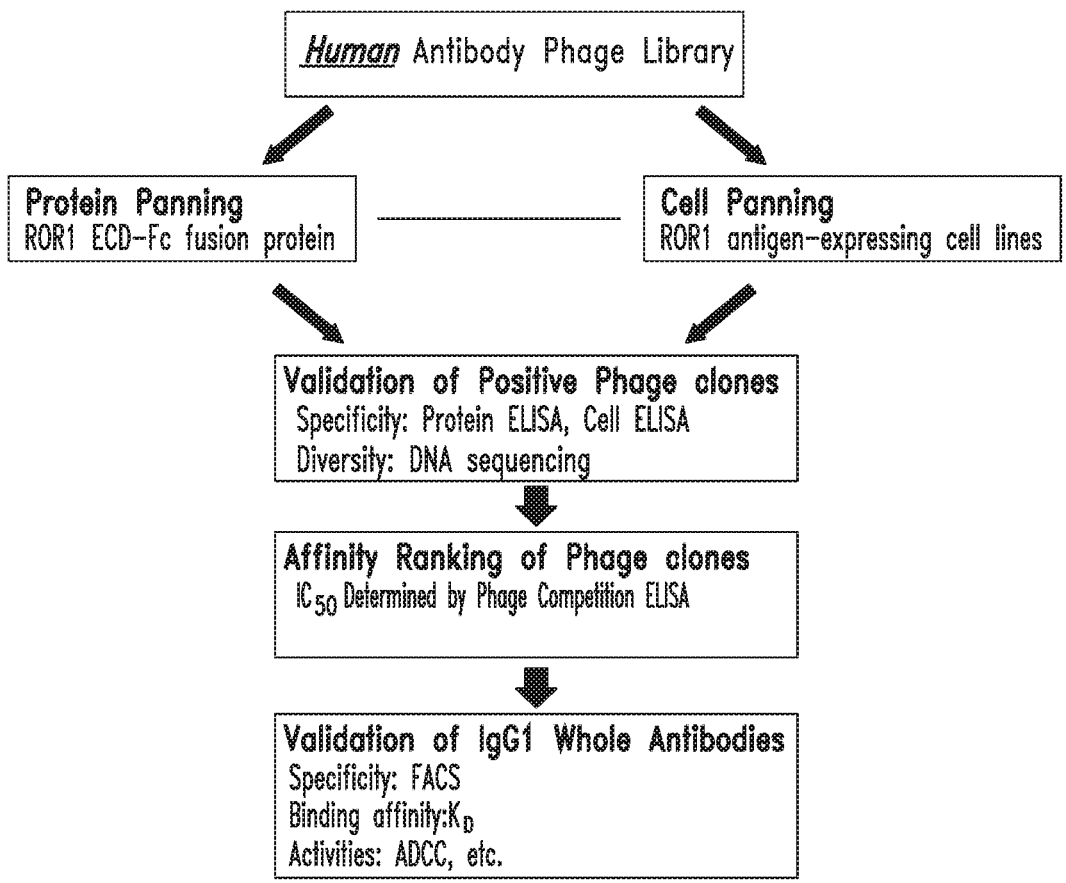
FIG. 4 represents the ROR1 phage display panning strategy.
Figure 5:
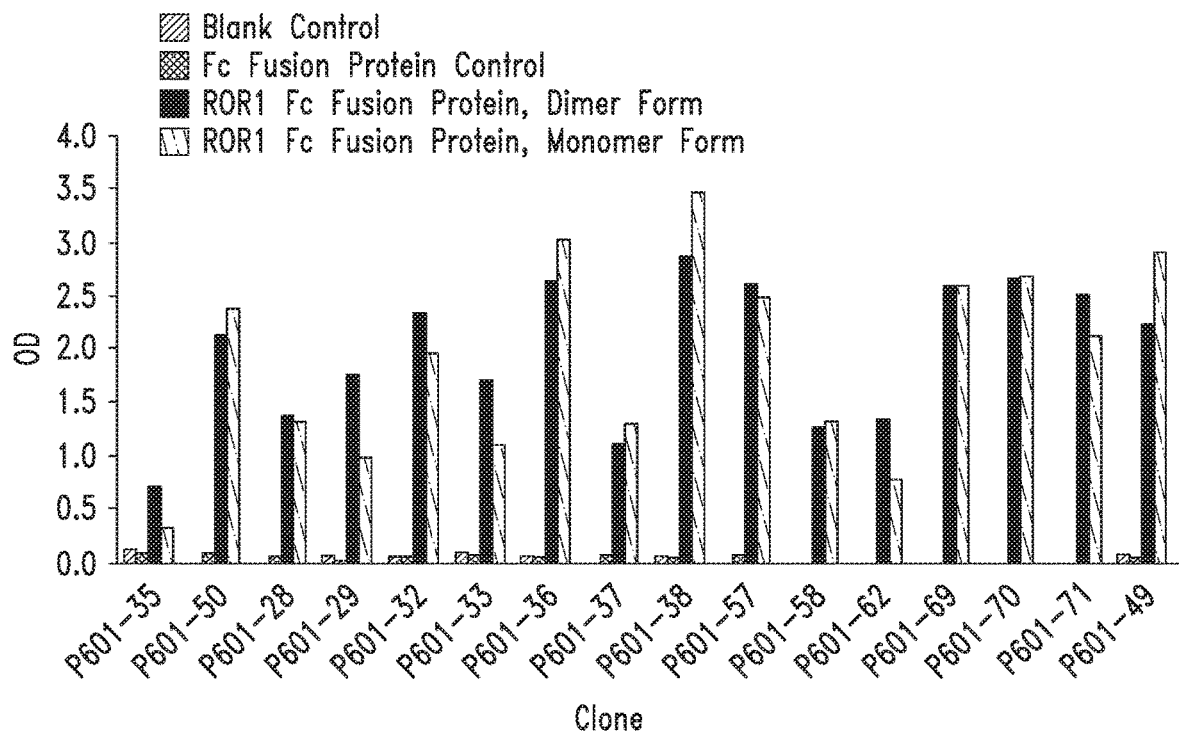
FIG. 5 is a graph showing an example of ROR1 phage antibody ELISA results.

The process is described in the flow chart shown in FIG. 4. A total of 1519 single-chain variable fragment (scFv) and fragment antigen-binding (Fab) phage antibodies were screened from enriched panning pools by protein ELISA and cell ELISA to identify antibodies recognizing native conformation of human ROR1 ECD. Using protein ELISA, the inventors selected over 100 unique clones exhibiting positive binding to both human ROR1 (hROR1) monomeric and dimeric ECD-Fc fusion proteins, and negative binding to the control Fc-fusion protein and blank control (FIG. 5).

Figure 6:
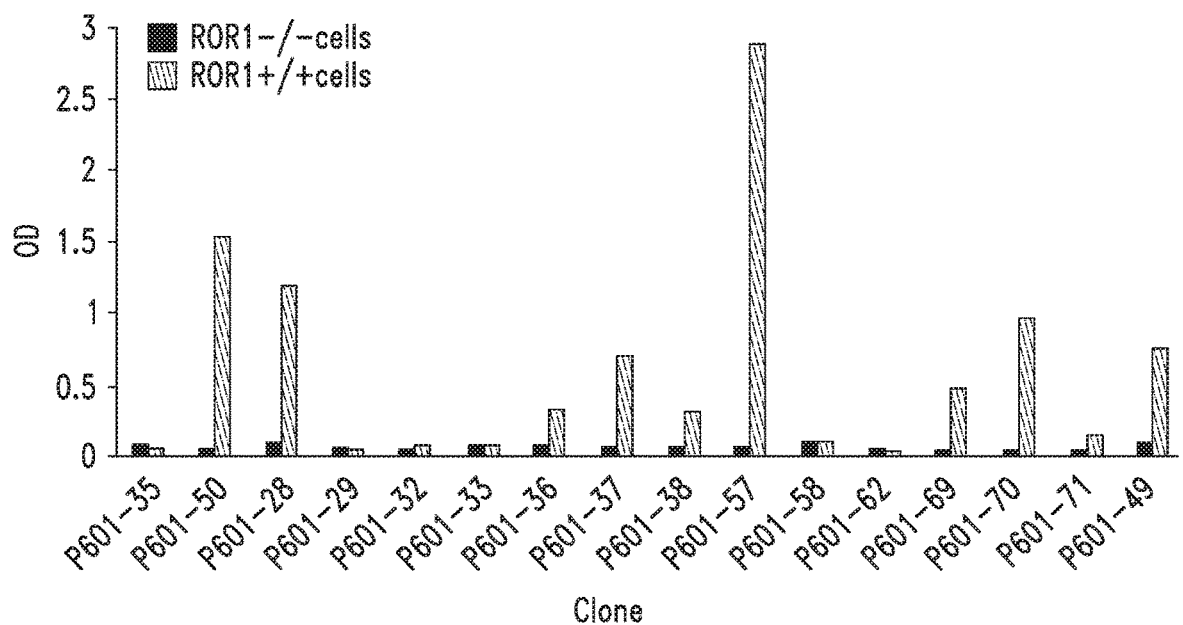
FIG. 6 is a graph showing an example of ROR1 phage antibody cell ELISA results.

Through cell ELISA, the inventors further identified 45 unique clones recognizing ROR1 positive cells, but not ROR1 negative cells (FIG. 6). These 45 cell ELISA-positive phage antibody clones possessing unique DNA coding sequences (as shown in Table 2) were then subjected to further characterization.

TABLE 2

ROR1 phage antibody display panning summary

| Type of Libraries | Planning methods | ELISA positive rate | Unique clone | Cell ELISA positive |
|---|---|---|---|---|
| scFv naïve | Plastic panning | 87/120 | 15/120 | 5/120 |
| scFv naïve | Plastic panning | 574/1079 | 119/1079 | 38/1079 |
|  | Panning in solution | 24/96 | 5/96 | 0/96 |
|  | Cell panning | 29/92 | 4/92 | 2/92 |
| Fab naïve | Plastic panning | 83/108 | 14/108 | — |
| Spleen | Panning in solution | 11/24 | 2/24 | — |

Figure 7:
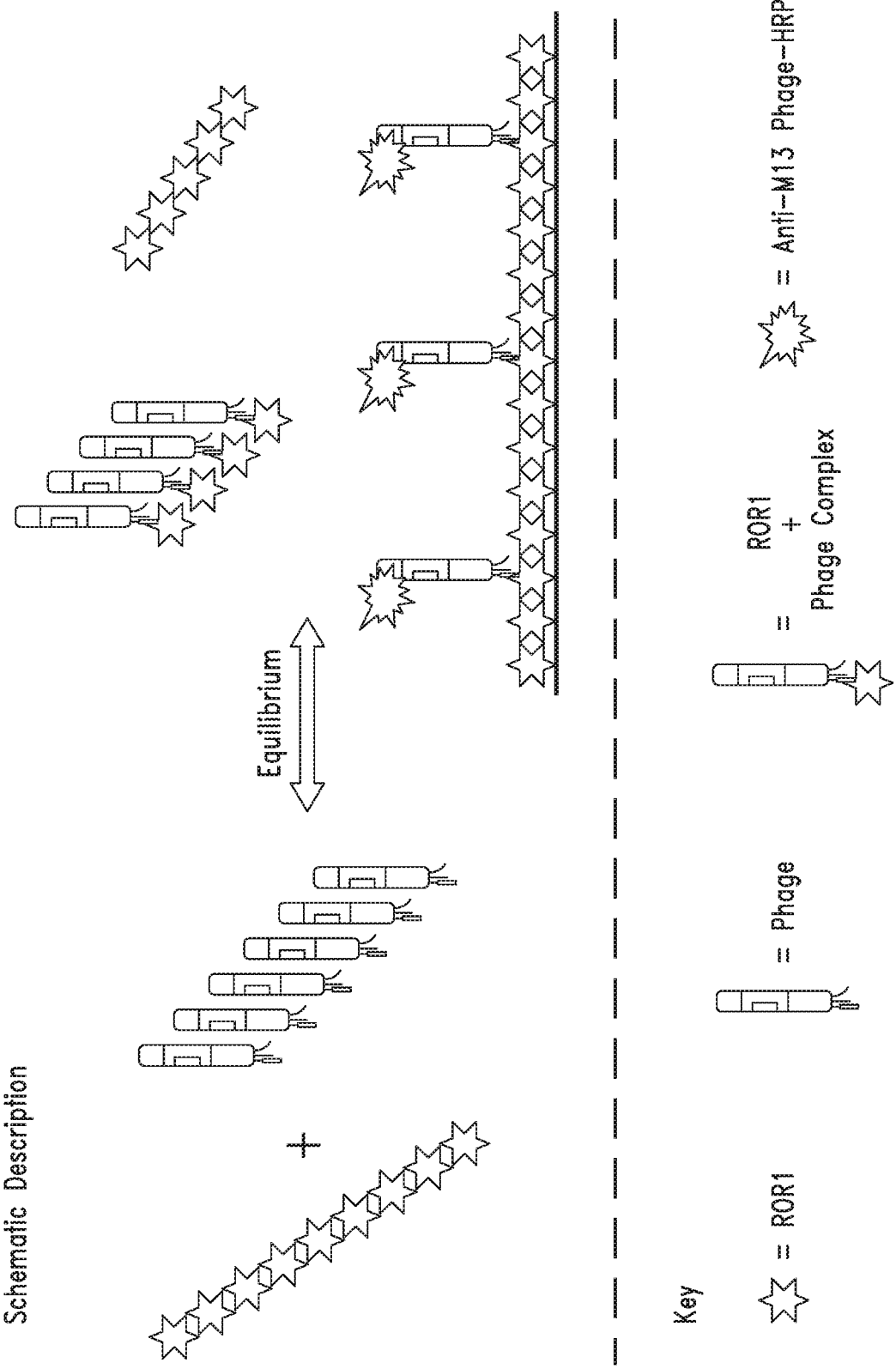
FIG. 7 illustrates methodology for affinity ranking by phage competition ELISA.

Binding affinities of the 45 unique cell ELISA-positive phage clones were estimated by competitive phage-binding ELISA. A diagram demonstrating the design of ROR1 competitive ELISA is shown in FIG. 7. Purified phage antibodies were first diluted serially in PBST buffer, and tested for binding to a ROR1-coated plate. The dilution that gave 50-80% saturating signal was used in the solution binding assay in which phage were first incubated with increasing concentration of ROR1 for one to two hours, and then transferred to a ROR1-coated plate for $10^{-15}$ minutes to capture the unbound phage. IC50 was calculated as the concentration of ROR1 in solution-binding stage that inhibited 50% of the phage from binding to immobilized ROR1, and Table 1 summarizes the IC50s of the 45 clones tested.

By epitope grouping assay, the 45 unique phage antibodies were then grouped into four different classes according to their distinct binding epitopes on ROR1, as shown in Table 3).

TABLE 3

Epitope bucket summary of ROR1-positive phage clones

| Total | 45 |
|---|---|
| Epitope Class I | 16 |
| Epitope Class II | 10 |
| Epitope Class III | 11 |
| Epitope Class IV | 8 |

In this assay, ROR1 was captured by immobilized anti-ROR1 monoclonal full-length antibodies with known and distinct binding epitopes. Then, purified phage antibodies were added to the solution. In cases where the binding between ROR1 and immobilized mAb blocked the binding of the phage antibody to ROR1, this phage antibody was considered to have a binding epitope very close to, or the same as, the immobilized mAb. Otherwise, the phage antibody is thought to have a different epitope.

Figure 8:
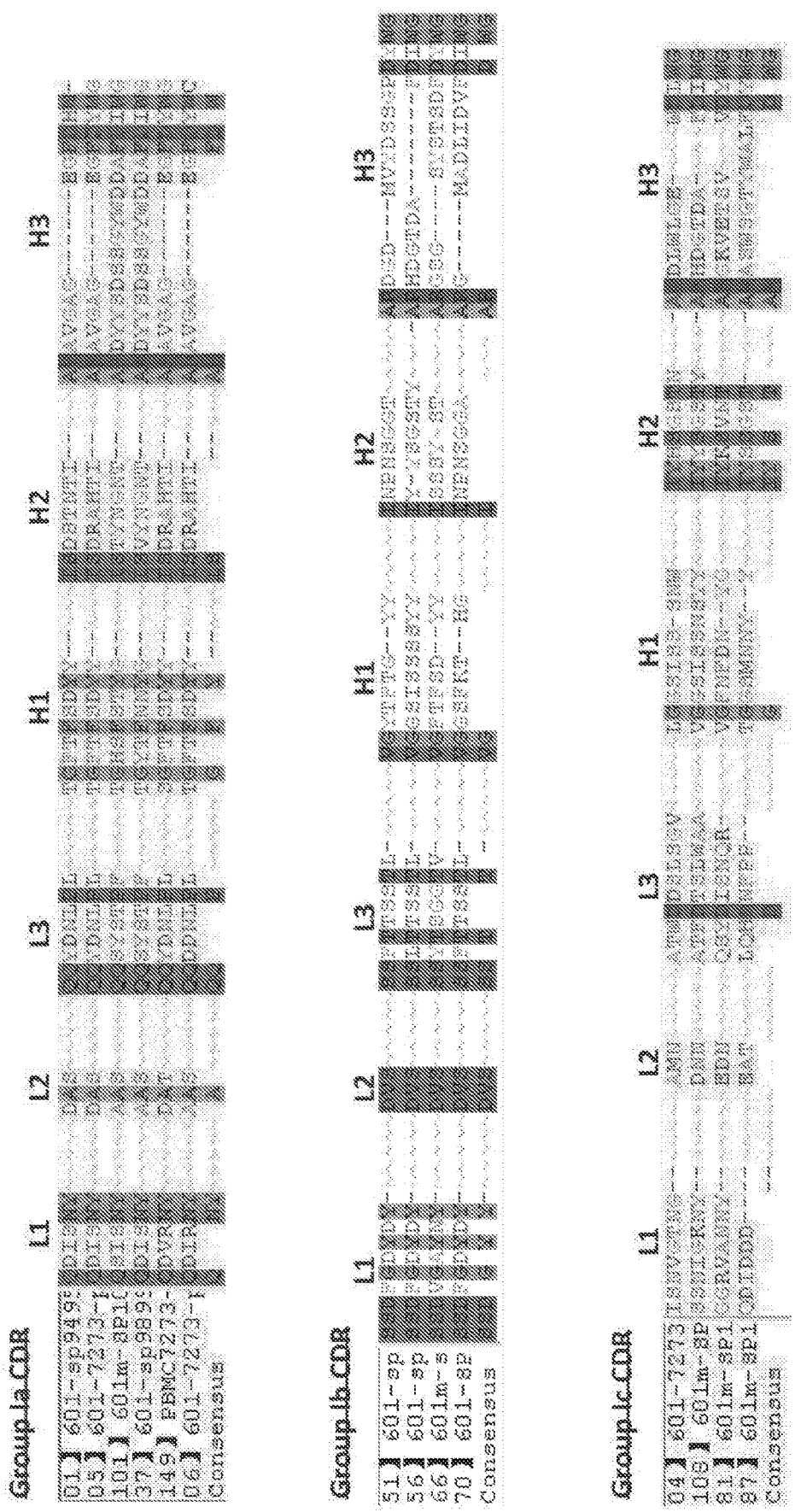
FIG. 8 illustrates epitope Class I antibody CDR sequence analysis.
Figure 9:
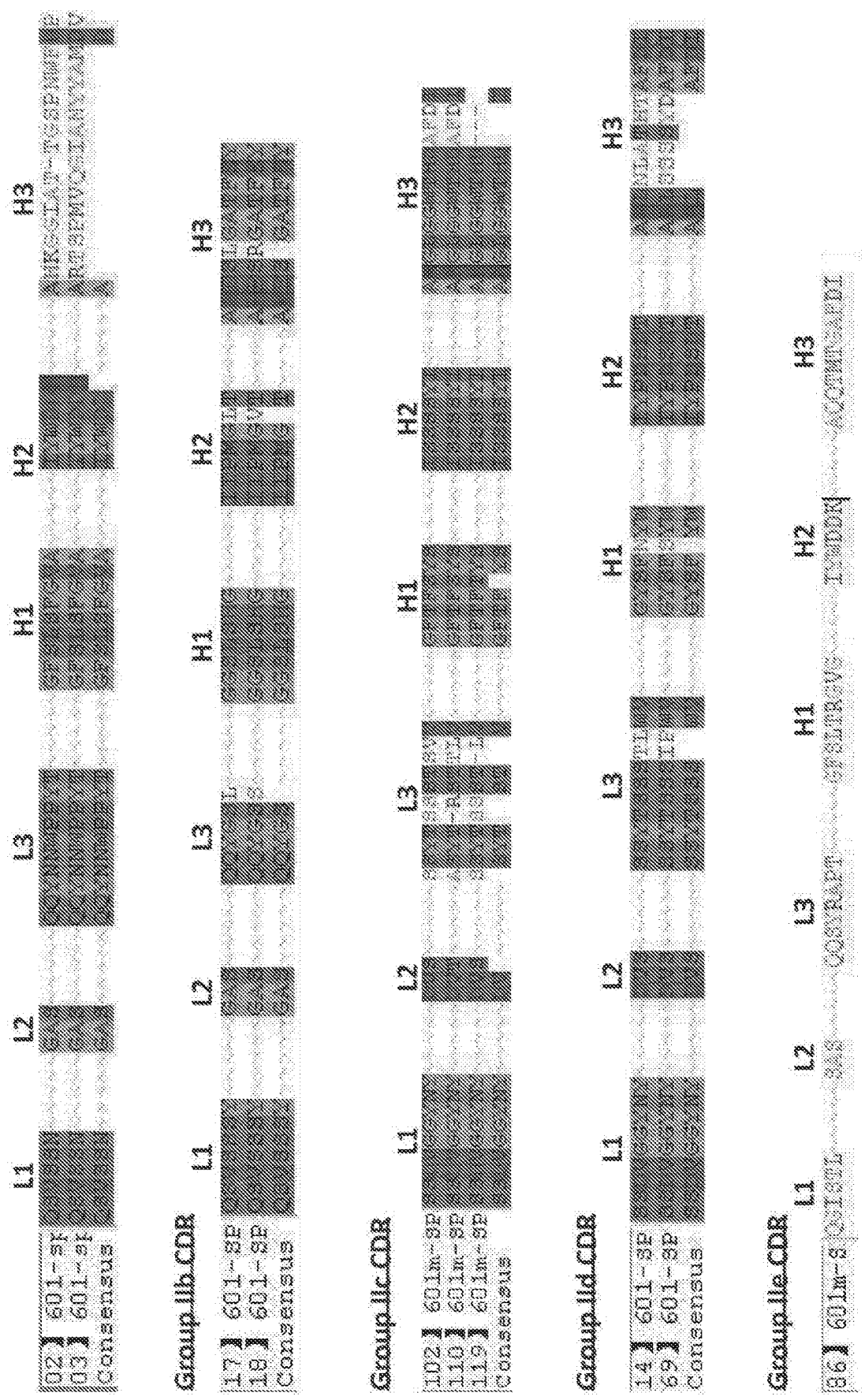
FIG. 9 illustrates epitope Class II antibody CDR sequence analysis.
Figure 10:
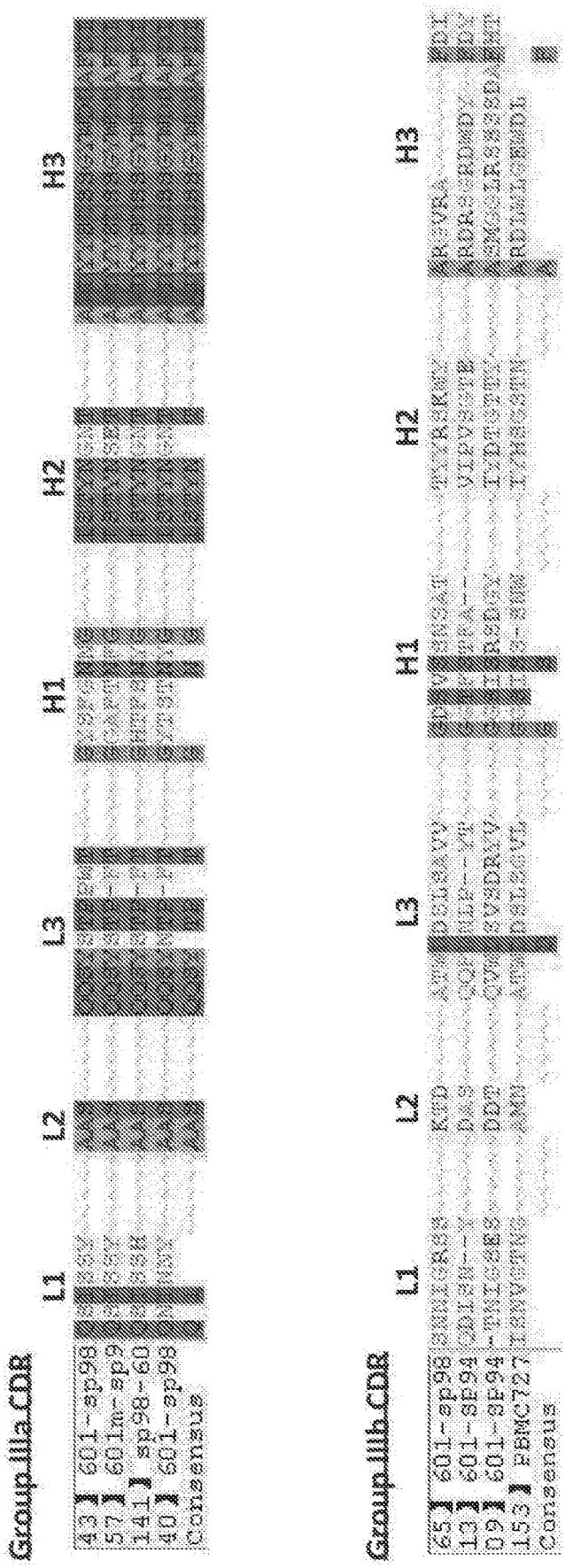
FIG. 10 illustrates epitope Class III antibody CDR sequence analysis.
Figure 11:
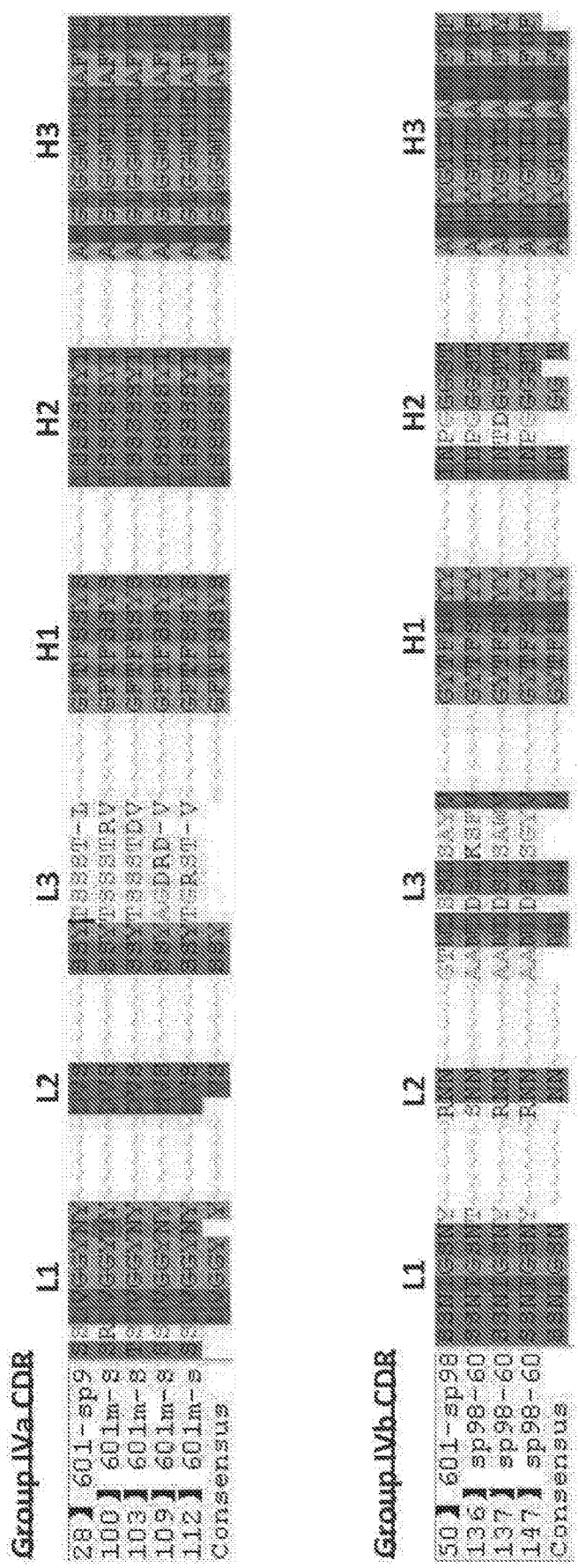
FIG. 11 illustrates epitope Class IV antibody CDR sequence analysis.

The complementary determining regions (CDR) regions of both heavy chain and light chain of ROR1-specific antibodies have been analyzed and highly conserved motifs have been identified within each epitope class (Class I to IV), as illustrated in FIGS. 8-11. FIG. 8 illustrates epitope Class I antibody CDR sequence analysis, FIG. 9 illustrates epitope Class II CDR sequence analysis, FIG. 10 illustrates epitope Class III CDR sequence analysis, and FIG. 11 illustrates epitope Class IV CDR sequence analysis.

As can be seen in the Figures, there are three subgroups in epitope Class I, five subgroups in epitope Class II, and two subgroups in each of epitope classes III and IV. The conserved residues are important for defining the antibodies' binding specificity and affinity to hROR1-ECD, and provide useful information for future protein engineering to modify the binding profile.

Figure 12:
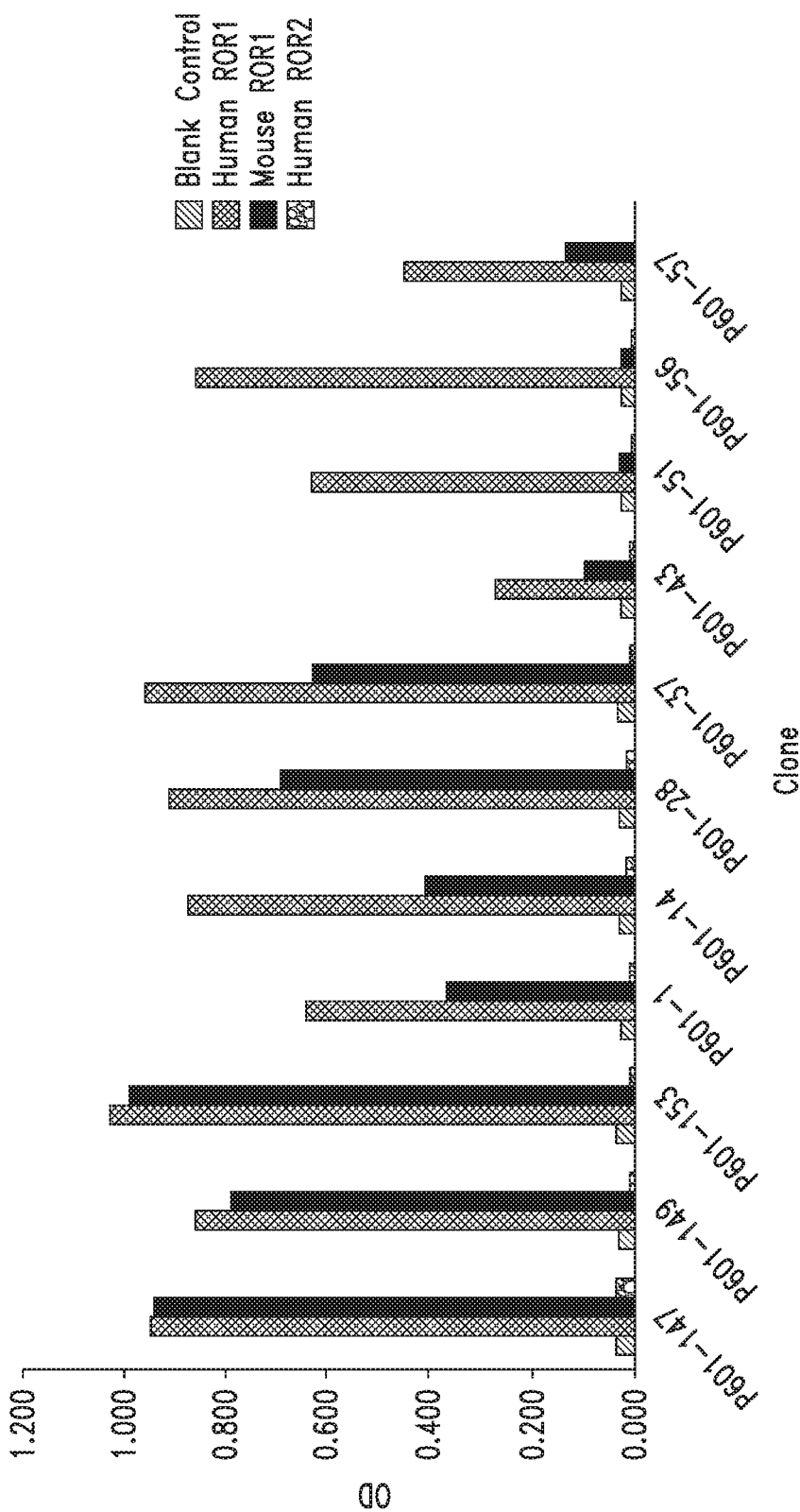
FIG. 12 is a graph showing an example of the binding specificity of ROR1 positive phage clones by ELISA.

Binding specificities of the 45 phage antibodies were determined by protein ELISA against human ROR1-ECD, human ROR2-ECD and mouse ROR1-ECD (FIG. 12). All 45 antibodies show specific binding to ROR1. Thirty-eight out of the 45 antibodies recognize both human and mouse ROR1-ECD (hROR1 and mROR1, respectively), as summarized in Table 4, which is a desired property facilitating future preclinical animal studies.

TABLE 4

Binding specificity of ROR1 phage antibodies

| Specificity | Positive rate |
| --- | --- |
| hROR1 positive only | 7/45 |
| hROR1 and mROR1 positive | 38/45 |
| hROR1 and hROR2 positive | 0/45 |

Figure 13:
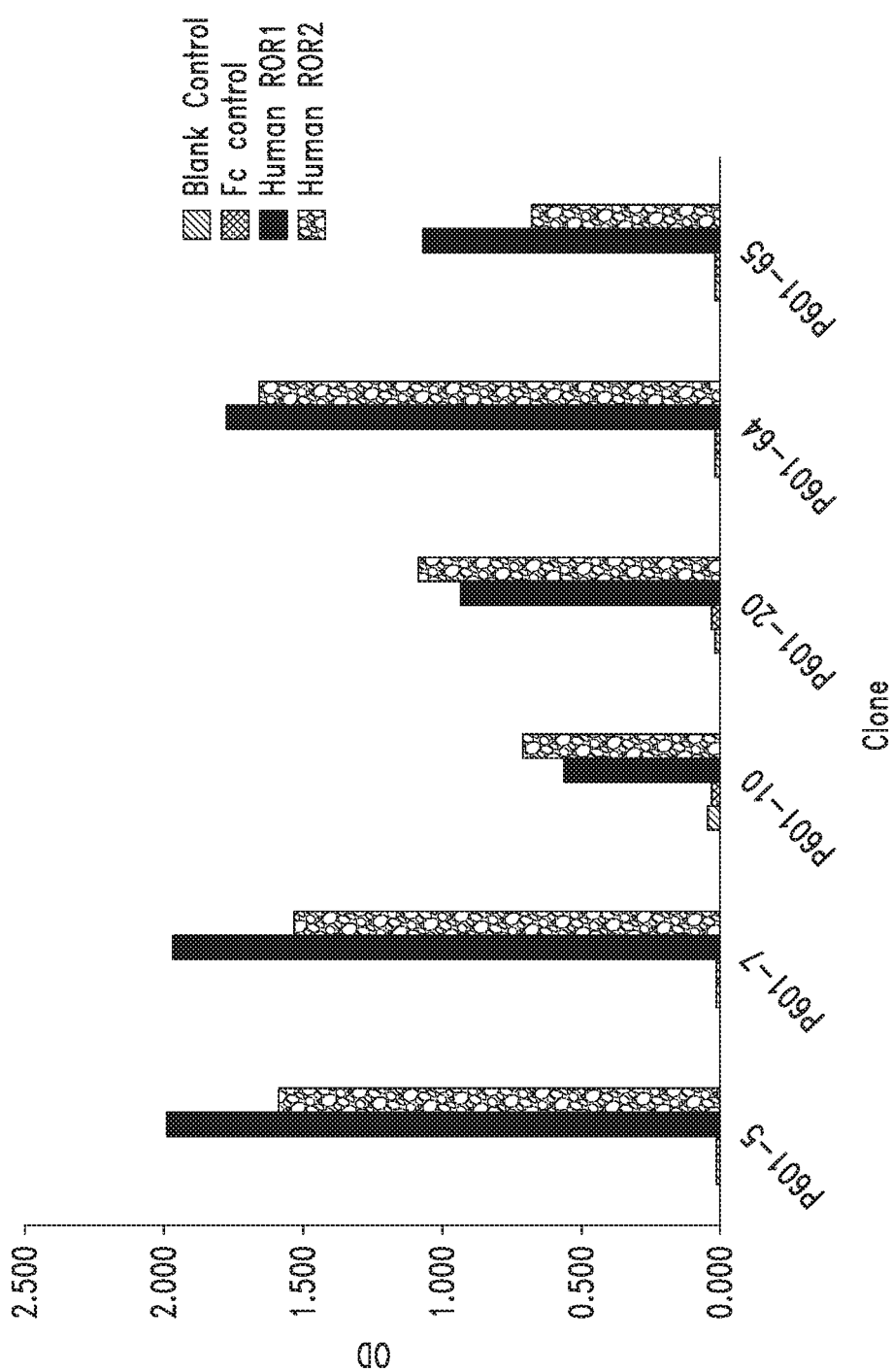
FIG. 13 is a graph showing an example of positive phage clones binding to both human ROR1 and human ROR2 by ELISA.

In another panning effort, the inventors discovered clones that bind to both Ror1 and Ror2, demonstrating that development of ROR1/ROR2 bi-specific antibodies is highly feasible (FIG. 13).

Example 2—Summary of Preferred ROR1 Specific Antibodies

The inventors isolated 45 antibodies according to the invention. The antibodies may be developed for therapeutic or diagnostic use. Fourteen antibodies were selected by the following criteria:

1. They represent all epitope classes and sub-groups;
2. They have high ROR1-binding affinity; and
3. They form the pool that is likely to be converted into full IgG molecules for further analysis.

For each antibody, the information is organized as following:

1. Name of antibody;
2. Epitope class and sub-group;
3. Light chain variable region DNA sequence;
4. Light chain variable region protein sequence;
5. Light chain CDRs: L1, L2, L3 DNA sequence;
6. Light chain CDRs: L1, L2, L3 amino acid sequence;
7. Heavy chain variable region DNA sequence;
8. Heavy chain variable region protein sequence;
9. Heavy chain CDRs: H1, H2, H3 DNA sequence; and
10. Heavy chain CDRs: H1, H2, H3 amino acid sequence.

1) Antibody 601-1; Epitope Class I; Subgroup 1a 601-1 Light Chain Variable Region (DNA Sequence)

[SEQ ID NO: 3]
Gccatccggatgacccagtctccatcctccctgtctgcatctgtaggaga cagagtcaccatcacttgccaggcgagtcaggacattagcaactatttaa attggtatcagcagaaaccagggaaagcccctaagctcctgatctacgat gcatccaatttggaaacaggggtcccatcaaggttcagtggaagtggatc tgggacagattttactttcaccatcagcagcctgcagcctgaagatattg caacatattactgtcaacagtatgataatctcccctcactttcggcgga gggaccaaggtggaaatcaaacgt 601-1 Light chain variable region (protein sequence)

[SEQ ID NO: 4]
AIRMTQSPSSLSASVGDRVTITCQASQDISNYLNWYQQKPGKAPKLLIYD
ASNLETGVPSRFSGSGSGTDFTFTISSLQPEDIATYYCQQYDNLPLTFGG
GTKVEIKR 601-1 Light chain CDRs: L1, L2, L3 (DNA sequence)

[SEQ ID NO: 5]
caggcgagtcaggacattagcaactatttaaat

[SEQ ID NO: 6]
gatgcatccaatttggaaaca

[SEQ ID NO: 7]
caacagtatgataatctcccctcact 601-1 Light chain CDRs: L1, L2, L3 (protein sequence)

[SEQ ID NO: 8]
QASQDISNYLN

[SEQ ID NO: 9]
DASNLET

[SEQ ID NO: 10]
QQYDNLPLT 601-1 heavy chain variable region (DNA sequence)

[SEQ ID NO: 11]
gaggtgcagctggtggagtctgggggaggcttggtcaagcctggaggatc cctgagactctcctgtgcagcctctggattcaccttcagtgactactaca tgagctggatccgccaggctccagggaaggggctggagtgggtttcatac attagtgatagtactaataccatatactacgcagactctgtgaagggccg attcaccgtctccagggacaacccaaaaactcactctatctgcaaatga tcagcctgagagccgaggacacggccgtgtattattgtgcgagagctgtg ggagctggcgagggctttgaccactggggccagggaaccctggtcaccgt ctcctca 601-1 heavy chain variable region (protein sequence)

[SEQ ID NO: 12]
EVQLVESGGGLVKPGGSLRLSCAASGFTFSDYYMSWIRQAPGKGLEWVSY
ISDSTNTIYYADSVKGRFTVSRDNPKNSLYLQMISLRAEDTAVYYCARAV
GAGEGFDHWGQGTLVTVSS 601-1 heavy chain CDRs: H1, H2, H3 (DNA sequence)

[SEQ ID NO: 13]
gactactacatgagc

[SEQ ID NO: 14]
tacattagtgatagtactaataccatatactacgcagactctgtgaaggg
c

[SEQ ID NO: 15]
gctgtgggagctggcgagggctttgaccac 601-1 heavy chain CDRs: H1, H2, H3 (protein sequence)

[SEQ ID NO: 16]
DYYMS

[SEQ ID NO: 17]
YISDSTNTIYYADSVKG

[SEQ ID NO: 18]
AVGAGEGFDH

2) Antibody 601-5; Epitope Class I; Subgroup 1a 601-5 Light chain variable region (DNA sequence)
[SEQ ID NO: 19]
gacatccagatgacccagtctccatcctccctgtctgcatctgtaggaga cagagtcaccatcacttgccaggcgagtcaggacattagcaactatttaa attggtatcagcagaaaccagggaaagcccctaagctcctgatctacgat gcatccaatttggaaacaggggtcccatcaaggttcagtggaagtggatc tgggacagattttaccttcaccatcagcagcctgcagcctgaagatattg caacatattactgtcaacagtatgataatctcccccctcactttcggcgga gggaccaagctggagatcaaacgt 601-5 Light chain variable region (protein sequence)
[SEQ ID NO: 20]
DIQMTQSPSSLSASVGDRVTITCQASQDISNYLNWYQQKPGKAPKLLIYD
ASNLETGVPSRFSGSGSGTDFTFTISSLQPEDIATYYCQQYDNLPLTFGG
GTKLEIKR 601-5 Light chain CDRs: L1, L2, L3 (DNA sequence)
[SEQ ID NO: 21]
caggcgagtcaggacattagcaactatttaaat

[SEQ ID NO: 22]
gatgcatccaatttggaaaca

[SEQ ID NO: 23]
caacagtatgataatctcccccctcact 601-5 Light chain CDRs: L1, L2, L3 (protein sequence)
[SEQ ID NO: 24]
QASQDISNYLN

[SEQ ID NO: 25]
DASNLET

[SEQ ID NO: 26]
QQYDNLPLT 601-5 heavy chain variable region (DNA sequence)
[SEQ ID NO: 27]
gaggtgcagctggtggagtctgggggaggcttggtcaagcctggagggtc cctgagactctcctgtgcagcctctggattcaccttcagtgactactaca tgggctgggtccgccaggctccggggaagggccttaagtggctttcatac attagtgatcgtgcgcataccatatacgacacagactctgtgaagggccg attcaccatttccagggacgacgccaagagttcgctttatctgcgaatga acaacctgagagtcgaggacacggccgtttactactgtgcgagggcagtg ggagctggggagggctttgactactggggccaaggcaccctggtgaccgt ctcctca 601-5 heavy chain variable region (protein sequence)
[SEQ ID NO: 28]
EVQLVESGGGLVKPGGSLRLSCAASGFTFSDYYMGWVRQAPGKGLKWLSY
ISDRAHTIYDTDSVKGRFTISRDDAKSSLYLRMNNLRVEDTAVYYCARAV
GAGEGFDYWGQGTLVTVSS 601-5 heavy chain CDRs: H1, H2, H3 (DNA sequence)
[SEQ ID NO: 29]
gactactacatgggc

[SEQ ID NO: 30]
tacattagtgatcgtgcgcataccatatacgacacagactctgtgaaggg
c

[SEQ ID NO: 31]
gcagtgggagctggggagggctttgactac 601-5 heavy chain CDRs: H1, H2, H3 (protein sequence)
[SEQ ID NO: 32]
DYYMG

[SEQ ID NO: 33]
YISDRAHTIYDTDSVKG

[SEQ ID NO: 34]
AVGAGEGFDY

3) Antibody 601-51; Epitope Class I; Subgroup 1b 601-51 Light chain variable region (DNA sequence)
[SEQ ID NO: 35]
cagtctgccctgactcagcctgcctccgtgtctgggtctcctggacagtc gatcaccatctcctgcactggaaccagcagtgactttggtgattatgact atgtctcttggtaccaacaacacccaggcaaagcccccaaactcatgatt tatgatgtcagtgatcggccctcaggggtttctaatcgcttctctggctc caagtctggcaacacggcctccctgaccatctctgggctccaggctgagg acgaggctgattatttctgcagctcatttacaaccagcagcactctggtg ttcggcggagggaccaagctgaccgtcctaggt 601-51 Light chain variable region (protein sequence)
[SEQ ID NO: 36]
QSALTQPASVSGSPGQSITISCTGTSSDFGDYDYVSWYQQHPGKAPKLMI
YDVSDRPSGVSNRFSGSKSGNTASLTISGLQAEDEADYFCSSFTTSSTLV
FGGGTKLTVLG 601-51 Light chain CDRs: L1, L2, L3 (DNA sequence)
[SEQ ID NO: 37]
actggaaccagcagtgactttggtgattatgactatgtctct

[SEQ ID NO: 38]
gatgtcagtgatcggccctca

[SEQ ID NO: 39]
agctcatttacaaccagcagcactctggtg 601-51 Light chain CDRs: L1, L2, L3 (protein sequence)
[SEQ ID NO: 40]
TGTSSDFGDYDYVS

[SEQ ID NO: 41]
DVSDRPS

[SEQ ID NO: 42]
SSFTTSSTLV 601-51 heavy chain variable region (DNA sequence)
[SEQ ID NO: 43]
caggtgcagctggtgcagtctggggctgaggtgaagaagcctggggcctc agtgaaggtctcctgcaaggcttctggatacaccttcaccggctactata tgcactgggtgcgacaggcccctggacaagggcttgagtggatgggatgg atcaaccctaacagtggtggcacaaactatgcacagaagtttcagggcag ggtcaccatgaccagggacacgtccatcagcacagcctacatggagctga gcaggctgagatctgacgacacggccgtgtattactgtgcgagagatggg gatatggtctatgatagtagtgggcctgactactggggccagggaaccct ggtcaccgtctcctca 601-51 heavy chain variable region (protein sequence)

[SEQ ID NO: 44]
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVYYCARDG
DMVYDSSGPDYWGQGTLVTVSS 601-51 heavy chain CDRs: H1, H2, H3 (DNA sequence)

[SEQ ID NO: 45]
Ggctactatatgcac

[SEQ ID NO: 46]
Tggatcaaccctaacagtggtggcacaaactatgcacagaagtttcaggg
c

[SEQ ID NO: 47]
Gatggggatatggtctatgatagtagtgggcctgactac 601-51 heavy chain CDRs: H1, H2, H3 (protein sequence)

[SEQ ID NO: 48]
GYYMH

[SEQ ID NO: 49]
WINPNSGGTNYAQKFQG

[SEQ ID NO: 50]
DGDMVYDSSGPDY

4) Antibody 601-4; Epitope Class I; Subgroup 1c 601-4 Light chain variable region (DNA sequence)
[SEQ ID NO: 51]
cagtctgtgctgactcagccaccctcagcgtctggggccccgggcagag ggtcaccatctcctgttccggaggcatctccaacgtcgggactaatggtg ttaactggtaccagcacctcccaggaacggcccccaaactcctcgtcgat gctatgaatcagcggccctcaggagtccctgaccgattctctggctccag gtctggcacgtcaggctccctggccatcactgggctccggtctgaagatg aggctgactattattgtgcaacatgggatgacagcctgagtggtgtacta ttcggcggagggaccaagctgaccgtcctaggt 601-4 Light chain variable region (protein sequence)
[SEQ ID NO: 52]
QSVLTQPPSASGAPGQRVTISCSGGISNVGTNGVNWYQHLPGTAPKLLVD
AMNQRPSGVPDRFSGSRSGTSGSLAITGLRSEDEADYYCATWDDSLSGVL
FGGGTKLTVLG 601-4 Light chain CDRs: L1, L2, L3 (DNA sequence)
[SEQ ID NO: 53]
tccggaggcatctccaacgtcgggactaatggtgttaac

[SEQ ID NO: 54]
gctatgaatcagcggccctca

[SEQ ID NO: 55]
gcaacatgggatgacagcctgagtggtgtacta 601-4 Light chain CDRs: L1, L2, L3 (protein sequence)
[SEQ ID NO: 56]
SGGISNVGTNGVN

[SEQ ID NO: 57]
AMNQRPS

[SEQ ID NO: 58]
ATWDDSLSGVL 601-4 heavy chain variable region (DNA sequence)
[SEQ ID NO: 59]
gaggtgcagctggtgcagtctggcccaggactggtgaagccttcggggac cctgtccctcacctgcgctgtctctggtggctccatcagcagtagtaact ggtggagttgggtccgccagcccccagggaaggggctggagtggattggg gaaatctatcatagtgggagcaccaactacaacccgtccctcaagagtcg agtcaccatatcagtagacaagtccaagaaccagttctccctgaagctgg gctctgtgaccgccgcggacacagccacatattactgtgcgcgcgatctg tggctgggtgagtgggatttgtggggccaaggcaccctggtcaccgtctc ctca 601-4 heavy chain variable region (protein sequence)
[SEQ ID NO: 60]
EVQLVQSGPGLVKPSGTLSLTCAVSGGSISSSNWWSWVRQPPGKGLEWIG
EIYHSGSTNYNPSLKSRVTISVDKSKNQFSLKLGSVTAADTATYYCARDL
WLGEWDLWGQGTLVTVSS 601-4 heavy chain CDRs: H1, H2, H3 (DNA sequence)
[SEQ ID NO: 61]
agtagtaactggtggagt

[SEQ ID NO: 62]
gaaatctatcatagtgggagcaccaactacaacccgtccctcaagagt

[SEQ ID NO: 63]
gatctgtggctgggtgagtgggatttg 601-4 heavy chain CDRs: H1, H2, H3 (protein sequence)
[SEQ ID NO: 64]
SSNWWS

[SEQ ID NO: 65]
EIYHSGSTNYNPSLKS

[SEQ ID NO: 66]
DLWLGEWDL

5) Antibody 601-2; Epitope Class II; Subgroup 2a 601-2 Light Chain Variable Region (DNA Sequence)

[SEQ ID NO: 67]
gaaattgtgttgacgcagtctccagacaccctgtccttgtctcagggga aagagccaccctctcctgcagggccagtcagagtgttagcagcaacttag cctggtaccagcagaaacctggccaggctcccaggctcctcatctatggt gcatccaccagggccactggtatcccagccaggttcagtggcagtgggtc tgggacagagttcactctcaccatcagcagcctgcagtctgaagattttg cagtttattactgtcagcagtataataactggcctccgtacacttttggc caggggaccaaggtggaaatcaaacgt 601-2 Light chain variable region (protein sequence)
[SEQ ID NO: 68]
EIVLTQSPDTLSLSPGERATLSCRASQSVSSNLAWYQQKPGQAPRLLIYG
ASTRATGIPARFSGSGSGTEFTLTISSLQSEDFAVYYCQQYNNWPPYTFG
QGTKVEIKR 601-2 Light chain CDRs: L1, L2, L3 (DNA sequence)
[SEQ ID NO: 69]
agggccagtcagagtgttagcagcaacttagcc

[SEQ ID NO: 70]
ggtgcatccaccagggccact

-continued cagcagtataataactggcctccgtacact [SEQ ID NO: 71]

601-2 Light chain CDRs: L1, L2, L3 (protein sequence)

RASQSVSSNLA [SEQ ID NO: 72]

GASTRAT [SEQ ID NO: 73]

QQYNNWPPYT [SEQ ID NO: 74]

601-2 heavy chain variable region (DNA sequence) [SEQ ID NO: 75]
caggtcaccttgaaggagtctggccctacgctggtgaaacccacacagac
cctcacgctgacgtgcaccttctctggcttctcactcagtagttttggag
tggctgtgggctggttccgtcagccccaggaaaggccctggagtggctt
ggacttatttattgggatgatgataagcgctacagcccatctctgaagac
caggctcaccatcaccaaggacacctccaaaaaccaggtggtccttacaa
tgaccaacatggaccctgtggacacagccacatattattgtgcccacaaa
gggggtatagcaacaactggcagccccaactggttcgacccctggggcca
gggaaccctggtcaccgtctcctca 601-2 heavy chain variable region (protein sequence)

QVTLKESGPTLVKPTQTLTLTCTFSGFSLSSFGVAVGWFRQPPGKALEWL
GLIYWDDDKRYSPSLKTRLTITKDTSKNQVVLTMTNMDPVDTATYYCAHK
GGIATTGSPNWFDPWGQGTLVTVSS [SEQ ID NO: 76]

601-2 heavy chain CDRs: H1, H2, H3 (DNA sequence)

agttttggagtggctgtgggc [SEQ ID NO: 77]

cttatttattgggatgatgataagcgctacagcccatctctgaagacc [SEQ ID NO: 78]

aaaggggtatagcaacaactggcagccccaactggttcgacccc [SEQ ID NO: 79]

601-2 heavy chain CDRs: H1, H2, H3 (protein sequence)

SFGVAVG [SEQ ID NO: 80]

LIYWDDDKRYSPSLKT [SEQ ID NO: 81]

KGGIATTGSPNWFDP [SEQ ID NO: 82]

6) Antibody 601-17; Epitope Class II; Subgroup 2b 601-17 Light chain variable region (DNA sequence) [SEQ ID NO: 83]
gaaattgtgttgacgcagtctccaggcaccctgtctttgtctccagggga
aagagccaccctctcctgcagggccagtcagagtgttagcagcagctact
tagcctggtaccagcagaaacctggccaggctcccaggctcctcatctat
ggtgcatccagcagggccactggcatcccagacaggttcagtggcagtgg
gtctgggacagacttcactctcaccatcagcagactggagcctgaagatt
ttgcagtgtattactgtcagcagtatggtagccttttggccaggggacc
aaggtggagatcaaacgt 601-17 Light chain variable region (protein sequence)

EIVLTQSPGTLSLSPGERATLSCRASQSVSSSYLAWYQQKPGQAPRLLIY
GASSRATGIPDRFSGSGSGTDFTLTISRLEPEDFAVYYCQQYGSLFGQGT
KVEIKR [SEQ ID NO: 84]

601-17 Light chain CDRs: L1, L2, L3 (DNA sequence)

agggccagtcagagtgttagcagcagctacttagcct [SEQ ID NO: 85]

ggtgcatccagcagggccact [SEQ ID NO: 86]

cagcagtatggtagcctt [SEQ ID NO: 87]

601-17 Light chain CDRs: L1, L2, L3 (protein sequence)

RASQSVSSSYLA [SEQ ID NO: 88]

GASSRAT [SEQ ID NO: 89]

QQYGSL [SEQ ID NO: 90]

601-17 heavy chain variable region (DNA sequence) [SEQ ID NO: 91]
gaggtccagctggtacagtctggggctgaggtgaggaaacctggtcctc
ggtgaaggtctcctgcaaggcctctggaggctccctcagcagtcatggtg
tcagttgggtgcgtcaggcccctggacaaggcttgagtggatggccagg
atcatccccatgtttggtctaacagactacgcacagaacttccaggccag
agtcacgatttccgcggacagatccacgaacacagtttacatggagatca
gcaacctgggatctgaagacacggccgtctatttctgtgcgagagagagt
ctgggagcaacatttgagtattggggccagggaaccctggtcaccgtctc
ctca 601-17 heavy chain variable region (protein sequence)

EVQLVQSGAEVRKPGSSVKVSCKASGGSLSSHGVSWVRQAPGQGLEWMAR
IIPMFGLTDYAQNFQARVTISADRSTNTVYMEISNLGSEDTAVYFCARES
LGATFEYWGQGTLVTVSS [SEQ ID NO: 92]

601-17 heavy chain CDRs: H1, H2, H3 (DNA sequence)

agtcatggtgtcagt [SEQ ID NO: 93]

aggatcatccccatgtttggtctaacagactacgcacagaacttccaggcc [SEQ ID NO: 94]

gagagtctgggagcaacatttgagtat [SEQ ID NO: 95]

601-17 heavy chain CDRs: H1, H2, H3 (protein sequence)

SHGVS [SEQ ID NO: 96]

RIIPMFGLTDYAQNFQA [SEQ ID NO: 97]

ESLGATFEY [SEQ ID NO: 98]

7) Antibody 601-119; Epitope Class II; Subgroup 2c 601-119 Light chain variable region (DNA sequence)
[SEQ ID NO: 99]
cagtctgccctgactcagcctgcctccgtgtctgcgtctcctggacagtc
gatcaccatctcctgcactggaaccagcagtgacgttggtggttataact
atgtcacctggtaccaacagcacccaggcaaagcccccaaactcatgatt
tatgatgtcagtaagcggccctcaggggtccttgatcgcttctctggctc
caagtctggcaacacggcctccctgaccatctctgggctccaggctgagg
acgaggctgattatttctgcagctcatatacaagcagttccaccctggtg
tttggcggagggaccaagctgaccgtcctaggt 601-119 Light chain variable region (protein sequence)
[SEQ ID NO: 100]
QSALTQPASVSASPGQSITISCTGTSSDVGGYNYVTWYQQHPGKAPKLMI
YDVSKRPSGVLDRFSGSKSGNTASLTISGLQAEDEADYFCSSYTSSSTLV
FGGGTKLTVLG 601-119 Light chain CDRs: L1, L2, L3 (DNA sequence)
[SEQ ID NO: 101]
actggaaccagcagtgacgttggtggttataactatgtcacc

[SEQ ID NO: 102]
gatgtcagtaagcggccctca

[SEQ ID NO: 103]
agctcatatacaagcagttccaccctggtg 601-119 Light chain CDRs: L1, L2, L3 (protein sequence)
[SEQ ID NO: 104]
TGTSSDVGGYNYVT

[SEQ ID NO: 105]
DVSKRPS

[SEQ ID NO: 106]
SSYTSSSTLV 601-119 heavy chain variable region (DNA sequence)
[SEQ ID NO: 107]
caggtgcagctggtgcaatctgggggaggcctggtcaagcctggggggtc
cctgagactctcctgtgcagcctctggattcaccttcggtacctatagca
tgaactgggtccgccaggctccaggaaaggggctggagtgggtctcatcc
attagtagtagtagtagttacatatactacgcagactcagtgaagggccg
attcaccatctccagagacaacgccaagaactcactgtatctgcaaatga
acagcctgagagccgaggacacggctgtgtattactgtgcgagaggtctc
ggtggctggacccatgatgcttttgatatctggggccaagggaccacggt
caccgtctcctca 601-119 heavy chain variable region (protein sequence)
[SEQ ID NO: 108]
QVQLVQSGGGLVKPGGSLRLSCAASGFTFGTYSMNWVRQAPGKGLEWVSS
ISSSSSYIYYADSVKGRFTISRDNAKNSLYLQMNSLRAEDTAVYYCARGL
GGWTHDAFDIWQGTTVTSS 601-119 heavy chain CDRs: H1, H2, H3 (DNA sequence)
[SEQ ID NO: 109]
acctatagcatgaac

[SEQ ID NO: 110]
tccattagtagtagtagtagttacatatactacgcagactcagtgaaggg
gc

[SEQ ID NO: 111]
ggtctcggtggctggacccatgatgcttttgatatc 601-119 heavy chain CDRs: H1, H2, H3 (protein sequence)
[SEQ ID NO: 112]
TYSMN

[SEQ ID NO: 113]
SISSSSSYIYYADSVKG

[SEQ ID NO: 114]
GLGGWTHDAFDI

8) Antibody 601-14; Epitope Class II; Subgroup 2d 601-14 Light chain variable region (DNA sequence)
[SEQ ID NO: 115]
cagtctgtgctgactcagcctgcctccgtgtctgggtctcctggacagtc
gatcaccatctcctgcactggaaccagcagtgacgttggtggttataact
atgtctcctggtaccaacaacacccaggcaaagcccccaaactcatgatt
tatgatgtcagtaatcggccctcaggggtttctaatcgcttctctggctc
caagtctggcaacacggcctccctgaccatctctgggctccaggctgagg
acgaggctgattattactgcagctcatatacaagcagcagcactctttgg
gtgttcggcggagggaccaagctgaccgtcctaggt 601-14 Light chain variable region (protein sequence)
[SEQ ID NO: 116]
QSVLTQPASVSGSPGQSITISCTGTSSDVGGYNYVSWYQQHPGKAPKLMI
YDVSNRPSGVSNRFSGSKSGNTASLTISGLQAEDEADYYCSSYTSSSTLW
VFGGGTKLTVLG 601-14 Light chain CDRs: L1, L2, L3 (DNA sequence)
[SEQ ID NO: 117]
actggaaccagcagtgacgttggtggttataactatgtctcc

[SEQ ID NO: 118]
gatgtcagtaatcggccctca

[SEQ ID NO: 119]
agctcatatacaagcagcagcactctttgggtg 601-14 Light chain CDRs: L1, L2, L3 (protein sequence)
[SEQ ID NO: 120]
TGTSSDVGGYNYVS

[SEQ ID NO: 121]
DVSNRPS

[SEQ ID NO: 122]
SSYTSSSTLWV 601-14 heavy chain variable region (DNA sequence)
[SEQ ID NO: 123]
caggtgcagctggtgcagtctggagcagaggtgaaaaagcccggggagtc
tctgaagatctcctgtaaggattctggatacagctttaccaactactggc
tcggctgggtgcgccagatgcccgggaaaggcctggagtggatgggaatc
atctatccgggtgactctgataccagatacagccgtccttcgaggcca
ggtcaccatctcagccgacaagtccatcagcaccgcctacctgcagtgga
gcagcctgaaggcctcggacaccgccatgtattactgtgcgagacttaat
cttgccacacatacagcttttgacatatggggccaagggaccacggtcac
cgtctcctca 601-14 heavy chain variable region (protein sequence)
[SEQ ID NO: 124]
QVQLVQSGAEVKKPGESLKISCKDSGYSFTNYWLGWVRQMPKGLEWMGI
IYPGDSDTRYSPSFRGQVTISADKSISTAYLQWSSLKASDTAMYYCARLN
LATHTAFDIWGQGTTVTVSS 601-14 heavy chain CDRs: H1, H2, H3 (DNA sequence)
[SEQ ID NO: 125]
aactactggctcggc

[SEQ ID NO: 126]
atcatctatccgggtgactctgataccagatacagcccgtccttccgag
gc

[SEQ ID NO: 127]
cttaatcttgccacacatacagcttttgacata 601-14 heavy chain CDRs: H1, H2, H3 (protein sequence)
[SEQ ID NO: 128]
NYWLG

[SEQ ID NO: 129]
IIYPGDSDTRYSPSFRG

[SEQ ID NO: 130]
LNLATHTAFDI

9) Antibody 601-86; Epitope Class II; Subgroup 2e 601-86 Light chain variable region (DNA sequence)
[SEQ ID NO: 131]
gacatccagatgacccagtctccatcttctgtgtctgcatctgtaggaga
cagagtcaccatcacttgtcgggcgagtcaaggtattagcaccttgttgg
cctggtatcagcagaaaccagggaaagcccctaagctcctgatatcttct
gcatccagtttgcaaagtggggtcccagcaaggttcagcggcagtggatc
tgggacagatttcactctcactatcagcagcctgcagcctgaggattttg
caacttactactgccagcaaagttacagagcccccgactttcggccagggg
accaaggtggagatcaaacgt 601-86 Light chain variable region (protein sequence)
[SEQ ID NO: 132]
DIQMTQSPSSVSASVGDRVTITCRASQGISTLLAWYQQKPGKAPKLLISS
ASSLQSGVPARFSGSGSGTDFTLTISSLQPEDFATYYCQQSYRAPTFGQG
TKVEIKR 601-86 Light chain CDRs: L1, L2, L3 (DNA sequence)
[SEQ ID NO: 133]
cgggcgagtcaaggtattagcaccttgttggcc

[SEQ ID NO: 134]
tctgcatccagtttgcaaagt

[SEQ ID NO: 135]
cagcaaagttacagagcccccgact 601-86 Light chain CDRs: L1, L2, L3 (protein sequence)
[SEQ ID NO: 136]
RASQGISTLLA

[SEQ ID NO: 137]
SASSLQS

[SEQ ID NO: 138]
QQSYRAPT 601-86 heavy chain variable region (DNA sequence)
[SEQ ID NO: 139]
caggtcaccttgaaggagtctggtcctacgctgctgaaacccacacagac
cctcacgctgacctgcaccttctctgggttctcactcagtactagaggag
tgggggtgggctggatccgtcagcccccaggacaggccctggagtggctt
acactcatttattgggatgatgataagcgctacagcccttctctaaagag
caggctcaccatcaccaaggacacatccaaaaaccaggtggtccttacaa
tgaccaacatggaatctgtggacacagccacatattactgtgcacagcag
actatgaccggtgcttttgatatctggggccaagggaccacggtcaccgt
ctcctca 601-86 heavy chain variable region (protein sequence)
[SEQ ID NO: 140]
QVTLKESGPTLLKPTQTLTLTCTFSGFSLSTRGVGVGWIRQPPGQALEWL
TLIYWDDDKRYSPSLKSRLTITKDTSKNQVVLTMTNMESVDTATYYCAQQ
TMTGAFDIWGQGTTVTVSS 601-86 heavy chain CDRs: H1, H2, H3 (DNA sequence)
[SEQ ID NO: 141]
actagaggagtggggtgggc

[SEQ ID NO: 142]
ctcatttattgggatgatgataagcgctacagcccttctctaaagagc

[SEQ ID NO: 143]
cagactatgaccggtgcttttgatatc 601-86 heavy chain CDRs: H1, H2, H3 (protein sequence)
[SEQ ID NO: 144]
TRGVGVG

[SEQ ID NO: 145]
LIYWDDDKRYSPSLKS

[SEQ ID NO: 146]
QTMTGAFDI

10) Antibody 601-40; Epitope Class III; Subgroup 3a 601-40 Light chain variable region (DNA sequence)
[SEQ ID NO: 147]
gacatccagttgacccagtctccatcctccctgtctgcatctgtaggaga
cagagtcaccatcacttgccgggcaagtcagaacattaacaactatttaa
attggtatcagcagaaaccagggaaagcccctaagctcctgctctatgct
gcatccagtttgcaaagtggggtcccatcaaggttcagtggcagtggatc
tgggacagaattcactctcaccatcagcagtctgcaccctgaagattttg
caacttactactgtcaacagagttacaatacccccattcaccttcggccct
gggaccaaagtggatatcaaacgt 601-40 Light chain variable region (protein sequence)
[SEQ ID NO: 148]
DIQLTQSPSSLSASVGDRVTITCRASQNINNYLNWYQQKPGKAPKLLLYA
ASSLQSGVPSRFSGSGSGTE
FTLTISSLHPEDFATYYCQQSYNTPFTFGPGTKVDIKR -continued 601-40 Light chain CDRs: L1, L2, L3 (DNA sequence)
[SEQ ID NO: 149]
cgggcaagtcagaacattaacaactatttaaat

[SEQ ID NO: 150]
gctgcatccagtttgcaaagt

[SEQ ID NO: 151]
caacagagttacaataccccattcacc 601-40 Light chain CDRs: L1, L2, L3
(protein sequence)
[SEQ ID NO: 152]
RASQNINNYLN

[SEQ ID NO: 153]
AASSLQS

[SEQ ID NO: 154]
QQSYNTPFT 601-40 heavy chain variable region (DNA sequence)
[SEQ ID NO: 155]
caggtacagctgcagcagtcaggagctgaggtgaagaagcctggggcctc agtgaaggtctcctgcaaggcttctggttacacctctaccaactatggta tcagctgggtgcgacaggcccctggacaagggcttgagtggatgggatgg atcagcacttacaatggtaacacaaactatgcacagaagctccagggcag agtcaccatgaccacagacacatccacgagcacagcctacatggagctga ggagcctgagatctgacgacacggccgtgtattactgtgcgagagactat tactctgatagtagtggttattgggacgatgcttttgatatctggggcca agggacaatggtcaccgtctcttca 601-40 heavy chain variable region
(protein sequence)
[SEQ ID NO: 156]
QVQLQQSGAEVKKPGASVKVSCKASGYTSTNYGISWVRQAPGQGLEWMGW

ISTYNGNTNYAQKLQGRVTMTTDTSTSTAYMELRSLRSDDTAVYYCARDY

YSDSSGYWDDAFDIWGQGTMVTVSS 601-40 heavy chain CDRs: H1, H2, H3 (DNA sequence)
[SEQ ID NO: 157]
aactatggtatcagc

[SEQ ID NO: 158]
tggatcagcacttacaatggtaacacaaactatgcacagaagctccaggg
c

[SEQ ID NO: 159]
gactattactctgatagtagtggttattgggacgatgcttttgatatc 601-40 heavy chain CDRs: H1, H2, H3
(protein sequence)
[SEQ ID NO: 160]
NYGIS

[SEQ ID NO: 161]
WISTYNGNTNYAQKLQG

[SEQ ID NO: 162]
DYYSDSSGYWDDAFDI

11) Antibody 601-13; Epitope Class III; Subgroup 3b 601-13 Light chain variable region (DNA sequence)
[SEQ ID NO: 163]
gacatcgtgatgacccagtctccatcctccctgtctgcatctgtaggaga cagagtcaccatcacttgccaggcgagtcaggacattagcaactatttaa attggtatcagcagaaaccagggaaagcccctaagctcctgatctacgat gcatccaatttggaaacaggggtcccatcaaggttcagtggaagtggatc tgggacagattttattttcaccatcagcagcctgcagcctgaagatattg caacatattactgtcaacagtttgataatctcccttacacttttggccag gggaccaaggtggagatcaaacgt 601-13 Light chain variable region
(protein sequence)
[SEQ ID NO: 164]
DIVMTQSPSSLSASVGDRVTITCQASQDISNYLNWYQQKPGKAPKLLIYD

ASNLETGVPSRFSGSGSGTDFIFTISSLQPEDIATYYCQQFDNLPYTFGQ

GTKVEIKR 601-13 Light chain CDRs: L1, L2, L3 (DNA sequence)
[SEQ ID NO: 165]
caggcgagtcaggacattagcaactatttaaat

[SEQ ID NO: 166]
gatgcatccaatttggaaaca

[SEQ ID NO: 167]
caacagtttgataatctcccttacact 601-13 Light chain CDRs: L1, L2, L3
(protein sequence)
[SEQ ID NO: 168]
QASQDISNYLN

[SEQ ID NO: 169]
DASNLET

[SEQ ID NO: 170]
QQFDNLPYT 601-13 heavy chain variable region (DNA sequence)
[SEQ ID NO: 171]
gaggtccagctggtgcagtctggggctgaggtgaagaagcctgggtcctc ggtgaaggtctcctgcaaggcttctggtggcaccttcagcacctttgcga tcaactgggtgcgacaggcccctggacaagggcttgagtggatgggaggg gtcatccctgtctctggaacagaagactactcacagaagttccagggcag actctcacttaccgcggacgagtccacgggcacagcctacatggagctga gcagcctgagatctgacgacacggccgtgtattactgtgcgagagatcga agtggccgcgattgggactactttgactattggggccagggaaccctggt caccgtctcctca 601-13 heavy chain variable region
(protein sequence)
[SEQ ID NO: 172]
EVQLVQSGAEVKKPGSSVKVSCKASGGTFSTFAINWVRQAPGQGLEWMGG

VIPVSGTEDYSQKFQGRLSLTADESTGTAYMELSSLRSDDTAVYYCARDR

SGRDWDYFDYWGQGTLVTVSS 601-13 heavy CDRs: H1, H2, H3 (DNA sequence)
[SEQ ID NO: 173]
acctttgcgatcaac

[SEQ ID NO: 174]
ggggtcatccctgtctctggaacagaagactactcacagaagttccaggg
c

[SEQ ID NO: 175]
gatcgaagtggccgcgattgggactactttgactat 601-13 heavy CDRs: H1, H2, H3 (protein sequence)
[SEQ ID NO: 176]
TFAIN

[SEQ ID NO: 177]
GVIPVSGTEDYSQKFQG

[SEQ ID NO: 178]
DRSGRDWDYFDY

12) Antibody 601-109; Epitope Class IV; Subgroup 4a 601-109 Light chain variable region (DNA sequence)
[SEQ ID NO: 179]
caatctgccctgactcagcctgcctccgtgtctgggtctcctggacagtc gatcaccatctcctgcactggaaccagcagtgacgttggtggttataact atgtctcctggtaccaacagcacccaggcaaagcccccaaactcttgatt tatgaggtcagtcagcggccctcaggggtccctgatcgattctctggctc caagtctggcaacacggcctccctgaccgtctctggcctccaggctgaag atgaggctgactattattgcagctcatatgcaggcgacagggacgtcttc ggaactgggacccagctcaccgttttaagt 601-109 Light chain variable region (protein sequence)
[SEQ ID NO: 180]
QSALTQPASVSGSPGQSITISCTGTSSDVGGYNYVSWYQQHPGKAPKLLI

YEVSQRPSGVPDRFSGSKSGNTASLTVSGLQAEDEADYYCSSYAGDRDVF

GTGTQLTVLS 601-109 Light chain CDRs: L1, L2, L3 (DNA sequence)
[SEQ ID NO: 181]
actggaaccagcagtgacgttggtggttataactatgtctcc

[SEQ ID NO: 182]
gaggtcagtcagcggccctca

[SEQ ID NO: 183]
agctcatatgcaggcgacagggacgtc 601-109 Light chain CDRs: L1, L2, L3 (protein sequence)
[SEQ ID NO: 184]
TGTSSDVGGYNYVS

[SEQ ID NO: 185]
EVSQRPS

[SEQ ID NO: 186]
SSYAGDRDV 601-109 heavy chain variable region (DNA sequence)
[SEQ ID NO: 187]
cagatgcagctggtgcagtctggggggagacttggtccagcctggggggtc cctgagactctcctgtgcagcctctggattcaccttcagtagctatagca tgaactgggtccgccaggctccaggaaaggggctggagtgggtctcatcc attagtagtagtagtagttacatatactacgcagactcagtgaagggccg attcaccatctccagagacaacgccaagaactcactgtatctgcaaatga acagcctgagagccgaggacacggctgtgtattactgtgcgagaggtctc ggtggctggacccatgatgcttttgatatctggggccaagggaccacggt caccgtctcctca 601-109 heavy chain variable region (protein sequence)
[SEQ ID NO: 188]
QMQLVQSGGDLVQPGGSLRLSCAASGFTFSSYSMNWVRQAPGKGLEWVSS

ISSSSSYIYYADSVKGRFTISRDNAKNSLYLQMNSLRAEDTAVYYCARGL

GGWTHDAFDIWGQGTTVTVSS 601-109 heavy chain CDRs: H1, H2, H3 (DNA sequence)
[SEQ ID NO: 189]
agctatagcatgaac

[SEQ ID NO: 190]
tccattagtagtagtagtagttacatatactacgcagactcagtgaaggg
c

[SEQ ID NO: 191]
ggtctcggtggctggacccatgatgcttttgatatc 601-109 heavy chain CDRs: H1, H2, H3 (protein sequence)
[SEQ ID NO: 192]
SYSMN

[SEQ ID NO: 193]
SISSSSSYIYYADSVKG

[SEQ ID NO: 194]
GLGGWTHDAFDI

13) Antibody 601-137; Epitope Class IV; Subgroup 4b 601-137 Light chain variable region (DNA sequence)
[SEQ ID NO: 195]
cagtctgccctgactcagccaccctcagcgtctgggaccccgggcagag ggtcaccatctcttgttctggaagcagctccaacatcggaagtaattatg tatactggtaccagcagctcccaggaacggccccaaactcctcatctat aggaataatcagcggccctcaggggtccctgaccgattctctggctccaa gtctggcacctcagcctccctggccatcagtgggctccggtccgaggatg aggctgattattactgtgcagcatgggatgacagcctgagtgcctgggtg ttcggcggagggaccaagctgaccgtcctaggt 601-137 Light chain variable region (protein sequence)
[SEQ ID NO: 196]
QSALTQPPSASGTPGQRVTISCSGSSSNIGSNYVYWYQQLPGTAPKLLIY

RNNQRPSGVPDRFSGSKSGTSASLAISGLRSEDEADYYCAAWDDSLSAWV

FGGGTKLTVLG 601-137 Light chain CDRs: L1, L2, L3 (DNA sequence)
[SEQ ID NO: 197]
tctggaagcagctccaacatcggaagtaattatgtatac

[SEQ ID NO: 198]
aggaataatcagcggccctca

[SEQ ID NO: 199]
gcagcatgggatgacagcctgagtgcctgggtg 601-137 Light chain CDRs: L1, L2, L3 (protein sequence)
[SEQ ID NO: 200]
SGSSSNIGSNYVY

[SEQ ID NO: 201]
RNNQRPS

```
[SEQ ID NO: 202]
AAWDDSLSAWV 601-137 heavy chain variable region (DNA sequence)
                                      [SEQ ID NO: 203]
caggtacagctgcagcagtcagggggctgaggtgaagaagcctggggcctc agtgaaggtttcctgcaaggcatctggatacaccttctccagatactata tccactgggtgcgacaggcccctggtcaagggcttgagtggatgggaata atcaacactgatggtggcaccacaacctacgcacagaagtttcagggcag actcaccatgaccagggacacgtccacgagcaccgtctacatggaactga gcagcctgagatctgacgacacggccgtctattactgtgcgagagattat gggactatagatgctcgtcgttttgactactggggccagggaaccctggt caccgtctcctca 601-137 heavy chain variable region
(protein sequence)
                                      [SEQ ID NO: 204]
QVQLQQSGAEVKKPGASVKVSCKASGYTFSRYYIHWVRQAPGQGLEWMGI

INTDGGTTTYAQKFQGRLTMTRDTSTSTVYMELSSLRSDDTAVYYCARDY

GTIDARRFDYWGQGTLVTVSS 601-137 heavy chain CDRs: H1, H2, H3
(DNA sequence)
                                      [SEQ ID NO: 205]
agatactatatccac

[SEQ ID NO: 206]
ataatcaacactgatggtggcaccacaacctacgcacagaagtttcaggg
c

[SEQ ID NO: 207]
gattatgggactatagatgctcgtcgttttgactac 601-137 heavy chain CDRs: H1, H2, H3
(protein sequence)
                                      [SEQ ID NO: 208]
RYYIH

[SEQ ID NO: 209]
IINTDGGTTTYAQKFQG

[SEQ ID NO: 210]
DYGTIDARRFDY
```

14) Antibody 601-3; Epitope Class II; Subgroup 2a

```
601-3 Light chain variable region (DNA sequence)
                                      [SEQ ID NO: 211]
gaaatagtgatgacgcagtccccagccaccctgtctgtgtctccaggga aagagccaccctctcctgcagggccagtcagagtgttagcagcaacttag cctggtaccagcagaaacctggccaggctcccaggctcctcatctatggt gcatccaccagggccactggtatcccagccaggttcagtggcagtgggtc tgggacagagttcactctcaccatcagcagcctgcagtctgaagatttg cagtttattactgtcagcagtataataactggcctccgtacacttttggc caggggaccaaggtggagatcaaacgt 601-3 Light chain variable region
(protein sequence)
                                      [SEQ ID NO: 212]
EIVMTQSPATLSVSPGERATLSCRASQSVSSNLAWYQQKPGQAPRLLIYG

ASTRATGIPARFSGSGSGTEFTLTISSLQSEDFAVYYCQQYNNWPPYTFG

QGTKVEIKR 601-3 Light chain CDRs: L1, L2, L3 (DNA sequence)
                                      [SEQ ID NO: 213]
agggccagtcagagtgttagcagcaacttagcc

[SEQ ID NO: 214]
ggtgcatccaccagggccact

[SEQ ID NO: 215]
cagcagtataataactggcctccgtacact 601-3 Light chain CDRs: L1, L2, L3
(protein sequence)
                                      [SEQ ID NO: 216]
RASQSVSSNLA

[SEQ ID NO: 217]
GASTRAT

[SEQ ID NO: 218]
QQYNNWPPYT 601-3 heavy chain variable region (DNA sequence)
                                      [SEQ ID NO: 219]
caggtcaccttgaaggagtctgggcccacgctggtgaaacccacacagac cctcacgctgacgtgcaccttctctggcttctcactcaatagttttggag tggctgtgggctggttccgtcagcccccaggaaaggccctggagtggctt ggacttatttattgggatgatgacaggcgctacttcccatcgctggaggg caggctctccatcaccaaggacgcctccgataacaacgtggtcctgacaa tgatgaacgtggaccctgcggacacagccacatattattgtgcacggact tcccctatggttcagggaattgcaaactactacgctatggacgtctgggg ccaagggaccacggtcaccgtctcctca 601-3 heavy chain variable region
(protein sequence)
                                      [SEQ ID NO: 220]
QVTLKESGPTLVKPTQTLTLTCTFSGFSLNSFGVAVGWFRQPPGKALEWL

GLIYWDDDRRYFPSLEGRLSITKDASDNNVVLTMMNVDPADTATYYCART

SPMVQGIANYYAMDVWGQGTTVTVSS 601-3 heavy chain CDRs: H1, H2, H3 (DNA sequence)
                                      [SEQ ID NO: 221]
agttttggagtggctgtgggc

[SEQ ID NO: 222]
cttatttattgggatgatgacaggcgctacttcccatcgctggaggc

[SEQ ID NO: 223]
acttcccctatggttcagggaattgcaaactactacgctatggacgtc 601-3 heavy chain CDRs: H1, H2, H3
(protein sequence)
                                      [SEQ ID NO: 224]
SFGVAVG

[SEQ ID NO: 225]
LIYWDDDRRYFPSLEG

[SEQ ID NO: 226]
TSPMVQGIANYYAMDV
```

The inventors have also determined the amino acid and DNA sequences for the constant regions of one embodiment of the antibody, as follows.

Antibody light chain constant region
(protein sequence)
[SEQ ID NO: 227]
EIVMTQSPATLSVSPGERATLSCRASQSVSSNLAWYQQKPGQAPRLLIYG

ASTRATGIPARFSGSGSGTEFTLTISSLQSEDFAVYYCQQYNNWPPYTFG

QGTKVEIKR

Antibody heavy chain constant region
(protein sequence)
[SEQ ID NO: 228]
QVTLKESGPTLVKPTQTLTLTCTFSGFSLNSFGVAVGWFRQPPGKALEWL

GLIYWDDDRRYFPSLEGRLSITKDASDNNVVLTMMNVDPADTATYYCART

SPMVQGIANYYAMDVWGQGTTVTVSS

Antibody light chain constant region
(DNA sequence)
[SEQ ID NO: 229]
gaaatagtgatgacgcagtccccagccaccctgtctgtgtctccagggga aagagccaccctctcctgcagggccagtcagagtgttagcagcaacttag cctggtaccagcagaaacctggccaggctcccaggctcctcatctatggt gcatccaccagggccactggtatcccagccaggttcagtggcagtgggtc tgggacagagttcactctcaccatcagcagcctgcagtctgaagattttg cagtttattactgtcagcagtataataactggcctccgtacacttttggc caggggaccaaggtggagatcaaacgt Antibody heavy chain constant region
(DNA sequence)
[SEQ ID NO: 230]
caggtcaccttgaaggagtctggacccacgctggtgaaacccacacagac cctcacgctgacgtgcacctttctctggcttctcactcaatagttttggag tggctgtgggctggttccgtcagccccaggaaaggccctggagtggctt ggacttatttattgggatgatgacaggcgctacttcccatcgctggaggg caggctctccatcaccaaggacgcctccgataacaacgtggtcctgacaa tgatgaacgtggaccctgcggacacagccacatattattgtgcacggact tccctatggttcagggaattgcaaactactacgctatggacgtctgggg ccaagggaccacggtcaccgtctcctca Example 3—Engineering Full Length Monoclonal Antibodies Using the Selected scFv Fragments Although the phage display technology allows for the rapid selection and production of antigen-specific scFv fragments, the complete monoclonal antibodies (mAbs) including the Fc domains have a number of advantages over the scFv. Firstly, only full lengths antibodies exert immunological function such as complement-dependent cytotoxicity (CDC) and antibody-dependent cytotoxicity (ADCC) mediated via the Fc domain. Secondly, bivalent monoclonal antibodies offer stronger antigen-binding affinity than monomeric Fab Abs. Thirdly, plasma half-life and renal clearance will be different with the Fab and bivalent mAb. Fourthly, bivalent mAb may be internalized at different rates from scFv, altering immune function or carrier function. Alpha emitters do not need to be internalized to kill the targets, but many drugs and toxins will benefit from internalization of the immune complex. Therefore, according to the affinity ranking result obtained through competitive ELISA (see Table 1), three clones with high binding affinity were then selected and reconstructed into full-length human IgG1 recombinant antibodies and characterized further.

Figure 16:
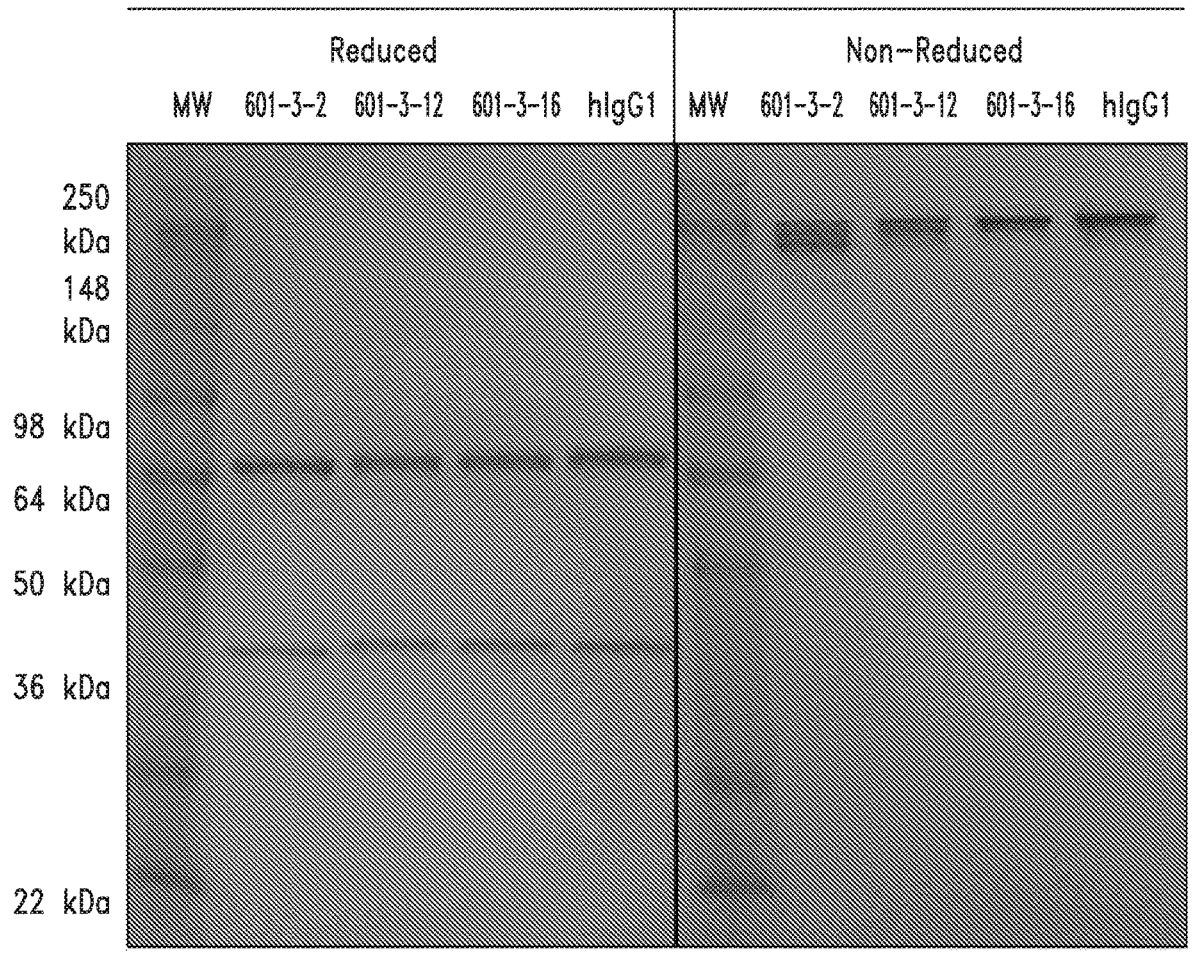
FIG. 16 illustrates SDS-PAGE of purified human anti-ROR1 full-length IgG1 antibodies.

To produce recombinant human monoclonal IgG in Chinese hamster ovary (CHO) cells, the inventors engineered full length IgG1 mAbs based on the method by Tomomatsu et al., 2009, Biosci Biotechnol Biochem 73(7): 1465-1469. Antibody variable regions were sub-cloned into mammalian expression vectors (FIGS. 14a and 14b), with matching Kappa light chain constant sequences and IgG1 subclass Fc (FIG. 15). Purified full-length IgG1 antibodies showed expected molecular weights under both reducing and non-reducing conditions (FIG. 16). Kinetic binding analysis confirmed specific binding of the full length IgG1 antibodies to hROR1-ECD, with a Kd in picomolar range (FIG. 17).

Example 4—Characterization of the ROR1-Specific Full Length IgG1 Monoclonal Antibodies 1. Epitope Mapping:

To better understand the structural basis of the ROR1-specific antibody as a drug candidate, a standard epitope mapping was performed by ELISA against a ROR1 peptide array. The peptide array covered the whole length of the ROR1 protein extracellular domain with 96 overlapping peptides (15 amino acids each with a 5 amino acid overlap). The peptides were biotinylated at the N-terminal to immobilize them onto streptavidin ELISA plates. A spacer (SGSG) was used to provide flexibility. ELISA assays were performed with the ROR1 antibodies as the primary antibody and an anti-human Fc AP-conjugated antibody was used for detection.

Figures 18A, 18B:
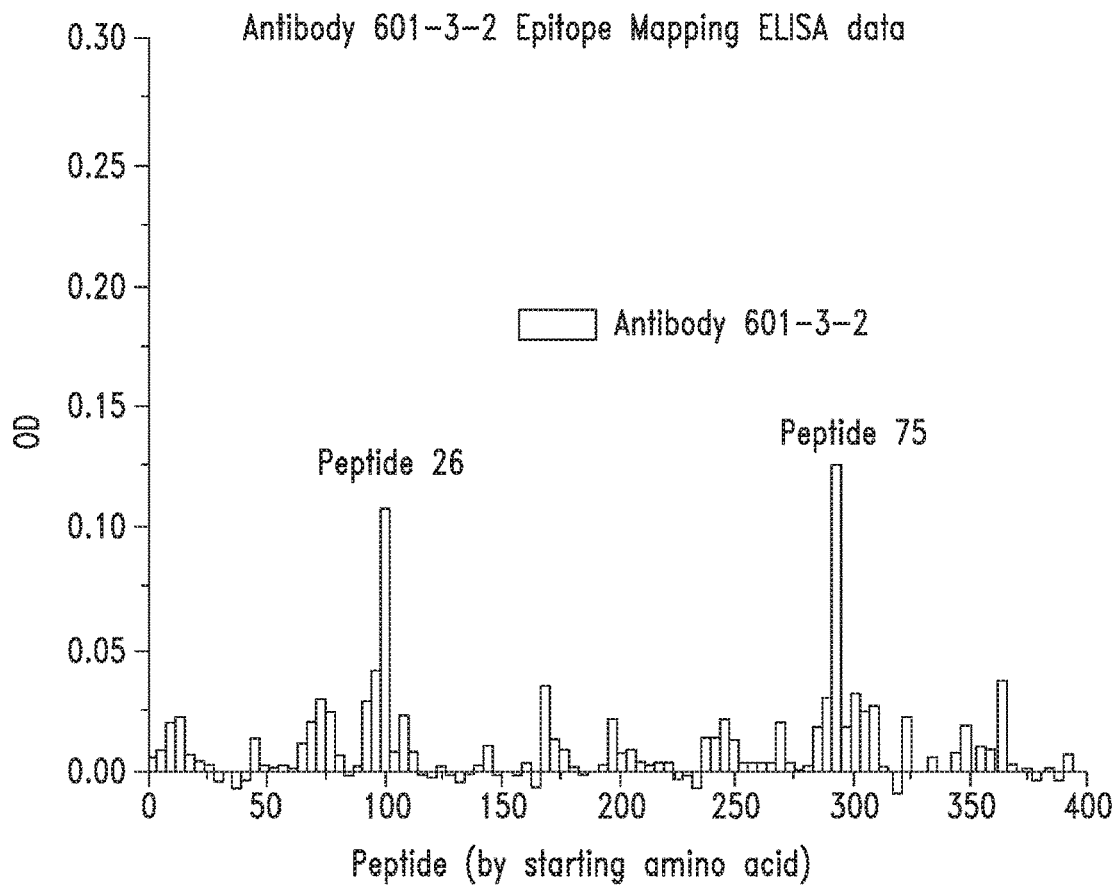
FIGS. 18A and 18B represent antibody 601-3-2 epitope mapping ELISA data. The highlighted regions illustrate the 601-3-2 epitope in human ROR1 protein sequence.
Figures 19A, 19B:
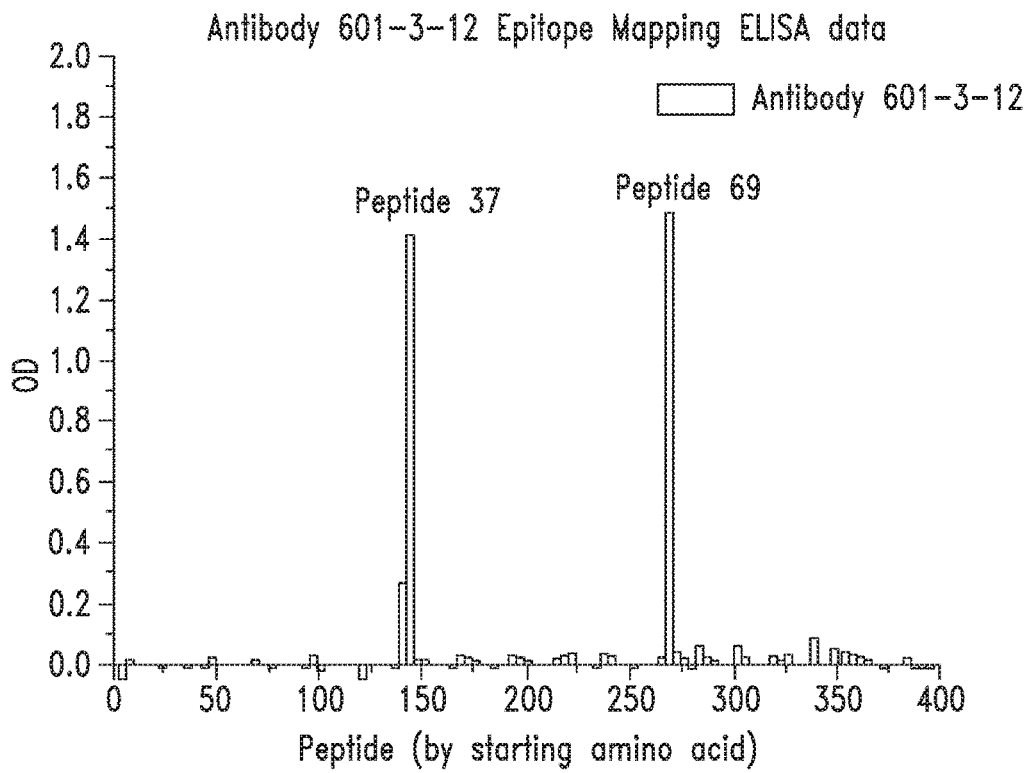
FIGS. 19A and 19B represent antibody 601-3-12 epitope mapping ELISA data. The highlighted regions illustrate the 601-3-12 epitope in human ROR1 protein sequence.
Figures 20A, 20B:
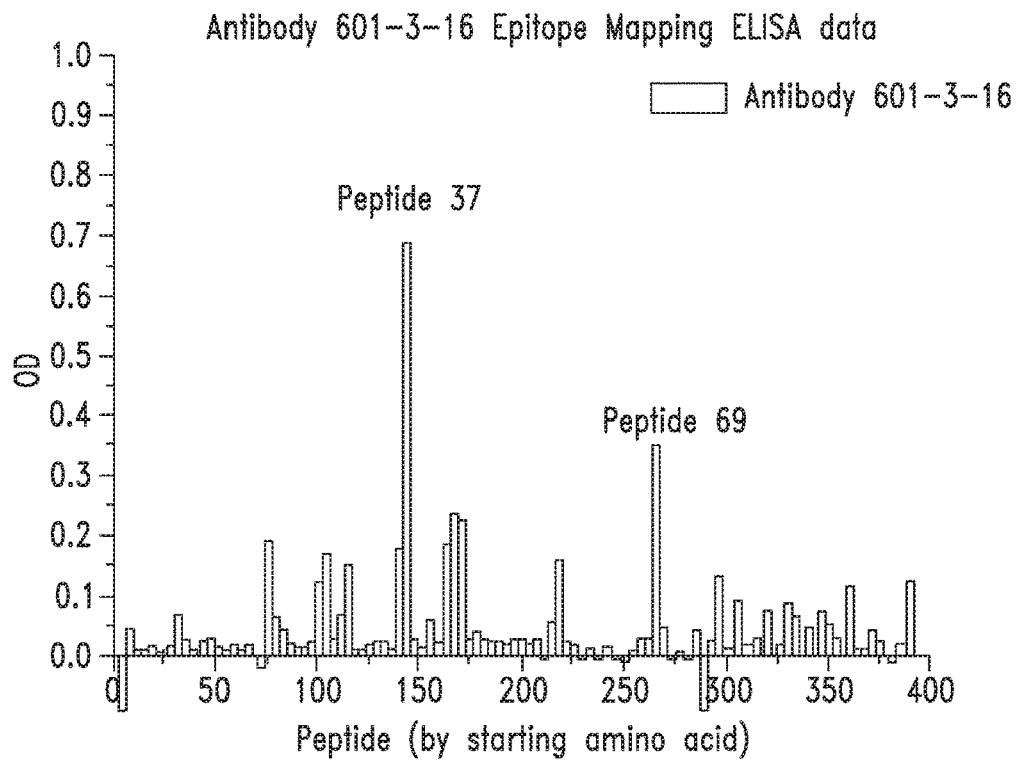
FIGS. 20A and 20B represent antibody 601-3-16 epitope mapping ELISA data. The highlighted regions illustrate the 601-3-16 epitope in human ROR1 protein sequence.

As shown in FIGS. 18, 19 and 20, antibody 601-3-12 (FIG. 19) and 601-3-16 (FIG. 20) share similar binding epitopes, while antibody 601-3-2 (FIG. 18) has distinct binding epitopes different from 601-3-12 and 601-3-16.

Figure 21A:
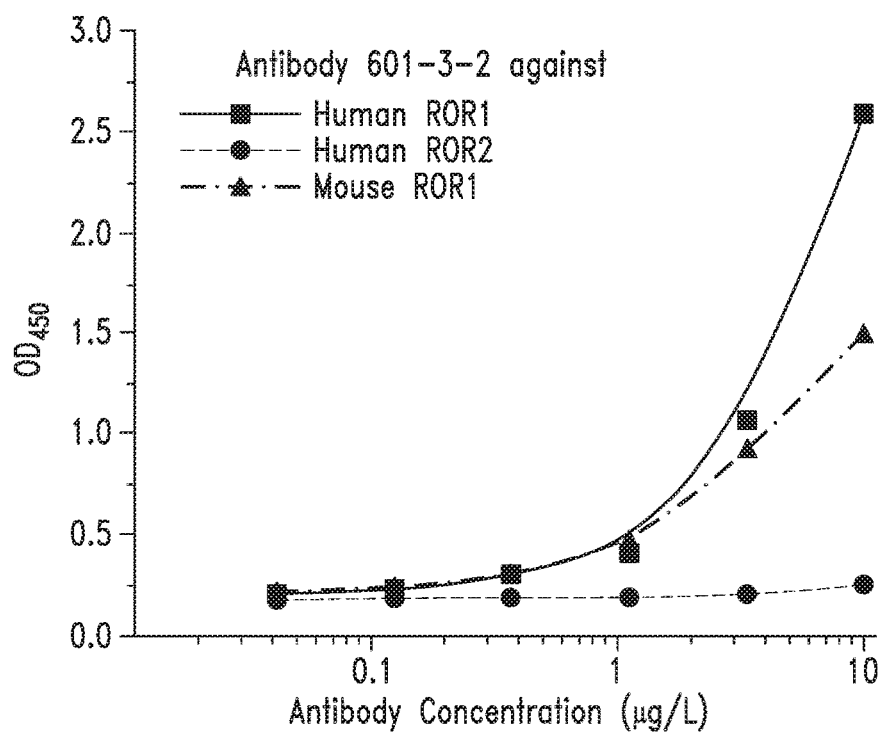
FIG. 21a-21c are graphs showing ELISA results of anti-ROR1 full-length IgG1 antibodies against human ROR1, human ROR2, and mouse ROR1.
Figure 21B:
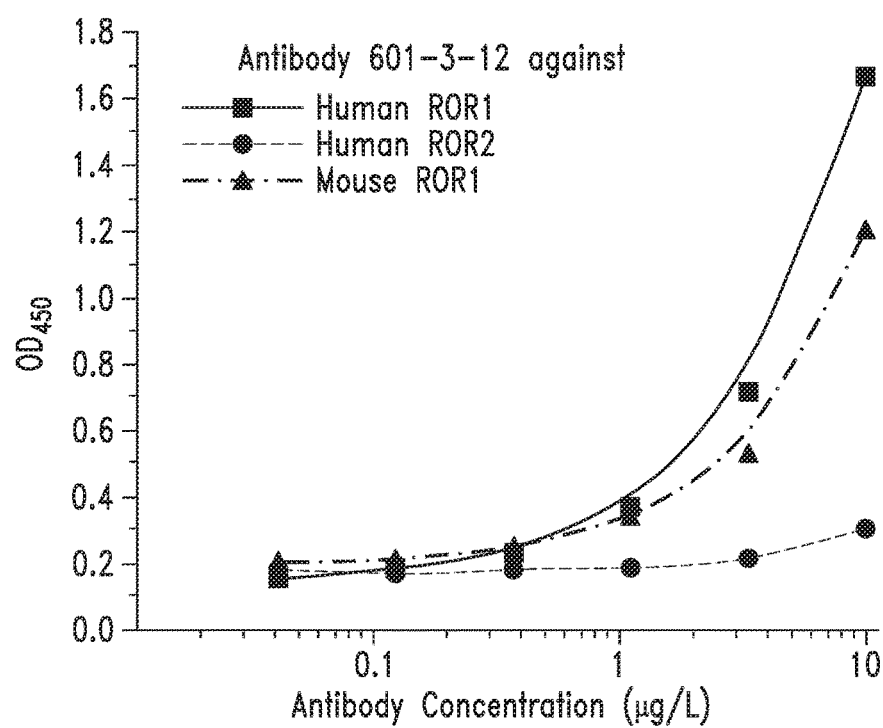
Figure 21C:
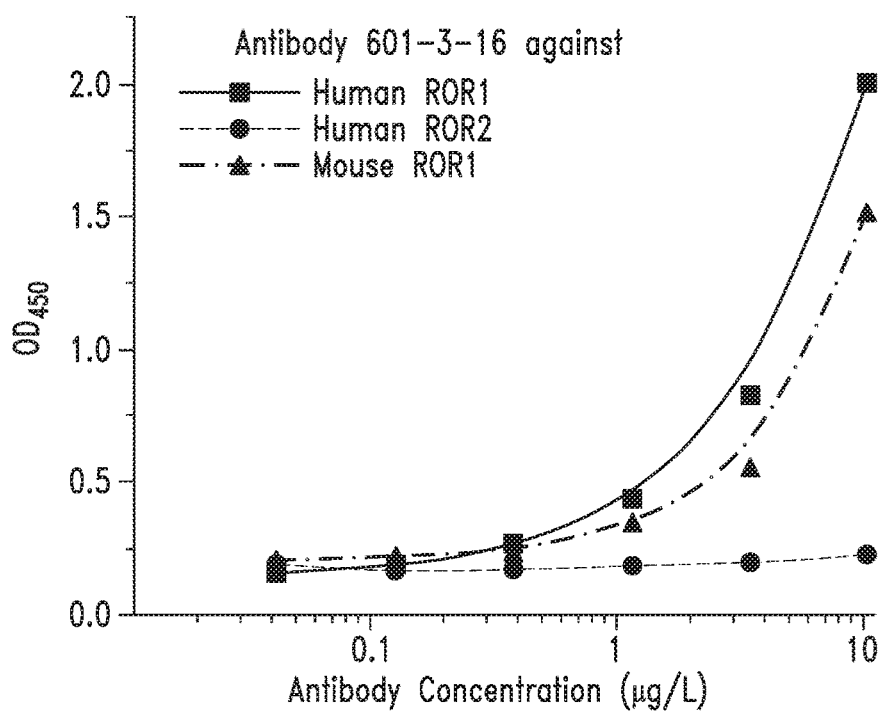

2. Binding Property:

Binding specificity was tested again using the three purified full length IgG1 antibodies. Protein ELISA confirmed that they all recognize both human and mouse ROR1 ECDs, but not human ROR2 ECD (FIG. 21).

Figure 22A:
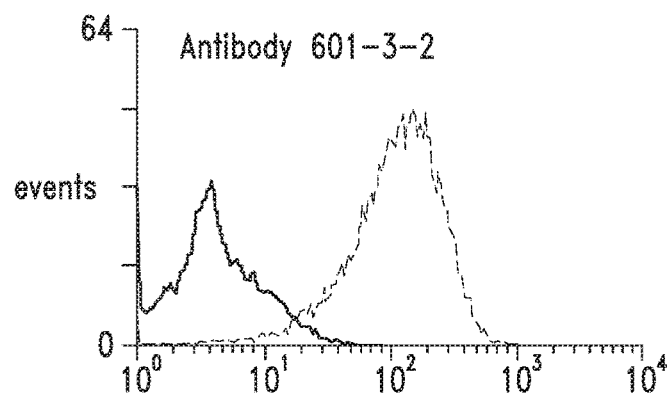
FIG. 22a-22c are graphs showing binding analysis of anti-ROR1 full-length IgG1 antibodies by FACS.
Figure 22B:
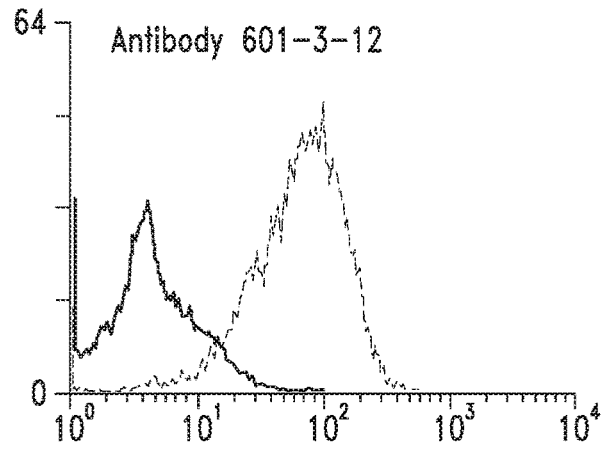
Figure 22C:
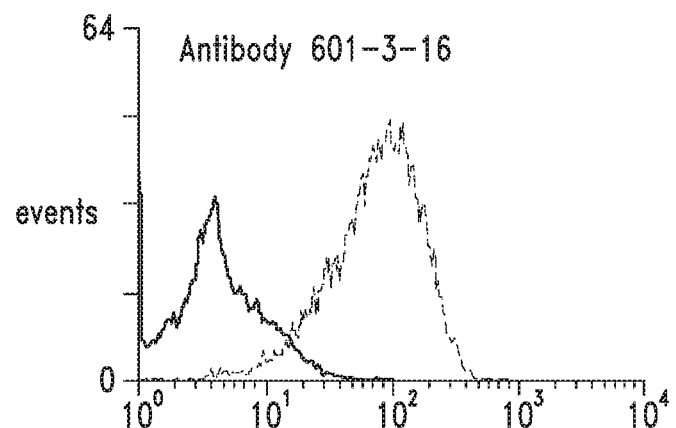

Binding of the hIgG1 mAbs to the cell surface ROR1 was determined by FACS analysis using different cancer cell lines positive for ROR1 expression, including MDA-MB-231, A549, H1299 and Jeko-1. All three antibodies recognize ROR1 expressed on the surface of cancer cells. An example of FACS using MDA-MB-231 cells is shown in FIG. 22. The antibodies at 0.1 ug/ml, 1 ug/ml, 10 ug/ml and 100 ug/ml were incubated with MDA-MB-231 cells, then with FITC-labeled secondary antibody after washing. The binding was measured by FACS and expressed as mean fluorescence intensity (MFI). Cells incubated with secondary antibody only were used as negative control. FIG. 22 shows the results of 10 ug/ml ROR1-specific mAbs.

3. Immune Activity:

The inventors then evaluated in vitro immune effector mechanisms of the ROR1-specific IgG1 mAbs, such as CDC and ADCC:

A) Complement-Dependent Cytotoxicity (CDC) Activity

An important mechanism by which mAbs kill cells is that antibody bound to target cell surface fixes complement, which results in initiation of the complement cascade and assembly of the membrane attack complex (MAC) that ultimately results in lysis of the target cell. The inventors investigated whether the ROR1-specific IgG mAbs were capable of attracting C1q binding, the first step of initiating complement complex formation. Various concentrations of ROR1 antibodies were coated onto plate, and 2 ug/mL of the C1q protein was used as a probe. Horse Radish Protein (HRP)-conjugated anti-C1q antibody was used to report the binding signal. As shown in FIG. 23, all three antibodies were able to bind to C1q in a dose-dependent manner, proving that the antibodies can mediate complement-dependent cytotoxicity (CDC) of the target cells.

B) Antibody-Dependent Cellular Cytotoxicity (ADCC) Against ROR1 Positive Cancer Cell Lines Antibody-dependent cellular cytotoxicity is one of the important effector mechanisms of mAb therapy. The antibody can bridge tumor cells expressing the target molecules and cytotoxic cells such as NK cells, and mediate NK-directed target cell killing. The ADCC assay was performed as follows. 100 ul of target cell suspension (MDA-MB-231 or Jeko-1) were pre-incubated with 50 ul of the testing mAbs at the various concentrations in 96-well plate at 37° C. for half hour. 50 ul of freshly isolated human peripheral blood mononuclear cells (PBMC) were then added at the effector/target cell ratio of 25:1. After incubated for 16 hours, the plate was spun down and 50 ul of cell-free supernatants were transferred to a new plate. The released LDH from killed cancer cells was measured by CYTOTOX96® Non-radioactive Cytotoxicity Assay from PROMEGA®. The cell lysis was calculated by the formula (E-S)/(M-S) (E: experimental release, S: spontaneous release, M: maximal release). Non-specific antibody was used as a negative control. The inventors found that all three antibodies were capable of mediating killing of ROR1-expressing tumor cells in the ADCC assay. FIG. 24 shows the results of ADCC against MDA-MB-231 cells by ROR1-specific mAbs.

4. Blockade of Wnt5a Ligand Binding:

Furthermore, the three mAbs were tested in three biological assays to evaluate their functional activities:

(i) Blocking of Wnt5a binding to ROR1; and
(ii) Blocking of Wnt-5a induced ROR1 phosphorylation A FORTEBIO® assay was designed to test the ability of the three antibody candidates to block Wnt-5a binding to ROR1. ROR1/Wnt5A interaction was measured using FORTEBIO OCTET®. Three anti-ROR1 mAbs and one hIgG1 negative control antibody M901 were then added, respectively, to measure the reduction of binding (measured a Pseudo ka (1/M·s). Compared with the negative control IgG1 antibody, all the three antibodies were able to block Wnt-5a binding to ROR1 to various extents (FIG. 25).

Upon binding to ROR1, Wnt5a triggers ROR1 phosphorylation and downstream signaling cascade activation. ROR1 phosphorylation leads to the slower migration of Ror1 on SDS-PAGE electrophoresis. To determine if their lead candidate antibodies against ROR1 could functionally block Wnt5a binding to ROR1, they made use of this assay as the surrogate experiment to test this possibility. They incubated serum-starved ROR1-expressing cell line Jeko-1 with 300 nM Wnt5a treated with or without 10 lag of the antibodies for 2 hours. The cells were lysed, separated by SDS-PAGE electrophoresis, and blotted with antibody against ROR1. Treating the cells with Wnt5a alone caused slower migration of ROR1 when compared to the non-phosphorylation.

However, the effect of Wnt5a on ROR1 migration was completely abrogated by two out of three lead candidates (clone 3-12 and clone 3-16) when both Wnt5a and the antibodies were co-incubated with the cells. The results demonstrate that these antibodies can effectively prevent Wnt5a from binding to ROR1, and that this blockade of the ligand binding abolishes ROR1 activation.

5. Inhibition of Cancer Cell Proliferation

Cell proliferation assays were performed to determine if the antibodies inhibit cancer cell proliferation. Target cells (MDA-MB-231 or SKBR3 cells) were plated into 96-well plate at $5 \times 10^3$ cells per well. 10 ug/ml ROR1-specific mAbs were added to the cells and incubated at 37° C. in a 5% CO2 incubator. After 72-h treatment, cells were assayed for proliferation using CELLTITER 96® AQueous One Solution Cell Proliferation Assay (PROMEGA®) according to the manufacturer's instructions. Untreated cell viability was set as 100% and data was shown as percentage compared to untreated cells. A non-specific antibody (901) was used as a negative control. Each data point represents mean±S.D. (n=3).

Example 5—Exploration of Further Improvement of ROR1 Antibody Drugability

1. Conjugation to Cytotoxic Moieties
1) Antibody Drug Conjugate

Antibody-drug conjugate (ADC) is used for an antibody to deliver a potent cytotoxic drug selectively to a target cell. Such methods, when applied to a tumor antigen target, can enhance the antitumor activity of antibodies and improve the tumor-to-normal tissue selectivity of chemotherapy. One key parameter for ADC development is that the antibody can be endocytosed once bound to target antigen, and therefore, deliver the conjugated drug into target cancer cells.

To explore the possibility of developing ADC strategy with the ROR1 antibodies of the invention, the inventors evaluated endocytosis of the antibodies induced by ROR1-antibody binding. In the assay, Jeko cells were surface-labeled for 60 min on ice with FITC-labeled ROR1 antibodies (10 ug/ml) in PBS with 5% FBS, and then washed three times with cold PBS and incubated at 37° C. in RPMI with 5% FBS for 3 hrs to internalize surface fluorescence. Cells were rapidly chilled, washed and incubated with (stripped) or without (non-stripped) 500 ul stripping buffer (150 mM NaCT+HCL, pH 2.5) for 5 min at RT, spin down, wash twice with PBS and then fixed with cold 1% PFA/PBS and immediately analyzed by flow cytometry. Internalized fluorescence was calculated from stripped and non-stripped sample data after correcting from incomplete surface stripping.

As shown in FIG. 26, the inventors found that ROR1 antibodies were slowly internalized.

2) Conjugation to Alpha Emitting Radionucleotides

Alpha particles are high energy, high linear energy transfer helium nuclei capable of strong, yet selective single cell cytotoxicity. Targetable nanogenerators are $^{225}$Ac-labeled monoclonal antibodies that have been demonstrated to be extremely potent and specific in killing leukemia, lymphoma, and other solid tumors (McDevitt et al., 2001, Science 294 (5546): 1537-1540). The inventors decided to conjugate the ROR1 antibodies to alpha particle emitters with bi-functional chelates. Given their exquisite specificity for the ROR1, full-length mAb and ScFv/Fab can be excellent vehicles for delivering potent anti-tumor reagents. Their small size, rapid clearance from blood and tumor penetration properties should make ScFv/Fab an ideal format of choice for tumor-targeted alpha emitters. The inventors conjugated all forms of mAbs (full length IgG, scFV and Fab) to alpha particle emitters using the two-step labeling method as described in Borchardt et al., 2003, Cancer Res 63: 5-84-5090.

3) Test the In Vitro Cytotoxicity of the Conjugates Against ROR1 Positive Cancer Cell Lines A panel of ROR1 positive cell lines was treated with or without conjugated ROR1 IgG antibodies ranging from 0.01-10 ug/ml and negative control antibody conjugates for 24-96 hours. Cell proliferation was determined by 3H-thymidine incorporation, and viability by ATPlite assay (Griffiths, et al., 2011, Methods Mol Biol 731: 451-65 Sun, et al., 2005, Oncogene 24: 7381-88).

4) Test the In Vivo Anti-Tumor Activity of the Conjugates in a NOD/SCID Mouse Bearing Cancer Cells Expressing ROR1.

A) Therapeutic Efficacy of the Constructs on NOD/SCID Xenograft Model

The NOD/SCID mice are characterized by a functional deficit in NK cells, an absence of circulating complement and defects in the differentiation and function of APCs (antigen-presenting cells). Therefore, the NOD/SCID model is suitable for xenografts of human tumor cell lines and to test the direct effects of mAb against tumor cells expressing targeted molecules. A similar protocol was used to establish the mouse model and to perform therapeutic studies to determine the therapeutic efficacy of the conjugated mAbs (Francisco, et al., 2003, Blood 102:1458-1465).

B) Bio-Distribution of the Conjugates

This was measured by labeling both forms of mAbs with $^{111}$In, and counting the radioactivity from various tissues from mice at different time points, after injection (Singh Jaggi et al., 2007, Plos One 2(3): e267). Based on the results obtained from the normal mice, the tumor uptake of the constructs was determined using the NOD/SCID xenograft of human leukemia, by gamma imaging as described previously.

5) Engineer Novel Forms of the Antibodies to Enhance their Cytotoxic Abilities

1. Bispecific Antibody

Bispecific antibodies were constructed to recognize both ROR1 and CD3 on immune T cells as described (Gunasekaran et al., 2010, J. Biol. Chem. 285: 19637-19646; Rossi E A et al., 2006, Proc Natl Aca Sci USA 103:6841-6) with a human IgG1 Fc. Bispecific antibodies were expected to recruit and target cytotoxic T cells to ROR1 positive cancer cells, while maintaining Fc effector functions and long half-life in vivo. Three mechanisms are involved in the specific killing of cancer cells mediated by bispecific antibodies: (i) killing by activated T cells; (ii) ADCC activity; (iii) CDC activity. Other formats of bispecific antibodies can be constructed, such tandem scFv molecules (taFv), diabodies (Db), or single chain diabodies (scDb), and fusion protein with human serum albumin (Asano et al., J. Biol. Chem. 286: 1812-1818; Loffler et al., Blood 95(6): 2098-2103; Weiner et al., J. Immunology 152(5): 2385-2392; Muller et al., J. Biol. Chem. 282: 12650-12660), but are devoid of Fc effector functions with distinct pharmacokinetic profiles.

2. ADCC Enhancement

ROR1 target specific ADCC activity was enhanced by expressing antibodies recombinantly in glycol-engineered CHO cells as described in PCT/US2010/0081195. The modified oligosaccharide N-glycan on Asn297 alters effector functions as follows: higher affinity binding to CD16/FcRIIIa for improved ADCC activity mediated by human Natural Killer cells; 2) reduced binding affinity to CD32b/FcRIIb, an inhibitory receptor expressed in multiple types of immune cells (except NK cells), for improved ADCC activity mediated by effector cells such as neutrophils and antigen presentation by macrophage and DC cells.

Example 6—Anti-ROR1 Antibody Binding Affinity

The binding affinities of ROR1 extracellular domain dimer and monomer for anti-ROR1 antibodies were determined by surface plasmon resonance (SPR). ROR1 extracellular domain Fc-fusion, "dimer," and ROR1 extracellular domain Fc fusion:Fc heterodimer, "monomer," are the dimer and monomeric forms of ROR1 used for affinity analysis, respectively. Briefly, ROR1 dimer and monomer were directly immobilized to a CM4 chip using an amine coupling kit and 100 mM ethylenediamine in 100 mM Sodium Borate buffer, pH 8.0 as the blocking reagent. Approximately 100-150 RU of ROR1 dimer and monomer were immobilized on separate flow cells and an un-derivatized flow cell was used as a reference control. Each anti-ROR1 antibody was diluted in HBS-P+ running buffer and injected at 5 or 6 concentrations (0 nM, 1.23 nM, 3.7 nM, 11.1 nM, 33.3 nM, and 100 nM) at 30 µl/min for 120 seconds. Dissociation was followed for 180 seconds. The association constant, dissociation constant, and affinity of each anti-ROR1 antibody was calculated using the BIACORE™ T200 Evaluation Software 1:1 binding model.

Figure 27:
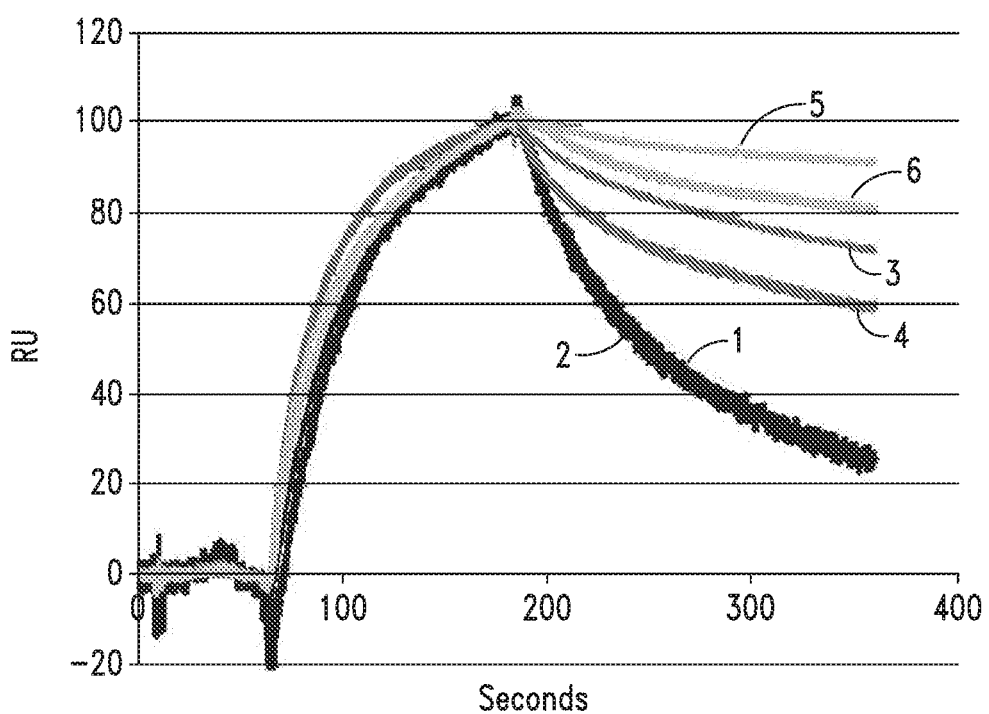
FIG. 27 shows normalized sensosgrams of anti-ROR1 antibodies binding to ROR1 extracellular domain monomer and dimer forms.

The binding studies demonstrated that 19 anti-ROR1 antibodies bind to both ROR1 monomer and dimer with similar affinity when fit with the 1:1 binding model, as shown in Table 5. While the interaction between anti-ROR1 and ROR1-Fc fusion dimer could be analyzed with the bivalent analyte, analysis was performed using the 1:1 binding model as binding curves for both ROR1 monomer and dimer are similar. Apparent affinity for anti-ROR1 antibody binding to ROR1 dimer is shown. FIG. 27 shows normalized sensorgrams of antibodies binding to both ROR1 monomer and dimer. Sensorgrams were normalized to 100 RU using the "binding stability point" at the end of the association phase but before the dissociation phase.

TABLE 5

ROR1 extracellular domain monomer and dimer binding kinetics and affinity to anti-ROR1 antibodies by SPR

| Anti-ROR1 Ab | ROR1 analyte | ka (1/Ms) | kd (1/s) | KD (nM)* |
|---|---|---|---|---|
| 601-13 | dimer | 1.6E+06 | 8.7E−04 | 0.5 |
|  | monomer | 1.8E+06 | 1.4E−03 | 0.8 |
| 601-14 | dimer | 2.7E+06 | 6.6E−04 | 0.2 |
|  | monomer | 3.2E+06 | 1.3E−03 | 0.4 |
| 601-17 | dimer | 1.8E+06 | 9.0E−04 | 0.5 |
|  | monomer | 2.3E+06 | 1.0E−03 | 0.4 |
| 601-18 | dimer | 4.9E+06 | 1.5E−03 | 0.3 |
|  | monomer | 6.0E+06 | 2.2E−03 | 0.4 |
| 601-100 | dimer | 4.4E+05 | 1.7E−03 | 3.9 |
|  | monomer | 3.5E+05 | 2.8E−03 | 8.2 |
| 601-103 | dimer | 1.7E+05 | 3.5E−03 | 20.7 |
|  | monomer | 1.2E+05 | 5.0E−03 | 40.2 |
| 601-112 | dimer | 3.4E+05 | 3.2E−04 | 1.0 |
|  | monomer | 2.7E+05 | 1.2E−03 | 4.6 |
| 601-119 | dimer | 4.4E+05 | 7.9E−02 | 178.0 |
|  | monomer | 2.3E+05 | 9.5E−02 | 407.3 |
| 601-128A | dimer | 4.1E+05 | 2.1E−03 | 5.0 |
|  | monomer | 3.4E+05 | 2.1E−03 | 6.3 |
| 601-128B | dimer | 4.3E+06 | 2.7E−03 | 0.6 |
|  | monomer | 3.6E+06 | 2.9E−03 | 0.8 |
| 601-130 | dimer | 5.2E+05 | 1.2E−03 | 2.2 |
|  | monomer | 4.5E+05 | 1.8E−03 | 4.1 |
| 601-134 | dimer | 1.8E+05 | 1.2E−03 | 6.7 |
|  | monomer | 3.2E+05 | 4.8E−03 | 14.9 |
| 601-14 | dimer | 2.4E+06 | 1.5E−03 | 0.6 |
|  | monomer | 2.4E+06 | 2.1E−03 | 0.8 |
| 601-141 | dimer | 1.8E+06 | 2.2E−02 | 11.9 |
|  | monomer | 1.2E+06 | 2.6E−02 | 20.6 |

TABLE 5-continued

ROR1 extracellular domain monomer and dimer binding
kinetics and affinity to anti-ROR1 antibodies by SPR

| Anti-ROR1 Ab | ROR1 analyte | ka (1/Ms) | kd (1/s) | KD (nM)* |
|---|---|---|---|---|
| 601-147 | dimer | 6.8E+05 | 6.3E−04 | 0.9 |
|  | monomer | 5.9E+05 | 1.7E−03 | 2.8 |
| 601-149 | dimer | 1.9E+06 | 2.3E−04 | 0.1 |
|  | monomer | 1.6E+06 | 6.9E−04 | 0.4 |
| 601-28 | dimer | 3.4E+05 | 9.7E−03 | 28.5 |
|  | monomer | 3.2E+05 | 1.2E−02 | 36.4 |
| 601-37 | dimer | 1.0E+06 | 1.8E−03 | 1.7 |
|  | monomer | 9.2E+05 | 2.7E−03 | 3.0 |
| 601-4 | dimer | 3.6E+06 | 7.6E−04 | 0.2 |
|  | monomer | 4.6E+06 | 1.6E−03 | 0.3 |
| 601-5 | dimer | 2.5E+06 | 2.9E−04 | 0.1 |
|  | monomer | 2.3E+06 | 8.4E−04 | 0.4 |
| 601-50 | dimer | 9.4E+05 | 1.1E−03 | 1.1 |
|  | monomer | 1.1E+06 | 1.6E−03 | 1.5 |
| 601-65 | dimer | 1.1E+06 | 7.2E−03 | 6.4 |
|  | monomer | 1.7E+06 | 1.1E−02 | 6.6 |
| 601-66 | dimer | 3.1E+06 | 5.1E−03 | 1.7 |
|  | monomer | 2.5E+06 | 5.9E−03 | 2.4 |
| 601-70 | dimer | 5.1E+06 | 1.8E−02 | 3.5 |
|  | monomer | 3.6E+06 | 1.9E−02 | 5.4 |
| 601-87 | dimer | 7.6E+05 | 5.8E−04 | 0.8 |
|  | monomer | 6.0E+05 | 1.3E−03 | 2.2 |
| 601-9 | dimer | 1.4E+06 | 2.1E−02 | 15.3 |
|  | monomer | 6.3E+05 | 1.7E−02 | 27.6 |

*Apparent affinity is reported for ROR1 dimer binding to antibody

Example 7—Anti-ROR1 Antibody Binding to CLL Cells

The ability of the antibodies to bind to ROR1 on the surface of primary chronic lymphocytic leukemia (CLL) cells was determined by flow cytometry. ROR1 is not expressed on normal, healthy adult blood cells, but is found on malignant cells of virtually all cases of CLL and on different types of solid tumors. Thirty-seven of the antibodies tested showed detectable binding to CLL cells by flow cytometry.

Methods
Cell Surface Staining of CLL Cells by the CD5, CD19, and Anti-ROR1 Antibodies Anti-ROR1 and control IgG1 antibodies were labeled using a ZENON® ALEXA FLUOR® 647 human IgG labeling kit (LIFE TECHNOLOGIES™) according to the manufacturer's directions. Frozen peripheral blood mononuclear cells (PBMC) from CLL patients (ALLCELLS® LLC) were thawed and washed in FACS buffer (PBS, 2% heat inactivated FBS, 0.1% NaN3). CLL cells were counted and resuspended at 4×10E6 cell/mL in FACS buffer. 2×10E5 cells per test were then incubated in 100 pt FACS buffer with phycoerythrin (PE)-labeled anti-CD5, flu601-5cein isothiocyanate (FITC)-labeled anti-CD19 (BD BIOSCIENCES™) and ZENON® ALEXA FLUOR® 647-labelled anti-ROR1 or control human IgG1 ET901 (Eureka Therapeutics) for 30 minutes on ice. Following incubation, the cells were washed twice in FACS buffer and fixed in 2% paraformaldehyde in PBS (final concentration). Cells were run on a BD LSRII flow cytometer (BD BIOSCIENCES™) and analyzed using FLOWJO™ software (TREESTAR™).

Figure 28:
FIG. 28 shows binding of anti-ROR1 antibodies to CLL cells from patient 13 at four different concentrations (10, 2.5, 0.63, 0.16 µg/mL from left to right for each antibody), with signal correction by subtracting MFI obtained for the same concentration of isotype control antibody.
Figure 29:
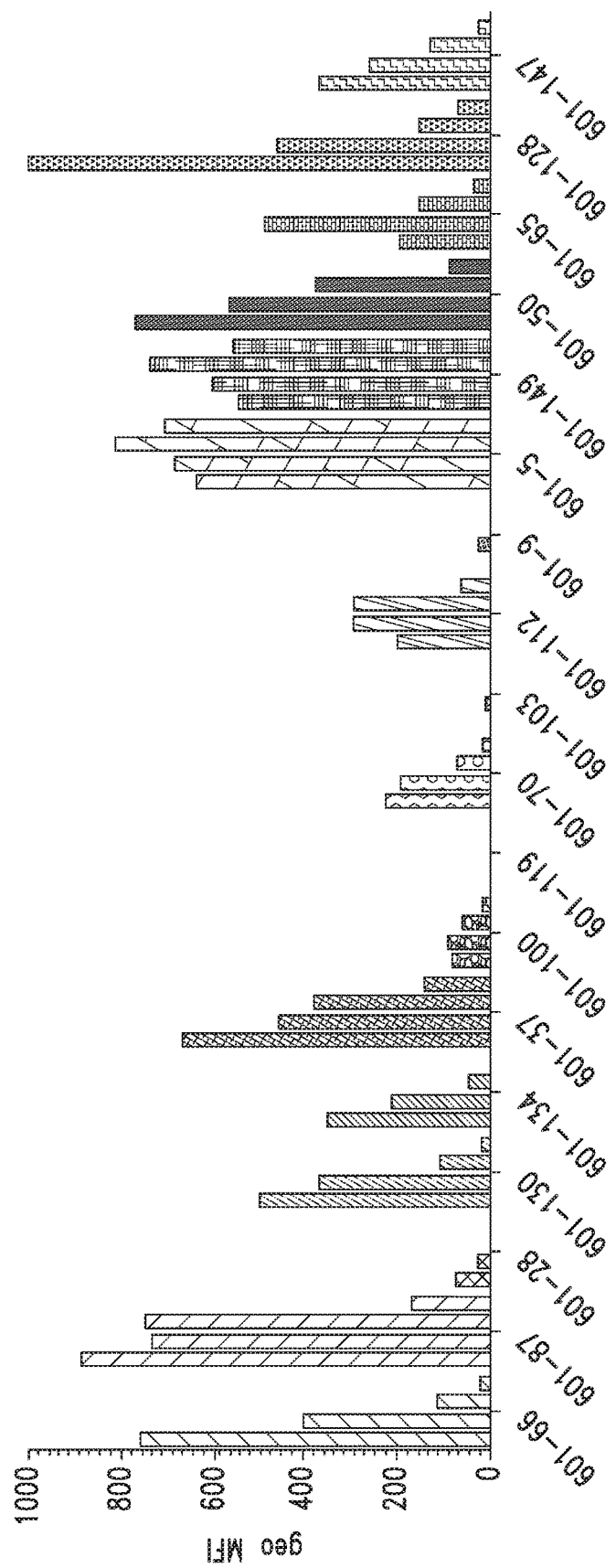
FIG. 29 shows binding of anti-ROR1 antibodies to CLL cells from patient 13 at four different concentrations (10, 2.5, 0.63, 0.16 µg/mL from left to right for each antibody) with signal correction by subtracting the MFI obtained for the same concentration of isotype control antibody.

CLL cells identified as CD5 and CD19 double positive were assessed for anti-ROR1 or control Ig staining. FIGS. 28 and 29 show the geometric mean fluorescence intensity (gMFI) of various concentrations of the anti-ROR1 antibody on CLL cells.

Summary

The invention is directed to a human ROR1-specific antibody. Advantageously, the antibody is human in origin, and is therefore likely to minimize any immune response upon administration to a human patient in contrast to using antibodies comprising non-human elements. In addition, the antibody or functional fragment thereof, amino acid sequences and nucleotide sequences encoding the antibody or functional fragment thereof, and conjugates described herein, may be effectively used for the manufacture of compositions and diagnostics, and uses thereof, for example, in treating cancer.

TABLE 6

Certain Light Chain Variable Region Sequences

| SEQ ID NO: | kappa/ lambda | Antibody name | Epitope class | Sequence |
|---|---|---|---|---|
| 4 | kappa | Antibody 601-1 | Epitope Class I | AIRMTQSPSS LSASVGDRVT ITCQASQDIS NYLNWYQQKP GKAPKLLIYD ASNLETGVPS RFSGSGSGTD FTFTISSLQP EDIATYYCQQ YDNLPLTFGG GTKVEIKR |
| 68 | kappa | Antibody 601-2(3-12) | Epitope Class II | EIVLTQSPDT LSLSPGERAT LSCRASQSVS SNLAWYQQKP GQAPRLLIYG ASTRATGIPA RFSGSGSGTE FTLTISSLQS EDFAVYYCQQ YNNWPPYTFG QGTKVEIKR |
| 212 | kappa | Antibody 601-3(3-16) | Epitope Class II | EIVMTQSPAT LSVSPGERAT LSCRASQSVS SNLAWYQQKP GQAPRLLIYG ASTRATGIPA RFSGSGSGTE FTLTISSLQS EDFAVYYCQQ YNNWPPYTFG QGTKVEIKR |
| 52 | lambda | Antibody 601-4 | Epitope Class I | QSVLTQPPSA SGAPGQRVTI SCSGGISNVG TNGVNWYQHL PGTAPKLLVD AMNQRPSGVP DRFSGSRSGT SGSLAITGLR SEDEADYYCA TWDDSLSGVL FGGGTKLTVL G |
| 20 | kappa | Antibody 601-5(3-2) | Epitope Class I | DIQMTQSPSS LSASVGDRVT ITCQASQDIS NYLNWYQQKP GKAPKLLIYD ASNLETGVPS RFSGSGSGTD FTFTISSLQP EDIATYYCQQ YDNLPLTFGG GTKLEIKR |

TABLE 6-continued

Certain Light Chain Variable Region Sequences

| SEQ ID NO: | kappa/ lambda | Antibody name | Epitope class | Sequence |
|---|---|---|---|---|
| 241 | kappa | Antibody 601-6 | Epitope Class I | DIQMTQSPSS LSASVGDRVT ITCQASQDIR NYLNWYQQKP GKAPKLLIYA ASNLETGVPS RFSGSGSGTD FTFTISSLQP EDIATYYCQQ DDNLPLTFGG GTKLEIKR |
| 242 | lambda | Antibody 601-9 | Epitope Class III | QSVLTQPPSV SVAPGETARI TCGGTNIGSE SVHWYQQRPG QAPVLVVYDD TDRPSGIPER FSGSNSGNTA TLTISRVEAG DGADYYCQVW DSVSDRYVFG TGTKVTVLG |
| 164 | kappa | Antibody 601-13 | Epitope Class III | DIVMTQSPSS LSASVGDRVT ITCQASQDIS NYLNWYQQKP GKAPKLLIYD ASNLETGVPS RFSGSGSGTD FIFTISSLQP EDIATYYCQQ FDNLPYTFGQ GTKVEIKR |
| 116 | lambda | Antibody 601-14 | Epitope Class II | QSVLTQPASV SGSPGQSITI SCTGTSSDVG GYNYVSWYQQ HPGKAPKLMI YDVSNRPSGV SNRFSGSKSG NTASLTISGL QAEDEADYYC SSYTSSSTLW VFGGGTKLTV LG |
| 84 | kappa | Antibody 601-17 | Epitope Class II | EIVLTQSPGT LSLSPGERAT LSCRASQSVS SSYLAWYQQK PGQAPRLLIY GASSRATGIP DRFSGSGSGT DFTLTISRLE PEDFAVYYCQ QYGSLFGQGT KVEIKR |
| 243 | kappa | Antibody 601-18 | Epitope Class II | EIVLTQSPGT LSLSPGERAT LSCRASQSVS SSYLAWYQQK PGQAPRLLIY GASSRATGIP DRFSGSGSGT DFTLTISRLE PEDFAVYYCQ QYGSSFGPGT KVDIKR |
| 244 | lambda | Antibody 601-28 | Epitope Class IV | QSALTQPASV SGSPGQSITI SCTGTSSDVG GYNYVSWYQQ HPGKAPKLMI FDVSNRPSGV SNRFSGSKSG NTASLTISGL QAEDEADYYC SSYTSSSTLF GGGTKLTVLG |
| 245 | kappa | Antibody 601-37 | Epitope Class I | AIRMTQSPSS LSASVGDRVT ITCQASQDIS NYLNWYQQKP GKAPKLLIYA ASSLQSGVPS RFSGSGSGTD FTLTISSLQP EDFATYYCQQ SYSTPFTFGP GTKVDIKR |
| 148 | kappa | Antibody 601-40 | Epitope Class III | DIQLTQSPSS LSASVGDRVT ITCRASQNIN NYLNWYQQKP GKAPKLLLYA ASSLQSGVPS RFSGSGSGTE FTLTISSLHP EDFATYYCQQ SYNTPFTFGP GTKVDIKR |
| 246 | kappa | Antibody 601-43 | Epitope Class III | DIQLTQSPSS LSASVGDRVT ITCRASQSIS SYLNWYQQKP GKAPKLLIYA ASSLQSGVPS RFSGSGSGTD FTLTISSLQP EDFATYYCQQ SYSTPPWTFG QGTKVEIKR |
| 247 | lambda | Antibody 601-50 | Epitope Class IV | QSALTQPPSA SGTPGQRVTI SCPGSSSNIG SNYVYWYQQL PGTAPKLLIY RNNQRPSGVP DRFSGSKSGT SATLGITGLQ TGDEADYYCG TWDSSLSAYV FGTGTKVTVLG |
| 36 | lambda | Antibody 601-51 | Epitope Class I | QSALTQPASV SGSPGQSITI SCTGTSSDFG DYDYVSWYQQ HPGKAPKLMI YDVSDRPSGV SNRFSGSKSG NTASLTISGL QAEDEADYFC SSFTTSSTLV FGGGTKLTVLG |
| 248 | lambda | Antibody 601-56 | Epitope Class I | QSVLTQPASV SGSPGQSITI SCTGTSSDFG DYDYVSWYQQ HPGKAPKLMI YDVSDRPSGV SNRFSGSKSG NTASLTISGL QAEDEADYFC SSLTTSSTLV FGGGTKLTVLG |
| 249 | kappa | Antibody 601-57 | Epitope Class III | AIQMTQSPSS LSASVGDRVT ITCRTSQSIS SYLNWYQQKP GKAPKLLIYA ASSLQSGVPS RFSGSGSGTD FTLTISSLQP EDFATYYCQQ SYSTPFTFGP GTKVDIKR |

TABLE 6-continued

Certain Light Chain Variable Region Sequences

| SEQ ID NO: | kappa/ lambda | Antibody name | Epitope class | Sequence |
|---|---|---|---|---|
| 250 | lambda | Antibody 601-65 | Epitope Class III | QSVLTQPPSV SGTPGQRVTI FCSGGSNNIG RSSVYWYRQA AGTAPKLLIY KTDQRPSGVP DRFAASKSGA SASLAISGLR SEDEADYHCA TWDDSLSAVV FGGGTKLTVLG |
| 251 | lambda | Antibody 601-66 | Epitope Class I | QSALTQPALT QPASVSGSPG QSITISCTGT SSDFGDYDYV SWYQQHPGKA PKLMIYDVSD RPSGVSNRFS GSKSGNTASL TISGLQAEDE ADYFCSSFTT SSTLVFGGGTKLTVLG |
| 252 | lambda | Antibody 601-69 | Epitope Class II | QSALTQPASV SGSPGQSITI SCTGTSSDVG GYNYVSWYQQ HPGKAPKLMI YDVSNRPSGV SNRFSGSKSG NTASLTISGL QAEDEADYYC SSYTSSSIPW VFGGGTKLTVLG |
| 253 | lambda | Antibody 601-70 | Epitope Class I | QSALTQPALT QPASVSGSPG QSITISCTGT SSDFGDYDYV SWYQQHPGKA PKLMIYDVSD RPSGVSNRFS GSKSGNTASL TISGLQAEDE ADYFCSSFTT SSTLVFGGGTKLTVLG |
| 254 | lambda | Antibody 601-81 | Epitope Class I | NFMLTQPRSV SESPGKTVTI SCTGNGGRVA NNYVQWYQQR PGSAPTTVIY EDNQRPSGVP ARFSGSIDSS SNSASLTISG LKTDDEADYY CQSYDISNQR VFGGGTKLTVLG |
| 132 | kappa | Antibody 601-86 | Epitope Class II | DIQMTQSPSS VSASVGDRVT ITCRASQGIS TLLAWYQQKP GKAPKLLISS ASSLQSGVPA RFSGSGSGTD FTLTISSLQP EDFATYYCQQ SYRAPTFGQG TKVEIKR |
| 255 | kappa | Antibody 601-87 | Epitope Class I | ETTLTQSPAF MSATPGDKVN ISCKASQDID DDLNWYQQKP GEAPILIIQE ATTLVPGIPP RFSGSGFGTD FTLTINSMQS EDVAYYFCLQ HDNFPPTFGQ GTKVEIKR |
| 256 | lambda | Antibody 601-100 | Epitope Class IV | QSALTQPASV SGSPGQSITI SCTGTSRDVG GYDYVSWYQQ YPGNAPKLMI YDVSRRPSGV SHRFSASKSG NTASLTISGL QTEDEADYYC SSYTSSSTRV FGGGTKVTVLG |
| 257 | kappa | Antibody 601-101 | Epitope Class I | DIQLAQSPSS LSASVGDRVT ITCRASQSIS NYLNWYQQKP GKAPKLLIYA ASSLQSGVPS RFSGSGSGTD FTLTISSLQP EDFATYYCQQ SYSTPFTFGP GTKVEIKR |
| 258 | lambda | Antibody 601-102 | Epitope Class II | QSALTQPASV SGSPGQSITI SCTGTSSDVG GYNYVSWYQQ HPGKAPKLMI YDVSKRPSGV SNRFSGSKSG NTASLTISGL QAEDEADYYC SSYTSSSTSV VFGGGTKLTVLG |
| 259 | lambda | Antibody 601-103 | Epitope Class IV | QSVLTQPASV SGSPGQSITI SCTGTTSDVG GYNYVSWYQQ HPGKAPKLMI YDVSKRPSGV SNRFSGSKSG NTASLTISGL QAEDEADYYC SSYTSSSTDV FGTGTKLTVLG |
| 260 | lambda | Antibody 601-108 | Epitope Class I | QSVVTQPPSV SAAPGQKVTI SCSGSSSNIG KNYVSWYQQF PGTAPKLLIY DNNERPSGIP ARFSGSKSGT SATLGITGLQ TGDEADYYCA TFDTSLWAAV FGGGTKLTVLG |
| 180 | lambda | Antibody 601-109 | Epitope Class IV | QSALTQPASV SGSPGQSITI SCTGTSSDVG GYNYVSWYQQ HPGKAPKLLI YEVSQRPSGV PDRFSGSKSG NTASLTVSGL QAEDEADYYC SSYAGDRDVF GTGTQLTVLS |
| 261 | lambda | Antibody 601-110 | Epitope Class II | QSALTQPASV SGSPGQSITL SCTGTSSDVG GYNYVSWYQQ HPGNGPKLII YDVTKRPSGV SNRFSGSKSG NTAYLTISGL QAEDEADYYC ASYTRSTTLV FGGGTKLTVLG |
| 262 | lambda | Antibody 601-112 | Epitope Class IV | QSALTQPASV SGSPGQSITI SCTGTSSDVG GYNYVSWYQQ HPGKAPKLMI YDVSKRPSGV SNRFSGSKSG NTASLTISGL QAEDEADYYC SSYTGRSTVF GGGTKLTVLG |

TABLE 6-continued

Certain Light Chain Variable Region Sequences

| SEQ ID NO: | kappa/ lambda | Antibody name | Epitope class | Sequence |
|---|---|---|---|---|
| 100 | lambda | Antibody 601-119 | Epitope Class II | QSALTQPASV SASPGQSITI SCTGTSSDVG GYNYVTWYQQ HPGKAPKLMI YDVSKRPSGV LDRFSGSKSG NTASLTISGL QAEDEADYFC SSYTSSSTLV FGGGTKLTVLG |
| 263 | lambda | Antibody 601-120 | Epitope Class IV | QSALTQPASV SGSPGQSITI SCTGTSSDVG GYNYVSWYQQ HPGKAPKLMI YDVSNRPSGV SNRFSGSKSG NTASLTISGL QAEDEADYYC SSYTSSSTRV FGGGTKLTVLG |
| 264 | kappa | Antibody 601-128 | Epitope Class IV | DIQMTQSPSS VSASVGDRVT ITCRASQGIS SWLAWYQQKP GKAPKLLIYA ASSLQSGVPS RFSGSGSGTD FTLTISSLQP EDFATYYCQQ ANSFPLTFGG GTKVEIKR |
| 265 | lambda | Antibody 601-130 | Epitope Class I | QSVLTQPPSV SGAPGQRVTI SCTGSSSNIG AGYDVHWYQQ LPGTAPKLLI YGNSNRPSGV PDRFSGSKSG TSASLAITGL QAEDEADYYC QSYDSSLSGY VFGTGTKLTV LG |
| 266 | lambda | Antibody 601-134 | Epitope Class I | SSELTQDPAV SVALGQTVRI TCQGDSLRSY YASWYQQKPG QAPVLVIYGK NNRPSGIPDR FSGSSSGNTA SLTITGAQAE DEADYYCNSR DSSGNHLVFG GGTKLTVLG |
| 267 | lambda | Antibody 601-136 | Epitope Class IV | QSVLTQPPSA SGTPGQRVTI SCSGSSSNIG SNTVNWYQQL PGTAPKLLIY SNNQRPSGVP DRFSGSKSGT SASLAIRGLQ SDDEAEYYCA AWDDSLKSFV FGKGTKVTVLG |
| 196 | lambda | Antibody 601-137 | Epitope Class IV | QSALTQPPSA SGTPGQRVTI SCSGSSSNIG SNYVYWYQQL PGTAPKLLIY RNNQRPSGVP DRFSGSKSGT SASLAISGLR SEDEADYYCA AWDDSLSAWV FGGGTKLTVLG |
| 268 | kappa | Antibody 601-141 | Epitope Class III | AIQMTQSPSS LSASVGDRVT ITCRASQSIS SHLNWYQQKP GKAPKLLIYA ASSLQSGVPS RFSGSGSGTD FTLTISSLQP EDFATYYCQQ SYSTPFTFGP GTKVDIKR |
| 269 | lambda | Antibody 601-147 | Epitope Class III | QSALTQPPSA SGTPGQRVTI SCSGSSSNIG SNYVYWYQQL PGTAPKLLIY RNNQRPSGVP DRFSGSKSGT SASLAISGLR SEDEADYYCA AWDDSLSGYV FGTGTKVTVLG |
| 270 | kappa | Antibody 601-149 | Epitope Class I | DIQLTQSPSS LSASVGDRVT ITCQASQDVR NYLNWYQQKP GKAPNLLIYD ATNLESGVPS RFSGSGSGTD FTFTISSLQP EDFATYYCQQ YDNLPLSFGG GTKVEIKR |
| 271 | lambda | Antibody 601-153 | Epitope Class III | QSALTQPASV SGSPGQSITI SCTGTSSDVG GYNYVSWYQQ HPGKAPKFMI YDVSKRPSGV SNRFSGSKSG NTASLTISGL QAEDEADYYC GSFTSSITYV FGTGTKVTVL G |

TABLE 7

Certain Heavy Chain Variable Region Sequences

| SEQ ID NO: | Antibody | Epitope Class | Sequence |
|---|---|---|---|
| 12 | Antibody 601-1 | Epitope Class I | EVQLVESGGG LVKPGGSLRL SCAASGFTFS DYYMSWIRQA PGKGLEWVSY ISDSTNTIYY ADSVKGRFTV SRDNPKNSLY LQMISLRAED TAVYYCARAV GAGEGFDHWG QGTLVTVSS |
| 76 | Antibody 601-2 (3-12) | Epitope Class II | QVTLKESGPT LVKPTQTLTL TCTFSGFSLS SFGVAVGWFR QPPGKALEWL GLIYWDDDKR YSPSLKTRLT ITKDTSKNQV VLTMTNMDPV DTATYYCAHK GGIATTGSPN WFDPWGQGTL VTVSS |

TABLE 7-continued

Certain Heavy Chain Variable Region Sequences

| SEQ ID NO: | Antibody | Epitope Class | Sequence |
|---|---|---|---|
| 220 | Antibody 601-3 (3-16) | Epitope Class II | QVTLKESGPT LVKPTQTLTL TCTFSGFSLN SFGVAVGWFR QPPGKALEWL GLIYWDDDRR YFPSLEGRLS ITKDASDNNV VLTMMNVDPA DTATYYCART SPMVQGIANY YAMDVWGQGT TVTVSS |
| 60 | Antibody 601-4 | Epitope Class I | EVQLVQSGPG LVKPSGTLSL TCAVSGGSIS SSNWWSWVRQ PPGKGLEWIG EIYHSGSTNY NPSLKSRVTI SVDKSKNQFS LKLGSVTAAD TATYYCARDL WLGEWDLWGQ GTLVTVSS |
| 28 | Antibody 601-5 (3-2) | Epitope Class I | EVQLVESGGG LVKPGGSLRL SCAASGFTFS DYYMGWVRQA PGKGLKWLSY ISDRAHTIYD TDSVKGRFTI SRDDAKSSLY LRMNNLRVED TAVYYCARAV GAGEGFDYWG QGTLVTVSS |
| 272 | Antibody 601-6 | Epitope Class I | EVQLVESGGG LVKPGGSLKL SCAASGFTFS DYYMGWVRQA PGKGLKWLSY ISDRAHTIYD THSVKGRFTI SRDDAKSSLY LRMNNLRVED TAVYYCARAV GAGEGFDYWC QGTLVTVSS |
| 273 | Antibody 601-9 | Epitope Class III | QLQLQESGPG VVKPSGTLSL TCTVSGGSIS RSDGYWGWVR QPPGKGLEWI GSIYDTGTTY YSPSLKSRLI ISVDTSKNQF SLTLNSVTAA DTAVYYCASM GGLRSSSSDA FHTWGPGTMV TVSS |
| 172 | Antibody 601-13 | Epitope Class III | EVQLVQSGAE VKKPGSSVKV SCKASGGTFS TFAINWVRQA PGQGLEWMGG VIPVSGTEDY SQKFQGRLSL TADESTGTAY MELSSLRSDD TAVYYCARDR SGRDWDYFDY WGQGTLVTVSS |
| 124 | Antibody 601-14 | Epitope Class II | QVQLVQSGAE VKKPGESLKI SCKDSGYSFT NYWLGWVRQM PGKGLEWMGI IYPGDSDTRY SPSFRGQVTI SADKSISTAY LQWSSLKASD TAMYYCARLN LATHTAFDIW GQGTTVTVSS |
| 92 | Antibody 601-17 | Epitope Class II | EVQLVQSGAE VRKPGSSVKV SCKASGGSLS SHGVSWVRQA PGQGLEWMAR IIPMFGLTDY AQNFQARVTI SADRSTNTVY MEISNLGSED TAVYFCARES LGATFEYWGQ GTLVTVSS |
| 274 | Antibody 601-18 | Epitope Class II | QVQLVQSGTE VKKPGSSVKV SCQASGGSLS SHGVSWLRQA PGQGLEWVGR IIPMFGVTDY AQKFQDRVTI TADKSTSTVY MELISLGSDD TAVYFCARES RGATFEYWGQ GTLVTVSS |
| 275 | Antibody 601-28 | Epitope Class IV | EVQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVSS |
| 276 | Antibody 601-37 | Epitope Class I | EVQLVQSGAE VKKPGASVKV SCKASGYTFN NYGFSWVRQA PGQGLEWMGW ISVYNGNTNY AQKLQGRVTM TTDTSTSTAY MELRSLRSDD TAVYYCARDY YSDSSGYWDD AFDIWGQGTM VTVSS |
| 156 | Antibody 601-40 | Epitope Class III | QVQLQQSGAE VKKPGASVKV SCKASGYTST NYGISWVRQA PGQGLEWMGW ISTYNGNTNY AQKLQGRVTM TTDTSTSTAY MELRSLRSDD TAVYYCARDY YSDSSGYWDD AFDIWGQGTM VTVSS |
| 277 | Antibody 601-43 | Epitope Class III | QVQLQQSGAE VKKPGASVRV SCKASGYSFG NNGITWVRQA PGQGLEWMGW ISTYNGNTNY AQKLQGRVTM TTDTSTSTAY MELRSLRSDD TAVYYCARDY YSDSSGYWDD AFDIWGQGTT VTVSS |
| 278 | Antibody 601-50 | Epitope Class IV | QVQLQQSGAE VKKPGASVKV SCKASGYTFS RYYIHWVRRA PGQGLEWMGL INPGGGSTNY AQKFQGRVTM TRDTSTNTVY LELSSLRSDD TAVYYCARDY GTIDARRFDF WGQGTLVTVS S |
| 44 | Antibody 601-51 | Epitope Class I | QVQLVQSGAE VKKPGASVKV SCKASGYTFT GYYMHWVRQA PGQGLEWMGW INPNSGGTNY AQKFQGRVTM TRDTSISTAY MELSRLRSDD TAVYYCARDG DMVYDSSGPD YWGQGTLVTV SS |
| 279 | Antibody 601-56 | Epitope Class I | QLQLQESGPG LVKPSETLSL TCTVSGGSIS SSSYYWGWIR QPPGKGLEWI GSIYYSGSTY YNPSLKSRVT ISVDTSKNQF SLKLGSVTAA DTAVYYCARH DGTDAFDIWG QGTTVTVSS |
| 280 | Antibody 601-57 | Epitope Class III | EVQLVQSGAE VKKPGSSVKI SCKASGGAFT NFGISWVRQA PGQGLEWMGW ISTYNSETNY AQKLQGRVTM TTDTSTSTAY MELRSLRSDD TAVYYCARDY YSDSSGYWDD AFDIWGQGTL VTVSS |
| 281 | Antibody 601-65 | Epitope Class III | QVQLQQSGPG LVKPSQTLSL TCAISGDSVS SNSATWNWIR QSPSRGLEWL GRTYYRSKWY NDYAVSVKSR IIINPDTSKN QFSLQLNSVT PEDTAVYYCA RGVRAFDIWG QGTTVTVSS |

TABLE 7-continued

Certain Heavy Chain Variable Region Sequences

| SEQ ID NO: | Antibody | Epitope Class | Sequence |
|---|---|---|---|
| 282 | Antibody 601-66 | Epitope Class I | QVQLVQSGAE VKEPGASVKV SCKASGYTFR NSGITWVRQA PGQGLEWMGW INPNSGGAMY VDNFQGRATM TRDTSINTAY MELRSLSSDD TAVYYCARGM ADLIDVFDIW GQGTLVTVSS |
| 283 | Antibody 601-69 | Epitope Class II | QVQLVQSGAE VKKPGESLKI SCKGSGYSFT SYWIGWVRQM PGKGLEWMGI IYPGDSDTRY SPSFQGQVTI SADKSISTAY LQWSSLKASD TAMYYCARLS SSSYDAFDIW GQGTMVTVSS |
| 284 | Antibody 601-70 | Epitope Class I | EVQLVQSGAE LKKPGSSVRV SCKTSGGSFK THGISWVRQA PGQGLEWMGW INPNSGGALY VDNFQGRATM TRDTSINTAY MELRSLSSDD TAVYYCARGM ADLIDVFDIW GQGTMVTVSS |
| 285 | Antibody 601-81 | Epitope Class I | EVQLVESGGG VVRPGGSLRL SCATSGFNFD NYGLSWVRQG PGKGLEWMGF IYKSVNTNYS PSLKSRLTIS MDTSKNQFSL NLASVTTADT AIYYCARGKV ETSVVDYWGQ GTLVTVSS |
| 140 | Antibody 601-86 | Epitope Class II | QVTLKESGPT LLKPTQTLTL TCTFSGFSLS TRGVGVGWIR QPPGQALEWL TLIYWDDDKR YSPSLKSRLT ITKDTSKNQV VLTMTNMESV DTATYYCAQQ TMTGAFDIWG QGTTVTVSS |
| 286 | Antibody 601-87 | Epitope Class I | QVQLQESGPG LVKSSETLSL TCTVSGGSMN NYYWSWIRQP AGKGLEWMGR IYSSGSTNYN PALKSRVTMS VDTSKNQFSL NLSSVTAADT AIYYCARASW SGTYWALFDY WGQGTLVTVSS |
| 287 | Antibody 601-100 | Epitope Class IV | EVQLVQSGGG VVQPGGPLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTMVTVS S |
| 288 | Antibody 601-101 | Epitope Class I | EVQLVQSGNE VKRPGASVKV SCKASGHSFS TYGFSWVRQA PGQGLEWMGW ISTYNGNTNY AQKLQGRVTM TTDTSTSTAY MELRSLRSDD TAVYYCARDY YSDSSGYWDD AFDIWGQGTL VTVSS |
| 289 | Antibody 601-102 | Epitope Class II | QMQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 290 | Antibody 601-103 | Epitope Class IV | EVQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 291 | Antibody 601-108 | Epitope Class I | QLQLQESGPG LVKPSETLSL TCTVSGGSIS SNSYYWGWIR QPPGKGLEWI GSIYYSGSTY YNPSLKSRVT ISVDTSKNQF SLKLGSVTAA DTAVYYCARH DGTDAFDIWG QGTTVTVSS |
| 188 | Antibody 601-109 | Epitope Class IV | QMQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 292 | Antibody 601-110 | Epitope Class II | QVQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 293 | Antibody 601-112 | Epitope Class IV | EVQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 108 | Antibody 601-119 | Epitope Class II | QVQLVQSGGG LVKPGGSLRL SCAASGFTFG TYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 294 | Antibody 601-120 | Epitope Class IV | EVQLVQSGGD LVQPGGSLRL SCAASGFTFS SYSMNWVRQA PGKGLEWVSS ISSSSSYIYY ADSVKGRFTI SRDNAKNSLY LQMNSLRAED TAVYYCARGL GGWTHDAFDI WGQGTTVTVS S |
| 295 | Antibody 601-128 | Epitope Class IV | EVQLVQSGAE VKKPGESLKI SCKGSGYSFS RYWIGWVRQM PGKGLEWMGI IYPRDSDTRY SPSFQGQVTI SADKSISTAY LQWSSLKASD TAMYYCATPV VTAGAFDIWG QGTMVTVSS |
| 296 | Antibody 601-130 | Epitope Class I | EVQLVETGGG LVKPGGSLRL SCEASGFSLS SYSMNWVRQA PGKGLEWVSS ISSSSTHIYY ADSLKGRFTI SRDNAKNSLF LQMDNLRAED TAVYYCARAT IGFDYWGQGT LVTVSS |

TABLE 7-continued

Certain Heavy Chain Variable Region Sequences

| SEQ ID NO: | Antibody | Epitope Class | Sequence |
|---|---|---|---|
| 297 | Antibody 601-134 | Epitope Class I | EVQLVQSGAE VKKPGASVKV SCKASGYTFT DYYIHWVRQA PGQGLEWMGW MNPNSGNSVS AQKFQGRVTM TRDTSINTAY MELSSLTSDD TAVYYCARNS EWHPWGYYDY WGQGTLVTVS S |
| 298 | Antibody 601-136 | Epitope Class IV | QVQLVQSGAE VKKPGASVKV SCKASGYTFS RYYIHWVRQA PGQGLEWMGL INPGGGSTNY AQKFQGRVTM TRDTSTNTVY LELSSLRSDD TAVYYCARDY GTIDARRFDF WGQGTLVTVS S |
| 204 | Antibody 601-137 | Epitope Class IV | QVQLQQSGAE VKKPGASVKV SCKASGYTFS RYYIHWVRQA PGQGLEWMGI INTDGGTTTY AQKFQGRLTM TRDTSTSTVY MELSSLRSDD TAVYYCARDY GTIDARRFDY WGQGTLVTVS S |
| 299 | Antibody 601 4 41 | Epitope Class III | QVQLQQSGAE VKKPGASVKV SCKASGHTFS NYGISWVRQA PGQGLEWMGW ISTYNGNTNY AQKLQGRVTM TTDTSTSTAY MELRSLRSDD TAVYYCARDY YSDSSGYWDD AFDIWGQGTT VTVSS |
| 300 | Antibody 601 4 47 | Epitope Class III | QMQLVQSGAE VKKPGASVKV SCKASGYTFS RYYIHWVRQA PGQGLEWMGL INPGGGSTNY AQKFQGRVTM TRDTSTNTVY LELSSLRSDD TAVYYCARDY GTIDARRFDF WGQGTLVTVS S |
| 301 | Antibody 601 4 49 | Epitope Class I | EAQLVESGGG LVKPGGSLRL SCAASGFTFS DYYMGWVRQA PGKGLKWLSY ISDRAHTIYD TDSVKGRFTI SRDDAKSSLY LRMNNLRVED TAVYYCARAV GAGEGFDYWG QGTLVTVSS |
| 302 | Antibody 601 4 53 | Epitope Class III | QMQLVQSGAE VKKPGASVKV SCKASGYTFT SYYMHWVRQA PGQGLEWMGI INPSGGSTSY AQKFQGRVTM TRDTSTSTVY MELSSLRSED TAVYYCARGG YTGWSPSDPW GQGTLVTVSS |

TABLE 8

Certain Light Chain CDR Sequences

| SEQ ID NOS: | Antibody | LC CDR1 | LC CDR2 | LC CDR3 |
|---|---|---|---|---|
| 8-10 | Antibody 601-1 | QASQDISNYLN | DASNLET | QQYDNLPLT |
| 72-74 | Antibody 601-2 (3-12) | RASQSVSSNLA | GASTRAT | QQYNNWPPYT |
| 216-218 | Antibody 601-3 (3-16) | RASQSVSSNLA | GASTRAT | QQYNNWPPYT |
| 56-58 | Antibody 601-4 | SGGISNVGTNGVN | AMNQRPS | ATWDDSLSGVL |
| 24-26 | Antibody 601-5 (3-2) | QASQDISNYLN | DASNLET | QQYDNLPLT |
| 303-305 | Antibody 601-6 | QASQDIRNYLN | AASNLET | QQDDNLPLT |
| 306-308 | Antibody 601-9 | GGTNIGSESVH | DDTDRPS | QVWDSVSDRYV |
| 168-170 | Antibody 601-13 | QASQDISNYLN | DASNLET | QQFDNLPYT |
| 120-122 | Antibody 601-14 | TGTSSDVGGYNYVS | DVSNRPS | SSYTSSSTLWV |
| 88-90 | Antibody 601-17 | RASQSVSSSYLA | GASSRAT | QQYGSL |
| 309-311 | Antibody 601-18 | RASQSVSSSYLA | GASSRAT | QQYGSS |
| 312-314 | Antibody 601-28 | TGTSSDVGGYNYVS | DVSNRPS | SSYTSSSTL |
| 315-317 | Antibody 601-37 | QASQDISNYLN | AASSLQS | QQSYSTPFT |
| 152-154 | Antibody 601-40 | RASQNINNYLN | AASSLQS | QQSYNTPFT |
| 318-320 | Antibody 601-43 | RASQSISSYLN | AASSLQS | QQSYSTPPWT |
| 321-323 | Antibody 601-50 | PGSSSNIGSNYVY | RNNQRPS | GTWDSSLSAYV |

TABLE 8-continued

Certain Light Chain CDR Sequences

| SEQ ID NOS: | Antibody | LC CDR1 | LC CDR2 | LC CDR3 |
|---|---|---|---|---|
| 40-42 | Antibody 601-51 | TGTSSDFGDYDYVS | DVSDRPS | SSFTTSSTLV |
| 324-326 | Antibody 601-56 | TGTSSDFGDYDYVS | DVSDRPS | SSLTTSSTLV |
| 327-329 | Antibody 601-57 | RTSQSISSYLN | AASSLQS | QQSYSTPFT |
| 330-332 | Antibody 601-65 | SGGSNNIGRSSVY | KTDQRPS | ATWDDSLSAVV |
| 333-335 | Antibody 601-66 | TGTSSDFGDYDYVS | DVSDRPS | SSFTTSSTLV |
| 336-338 | Antibody 601-69 | TGTSSDVGGYNYVS | DVSNRPS | SSYTSSSIPWV |
| 339-341 | Antibody 601-70 | TGTSSDFGDYDYVS | DVSDRPS | SSFTTSSTLV |
| 342-344 | Antibody 601-81 | TGNGGRVANNYVQ | EDNQRPS | QSYDISNQRV |
| 136-138 | Antibody 601-86 | RASQGISTLLA | SASSLQS | QSYRAPT |
| 345-347 | Antibody 601-87 | KASQDIDDDLN | EATTLVP | LQHDNFPPT |
| 348-350 | Antibody 601-100 | TGTSRDVGGYDYVS | DVSRRPS | SSYTSSSTRV |
| 351-353 | Antibody 601-101 | RASQSISNYLN | AASSLQS | QQSYSTPFT |
| 354-356 | Antibody 601-102 | TGTSSDVGGYNYVS | DVSKRPS | SSYTSSSTSVV |
| 357-359 | Antibody 601-103 | TGTTSDVGGYNYVS | DVSKRPS | SSYTSSSTDV |
| 360-362 | Antibody 601-108 | SGSSSNIGKNYVS | DNNERPS | ATFDTSLWAAV |
| 184-186 | Antibody 601-109 | TGTSSDVGGYNYVS | EVSQRPS | SSYAGDRDV |
| 363-365 | Antibody 601-110 | TGTSSDVGGYNYVS | DVTKRPS | ASYTRSTTLV |
| 366-368 | Antibody 601-112 | TGTSSDVGGYNYVS | DVSKRPS | SSYTGRSTV |
| 104-106 | Antibody 601-119 | TGTSSDVGGYNYVT | DVSKRPS | SSYTSSSTLV |
| 369-371 | Antibody 601-120 | TGTSSDVGGYNYVS | DVSNRPS | SSYTSSSTRV |
| 372-374 | Antibody 601-128 | RASQGISSWLA | AASSLQS | QQANSFPLT |
| 375-377 | Antibody 601-130 | TGSSSNIGAGYDVH | GNSNRPS | QSYDSSLSGYV |
| 378-380 | Antibody 601-134 | QGDSLRSYYAS | GKNNRPS | NSRDSSGNHLV |
| 381-383 | Antibody 601-136 | SGSSSNIGSNTVN | SNNQRPS | AAWDDSLKSFV |
| 200-202 | Antibody 601-137 | SGSSSNIGSNYVY | RNNQRPS | AAWDDSLSAWV |
| 384-386 | Antibody 601-141 | RASQNSISSHLN | AASSLQS | QQSYSTPFT |
| 387-389 | Antibody 601-147 | SGSSSIGSNYVY | RNNQRPS | AAWDDSLSGYV |
| 390-392 | Antibody 601-149 | QASQDVRNYLN | DATNLES | QQYDNLPLS |
| 393-395 | Antibody 601-153 | TGTSSDVGGYNYVS | DVSKRPS | GSFTSSITYV |

TABLE 9

Certain Heavy Chain CDR Sequences

| SEQ ID NOS | Antibody | HC CDR1 | HC CDR2 | HC CDR3 |
|---|---|---|---|---|
| 396, 17, 18 | Antibody 601-1 | GFTFSDYYMS | YISDSTNTIYYADSVKG | AVGAGEGFDH |
| 397, 81, 82 | Antibody 601-2 (3-12) | GFSLSSFGVAVG | LIYWDDDKRYSPSLKT | KGGIATTGSPNWFDP |

TABLE 9-continued

Certain Heavy Chain CDR Sequences

| SEQ ID NOS | Antibody | HC CDR1 | HC CDR2 | HC CDR3 |
|---|---|---|---|---|
| 398, 225, 226 | Antibody 601-3 (3-16) | GFSLNSFGVAVG | LIYWDDDRRYFPSLEG | TSPMVQGIANYYAMDV |
| 399, 65, 66 | Antibody 601-4 | GGSISSSNWWS | EIYHSGSTNYNPSLKS | DLWLGEWDL |
| 400, 33, 34 | Antibody 601-5(3-2) | GFTFSDYYMG | YISDRAHTIYDTDSVKG | AVGAGEGFDY |
| 401-403 | Antibody 601-6 | GFTFSDYYMG | YISDRAHTIYDTHSVKG | AVGAGEGFDY |
| 404-406 | Antibody 601-9 | GGSISRSDGYWG | SIYDTGTTYYSPSLKS | MGGLRSSSSDAFHT |
| 407, 177, 178 | Antibody 601-13 | GGTFSTFAIN | GVIPVSGTEDYSQKFQG | DRSGRDWDYFDY |
| 408, 129, 130 | Antibody 601-14 | GYSFTNYWLG | IIYPGDSDTRYSPSFRG | LNLATHTAFDI |
| 409, 97, 98 | Antibody 601-17 | GGSLSSHGVS | RIIPMFGLTDYAQNFQA | ESLGATFEY |
| 410-412 | Antibody 601-18 | GGSLSSHGVS | RIIPMFGVTDYAQKFQD | ESRGATFEY |
| 413-415 | Antibody 601-28 | GFTFSSYSMN | SISSSSSYIYYADSVKG | GLGGWTHDAFDI |
| 416-418 | Antibody 601-37 | GYTFNNYGFS | WISVYNGNTNYAQKLQG | DYYSDSSGYWDDAFDI |
| 419, 161, 162 | Antibody 601-40 | GYTSTNYGIS | WISTYNGNTNYAQKLQG | DYYSDSSGYWDDAFDI |
| 420-422 | Antibody 601-43 | GYSFGNNGIT | WISTYNGNTNYAQKLQG | DYYSDSSGYWDDAFDI |
| 423-425 | Antibody 601-50 | GYTFSRYYIH | LINPGGGSTNYAQKFQG | DYGTIDARRFDF |
| 426, 49, 50 | Antibody 601-51 | GYTFTGYYMH | WINPNSGGTNYAQKFQG | DGDMVYDSSGPDY |
| 427-429 | Antibody 601-56 | GGSISSSSYYWG | SIYYSGSTYYNPSLKS | HDGTDAFDI |
| 430-432 | Antibody 601-57 | GGAFTNFGIS | WISTYNSETNYAQKLQG | DYYSDSSGYWDDAFDI |
| 433-435 | Antibody 601-65 | GDSVSSNSATWN | RTYYRSKWYNDYAVSVKS | GVRAFDI |
| 436-438 | Antibody 601-66 | GYTFRNSGIT | WINPNSGGAMYVDNFQG | GMADLIDVFDI |
| 439-441 | Antibody 601-69 | GYSFTSYWIG | IIYPGDSDTRYSPSFQG | LSSSSYDAFDI |
| 442-444 | Antibody 601-70 | GGSFKTHGIS | WINPNSGGALYVDNFQG | GMADLIDVFDI |
| 445-447 | Antibody 601-81 | GFNFDNYGLS | FIYKSVNTNYSPSLKS | GKVETSVVDY |
| 448, 145, 146 | Antibody 601-86 | GFSLSTRGVGVG | LIYWDDDKRYSPSLKS | QTMTGAFDI |
| 449-451 | Antibody 601-87 | GGSMNNYYWS | RIYSSGSTNYNPALKS | ASWSGTYWALFDY |
| 452-454 | Antibody 601-100 | GFTFSSYSMN | SISSSSSYIYYADSVKG | GLGGWTHDAFDI |

TABLE 9-continued

Certain Heavy Chain CDR Sequences

| SEQ ID NOS | Antibody | HC CDR1 | HC CDR2 | HC CDR3 |
|---|---|---|---|---|
| 455-457 | Antibody 601-101 | GHSFSTYGFS | WISTYNGNTNYAQKLQG | DYYSDSSGYWDDAFDI |
| 458-460 | Antibody 601-102 | GFTFSSYSMN | SISSSSSYIYYADSVKG | GLGGWTHDAFDI |
| 461-463 | Antibody 601-103 | GFTFSSYSMN | SISSSSSYIYYADSVKG | GLGGWTHDAFDI |
| 464-466 | Antibody 601-108 | GGSISSNSYYWG | SIYYSGSTYYNPSLKS | HDGTDAFDI |
| 467, 193, 104 | Antibody 601-109 | GFTFSSYSMN | SISSSSSYIYYADSVKG | GLGGWTHDAFDI |
| 468-470 | Antibody 601-110 | GFTFSSYSMN | SISSSSSYIYYADSVKG | GLGGWTHDAFDI |
| 471-473 | Antibody 601-112 | GFTFSSYSMN | SISSSSSYIYYADSVKG | GLGGWTHDAFDI |
| 474, 113, 114 | Antibody 601-119 | GFTFGTYSMN | SISSSSSYIYYADSVKG | GLGGWTHDAFDI |
| 475-477 | Antibody 601-120 | GFTFSSYSMN | SISSSSSYIYYADSVKG | GLGGWTHDAFDI |
| 478-480 | Antibody 601-128 | GYSFSRYWIG | IIYPRDSDTRYSPSFQG | PVVTAGAFDI |
| 481-483 | Antibody 601-130 | GFSLSSYSMN | SISSSSTHIYYADSLKG | ATIGFDY |
| 484-486 | Antibody 601-134 | GYTFTDYYIH | WMNPNSGNSVSAQKFQG | NSEWHPWGYYDY |
| 487-489 | Antibody 601-136 | GYTFSRYYIH | LINPGGGSTNYAQKFQG | DYGTIDARRFDF |
| 490, 209, 210 | Antibody 601-137 | GYTFSRYYIH | IINTDGGTTTYAQKFQG | DYGTIDARRFDY |
| 491-493 | Antibody 601-141 | GHTFSNYGIS | WISTYNGNTNYAQKLQG | DYYSDSSGYWDDAFDI |
| 494-496 | Antibody 601-147 | GYTFSRYYIH | LINPGGGSTNYAQKFQG | DYGTIDARRFDF |
| 497-499 | Antibody 601-149 | GFTFSDYYMG | YISDRAHTIYDTDSVKG | AVGAGEGFDY |
| 500-502 | Antibody 601-153 | GYTFTSYYMH | IINPSGGSTSYAQKFQG | GGYTGWSPSDP |

The invention claimed is:

1. An isolated human anti-Receptor Tyrosine Kinase-Like Orphan Receptor 1 (ROR1) antibody or an antigen binding fragment thereof that binds to the ROR1 protein set forth in SEQ ID NO: 2, wherein the antibody or antigen binding fragment thereof comprises at least one antigen binding region comprising light chain complementary determining region (LCDR) amino acid sequences set forth in SEQ ID NOs: 309, 310, and 311 and heavy chain complementary determining region (HCDR) amino acid sequences set forth in SEQ ID NOs: 410, 411, and 412.

2. The isolated antibody or antigen binding fragment thereof according to claim 1, wherein the antibody is an scFv of wherein the antigen binding fragment is selected from the group consisting of Fv, Fab, Fab', and F(ab')2 fragments.

3. The isolated antibody or antigen binding fragment thereof according to claim 1, wherein the antibody or antigen binding fragment thereof selectively interacts with the ROR1 protein with an affinity constant of approximately $10^{-5}$ to $10^{-13}$ M$^{-1}$.

4. The isolated antibody or antigen binding fragment thereof according to claim 1, wherein the antibody or antigen binding fragment thereof exhibits an IC50 for the ROR1 protein of about $10^{-7}$ to $10^{-10}$ M$^{-1}$ in a competitive phage-binding enzyme-linked immunosorbent assay (ELISA).

5. The isolated antibody or antigen binding fragment thereof according to claim 1, wherein the antibody or antigen binding thereof is capable of binding to residues SSTGVLFVKFGPPPTASPG (SEQ ID NO:239) and SNPMILMRLKLPNCE (SEQ ID NO:240) of the ROR1 protein.

6. The isolated antibody or antigen binding fragment thereof according to claim 1, wherein the antibody or antigen binding fragment thereof comprises a light chain variable region (VL) and a heavy chain variable region (VH), the light chain variable region comprising an amino acid sequence set forth in SEQ ID NO: 243, and the heavy chain variable region comprising the amino acid sequence set forth in in SEQ ID NO: 274.

7. An antibody-drug conjugate (ADC) comprising the antibody or antigen binding fragment thereof according to claim 1, and a cytotoxic moiety.

8. The conjugate according to claim 7, wherein the cytotoxic moiety is a toxin or an alpha-emitting radionucleotide.

9. A pharmaceutical composition comprising an antibody or an antigen binding fragment thereof as defined in claim 1; and a pharmaceutically acceptable vehicle.

10. A process for making the composition according to claim 9, the process comprising combining an antibody or an antigen binding fragment thereof as defined in claim 1 with a pharmaceutically acceptable vehicle.

11. An isolated nucleic acid encoding an antibody or an antigen binding fragment thereof according to claim 1.

12. An expression cassette comprising the nucleic acid according to claim 11, a recombinant vector comprising the expression cassette, or a host cell comprising the expression cassette.

13. A method of preparing a recombinant antibody or antigen binding fragment thereof according to claim 1, the method comprising (i) culturing at least one cell defined in claim 12 capable of expressing the antibody or antigen binding fragment thereof; and (ii) isolating the antibody or antigen binding fragment thereof.

* * * * *

SEQUENCE LISTING

<160> NUMBER OF SEQ ID NOS: 502

<210> SEQ ID NO 1
<211> LENGTH: 2814
<212> TYPE: DNA
<213> ORGANISM: Homo sapiens

<400> SEQUENCE: 1

```
atgcaccggc cgcgccgccg cgggacgcgc ccgccgctcc tggcgctgct ggccgcgctg      60
ctgctggccg cacgcgggc tgctgcccaa gaaacagagc tgtcagtcag tgctgaatta     120
gtgcctacct catcatggaa catctcaagt gaactcaaca agattcttta cctgaccctc     180
```

```
gatgaaccaa tgaataacat caccacgtct ctgggccaga cagcagaact gcactgcaaa    240
gtctctggga atccacctcc caccatccgc tggttcaaaa atgatgctcc tgtggtccag    300
gagcccggga ggctctcctt tcggtccacc atctatggct ctcggctgcg gattagaaac    360
ctcgacacca cagacacagg ctacttccag tgcgtggcaa caaacggcaa ggaggtggtt    420
tcttccactg gagtcttgtt tgtcaagttt ggccccctc ccactgcaag tccaggatac     480
tcagatgagt atgaagaaga tggattctgt cagccataca gagggattgc atgtgcaaga    540
tttattggca accgcaccgt ctatatggag tctttgcaca tgcaagggga aatagaaaat    600
cagatcacag ctgccttcac tatgattggc acttccagtc acttatctga taagtgttct    660
cagttcgcca ttccttccct gtgccactat gccttcccgt actgcgatga aacttcatcc    720
gtcccaaagc cccgtgactt tgtcgcgat gaatgtgaaa tcctggagaa tgtcctgtgt     780
caaacagagt acattttgc aagatcaaat cccatgattc tgatgaggct gaaactgcca      840
aactgtgaag atctccccca gccagagagc ccagaagctg cgaactgtat ccggattgga    900
attcccatgg cagatcctat aaataaaaat cacaagtgtt ataacagcac aggtgtggac    960
taccggggga ccgtcagtgt gaccaaatca gggcgccagt gccagccatg gaattcccag    1020
tatccccaca cacacacttt caccgcccctt cgtttcccag agctgaatgg aggccattcc   1080
tactgccgca acccagggaa tcaaaaggaa gctccctggt gcttcacctt ggatgaaaac    1140
tttaagtctg atctgtgtga catcccagcg tgcgattcaa aggattccaa ggagaagaat    1200
aaaatggaaa tcctgtacat actagtgcca agtgtggcca ttcccctggc cattgcttta    1260
ctcttcttct tcatttgcgt ctgtcggaat aaccagaagt catcgtcggc accagtccag    1320
aggcaaccaa aacacgtcag aggtcaaaat gtagagatgt caatgctgaa tgcatataaa    1380
cccaagagca aggctaaaga gctacctctt tctgctgtac gctttatgga agaattgggt    1440
gagtgtgcct ttggaaaaat ctataaaggc catctctatc tcccaggcat ggaccatgct    1500
cagctggttg ctatcaagac cttgaaagac tataacaacc ccagcaatg gacggaattt    1560 caacaagaag cctccctaat ggcagaactg caccaccca atattgtctg ccttctaggt     1620
gccgtcactc aggaacaacc tgtgtgcatg cttttgagt atattaatca ggggatctc     1680 catgagttcc tcatcatgag atccccacac tctgatgttg gctgcagcag tgatgaagat    1740
gggactgtga atccagcct ggaccacgga gattttctgc acattgcaat tcagattgca     1800
gctggcatgg aatacctgtc tagtcacttc tttgtccaca aggaccttgc agctcgcaat    1860 atttaatcg gagagcaact tcatgtaaag atttcagact tggggctttc cagagaaatt    1920
tactccgctg attactacag ggtccagagt aagtccttgc tgcccattcg ctggatgccc    1980
cctgaagcca tcatgtatgg caaattctct tctgattcag atatctggtc ctttgggtt    2040 gtcttgtggg agattttcag tttttggactc cagccatatt atggattcag taaccaggaa   2100
gtgattgaga tggtgagaaa acggcagctc ttaccatgct ctgaagactg cccacccaga    2160
atgtacagcc tcatgacaga gtgctggaat gagattcctt ctaggagacc aagatttaaa    2220
gatattcacg tccggcttcg gtcctgggag ggactctcaa gtcacacaag ctctactact    2280
ccttcagggg gaaatgccac cacacagaca acctcccctca gtgccagccc agtgagtaat   2340
ctcagtaacc ccagatatcc taattacatg ttcccgagcc agggtattac accacagggc    2400
cagattgctg gtttcattgg cccgccaata cctcagaacc agcgattcat tcccatcaat    2460
ggatacccaa tacctcctgg atatgcagcg tttccagctg cccactacca gccaacaggt    2520
```

```
cctcccagag tgattcagca ctgcccacct cccaagagtc ggtccccaag cagtgccagt    2580
gggtcgacta gcactggcca tgtgactagc ttgccctcat caggatccaa tcaggaagca    2640
aatattcctt tactaccaca catgtcaatt ccaaatcatc ctggtggaat gggtatcacc    2700
gtttttggca acaaatctca aaaccctac aaaattgact caaagcaagc atctttacta    2760
ggagacgcca atattcatgg acacaccgaa tctatgattt ctgcagaact gtaa         2814
```

<210> SEQ ID NO 2
<211> LENGTH: 937
<212> TYPE: PRT
<213> ORGANISM: Homo sapiens

<400> SEQUENCE: 2

```
Met His Arg Pro Arg Arg Gly Thr Arg Pro Pro Leu Leu Ala Leu
1               5                   10                  15

Leu Ala Ala Leu Leu Ala Ala Arg Gly Ala Ala Gln Glu Thr
            20                  25                  30

Glu Leu Ser Val Ser Ala Glu Leu Val Pro Thr Ser Ser Trp Asn Ile
35                  40                  45

Ser Ser Glu Leu Asn Lys Asp Ser Tyr Leu Thr Leu Asp Glu Pro Met
50                  55                  60

Asn Asn Ile Thr Thr Ser Leu Gly Gln Thr Ala Glu Leu His Cys Lys
65                  70                  75                  80

Val Ser Gly Asn Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
```

```
                    325                 330                 335
Trp Asn Ser Gln Tyr Pro His Thr His Thr Phe Thr Ala Leu Arg Phe
                340                 345                 350
Pro Glu Leu Asn Gly Gly His Ser Tyr Cys Arg Asn Pro Gly Asn Gln
                355                 360                 365
Lys Glu Ala Pro Trp Cys Phe Thr Leu Asp Glu Asn Phe Lys Ser Asp
            370                 375                 380
Leu Cys Asp Ile Pro Ala Cys Asp Ser Lys Asp Ser Lys Glu Lys Asn
385                 390                 395                 400
Lys Met Glu Ile Leu Tyr Ile Leu Val Pro Ser Val Ala Ile Pro Leu
                405                 410                 415
Ala Ile Ala Leu Leu Phe Phe Ile Cys Val Cys Arg Asn Asn Gln
                420                 425                 430
Lys Ser Ser Ser Ala Pro Val Gln Arg Gln Pro Lys His Val Arg Gly
            435                 440                 445
Gln Asn Val Glu Met Ser Met Leu Asn Ala Tyr Lys Pro Lys Ser Lys
        450                 455                 460
Ala Lys Glu Leu Pro Leu Ser Ala Val Arg Phe Met Glu Glu Leu Gly
465                 470                 475                 480
Glu Cys Ala Phe Gly Lys Ile Tyr Lys Gly His Leu Tyr Leu Pro Gly
                485                 490                 495
Met Asp His Ala Gln Leu Val Ala Ile Lys Thr Leu Lys Asp Tyr Asn
            500                 505                 510
Asn Pro Gln Gln Trp Thr Glu Phe Gln Gln Glu Ala Ser Leu Met Ala
            515                 520                 525
Glu Leu His His Pro Asn Ile Val Cys Leu Leu Gly Ala Val Thr Gln
        530                 535                 540
Glu Gln Pro Val Cys Met Leu Phe Glu Tyr Ile Asn Gln Gly Asp Leu
545                 550                 555                 560
His Glu Phe Leu Ile Met Arg Ser Pro His Ser Asp Val Gly Cys Ser
                565                 570                 575
Ser Asp Glu Asp Gly Thr Val Lys Ser Ser Leu Asp His Gly Asp Phe
            580                 585                 590
Leu His Ile Ala Ile Gln Ile Ala Ala Gly Met Glu Tyr Leu Ser Ser
        595                 600                 605
His Phe Phe Val His Lys Asp Leu Ala Ala Arg Asn Ile Leu Ile Gly
        610                 615                 620
Glu Gln Leu His Val Lys Ile Ser Asp Leu Gly Leu Ser Arg Glu Ile
625                 630                 635                 640
Tyr Ser Ala Asp Tyr Tyr Arg Val Gln Ser Lys Ser Leu Leu Pro Ile
                645                 650                 655
Arg Trp Met Pro Pro Glu Ala Ile Met Tyr Gly Lys Phe Ser Ser Asp
                660                 665                 670
Ser Asp Ile Trp Ser Phe Gly Val Val Leu Trp Glu Ile Phe Ser Phe
            675                 680                 685
Gly Leu Gln Pro Tyr Tyr Gly Phe Ser Asn Gln Glu Val Ile Glu Met
        690                 695                 700
Val Arg Lys Arg Gln Leu Leu Pro Cys Ser Glu Asp Cys Pro Pro Arg
705                 710                 715                 720
Met Tyr Ser Leu Met Thr Glu Cys Trp Asn Glu Ile Pro Ser Arg Arg
                725                 730                 735
Pro Arg Phe Lys Asp Ile His Val Arg Leu Arg Ser Trp Glu Gly Leu
                740                 745                 750
```

Ser Ser His Thr Ser Ser Thr Thr Pro Ser Gly Gly Asn Ala Thr Thr
          755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
            805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
    850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
    930                 935

<210> SEQ ID NO 3
<211> LENGTH: 324
<212> TYPE: DNA
<213> ORGANISM: Homo sapiens

<400> SEQUENCE: 3
gccatccgga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tccccctcac tttcggcgga   300
gggaccaagg tggaaatcaa acgt                                          324

<210> SEQ ID NO 4
<211> LENGTH: 108
<212> TYPE: PRT
<213> ORGANISM: Homo sapiens

<400> SEQUENCE: 4

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg
            100                 105

<210> SEQ ID NO 5
<211> LENGTH: 33
<212> TYPE: DNA
<213> ORGANISM: Homo sapiens

<400> SEQUENCE: 5
caggcgagtc aggacattag caactattta aat                                    33

<210> SEQ ID NO 6
<211> LENGTH: 21
<212> TYPE: DNA
<213> ORGANISM: Homo sapiens

<400> SEQUENCE: 6
gatgcatcca atttggaaac a                                                 21

<210> SEQ ID NO 7
<211> LENGTH: 27
<212> TYPE: DNA
<213> ORGANISM: Homo sapiens

<400> SEQUENCE: 7
caacagtatg ataatctccc cctcact                                           27

<210> SEQ ID NO 8
<211> LENGTH: 11
<212> TYPE: PRT
<213> ORGANISM: Homo sapiens

<400> SEQUENCE: 8

Gln Ala Ser Gln Asp Ile Ser Asn Tyr Leu Asn
1               5                   10

<210> SEQ ID NO 9
<211> LENGTH: 7
<212> TYPE: PRT
<213> ORGANISM: Homo sapiens

<400> SEQUENCE: 9

Asp Ala Ser Asn Leu Glu Thr
1               5

<210> SEQ ID NO 10
<211> LENGTH: 9
<212> TYPE: PRT
<213> ORGANISM: Homo sapiens

<400> SEQUENCE: 10

Gln Gln Tyr Asp Asn Leu Pro Leu Thr
1               5

<210> SEQ ID NO 11
<211> LENGTH: 357
<212> TYPE: DNA
<213> ORGANISM: Homo sapiens

<400> SEQUENCE: 11
gaggtgcagc tggtggagtc tgggggaggc ttggtcaagc ctggaggatc cctgagactc       60

```
tcctgtgcag cctctggatt caccttcagt gactactaca tgagctggat ccgccaggct    120
ccagggaagg ggctggagtg ggtttcatac attagtgata gtactaatac catatactac    180
gcagactctg tgaagggccg attcaccgtc tccagggaca accccaaaaa ctcactctat    240
ctgcaaatga tcagcctgag agccgaggac acggccgtgt attattgtgc gagagctgtg    300
ggagctggcg agggctttga ccactggggc cagggaaccc tggtcaccgt ctcctca      357
```

<210> SEQ ID NO 12
<211> LENGTH: 119
<212> TYPE: PRT
<213> ORGANISM: Homo sapiens

<400> SEQUENCE: 12

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Asp Ser Thr Asn Thr Ile Tyr Tyr Ala Asp Ser Val
    50                  55                  60

Lys Gly Arg Phe Thr Val Ser Arg Asp Asn Pro Lys Asn Ser Leu Tyr
65                  70                  75                  80

Leu Gln Met Ile Ser Leu Arg Ala Glu Asp Thr Ala Val Tyr Tyr Cys
                85                  90                  95

Ala Arg Ala Val Gly Ala Gly Glu Gly Phe Asp His Trp Gly Gln Gly
            100                 105                 110

Thr Leu Val Thr Val Ser Ser
        115
```

<210> SEQ ID NO 13
<211> LENGTH: 15
<212> TYPE: DNA
<213> ORGANISM: Homo sapiens

<400> SEQUENCE: 13

```
gactactaca tgagc                                                     15
```

<210> SEQ ID NO 14
<211> LENGTH: 51
<212> TYPE: DNA
<213> ORGANISM: Homo sapiens

<400> SEQUENCE: 14

```
tacattagtg atagtactaa taccatatac tacgcagact ctgtgaaggg c              51
```

<210> SEQ ID NO 15
<211> LENGTH: 30
<212> TYPE: DNA
<213> ORGANISM: Homo sapiens

<400> SEQUENCE: 15

```
gctgtgggag ctggcgaggg ctttgaccac                                      30
```

<210> SEQ ID NO 16
<211> LENGTH: 5
<212> TYPE: PRT
<213> ORGANISM: Homo sapiens

<400> SEQUENCE: 16

Asp Tyr Tyr Met Ser
1               5

<210> SEQ ID NO 17
<211> LENGTH: 17
<212> TYPE: PRT
<213> ORGANISM: Homo sapiens

<400> SEQUENCE: 17

Tyr Ile Ser Asp Ser Thr Asn Thr Ile Tyr Tyr Ala Asp Ser Val Lys
1               5                   10                  15

Gly

<210> SEQ ID NO 18
<211> LENGTH: 10
<212> TYPE: PRT
<213> ORGANISM: Homo sapiens

<400> SEQUENCE: 18

Ala Val Gly Ala Gly Glu Gly Phe Asp His
1               5                   10

<210> SEQ ID NO 19
<211> LENGTH: 324
<212> TYPE: DNA
<213> ORGANISM: Homo sapiens

<400> SEQUENCE: 19
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttaccttca ccatcagcag cctgcagcct     240
gaagatattg caacatatta ctgtcaacag tatgataatc tccccctcac tttcggcgga     300
gggaccaagc tggagatcaa acgt                                            324

<210> SEQ ID NO 20
<211> LENGTH: 108
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Leu Glu Ile Lys Arg
            100                 105

<210> SEQ ID NO 21
<211> LENGTH: 33
<212> TYPE: DNA
<213> ORGANISM: Homo sapiens

<400> SEQUENCE: 21
caggcgagtc aggacattag caactattta aat                          33

<210> SEQ ID NO 22
<211> LENGTH: 21
<212> TYPE: DNA
<213> ORGANISM: Homo sapiens

<400> SEQUENCE: 22
gatgcatcca atttggaaac a                                       21

<210> SEQ ID NO 23
<211> LENGTH: 27
<212> TYPE: DNA
<213> ORGANISM: Homo sapiens

<400> SEQUENCE: 23
caacagtatg ataatctccc cctcact                                 27

<210> SEQ ID NO 24
<211> LENGTH: 11
<212> TYPE: PRT
<213> ORGANISM: Homo sapiens

<400> SEQUENCE: 24

Gln Ala Ser Gln Asp Ile Ser Asn Tyr Leu Asn
1               5                   10

<210> SEQ ID NO 25
<211> LENGTH: 7
<212> TYPE: PRT
<213> ORGANISM: Homo sapiens

<400> SEQUENCE: 25

Asp Ala Ser Asn Leu Glu Thr
1               5

<210> SEQ ID NO 26
<211> LENGTH: 9
<212> TYPE: PRT
<213> ORGANISM: Homo sapiens

<400> SEQUENCE: 26

Gln Gln Tyr Asp Asn Leu Pro Leu Thr
1               5

<210> SEQ ID NO 27
<211> LENGTH: 357
<212> TYPE: DNA
<213> ORGANISM: Homo sapiens

<400> SEQUENCE: 27
gaggtgcagc tggtggagtc tgggggaggc ttggtcaagc ctggagggtc cctgagactc    60
tcctgtgcag cctctggatt caccttcagt gactactaca tgggctgggt ccgccaggct   120
ccggggaagg gccttaagtg gctttcatac attagtgatc gtgcgcatac catatacgac   180
acagactctg tgaagggccg attcaccatt tccaggacg acgccaagag ttcgctttat   240
ctgcgaatga acaacctgag agtcgaggac acggccgttt actactgtgc gagggcagtg   300

```
ggagctgggg agggctttga ctactggggc caaggcaccc tggtgaccgt ctcctca      357
```

<210> SEQ ID NO 28
<211> LENGTH: 119
<212> TYPE: PRT
<213> ORGANISM: Homo sapiens

<400> SEQUENCE: 28

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Gly Trp Val Arg Gln Ala Pro Gly Lys Gly Leu Lys Trp Leu
        35                  40                  45

Ser Tyr Ile Ser Asp Arg Ala His Thr Ile Tyr Asp Thr Asp Ser Val
    50                  55                  60

Lys Gly Arg Phe Thr Ile Ser Arg Asp Asp Ala Lys Ser Ser Leu Tyr
65                  70                  75                  80

Leu Arg Met Asn Asn Leu Arg Val Glu Asp Thr Ala Val Tyr Tyr Cys
                85                  90                  95

Ala Arg Ala Val Gly Ala Gly Glu Gly Phe Asp Tyr Trp Gly Gln Gly
            100                 105                 110

Thr Leu Val Thr Val Ser Ser
        115
```

<210> SEQ ID NO 29
<211> LENGTH: 15
<212> TYPE: DNA
<213> ORGANISM: Homo sapiens

<400> SEQUENCE: 29

```
gactactaca tgggc                                                   15
```

<210> SEQ ID NO 30
<211> LENGTH: 51
<212> TYPE: DNA
<213> ORGANISM: Homo sapiens

<400> SEQUENCE: 30

```
tacattagtg atcgtgcgca taccatatac gacacagact ctgtgaaggg c            51
```

<210> SEQ ID NO 31
<211> LENGTH: 30
<212> TYPE: DNA
<213> ORGANISM: Homo sapiens

<400> SEQUENCE: 31

```
gcagtgggag ctggggaggg ctttgactac                                   30
```

<210> SEQ ID NO 32
<211> LENGTH: 5
<212> TYPE: PRT
<213> ORGANISM: Homo sapiens

<400> SEQUENCE: 32

```
Asp Tyr Tyr Met Gly
1               5
```

<210> SEQ ID NO 33
<211> LENGTH: 17

<212> TYPE: PRT
<213> ORGANISM: Homo sapiens

<400> SEQUENCE: 33

Tyr Ile Ser Asp Arg Ala His Thr Ile Tyr Asp Thr Asp Ser Val Lys
1               5                   10                  15

Gly

<210> SEQ ID NO 34
<211> LENGTH: 10
<212> TYPE: PRT
<213> ORGANISM: Homo sapiens

<400> SEQUENCE: 34

Ala Val Gly Ala Gly Glu Gly Phe Asp Tyr
1               5                   10

<210> SEQ ID NO 35
<211> LENGTH: 333
<212> TYPE: DNA
<213> ORGANISM: Homo sapiens

<400> SEQUENCE: 35
cagtctgccc tgactcagcc tgcctccgtg tctgggtctc ctggacagtc gatcaccatc      60
tcctgcactg gaaccagcag tgactttggt gattatgact atgtctcttg gtaccaacaa     120
cacccaggca aagcccccaa actcatgatt tatgatgtca gtgatcggcc ctcaggggtt     180
tctaatcgct tctctggctc caagtctggc aacacggcct ccctgaccat ctctgggctc     240
caggctgagg acgaggctga ttatttctgc agctcattta caaccagcag cactctggtg     300
ttcggcggag ggaccaagct gaccgtccta ggt                                  333

<210> SEQ ID NO 36
<211> LENGTH: 111
<212> TYPE: PRT
<213> ORGANISM: Homo sapiens

<400> SEQUENCE: 36

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Phe Gly Asp Tyr
                20                  25                  30

Asp Tyr Val Ser Trp Tyr Gln Gln His Pro Gly Lys Ala Pro Lys Leu
            35                  40                  45

Met Ile Tyr Asp Val Ser Asp Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Phe Thr Thr Ser
                85                  90                  95

Ser Thr Leu Val Phe Gly Gly Gly Thr Lys Leu Thr Val Leu Gly
            100                 105                 110

<210> SEQ ID NO 37
<211> LENGTH: 42
<212> TYPE: DNA
<213> ORGANISM: Homo sapiens

<400> SEQUENCE: 37
actggaacca gcagtgactt tggtgattat gactatgtct ct                         42

-continued

<210> SEQ ID NO 38
<211> LENGTH: 21
<212> TYPE: DNA
<213> ORGANISM: Homo sapiens

<400> SEQUENCE: 38
gatgtcagtg atcggccctc a                                              21

<210> SEQ ID NO 39
<211> LENGTH: 30
<212> TYPE: DNA
<213> ORGANISM: Homo sapiens

<400> SEQUENCE: 39
agctcattta caaccagcag cactctggtg                                     30

<210> SEQ ID NO 40
<211> LENGTH: 14
<212> TYPE: PRT
<213> ORGANISM: Homo sapiens

<400> SEQUENCE: 40

Thr Gly Thr Ser Ser Asp Phe Gly Asp Tyr Asp Tyr Val Ser
1               5                   10

<210> SEQ ID NO 41
<211> LENGTH: 7
<212> TYPE: PRT
<213> ORGANISM: Homo sapiens

<400> SEQUENCE: 41

Asp Val Ser Asp Arg Pro Ser
1               5

<210> SEQ ID NO 42
<211> LENGTH: 10
<212> TYPE: PRT
<213> ORGANISM: Homo sapiens

<400> SEQUENCE: 42

Ser Ser Phe Thr Thr Ser Ser Thr Leu Val
1               5                   10

<210> SEQ ID NO 43
<211> LENGTH: 366
<212> TYPE: DNA
<213> ORGANISM: Homo sapiens

<400> SEQUENCE: 43
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccta acagtggtgg cacaaactat     180
gcacagaagt ttcagggcag ggtcaccatg accaggaca cgtccatcag cacagcctac    240
atggagctga gcaggctgag atctgacgac acggccgtgt attactgtgc gagagatggg    300
gatatggtct atgatagtag tgggcctgac tactggggcc agggaaccct ggtcaccgtc    360
tcctca                                                              366

<210> SEQ ID NO 44
<211> LENGTH: 122
<212> TYPE: PRT
<213> ORGANISM: Homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Asp Met Val Tyr Ser Ser Gly Pro Asp Tyr Trp
            100                 105                 110

Gly Gln Gly Thr Leu Val Thr Val Ser Ser
        115                 120

<210> SEQ ID NO 45
<211> LENGTH: 15
<212> TYPE: DNA
<213> ORGANISM: Homo sapiens

<400> SEQUENCE: 45
ggctactata tgcac                                                15

<210> SEQ ID NO 46
<211> LENGTH: 51
<212> TYPE: DNA
<213> ORGANISM: Homo sapiens

<400> SEQUENCE: 46
tggatcaacc ctaacagtgg tggcacaaac tatgcacaga gtttcaggg c          51

<210> SEQ ID NO 47
<211> LENGTH: 39
<212> TYPE: DNA
<213> ORGANISM: Homo sapiens

<400> SEQUENCE: 47
gatggggata tggtctatga tagtagtggg cctgactac                      39

<210> SEQ ID NO 48
<211> LENGTH: 5
<212> TYPE: PRT
<213> ORGANISM: Homo sapiens

<400> SEQUENCE: 48

Gly Tyr Tyr Met His
1               5

<210> SEQ ID NO 49
<211> LENGTH: 17
<212> TYPE: PRT
<213> ORGANISM: Homo sapiens

<400> SEQUENCE: 49

Trp Ile Asn Pro Asn Ser Gly Gly Thr Asn Tyr Ala Gln Lys Phe Gln
1               5                   10                  15

Gly

<210> SEQ ID NO 50
<211> LENGTH: 13
<212> TYPE: PRT
<213> ORGANISM: Homo sapiens

<400> SEQUENCE: 50

Asp Gly Asp Met Val Tyr Asp Ser Ser Gly Pro Asp Tyr
1               5                   10

<210> SEQ ID NO 51
<211> LENGTH: 333
<212> TYPE: DNA
<213> ORGANISM: Homo sapiens

<400> SEQUENCE: 51

```
cagtctgtgc tgactcagcc accctcagcg tctggggccc ccgggcagag ggtcaccatc      60
tcctgttccg gaggcatctc caacgtcggg actaatggtg ttaactggta ccagcacctc     120
ccaggaacgg cccccaaact cctcgtcgat gctatgaatc agcggccctc aggagtccct     180
gaccgattct ctggctccag gtctggcacg tcaggctccc tggccatcac tgggctccgg     240
tctgaagatg aggctgacta ttattgtgca acatgggatg acagcctgag tggtgtacta     300
ttcggcggag ggaccaagct gaccgtccta ggt                                  333
```

<210> SEQ ID NO 52
<211> LENGTH: 111
<212> TYPE: PRT
<213> ORGANISM: Homo sapiens

<400> SEQUENCE: 52

Gln Ser Val Leu Thr Gln Pro Pro Ser Ala Ser Gly Ala Pro Gly Gln
1               5                   10                  15

Arg Val Thr Ile Ser Cys Ser Gly Gly Ile Ser Asn Val Gly Thr Asn
            20                  25                  30

Gly Val Asn Trp Tyr Gln His Leu Pro Gly Thr Ala Pro Lys Leu Leu
        35                  40                  45

Val Asp Ala Met Asn Gln Arg Pro Ser Gly Val Pro Asp Arg Phe Ser
    50                  55                  60

Gly Ser Arg Ser Gly Thr Ser Gly Ser Leu Ala Ile Thr Gly Leu Arg
65                  70                  75                  80

Ser Glu Asp Glu Ala Asp Tyr Tyr Cys Ala Thr Trp Asp Asp Ser Leu
                85                  90                  95

Ser Gly Val Leu Phe Gly Gly Gly Thr Lys Leu Thr Val Leu Gly
            100                 105                 110

<210> SEQ ID NO 53
<211> LENGTH: 39
<212> TYPE: DNA
<213> ORGANISM: Homo sapiens

<400> SEQUENCE: 53

```
tccggaggca tctccaacgt cgggactaat ggtgttaac                             39
```

<210> SEQ ID NO 54
<211> LENGTH: 21
<212> TYPE: DNA
<213> ORGANISM: Homo sapiens

<400> SEQUENCE: 54

```
gctatgaatc agcggccctc a                                              21

<210> SEQ ID NO 55
<211> LENGTH: 33
<212> TYPE: DNA
<213> ORGANISM: Homo sapiens

<400> SEQUENCE: 55
gcaacatggg atgacagcct gagtggtgta cta                                 33

<210> SEQ ID NO 56
<211> LENGTH: 13
<212> TYPE: PRT
<213> ORGANISM: Homo sapiens

<400> SEQUENCE: 56

Ser Gly Gly Ile Ser Asn Val Gly Thr Asn Gly Val Asn
1               5                   10

<210> SEQ ID NO 57
<211> LENGTH: 7
<212> TYPE: PRT
<213> ORGANISM: Homo sapiens

<400> SEQUENCE: 57

Ala Met Asn Gln Arg Pro Ser
1               5

<210> SEQ ID NO 58
<211> LENGTH: 11
<212> TYPE: PRT
<213> ORGANISM: Homo sapiens

<400> SEQUENCE: 58

Ala Thr Trp Asp Asp Ser Leu Ser Gly Val Leu
1               5                   10

<210> SEQ ID NO 59
<211> LENGTH: 354
<212> TYPE: DNA
<213> ORGANISM: Homo sapiens

<400> SEQUENCE: 59
gaggtgcagc tggtgcagtc tggcccagga ctggtgaagc cttcgggac cctgtccctc     60 acctgcgctg tctctggtgg ctccatcagc agtagtaact ggtggagttg ggtccgccag    120
cccccaggga aggggctgga gtggattggg gaaatctatc atagtgggag caccaactac    180
aacccgtccc tcaagagtcg agtcaccata tcagtagaca gtccaagaa ccagttctcc    240 ctgaagctgg gctctgtgac cgccgcggac acagccacat attactgtgc gcgcgatctg    300
tggctgggtg agtgggattt gtggggccaa ggcaccctgg tcaccgtctc ctca          354

<210> SEQ ID NO 60
<211> LENGTH: 118
<212> TYPE: PRT
<213> ORGANISM: Homo sapiens

<400> SEQUENCE: 60

Glu Val Gln Leu Val Gln Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30
```

```
Asn Trp Trp Ser Trp Val Arg Gln Pro Pro Gly Lys Gly Leu Glu Trp
        35                  40                  45
Ile Gly Glu Ile Tyr His Ser Gly Ser Thr Asn Tyr Asn Pro Ser Leu
 50                  55                  60
Lys Ser Arg Val Thr Ile Ser Val Asp Lys Ser Lys Asn Gln Phe Ser
 65                  70                  75                  80
Leu Lys Leu Gly Ser Val Thr Ala Ala Asp Thr Ala Thr Tyr Tyr Cys
                 85                  90                  95
Ala Arg Asp Leu Trp Leu Gly Glu Trp Asp Leu Trp Gly Gln Gly Thr
            100                 105                 110
Leu Val Thr Val Ser Ser
            115

<210> SEQ ID NO 61
<211> LENGTH: 18
<212> TYPE: DNA
<213> ORGANISM: Homo sapiens

<400> SEQUENCE: 61
agtagtaact ggtggagt                                                    18

<210> SEQ ID NO 62
<211> LENGTH: 48
<212> TYPE: DNA
<213> ORGANISM: Homo sapiens

<400> SEQUENCE: 62
gaaatctatc atagtgggag caccaactac aacccgtccc tcaagagt                   48

<210> SEQ ID NO 63
<211> LENGTH: 27
<212> TYPE: DNA
<213> ORGANISM: Homo sapiens

<400> SEQUENCE: 63
gatctgtggc tgggtgagtg ggatttg                                          27

<210> SEQ ID NO 64
<211> LENGTH: 6
<212> TYPE: PRT
<213> ORGANISM: Homo sapiens

<400> SEQUENCE: 64

Ser Ser Asn Trp Trp Ser
 1               5

<210> SEQ ID NO 65
<211> LENGTH: 16
<212> TYPE: PRT
<213> ORGANISM: Homo sapiens

<400> SEQUENCE: 65

Glu Ile Tyr His Ser Gly Ser Thr Asn Tyr Asn Pro Ser Leu Lys Ser
 1               5                  10                  15

<210> SEQ ID NO 66
<211> LENGTH: 9
<212> TYPE: PRT
<213> ORGANISM: Homo sapiens

<400> SEQUENCE: 66
```

```
Asp Leu Trp Leu Gly Glu Trp Asp Leu
1               5
```

<210> SEQ ID NO 67
<211> LENGTH: 327
<212> TYPE: DNA
<213> ORGANISM: Homo sapiens

<400> SEQUENCE: 67

```
gaaattgtgt tgacgcagtc tccagacacc ctgtccttgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctccgta cacttttggc    300
caggggacca aggtggaaat caaacgt                                         327
```

<210> SEQ ID NO 68
<211> LENGTH: 109
<212> TYPE: PRT
<213> ORGANISM: Homo sapiens

<400> SEQUENCE: 68

```
Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Val Glu Ile Lys Arg
            100                 105
```

<210> SEQ ID NO 69
<211> LENGTH: 33
<212> TYPE: DNA
<213> ORGANISM: Homo sapiens

<400> SEQUENCE: 69

```
agggccagtc agagtgttag cagcaactta gcc                                   33
```

<210> SEQ ID NO 70
<211> LENGTH: 21
<212> TYPE: DNA
<213> ORGANISM: Homo sapiens

<400> SEQUENCE: 70

```
ggtgcatcca ccagggccac t                                                21
```

<210> SEQ ID NO 71
<211> LENGTH: 30
<212> TYPE: DNA
<213> ORGANISM: Homo sapiens

<400> SEQUENCE: 71
cagcagtata ataactggcc tccgtacact         30

<210> SEQ ID NO 72
<211> LENGTH: 11
<212> TYPE: PRT
<213> ORGANISM: Homo sapiens

<400> SEQUENCE: 72

Arg Ala Ser Gln Ser Val Ser Ser Asn Leu Ala
1               5                   10

<210> SEQ ID NO 73
<211> LENGTH: 7
<212> TYPE: PRT
<213> ORGANISM: Homo sapiens

<400> SEQUENCE: 73

Gly Ala Ser Thr Arg Ala Thr
1               5

<210> SEQ ID NO 74
<211> LENGTH: 10
<212> TYPE: PRT
<213> ORGANISM: Homo sapiens

<400> SEQUENCE: 74

Gln Gln Tyr Asn Asn Trp Pro Pro Tyr Thr
1               5                   10

<210> SEQ ID NO 75
<211> LENGTH: 375
<212> TYPE: DNA
<213> ORGANISM: Homo sapiens

<400> SEQUENCE: 75
caggtcacct tgaaggagtc tgggcccacg ctggtgaaac ccacacagac cctcacgctg         60
acgtgcacct tctctggctt ctcactcagt agttttggag tggctgtggg ctggttccgt        120
cagcccccag gaaaggccct ggagtggctt ggacttattt attgggatga tgataagcgc        180
tacagcccat ctctgaagac caggctcacc atcaccaagg acacctccaa aaaccaggtg        240
gtccttacaa tgaccaacat ggaccctgtg gacacagcca catattattg tgcccacaaa        300
gggggtatag caacaactgg cagccccaac tggttcgacc cctggggcca gggaaccctg        360
gtcaccgtct cctca                                                        375

<210> SEQ ID NO 76
<211> LENGTH: 125
<212> TYPE: PRT
<213> ORGANISM: Homo sapiens

<400> SEQUENCE: 76

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ser Phe
            20                  25                  30

Gly Val Ala Val Gly Trp Phe Arg Gln Pro Pro Gly Lys Ala Leu Glu
        35                  40                  45

Trp Leu Gly Leu Ile Tyr Trp Asp Asp Asp Lys Arg Tyr Ser Pro Ser
    50                  55                  60

Leu Lys Thr Arg Leu Thr Ile Thr Lys Asp Thr Ser Lys Asn Gln Val

```
            65                  70                  75                  80
Val Leu Thr Met Thr Asn Met Asp Pro Val Asp Thr Ala Thr Tyr Tyr
                    85                  90                  95

Cys Ala His Lys Gly Gly Ile Ala Thr Thr Gly Ser Pro Asn Trp Phe
                100                 105                 110

Asp Pro Trp Gly Gln Gly Thr Leu Val Thr Val Ser Ser
                115                 120                 125
```

<210> SEQ ID NO 77
<211> LENGTH: 21
<212> TYPE: DNA
<213> ORGANISM: Homo sapiens

<400> SEQUENCE: 77
agttttggag tggctgtggg c                                        21

<210> SEQ ID NO 78
<211> LENGTH: 48
<212> TYPE: DNA
<213> ORGANISM: Homo sapiens

<400> SEQUENCE: 78
cttatttatt gggatgatga taagcgctac agcccatctc tgaagacc           48

<210> SEQ ID NO 79
<211> LENGTH: 45
<212> TYPE: DNA
<213> ORGANISM: Homo sapiens

<400> SEQUENCE: 79 aaaggggta tagcaacaac tggcagcccc aactggttcg acccc               45

<210> SEQ ID NO 80
<211> LENGTH: 7
<212> TYPE: PRT
<213> ORGANISM: Homo sapiens

<400> SEQUENCE: 80

Ser Phe Gly Val Ala Val Gly
1               5

<210> SEQ ID NO 81
<211> LENGTH: 16
<212> TYPE: PRT
<213> ORGANISM: Homo sapiens

<400> SEQUENCE: 81

Leu Ile Tyr Trp Asp Asp Asp Lys Arg Tyr Ser Pro Ser Leu Lys Thr
1               5                   10                  15

<210> SEQ ID NO 82
<211> LENGTH: 15
<212> TYPE: PRT
<213> ORGANISM: Homo sapiens

<400> SEQUENCE: 82

Lys Gly Gly Ile Ala Thr Thr Gly Ser Pro Asn Trp Phe Asp Pro
1               5                   10                  15

<210> SEQ ID NO 83
<211> LENGTH: 318
<212> TYPE: DNA
<213> ORGANISM: Homo sapiens

<400> SEQUENCE: 83

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gcctttttgg ccaggggacc   300
aaggtggaga tcaaacgt                                                 318
```

<210> SEQ ID NO 84
<211> LENGTH: 106
<212> TYPE: PRT
<213> ORGANISM: Homo sapiens

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Phe
                85                  90                  95

Gly Gln Gly Thr Lys Val Glu Ile Lys Arg
            100                 105

<210> SEQ ID NO 85
<211> LENGTH: 37
<212> TYPE: DNA
<213> ORGANISM: Homo sapiens

<400> SEQUENCE: 85

```
agggccagtc agagtgttag cagcagctac ttagcct                             37
```

<210> SEQ ID NO 86
<211> LENGTH: 21
<212> TYPE: DNA
<213> ORGANISM: Homo sapiens

<400> SEQUENCE: 86

```
ggtgcatcca gcagggccac t                                              21
```

<210> SEQ ID NO 87
<211> LENGTH: 18
<212> TYPE: DNA
<213> ORGANISM: Homo sapiens

<400> SEQUENCE: 87

```
cagcagtatg gtagcctt                                                  18
```

<210> SEQ ID NO 88
<211> LENGTH: 12
<212> TYPE: PRT
<213> ORGANISM: Homo sapiens

<400> SEQUENCE: 88

Arg Ala Ser Gln Ser Val Ser Ser Ser Tyr Leu Ala
1               5                   10

<210> SEQ ID NO 89
<211> LENGTH: 7
<212> TYPE: PRT
<213> ORGANISM: Homo sapiens

<400> SEQUENCE: 89

Gly Ala Ser Ser Arg Ala Thr
1               5

<210> SEQ ID NO 90
<211> LENGTH: 6
<212> TYPE: PRT
<213> ORGANISM: Homo sapiens

<400> SEQUENCE: 90

Gln Gln Tyr Gly Ser Leu
1               5

<210> SEQ ID NO 91
<211> LENGTH: 354
<212> TYPE: DNA
<213> ORGANISM: Homo sapiens

<400> SEQUENCE: 91

```
gaggtccagc tggtacagtc tggggctgag gtgaggaaac ctgggtcctc ggtgaaggtc      60
tcctgcaagg cctctggagg ctccctcagc agtcatggtg tcagttgggt cgtcaggcc     120 cctggacaag gcttgagtg gatggccagg atcatcccca tgtttggtct aacagactac     180
gcacagaact tccaggccag agtcacgatt ccgcggaca gatccacgaa cacagtttac     240
atggagatca gcaacctggg atctgaagac acggccgtct atttctgtgc gagagagagt     300
ctgggagcaa catttgagta ttggggccag ggaaccctgg tcaccgtctc ctca          354
```

<210> SEQ ID NO 92
<211> LENGTH: 118
<212> TYPE: PRT
<213> ORGANISM: Homo sapiens

<400> SEQUENCE: 92

Glu Val Gln Leu Val Gln Ser Gly Ala Glu Val Arg Lys Pro Gly Ser
1               5                   10                  15

Ser Val Lys Val Ser Cys Lys Ala Ser Gly Gly Ser Leu Ser Ser His
                20                  25                  30

Gly Val Ser Trp Val Arg Gln Ala Pro Gly Gln Gly Leu Glu Trp Met
            35                  40                  45

Ala Arg Ile Ile Pro Met Phe Gly Leu Thr Asp Tyr Ala Gln Asn Phe
        50                  55                  60

Gln Ala Arg Val Thr Ile Ser Ala Asp Arg Ser Thr Asn Thr Val Tyr
65                  70                  75                  80

Met Glu Ile Ser Asn Leu Gly Ser Glu Asp Thr Ala Val Tyr Phe Cys
                85                  90                  95

Ala Arg Glu Ser Leu Gly Ala Thr Phe Glu Tyr Trp Gly Gln Gly Thr
            100                 105                 110

Leu Val Thr Val Ser Ser
            115

<210> SEQ ID NO 93
<211> LENGTH: 15
<212> TYPE: DNA
<213> ORGANISM: Homo sapiens

<400> SEQUENCE: 93
agtcatggtg tcagt                                                    15

<210> SEQ ID NO 94
<211> LENGTH: 51
<212> TYPE: DNA
<213> ORGANISM: Homo sapiens

<400> SEQUENCE: 94
aggatcatcc ccatgtttgg tctaacagac tacgcacaga acttccaggc c            51

<210> SEQ ID NO 95
<211> LENGTH: 27
<212> TYPE: DNA
<213> ORGANISM: Homo sapiens

<400> SEQUENCE: 95
gagagtctgg gagcaacatt tgagtat                                       27

<210> SEQ ID NO 96
<211> LENGTH: 5
<212> TYPE: PRT
<213> ORGANISM: Homo sapiens

<400> SEQUENCE: 96

Ser His Gly Val Ser
1               5

<210> SEQ ID NO 97
<211> LENGTH: 17
<212> TYPE: PRT
<213> ORGANISM: Homo sapiens

<400> SEQUENCE: 97

Arg Ile Ile Pro Met Phe Gly Leu Thr Asp Tyr Ala Gln Asn Phe Gln
1               5                   10                  15

Ala

<210> SEQ ID NO 98
<211> LENGTH: 9
<212> TYPE: PRT
<213> ORGANISM: Homo sapiens

<400> SEQUENCE: 98

Glu Ser Leu Gly Ala Thr Phe Glu Tyr
1               5

<210> SEQ ID NO 99
<211> LENGTH: 333
<212> TYPE: DNA
<213> ORGANISM: Homo sapiens

<400> SEQUENCE: 99
cagtctgccc tgactcagcc tgcctccgtg tctgcgtctc ctggacagtc gatcaccatc    60
tcctgcactg gaaccagcag tgacgttggt ggttataact atgtcacctg gtaccaacag   120
cacccaggca aagcccccaa actcatgatt tatgatgtca gtaagcggcc ctcagggggtc   180

```
cttgatcgct tctctggctc caagtctggc aacacggcct ccctgaccat ctctgggctc     240
caggctgagg acgaggctga ttatttctgc agctcatata caagcagttc caccctggtg     300
tttggcggag ggaccaagct gaccgtccta ggt                                  333
```

<210> SEQ ID NO 100
<211> LENGTH: 111
<212> TYPE: PRT
<213> ORGANISM: Homo sapiens

<400> SEQUENCE: 100

```
Gln Ser Ala Leu Thr Gln Pro Ala Ser Val Ser Ala Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Thr Trp Tyr Gln Gln His Pro Gly Lys Ala Pro Lys Leu
         35                  40                  45

Met Ile Tyr Asp Val Ser Lys Arg Pro Ser Gly Val Leu Asp Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Ser Ser Tyr Thr Ser Ser
                 85                  90                  95

Ser Thr Leu Val Phe Gly Gly Gly Thr Lys Leu Thr Val Leu Gly
            100                 105                 110
```

<210> SEQ ID NO 101
<211> LENGTH: 42
<212> TYPE: DNA
<213> ORGANISM: Homo sapiens

<400> SEQUENCE: 101

```
actggaacca gcagtgacgt tggtggttat aactatgtca cc                         42
```

<210> SEQ ID NO 102
<211> LENGTH: 21
<212> TYPE: DNA
<213> ORGANISM: Homo sapiens

<400> SEQUENCE: 102

```
gatgtcagta agcggccctc a                                                21
```

<210> SEQ ID NO 103
<211> LENGTH: 30
<212> TYPE: DNA
<213> ORGANISM: Homo sapiens

<400> SEQUENCE: 103

```
agctcatata caagcagttc caccctggtg                                       30
```

<210> SEQ ID NO 104
<211> LENGTH: 14
<212> TYPE: PRT
<213> ORGANISM: Homo sapiens

<400> SEQUENCE: 104

```
Thr Gly Thr Ser Ser Asp Val Gly Gly Tyr Asn Tyr Val Thr
 1               5                  10
```

<210> SEQ ID NO 105

```
<211> LENGTH: 7
<212> TYPE: PRT
<213> ORGANISM: Homo sapiens

<400> SEQUENCE: 105

Asp Val Ser Lys Arg Pro Ser
1               5

<210> SEQ ID NO 106
<211> LENGTH: 10
<212> TYPE: PRT
<213> ORGANISM: Homo sapiens

<400> SEQUENCE: 106

Ser Ser Tyr Thr Ser Ser Ser Thr Leu Val
1               5                   10

<210> SEQ ID NO 107
<211> LENGTH: 363
<212> TYPE: DNA
<213> ORGANISM: Homo sapiens

<400> SEQUENCE: 107
caggtgcagc tggtgcaatc tggggggaggc ctggtcaagc ctggggggtc cctgagactc      60
tcctgtgcag cctctggatt caccttcggt acctatagca tgaactgggt ccgccaggct     120
ccaggaaagg ggctggagtg ggtctcatcc attagtagta gtagtagtta catatactac     180
gcagactcag tgaagggccg attcaccatc tccagagaca acgccaagaa ctcactgtat     240
ctgcaaatga acagcctgag agccgaggac acggctgtgt attactgtgc gagaggtctc     300
ggtggctgga cccatgatgc ttttgatatc tggggccaag ggaccacggt caccgtctcc     360
tca                                                                   363

<210> SEQ ID NO 108
<211> LENGTH: 121
<212> TYPE: PRT
<213> ORGANISM: Homo sapiens

<400> SEQUENCE: 108

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Gly Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Gly Trp Thr His Asp Ala Phe Asp Ile Trp Gly
            100                 105                 110

Gln Gly Thr Thr Val Thr Val Ser Ser
        115                 120

<210> SEQ ID NO 109
<211> LENGTH: 15
<212> TYPE: DNA
<213> ORGANISM: Homo sapiens
```

<400> SEQUENCE: 109
acctatagca tgaac                                                          15

<210> SEQ ID NO 110
<211> LENGTH: 51
<212> TYPE: DNA
<213> ORGANISM: Homo sapiens

<400> SEQUENCE: 110
tccattagta gtagtagtag ttacatatac tacgcagact cagtgaaggg c                  51

<210> SEQ ID NO 111
<211> LENGTH: 36
<212> TYPE: DNA
<213> ORGANISM: Homo sapiens

<400> SEQUENCE: 111
ggtctcggtg gctggaccca tgatgctttt gatatc                                   36

<210> SEQ ID NO 112
<211> LENGTH: 5
<212> TYPE: PRT
<213> ORGANISM: Homo sapiens

<400> SEQUENCE: 112

Thr Tyr Ser Met Asn
1               5

<210> SEQ ID NO 113
<211> LENGTH: 17
<212> TYPE: PRT
<213> ORGANISM: Homo sapiens

<400> SEQUENCE: 113

Ser Ile Ser Ser Ser Ser Ser Tyr Ile Tyr Tyr Ala Asp Ser Val Lys
1               5                   10                  15

Gly

<210> SEQ ID NO 114
<211> LENGTH: 12
<212> TYPE: PRT
<213> ORGANISM: Homo sapiens

<400> SEQUENCE: 114

Gly Leu Gly Gly Trp Thr His Asp Ala Phe Asp Ile
1               5                   10

<210> SEQ ID NO 115
<211> LENGTH: 336
<212> TYPE: DNA
<213> ORGANISM: Homo sapiens

<400> SEQUENCE: 115
cagtctgtgc tgactcagcc tgcctccgtg tctgggtctc ctggacagtc gatcaccatc          60
tcctgcactg gaaccagcag tgacgttggt ggttataact atgtctcctg gtaccaacaa         120
cacccaggca aagcccccaa actcatgatt tatgatgtca gtaatcggcc ctcaggggtt         180
tctaatcgct tctctggctc caagtctggc aacacggcct ccctgaccat ctctgggctc         240
caggctgagg acgaggctga ttattactgc agctcatata caagcagcag cactctttgg         300
gtgttcggcg gagggaccaa gctgaccgtc ctaggt                                  336

<210> SEQ ID NO 116
<211> LENGTH: 112
<212> TYPE: PRT
<213> ORGANISM: Homo sapiens

<400> SEQUENCE: 116

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Trp Val Phe Gly Gly Gly Thr Lys Leu Thr Val Leu Gly
            100                 105                 110
```

<210> SEQ ID NO 117
<211> LENGTH: 42
<212> TYPE: DNA
<213> ORGANISM: Homo sapiens

<400> SEQUENCE: 117
actggaacca gcagtgacgt tggtggttat aactatgtct cc                          42

<210> SEQ ID NO 118
<211> LENGTH: 21
<212> TYPE: DNA
<213> ORGANISM: Homo sapiens

<400> SEQUENCE: 118
gatgtcagta atcggccctc a                                                 21

<210> SEQ ID NO 119
<211> LENGTH: 33
<212> TYPE: DNA
<213> ORGANISM: Homo sapiens

<400> SEQUENCE: 119
agctcatata caagcagcag cactctttgg gtg                                    33

<210> SEQ ID NO 120
<211> LENGTH: 14
<212> TYPE: PRT
<213> ORGANISM: Homo sapiens

<400> SEQUENCE: 120

```
Thr Gly Thr Ser Ser Asp Val Gly Gly Tyr Asn Tyr Val Ser
 1               5                  10
```

<210> SEQ ID NO 121
<211> LENGTH: 7
<212> TYPE: PRT
<213> ORGANISM: Homo sapiens

<400> SEQUENCE: 121

Asp Val Ser Asn Arg Pro Ser
1               5

<210> SEQ ID NO 122
<211> LENGTH: 11
<212> TYPE: PRT
<213> ORGANISM: Homo sapiens

<400> SEQUENCE: 122

Ser Ser Tyr Thr Ser Ser Ser Thr Leu Trp Val
1               5                   10

<210> SEQ ID NO 123
<211> LENGTH: 360
<212> TYPE: DNA
<213> ORGANISM: Homo sapiens

<400> SEQUENCE: 123
caggtgcagc tggtgcagtc tggagcagag gtgaaaaagc ccggggagtc tctgaagatc    60
tcctgtaagg attctggata cagctttacc aactactggc tcggctgggt gcgccagatg   120
cccgggaaag gcctggagtg gatgggaatc atctatccgg gtgactctga taccagatac   180
agcccgtcct tccgaggcca ggtcaccatc tcagccgaca gtccatcag caccgcctac   240 ctgcagtgga gcagcctgaa ggcctcggac accgccatgt attactgtgc gagacttaat   300
cttgccacac atacagcttt tgacatatgg ggccaaggga ccacggtcac cgtctcctca   360

<210> SEQ ID NO 124
<211> LENGTH: 120
<212> TYPE: PRT
<213> ORGANISM: Homo sapiens

<400> SEQUENCE: 124

Gln Val Gln Leu Val Gln Ser Gly Ala Glu Val Lys Lys Pro Gly Glu
1               5                   10                  15

Ser Leu Lys Ile Ser Cys Lys Asp Ser Gly Tyr Ser Phe Thr Asn Tyr
                20                  25                  30

Trp Leu Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Asn Leu Ala Thr His Thr Ala Phe Asp Ile Trp Gly Gln
            100                 105                 110

Gly Thr Thr Val Thr Val Ser Ser
        115                 120

<210> SEQ ID NO 125
<211> LENGTH: 15
<212> TYPE: DNA
<213> ORGANISM: Homo sapiens

<400> SEQUENCE: 125
aactactggc tcggc                                                     15

<210> SEQ ID NO 126
<211> LENGTH: 51

```
<212> TYPE: DNA
<213> ORGANISM: Homo sapiens

<400> SEQUENCE: 126
atcatctatc cgggtgactc tgataccaga tacagcccgt ccttccgagg c        51

<210> SEQ ID NO 127
<211> LENGTH: 33
<212> TYPE: DNA
<213> ORGANISM: Homo sapiens

<400> SEQUENCE: 127
cttaatcttg ccacacatac agcttttgac ata                            33

<210> SEQ ID NO 128
<211> LENGTH: 5
<212> TYPE: PRT
<213> ORGANISM: Homo sapiens

<400> SEQUENCE: 128

Asn Tyr Trp Leu Gly
1               5

<210> SEQ ID NO 129
<211> LENGTH: 17
<212> TYPE: PRT
<213> ORGANISM: Homo sapiens

<400> SEQUENCE: 129

Ile Ile Tyr Pro Gly Asp Ser Asp Thr Arg Tyr Ser Pro Ser Phe Arg
1               5                   10                  15

Gly

<210> SEQ ID NO 130
<211> LENGTH: 11
<212> TYPE: PRT
<213> ORGANISM: Homo sapiens

<400> SEQUENCE: 130

Leu Asn Leu Ala Thr His Thr Ala Phe Asp Ile
1               5                   10

<210> SEQ ID NO 131
<211> LENGTH: 321
<212> TYPE: DNA
<213> ORGANISM: Homo sapiens

<400> SEQUENCE: 131
gacatccaga tgacccagtc tccatcttct gtgtctgcat ctgtaggaga cagagtcacc    60
atcacttgtc gggcgagtca aggtattagc accttgttgg cctggtatca gcagaaacca   120
gggaaagccc ctaagctcct gatatcttct gcatccagtt tgcaaagtgg ggtcccagca   180
aggttcagcg gcagtggatc tgggacagat ttcactctca ctatcagcag cctgcagcct   240
gaggattttg caacttacta ctgccagcaa agttacagag ccccgacttt cggccagggg   300
accaaggtgg agatcaaacg t                                             321

<210> SEQ ID NO 132
<211> LENGTH: 107
<212> TYPE: PRT
<213> ORGANISM: Homo sapiens

<400> SEQUENCE: 132
```

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Leu
            20                  25                  30

Leu Ala Trp Tyr Gln Lys Pro Gly Lys Ala Pro Lys Leu Leu Ile
        35                  40                  45

Ser Ser Ala Ser Ser Leu Gln Ser Gly Val Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ala Pro Thr
                85                  90                  95

Phe Gly Gln Gly Thr Lys Val Glu Ile Lys Arg
            100                 105
```

<210> SEQ ID NO 133
<211> LENGTH: 33
<212> TYPE: DNA
<213> ORGANISM: Homo sapiens

<400> SEQUENCE: 133
cgggcgagtc aaggtattag caccttgttg gcc          33

<210> SEQ ID NO 134
<211> LENGTH: 21
<212> TYPE: DNA
<213> ORGANISM: Homo sapiens

<400> SEQUENCE: 134
tctgcatcca gtttgcaaag t                      21

<210> SEQ ID NO 135
<211> LENGTH: 24
<212> TYPE: DNA
<213> ORGANISM: Homo sapiens

<400> SEQUENCE: 135
cagcaaagtt acagagcccc gact                   24

<210> SEQ ID NO 136
<211> LENGTH: 11
<212> TYPE: PRT
<213> ORGANISM: Homo sapiens

<400> SEQUENCE: 136

```
Arg Ala Ser Gln Gly Ile Ser Thr Leu Leu Ala
1               5                   10
```

<210> SEQ ID NO 137
<211> LENGTH: 7
<212> TYPE: PRT
<213> ORGANISM: Homo sapiens

<400> SEQUENCE: 137

```
Ser Ala Ser Ser Leu Gln Ser
1               5
```

<210> SEQ ID NO 138
<211> LENGTH: 8
<212> TYPE: PRT
<213> ORGANISM: Homo sapiens

<400> SEQUENCE: 138

Gln Gln Ser Tyr Arg Ala Pro Thr
1               5

<210> SEQ ID NO 139
<211> LENGTH: 357
<212> TYPE: DNA
<213> ORGANISM: Homo sapiens

<400> SEQUENCE: 139
caggtcacct tgaaggagtc tggtcctacg ctgctgaaac ccacacagac cctcacgctg    60
acctgcacct tctctgggtt ctcactcagt actagaggag tggggggtggg ctggatccgt    120 cagcccccag acaggccct ggagtggctt acactcattt attgggatga tgataagcgc    180
tacagccctt ctctaaagag caggctcacc atcaccaagg acacatccaa aaaccaggtg    240
gtccttacaa tgaccaacat ggaatctgtg acacagcca catattactg tgcacagcag    300
actatgaccg gtgcttttga tatctggggc caagggacca cggtcaccgt ctcctca       357

<210> SEQ ID NO 140
<211> LENGTH: 119
<212> TYPE: PRT
<213> ORGANISM: Homo sapiens

<400> SEQUENCE: 140

Gln Val Thr Leu Lys Glu Ser Gly Pro Thr Leu Leu Lys Pro Thr Gln
1               5                   10                  15

Thr Leu Thr Leu Thr Cys Thr Phe Ser Gly Phe Ser Leu Ser Thr Arg
            20                  25                  30

Gly Val Gly Val Gly Trp Ile Arg Gln Pro Pro Gly Gln Ala Leu Glu
        35                  40                  45

Trp Leu Thr Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Glu Ser Val Thr Ala Thr Tyr Tyr
                85                  90                  95

Cys Ala Gln Gln Thr Met Thr Gly Ala Phe Asp Ile Trp Gly Gln Gly
            100                 105                 110

Thr Thr Val Thr Val Ser Ser
        115

<210> SEQ ID NO 141
<211> LENGTH: 21
<212> TYPE: DNA
<213> ORGANISM: Homo sapiens

<400> SEQUENCE: 141
actagaggag tgggggtggg c                                              21

<210> SEQ ID NO 142
<211> LENGTH: 48
<212> TYPE: DNA
<213> ORGANISM: Homo sapiens

<400> SEQUENCE: 142
ctcatttatt gggatgatga taagcgctac agcccttctc taaagagc                 48

```
<210> SEQ ID NO 143
<211> LENGTH: 27
<212> TYPE: DNA
<213> ORGANISM: Homo sapiens

<400> SEQUENCE: 143
cagactatga ccggtgcttt tgatatc                                           27

<210> SEQ ID NO 144
<211> LENGTH: 7
<212> TYPE: PRT
<213> ORGANISM: Homo sapiens

<400> SEQUENCE: 144

Thr Arg Gly Val Gly Val Gly
1               5

<210> SEQ ID NO 145
<211> LENGTH: 16
<212> TYPE: PRT
<213> ORGANISM: Homo sapiens

<400> SEQUENCE: 145

Leu Ile Tyr Trp Asp Asp Asp Lys Arg Tyr Ser Pro Ser Leu Lys Ser
1               5                   10                  15

<210> SEQ ID NO 146
<211> LENGTH: 9
<212> TYPE: PRT
<213> ORGANISM: Homo sapiens

<400> SEQUENCE: 146

Gln Thr Met Thr Gly Ala Phe Asp Ile
1               5

<210> SEQ ID NO 147
<211> LENGTH: 324
<212> TYPE: DNA
<213> ORGANISM: Homo sapiens

<400> SEQUENCE: 147
gacatccagt tgacccagtc tccatcctcc ctgtctgcat ctgtaggaga cagagtcacc        60
atcacttgcc gggcaagtca gaacattaac aactatttaa attggtatca gcagaaacca       120
gggaaagccc ctaagctcct gctctatgct gcatccagtt tgcaaagtgg ggtcccatca       180
aggttcagtg gcagtggatc tgggacagaa ttcactctca ccatcagcag tctgcaccct       240
gaagattttg caacttacta ctgtcaacag agttacaata ccccattcac cttcggccct       300
gggaccaaag tggatatcaa acgt                                              324

<210> SEQ ID NO 148
<211> LENGTH: 108
<212> TYPE: PRT
<213> ORGANISM: Homo sapiens

<400> SEQUENCE: 148

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Leu Leu Leu
        35                  40                  45
```

```
Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu His Pro
 65                  70                  75                  80

Glu Asp Phe Ala Thr Tyr Tyr Cys Gln Gln Ser Tyr Asn Thr Pro Phe
                 85                  90                  95

Thr Phe Gly Pro Gly Thr Lys Val Asp Ile Lys Arg
            100                 105
```

<210> SEQ ID NO 149
<211> LENGTH: 33
<212> TYPE: DNA
<213> ORGANISM: Homo sapiens

<400> SEQUENCE: 149
cgggcaagtc agaacattaa caactattta aat                               33

<210> SEQ ID NO 150
<211> LENGTH: 21
<212> TYPE: DNA
<213> ORGANISM: Homo sapiens

<400> SEQUENCE: 150
gctgcatcca gtttgcaaag t                                           21

<210> SEQ ID NO 151
<211> LENGTH: 27
<212> TYPE: DNA
<213> ORGANISM: Homo sapiens

<400> SEQUENCE: 151
caacagagtt acaataccccc attcacc                                    27

<210> SEQ ID NO 152
<211> LENGTH: 11
<212> TYPE: PRT
<213> ORGANISM: Homo sapiens

<400> SEQUENCE: 152

```
Arg Ala Ser Gln Asn Ile Asn Asn Tyr Leu Asn
 1               5                   10
```

<210> SEQ ID NO 153
<211> LENGTH: 7
<212> TYPE: PRT
<213> ORGANISM: Homo sapiens

<400> SEQUENCE: 153

```
Ala Ala Ser Ser Leu Gln Ser
 1               5
```

<210> SEQ ID NO 154
<211> LENGTH: 9
<212> TYPE: PRT
<213> ORGANISM: Homo sapiens

<400> SEQUENCE: 154

```
Gln Gln Ser Tyr Asn Thr Pro Phe Thr
 1               5
```

<210> SEQ ID NO 155
<211> LENGTH: 375
<212> TYPE: DNA

<213> ORGANISM: Homo sapiens

<400> SEQUENCE: 155

```
caggtacagc tgcagcagtc aggagctgag gtgaagaagc ctggggcctc agtgaaggtc      60
tcctgcaagg cttctggtta cacctctacc aactatggta tcagctgggt gcgacaggcc     120
cctggacaag ggcttgagtg gatgggatgg atcagcactt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagactat     300
tactctgata gtagtggtta ttgggacgat gcttttgata tctggggcca agggacaatg     360
gtcaccgtct cttca                                                      375
```

<210> SEQ ID NO 156
<211> LENGTH: 125
<212> TYPE: PRT
<213> ORGANISM: Homo sapiens

<400> SEQUENCE: 156

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Ser Thr Asn Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Ser Asp Ser Ser Gly Tyr Trp Asp Asp Ala Phe
            100                 105                 110

Asp Ile Trp Gly Gln Gly Thr Met Val Thr Val Ser Ser
        115                 120                 125
```

<210> SEQ ID NO 157
<211> LENGTH: 15
<212> TYPE: DNA
<213> ORGANISM: Homo sapiens

<400> SEQUENCE: 157

```
aactatggta tcagc                                                       15
```

<210> SEQ ID NO 158
<211> LENGTH: 51
<212> TYPE: DNA
<213> ORGANISM: Homo sapiens

<400> SEQUENCE: 158

```
tggatcagca cttacaatgg taacacaaac tatgcacaga agctccaggg c               51
```

<210> SEQ ID NO 159
<211> LENGTH: 48
<212> TYPE: DNA
<213> ORGANISM: Homo sapiens

<400> SEQUENCE: 159

```
gactattact ctgatagtag tggttattgg gacgatgctt ttgatatc                   48
```

<210> SEQ ID NO 160
<211> LENGTH: 5
<212> TYPE: PRT
<213> ORGANISM: Homo sapiens

<400> SEQUENCE: 160

Asn Tyr Gly Ile Ser
1               5

<210> SEQ ID NO 161
<211> LENGTH: 17
<212> TYPE: PRT
<213> ORGANISM: Homo sapiens

<400> SEQUENCE: 161

Trp Ile Ser Thr Tyr Asn Gly Asn Thr Asn Tyr Ala Gln Lys Leu Gln
1               5                   10                  15

Gly

<210> SEQ ID NO 162
<211> LENGTH: 16
<212> TYPE: PRT
<213> ORGANISM: Homo sapiens

<400> SEQUENCE: 162

Asp Tyr Tyr Ser Asp Ser Ser Gly Tyr Trp Asp Ala Phe Asp Ile
1               5                   10                  15

<210> SEQ ID NO 163
<211> LENGTH: 324
<212> TYPE: DNA
<213> ORGANISM: Homo sapiens

<400> SEQUENCE: 163
gacatcgtga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttattttca ccatcagcag cctgcagcct    240
gaagatattg caacatatta ctgtcaacag tttgataatc tcccttacac ttttggccag    300
gggaccaagg tggagatcaa acgt                                            324

<210> SEQ ID NO 164
<211> LENGTH: 108
<212> TYPE: PRT
<213> ORGANISM: Homo sapiens

<400> SEQUENCE: 164

Asp Ile Val Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Ile Phe Thr Ile Ser Ser Leu Gln Pro
65                  70                  75                  80

Glu Asp Ile Ala Thr Tyr Tyr Cys Gln Gln Phe Asp Asn Leu Pro Tyr
            85                  90                  95

Thr Phe Gly Gln Gly Thr Lys Val Glu Ile Lys Arg
            100                 105

<210> SEQ ID NO 165
<211> LENGTH: 33
<212> TYPE: DNA
<213> ORGANISM: Homo sapiens

<400> SEQUENCE: 165
caggcgagtc aggacattag caactattta aat                                    33

<210> SEQ ID NO 166
<211> LENGTH: 21
<212> TYPE: DNA
<213> ORGANISM: Homo sapiens

<400> SEQUENCE: 166
gatgcatcca atttggaaac a                                                 21

<210> SEQ ID NO 167
<211> LENGTH: 27
<212> TYPE: DNA
<213> ORGANISM: Homo sapiens

<400> SEQUENCE: 167
caacagtttg ataatctccc ttacact                                           27

<210> SEQ ID NO 168
<211> LENGTH: 11
<212> TYPE: PRT
<213> ORGANISM: Homo sapiens

<400> SEQUENCE: 168

Gln Ala Ser Gln Asp Ile Ser Asn Tyr Leu Asn
1               5                   10

<210> SEQ ID NO 169
<211> LENGTH: 7
<212> TYPE: PRT
<213> ORGANISM: Homo sapiens

<400> SEQUENCE: 169

Asp Ala Ser Asn Leu Glu Thr
1               5

<210> SEQ ID NO 170
<211> LENGTH: 9
<212> TYPE: PRT
<213> ORGANISM: Homo sapiens

<400> SEQUENCE: 170

Gln Gln Phe Asp Asn Leu Pro Tyr Thr
1               5

<210> SEQ ID NO 171
<211> LENGTH: 363
<212> TYPE: DNA
<213> ORGANISM: Homo sapiens

<400> SEQUENCE: 171
gaggtccagc tggtgcagtc tggggctgag gtgaagaagc ctgggtcctc ggtgaaggtc        60

```
tcctgcaagg cttctggtgg caccttcagc acctttgcga tcaactgggt gcgacaggcc    120
cctggacaag ggcttgagtg gatgggaggg gtcatccctg tctctggaac agaagactac    180
tcacagaagt tccagggcag actctcactt accgcggacg agtccacggg cacagcctac    240
atggagctga gcagcctgag atctgacgac acggccgtgt attactgtgc gagagatcga    300
agtggccgcg attgggacta ctttgactat tggggccagg aaccctggt caccgtctcc    360 tca                                                                   363
```

<210> SEQ ID NO 172
<211> LENGTH: 121
<212> TYPE: PRT
<213> ORGANISM: Homo sapiens

<400> SEQUENCE: 172

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Phe
            20                  25                  30

Ala Ile Asn Trp Val Arg Gln Ala Pro Gly Gln Gly Leu Glu Trp Met
        35                  40                  45

Gly Gly Val Ile Pro Val Ser Gly Thr Glu Asp Tyr Ser Gln Lys Phe
    50                  55                  60

Gln Gly Arg Leu Ser Leu Thr Ala Asp Glu Ser Thr Gly Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Arg Ser Gly Arg Asp Trp Asp Tyr Phe Asp Tyr Trp Gly
            100                 105                 110

Gln Gly Thr Leu Val Thr Val Ser Ser
        115                 120
```

<210> SEQ ID NO 173
<211> LENGTH: 15
<212> TYPE: DNA
<213> ORGANISM: Homo sapiens

<400> SEQUENCE: 173

```
acctttgcga tcaac                                                      15
```

<210> SEQ ID NO 174
<211> LENGTH: 51
<212> TYPE: DNA
<213> ORGANISM: Homo sapiens

<400> SEQUENCE: 174

```
ggggtcatcc ctgtctctgg aacagaagac tactcacaga gttccaggg c              51
```

<210> SEQ ID NO 175
<211> LENGTH: 36
<212> TYPE: DNA
<213> ORGANISM: Homo sapiens

<400> SEQUENCE: 175

```
gatcgaagtg gccgcgattg ggactacttt gactat                              36
```

<210> SEQ ID NO 176
<211> LENGTH: 5
<212> TYPE: PRT
<213> ORGANISM: Homo sapiens

<400> SEQUENCE: 176

Thr Phe Ala Ile Asn
1               5

<210> SEQ ID NO 177
<211> LENGTH: 17
<212> TYPE: PRT
<213> ORGANISM: Homo sapiens

<400> SEQUENCE: 177

Gly Val Ile Pro Val Ser Gly Thr Glu Asp Tyr Ser Gln Lys Phe Gln
1               5                   10                  15

Gly

<210> SEQ ID NO 178
<211> LENGTH: 12
<212> TYPE: PRT
<213> ORGANISM: Homo sapiens

<400> SEQUENCE: 178

Asp Arg Ser Gly Arg Asp Trp Asp Tyr Phe Asp Tyr
1               5                   10

<210> SEQ ID NO 179
<211> LENGTH: 330
<212> TYPE: DNA
<213> ORGANISM: Homo sapiens

<400> SEQUENCE: 179

```
caatctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca agcccccaa actcttgatt tatgaggtca gtcagcggcc ctcaggggtc      180
cctgatcgat tctctggctc caagtctggc aacacggcct ccctgaccgt ctctggcctc     240
caggctgaag atgaggctga ctattattgc agctcatatg caggcgacag ggacgtcttc     300
ggaactggga cccagctcac cgttttaagt                                       330
```

<210> SEQ ID NO 180
<211> LENGTH: 110
<212> TYPE: PRT
<213> ORGANISM: Homo sapiens

<400> SEQUENCE: 180

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Glu Val Ser Gln Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asp
                85                  90                  95

Arg Asp Val Phe Gly Thr Gly Thr Gln Leu Thr Val Leu Ser
            100                 105                 110

<210> SEQ ID NO 181
<211> LENGTH: 42
<212> TYPE: DNA
<213> ORGANISM: Homo sapiens

<400> SEQUENCE: 181
actggaacca gcagtgacgt tggtggttat aactatgtct cc                          42

<210> SEQ ID NO 182
<211> LENGTH: 21
<212> TYPE: DNA
<213> ORGANISM: Homo sapiens

<400> SEQUENCE: 182
gaggtcagtc agcggccctc a                                                 21

<210> SEQ ID NO 183
<211> LENGTH: 27
<212> TYPE: DNA
<213> ORGANISM: Homo sapiens

<400> SEQUENCE: 183
agctcatatg caggcgacag ggacgtc                                           27

<210> SEQ ID NO 184
<211> LENGTH: 14
<212> TYPE: PRT
<213> ORGANISM: Homo sapiens

<400> SEQUENCE: 184

Thr Gly Thr Ser Ser Asp Val Gly Gly Tyr Asn Tyr Val Ser
1               5                   10

<210> SEQ ID NO 185
<211> LENGTH: 7
<212> TYPE: PRT
<213> ORGANISM: Homo sapiens

<400> SEQUENCE: 185

Glu Val Ser Gln Arg Pro Ser
1               5

<210> SEQ ID NO 186
<211> LENGTH: 9
<212> TYPE: PRT
<213> ORGANISM: Homo sapiens

<400> SEQUENCE: 186

Ser Ser Tyr Ala Gly Asp Arg Asp Val
1               5

<210> SEQ ID NO 187
<211> LENGTH: 363
<212> TYPE: DNA
<213> ORGANISM: Homo sapiens

<400> SEQUENCE: 187
cagatgcagc tggtgcagtc tggggggagac ttggtccagc ctggggggtc cctgagactc        60
tcctgtgcag cctctggatt caccttcagt agctatagca tgaactgggt ccgccaggct       120
ccaggaaagg ggctggagtg gtctctcatcc attagtagta gtagtagtta catatactac      180
gcagactcag tgaagggccg attcaccatc tccagagaca acgccaagaa ctcactgtat       240
ctgcaaatga acagcctgag agccgaggac acggctgtgt attactgtgc gagaggtctc    300
ggtggctgga cccatgatgc ttttgatatc tggggccaag ggaccacggt caccgtctcc    360
tca    363

<210> SEQ ID NO 188
<211> LENGTH: 121
<212> TYPE: PRT
<213> ORGANISM: Homo sapiens

<400> SEQUENCE: 188

Gln Met Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Gly Trp Thr His Asp Ala Phe Asp Ile Trp Gly
            100                 105                 110

Gln Gly Thr Thr Val Thr Val Ser Ser
        115                 120

<210> SEQ ID NO 189
<211> LENGTH: 15
<212> TYPE: DNA
<213> ORGANISM: Homo sapiens

<400> SEQUENCE: 189
agctatagca tgaac    15

<210> SEQ ID NO 190
<211> LENGTH: 51
<212> TYPE: DNA
<213> ORGANISM: Homo sapiens

<400> SEQUENCE: 190
tccattagta gtagtagtag ttacatatac tacgcagact cagtgaaggg c    51

<210> SEQ ID NO 191
<211> LENGTH: 36
<212> TYPE: DNA
<213> ORGANISM: Homo sapiens

<400> SEQUENCE: 191
ggtctcggtg gctggaccca tgatgctttt gatatc    36

<210> SEQ ID NO 192
<211> LENGTH: 5
<212> TYPE: PRT
<213> ORGANISM: Homo sapiens

<400> SEQUENCE: 192

Ser Tyr Ser Met Asn
1               5

<210> SEQ ID NO 193
<211> LENGTH: 17
<212> TYPE: PRT
<213> ORGANISM: Homo sapiens

<400> SEQUENCE: 193

Ser Ile Ser Ser Ser Ser Ser Tyr Ile Tyr Tyr Ala Asp Ser Val Lys
1               5                   10                  15

Gly

<210> SEQ ID NO 194
<211> LENGTH: 12
<212> TYPE: PRT
<213> ORGANISM: Homo sapiens

<400> SEQUENCE: 194

Gly Leu Gly Gly Trp Thr His Asp Ala Phe Asp Ile
1               5                   10

<210> SEQ ID NO 195
<211> LENGTH: 333
<212> TYPE: DNA
<213> ORGANISM: Homo sapiens

<400> SEQUENCE: 195
cagtctgccc tgactcagcc accctcagcg tctgggaccc ccgggcagag ggtcaccatc     60
tcttgttctg gaagcagctc caacatcgga agtaattatg tatactggta ccagcagctc    120
ccaggaacgg ccccccaaact cctcatctat aggaataatc agcggccctc aggggtccct   180
gaccgattct ctggctccaa gtctggcacc tcagcctccc tggccatcag tgggctccgg    240
tccgaggatg aggctgatta ttactgtgca gcatgggatg acagcctgag tgcctgggtg    300
ttcggcggag ggaccaagct gaccgtccta ggt                                  333

<210> SEQ ID NO 196
<211> LENGTH: 111
<212> TYPE: PRT
<213> ORGANISM: Homo sapiens

<400> SEQUENCE: 196

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95

Ser Ala Trp Val Phe Gly Gly Gly Thr Lys Leu Thr Val Leu Gly
            100                 105                 110

<210> SEQ ID NO 197
<211> LENGTH: 39
<212> TYPE: DNA
<213> ORGANISM: Homo sapiens

<400> SEQUENCE: 197
tctggaagca gctccaacat cggaagtaat tatgtatac                    39

<210> SEQ ID NO 198
<211> LENGTH: 21
<212> TYPE: DNA
<213> ORGANISM: Homo sapiens

<400> SEQUENCE: 198
aggaataatc agcggccctc a                                       21

<210> SEQ ID NO 199
<211> LENGTH: 33
<212> TYPE: DNA
<213> ORGANISM: Homo sapiens

<400> SEQUENCE: 199
gcagcatggg atgacagcct gagtgcctgg gtg                          33

<210> SEQ ID NO 200
<211> LENGTH: 13
<212> TYPE: PRT
<213> ORGANISM: Homo sapiens

<400> SEQUENCE: 200

Ser Gly Ser Ser Ser Asn Ile Gly Ser Asn Tyr Val Tyr
1               5                   10

<210> SEQ ID NO 201
<211> LENGTH: 7
<212> TYPE: PRT
<213> ORGANISM: Homo sapiens

<400> SEQUENCE: 201

Arg Asn Asn Gln Arg Pro Ser
1               5

<210> SEQ ID NO 202
<211> LENGTH: 11
<212> TYPE: PRT
<213> ORGANISM: Homo sapiens

<400> SEQUENCE: 202

Ala Ala Trp Asp Asp Ser Leu Ser Ala Trp Val
1               5                   10

<210> SEQ ID NO 203
<211> LENGTH: 363
<212> TYPE: DNA
<213> ORGANISM: Homo sapiens

<400> SEQUENCE: 203
caggtacagc tgcagcagtc aggggctgag gtgaagaagc ctggggcctc agtgaaggtt    60
tcctgcaagg catctggata caccttctcc agatactata tccactgggt gcgacaggcc   120
cctggtcaag gcttgagtg gatgggaata tcaacactg atggtggcac cacaacctac   180
gcacagaagt ttcagggcag actcaccatg accaggaca cgtccacgag caccgtctac   240
atggaactga gcagcctgag atctgacgac acggccgtct attactgtgc gagagattat   300
gggactatag atgctcgtcg ttttgactac tggggccagg gaaccctggt caccgtctcc   360
tca                                                          363

<210> SEQ ID NO 204
<211> LENGTH: 121
<212> TYPE: PRT
<213> ORGANISM: Homo sapiens

<400> SEQUENCE: 204

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Ile His Trp Val Arg Gln Ala Pro Gly Gln Gly Leu Glu Trp Met
        35                  40                  45

Gly Ile Ile Asn Thr Asp Gly Gly Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp Tyr Gly Thr Ile Asp Ala Arg Arg Phe Asp Tyr Trp Gly
            100                 105                 110

Gln Gly Thr Leu Val Thr Val Ser Ser
        115                 120

<210> SEQ ID NO 205
<211> LENGTH: 15
<212> TYPE: DNA
<213> ORGANISM: Homo sapiens

<400> SEQUENCE: 205
agatactata tccac                                                    15

<210> SEQ ID NO 206
<211> LENGTH: 51
<212> TYPE: DNA
<213> ORGANISM: Homo sapiens

<400> SEQUENCE: 206
ataatcaaca ctgatggtgg caccacaacc tacgcacaga gtttcaggg c              51

<210> SEQ ID NO 207
<211> LENGTH: 36
<212> TYPE: DNA
<213> ORGANISM: Homo sapiens

<400> SEQUENCE: 207
gattatggga ctatagatgc tcgtcgtttt gactac                              36

<210> SEQ ID NO 208
<211> LENGTH: 5
<212> TYPE: PRT
<213> ORGANISM: Homo sapiens

<400> SEQUENCE: 208

Arg Tyr Tyr Ile His
1               5

<210> SEQ ID NO 209
<211> LENGTH: 17
<212> TYPE: PRT
<213> ORGANISM: Homo sapiens

<400> SEQUENCE: 209

Ile Ile Asn Thr Asp Gly Gly Thr Thr Thr Tyr Ala Gln Lys Phe Gln
1               5                   10                  15

Gly

<210> SEQ ID NO 210
<211> LENGTH: 12
<212> TYPE: PRT
<213> ORGANISM: Homo sapiens

<400> SEQUENCE: 210

Asp Tyr Gly Thr Ile Asp Ala Arg Arg Phe Asp Tyr
1               5                   10

<210> SEQ ID NO 211
<211> LENGTH: 327
<212> TYPE: DNA
<213> ORGANISM: Homo sapiens

<400> SEQUENCE: 211
gaaatagtga tgacgcagtc cccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctccgta cactttggc    300
caggggacca aggtggagat caaacgt                                       327

<210> SEQ ID NO 212
<211> LENGTH: 109
<212> TYPE: PRT
<213> ORGANISM: Homo sapiens

<400> SEQUENCE: 212

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Val Glu Ile Lys Arg
            100                 105

<210> SEQ ID NO 213
<211> LENGTH: 33
<212> TYPE: DNA
<213> ORGANISM: Homo sapiens

<400> SEQUENCE: 213
agggccagtc agagtgttag cagcaactta gcc                                 33

<210> SEQ ID NO 214

```
<211> LENGTH: 21
<212> TYPE: DNA
<213> ORGANISM: Homo sapiens

<400> SEQUENCE: 214
ggtgcatcca ccagggccac t                                              21

<210> SEQ ID NO 215
<211> LENGTH: 30
<212> TYPE: DNA
<213> ORGANISM: Homo sapiens

<400> SEQUENCE: 215
cagcagtata ataactggcc tccgtacact                                     30

<210> SEQ ID NO 216
<211> LENGTH: 11
<212> TYPE: PRT
<213> ORGANISM: Homo sapiens

<400> SEQUENCE: 216

Arg Ala Ser Gln Ser Val Ser Ser Asn Leu Ala
1               5                   10

<210> SEQ ID NO 217
<211> LENGTH: 7
<212> TYPE: PRT
<213> ORGANISM: Homo sapiens

<400> SEQUENCE: 217

Gly Ala Ser Thr Arg Ala Thr
1               5

<210> SEQ ID NO 218
<211> LENGTH: 10
<212> TYPE: PRT
<213> ORGANISM: Homo sapiens

<400> SEQUENCE: 218

Gln Gln Tyr Asn Asn Trp Pro Pro Tyr Thr
1               5                   10

<210> SEQ ID NO 219
<211> LENGTH: 378
<212> TYPE: DNA
<213> ORGANISM: Homo sapiens

<400> SEQUENCE: 219
caggtcacct tgaaggagtc tgggcccacg ctggtgaaac ccacacagac cctcacgctg    60
acgtgcacct tctctggctt ctcactcaat agttttggag tgctgtggg ctggttccgt     120 cagcccccag gaaaggccct ggagtggctt ggacttattt attgggatga tgacaggcgc   180
tacttcccat cgctggaggg caggctctcc atcaccaagg acgcctccga taacaacgtg   240
gtcctgacaa tgatgaacgt ggaccctgcg gacacagcca catattattg tgcacggact   300
tcccctatgg ttcagggaat tgcaaactac tacgctatgg acgtctgggg ccaagggacc   360
acggtcaccg tctcctca                                                 378

<210> SEQ ID NO 220
<211> LENGTH: 126
<212> TYPE: PRT
<213> ORGANISM: Homo sapiens
```

```
<400> SEQUENCE: 220

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Ser Phe
            20                  25                  30

Gly Val Ala Val Gly Trp Phe Arg Gln Pro Pro Gly Lys Ala Leu Glu
        35                  40                  45

Trp Leu Gly Leu Ile Tyr Trp Asp Asp Asp Arg Arg Tyr Phe Pro Ser
    50                  55                  60

Leu Glu Gly Arg Leu Ser Ile Thr Lys Asp Ala Ser Asp Asn Asn Val
65                  70                  75                  80

Val Leu Thr Met Met Asn Val Asp Pro Ala Asp Thr Ala Thr Tyr Tyr
                85                  90                  95

Cys Ala Arg Thr Ser Pro Met Val Gln Gly Ile Ala Asn Tyr Tyr Ala
            100                 105                 110

Met Asp Val Trp Gly Gln Gly Thr Thr Val Thr Val Ser Ser
        115                 120                 125

<210> SEQ ID NO 221
<211> LENGTH: 21
<212> TYPE: DNA
<213> ORGANISM: Homo sapiens

<400> SEQUENCE: 221
agttttggag tggctgtggg c                                          21

<210> SEQ ID NO 222
<211> LENGTH: 48
<212> TYPE: DNA
<213> ORGANISM: Homo sapiens

<400> SEQUENCE: 222
cttatttatt gggatgatga caggcgctac ttcccatcgc tggagggc             48

<210> SEQ ID NO 223
<211> LENGTH: 48
<212> TYPE: DNA
<213> ORGANISM: Homo sapiens

<400> SEQUENCE: 223
acttccccta tggttcaggg aattgcaaac tactacgcta tggacgtc             48

<210> SEQ ID NO 224
<211> LENGTH: 7
<212> TYPE: PRT
<213> ORGANISM: Homo sapiens

<400> SEQUENCE: 224

Ser Phe Gly Val Ala Val Gly
1               5

<210> SEQ ID NO 225
<211> LENGTH: 16
<212> TYPE: PRT
<213> ORGANISM: Homo sapiens

<400> SEQUENCE: 225

Leu Ile Tyr Trp Asp Asp Asp Arg Arg Tyr Phe Pro Ser Leu Glu Gly
1               5                   10                  15
```

<210> SEQ ID NO 226
<211> LENGTH: 16
<212> TYPE: PRT
<213> ORGANISM: Homo sapiens

<400> SEQUENCE: 226

```
Thr Ser Pro Met Val Gln Gly Ile Ala Asn Tyr Tyr Ala Met Asp Val
1               5                   10                  15
```

<210> SEQ ID NO 227
<211> LENGTH: 109
<212> TYPE: PRT
<213> ORGANISM: Homo sapiens

<400> SEQUENCE: 227

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Val Glu Ile Lys Arg
            100                 105
```

<210> SEQ ID NO 228
<211> LENGTH: 126
<212> TYPE: PRT
<213> ORGANISM: Homo sapiens

<400> SEQUENCE: 228

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Ser Phe
            20                  25                  30

Gly Val Ala Val Gly Trp Phe Arg Gln Pro Pro Gly Lys Ala Leu Glu
        35                  40                  45

Trp Leu Gly Leu Ile Tyr Trp Asp Asp Asp Arg Arg Tyr Phe Pro Ser
    50                  55                  60

Leu Glu Gly Arg Leu Ser Ile Thr Lys Asp Ala Ser Asp Asn Asn Val
65                  70                  75                  80

Val Leu Thr Met Met Asn Val Asp Pro Ala Asp Thr Ala Thr Tyr Tyr
                85                  90                  95

Cys Ala Arg Thr Ser Pro Met Val Gln Gly Ile Ala Asn Tyr Tyr Ala
            100                 105                 110

Met Asp Val Trp Gly Gln Gly Thr Thr Val Thr Val Ser Ser
        115                 120                 125
```

<210> SEQ ID NO 229
<211> LENGTH: 327
<212> TYPE: DNA
<213> ORGANISM: Homo sapiens

<400> SEQUENCE: 229

```
gaaatagtga tgacgcagtc cccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctccgta cacttttggc   300
caggggacca aggtggagat caaacgt                                        327
```

<210> SEQ ID NO 230
<211> LENGTH: 378
<212> TYPE: DNA
<213> ORGANISM: Homo sapiens

<400> SEQUENCE: 230

```
caggtcacct tgaaggagtc tggacccacg ctggtgaaac ccacacagac cctcacgctg    60
acgtgcacct ctctctggctt ctcactcaat agttttggag tggctgtggg ctggttccgt   120
cagcccccag gaaaggccct ggagtggctt ggacttattt attgggatga tgacaggcgc   180
tacttcccat cgctggaggg caggctctcc atcaccaagg acgcctccga taacaacgtg   240
gtcctgacaa tgatgaacgt ggaccctgcg gacacagcca catattattg tgcacggact   300
tcccctatgg ttcagggaat tgcaaactac tacgctatgg acgtctgggg ccaagggacc   360
acggtcaccg tctcctca                                                  378
```

<210> SEQ ID NO 231
<211> LENGTH: 16
<212> TYPE: PRT
<213> ORGANISM: Homo sapiens

<400> SEQUENCE: 231

Arg Ser Ser Gln Ser Leu Val His Ser Asp Gly Asn Thr Tyr Leu Asn
1               5                   10                  15

<210> SEQ ID NO 232
<211> LENGTH: 7
<212> TYPE: PRT
<213> ORGANISM: Homo sapiens

<400> SEQUENCE: 232

Lys Val Ser Asn Arg Asp Ser
1               5

<210> SEQ ID NO 233
<211> LENGTH: 9
<212> TYPE: PRT
<213> ORGANISM: Homo sapiens

<400> SEQUENCE: 233

Met Gln Gly Thr Gln Trp Pro Ile Thr
1               5

<210> SEQ ID NO 234
<211> LENGTH: 5
<212> TYPE: PRT
<213> ORGANISM: Homo sapiens

<400> SEQUENCE: 234

Ser Tyr Ser Met Asn
1               5

```
<210> SEQ ID NO 235
<211> LENGTH: 17
<212> TYPE: PRT
<213> ORGANISM: Homo sapiens

<400> SEQUENCE: 235

Tyr Ile Ser Ser Ser Ser Ser Thr Ile Tyr Tyr Ala Asp Ser Val Lys
1               5                   10                  15

Gly

<210> SEQ ID NO 236
<211> LENGTH: 16
<212> TYPE: PRT
<213> ORGANISM: Homo sapiens

<400> SEQUENCE: 236

Asp Tyr Gly Gly Asn Ser Gly Tyr Tyr Tyr Tyr Tyr Tyr Met Asp Val
1               5                   10                  15

<210> SEQ ID NO 237
<211> LENGTH: 23
<212> TYPE: PRT
<213> ORGANISM: Homo sapiens

<400> SEQUENCE: 237

Lys Asn Asp Ala Pro Val Val Gln Glu Pro Arg Arg Leu Ser Phe Arg
1               5                   10                  15

Ser Thr Ile Tyr Gly Ser Arg
            20

<210> SEQ ID NO 238
<211> LENGTH: 15
<212> TYPE: PRT
<213> ORGANISM: Homo sapiens

<400> SEQUENCE: 238

Ala Ala Asn Cys Ile Arg Ile Gly Ile Pro Met Ala Asp Pro Ile
1               5                   10                  15

<210> SEQ ID NO 239
<211> LENGTH: 19
<212> TYPE: PRT
<213> ORGANISM: Homo sapiens

<400> SEQUENCE: 239

Ser Ser Thr Gly Val Leu Phe Val Lys Phe Gly Pro Pro Thr Ala
1               5                   10                  15

Ser Pro Gly

<210> SEQ ID NO 240
<211> LENGTH: 15
<212> TYPE: PRT
<213> ORGANISM: Homo sapiens

<400> SEQUENCE: 240

Ser Asn Pro Met Ile Leu Met Arg Leu Lys Leu Pro Asn Cys Glu
1               5                   10                  15

<210> SEQ ID NO 241
<211> LENGTH: 108
<212> TYPE: PRT
<213> ORGANISM: Homo sapiens

<400> SEQUENCE: 241
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asn Leu Pro Leu
                85                  90                  95

Thr Phe Gly Gly Gly Thr Lys Leu Glu Ile Lys Arg
            100                 105
```

<210> SEQ ID NO 242
<211> LENGTH: 109
<212> TYPE: PRT
<213> ORGANISM: Homo sapiens

<400> SEQUENCE: 242

```
Gln Ser Val Leu Thr Gln Pro Pro Ser Val Ser Val Ala Pro Gly Glu
1               5                   10                  15

Thr Ala Arg Ile Thr Cys Gly Gly Thr Asn Ile Gly Ser Glu Ser Val
            20                  25                  30

His Trp Tyr Gln Gln Arg Pro Gly Gln Ala Pro Val Leu Val Val Tyr
        35                  40                  45

Asp Asp Thr Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Gly Ala Asp Tyr Tyr Cys Gln Val Trp Asp Ser Val Ser Asp Arg
                85                  90                  95

Tyr Val Phe Gly Thr Gly Thr Lys Val Thr Val Leu Gly
            100                 105
```

<210> SEQ ID NO 243
<211> LENGTH: 106
<212> TYPE: PRT
<213> ORGANISM: Homo sapiens

<400> SEQUENCE: 243

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Gly Pro Gly Thr Lys Val Asp Ile Lys Arg
            100                 105
```

<210> SEQ ID NO 244
<211> LENGTH: 110
<212> TYPE: PRT
<213> ORGANISM: Homo sapiens

<400> SEQUENCE: 244

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Phe Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Phe Gly Gly Gly Thr Lys Leu Thr Val Leu Gly
            100                 105                 110

<210> SEQ ID NO 245
<211> LENGTH: 108
<212> TYPE: PRT
<213> ORGANISM: Homo sapiens

<400> SEQUENCE: 245

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 246
<211> LENGTH: 109
<212> TYPE: PRT
<213> ORGANISM: Homo sapiens

<400> SEQUENCE: 246

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Trp Thr Phe Gly Gln Gly Thr Lys Val Glu Ile Lys Arg
            100                 105
```

<210> SEQ ID NO 247
<211> LENGTH: 111
<212> TYPE: PRT
<213> ORGANISM: Homo sapiens

<400> SEQUENCE: 247

```
Gln Ser Ala Leu Thr Gln Pro Pro Ser Ala Ser Gly Thr Pro Gly Gln
  1               5                  10                  15

Arg Val Thr Ile Ser Cys Pro Gly Ser Ser Ser Asn Ile Gly Ser Asn
                 20                  25                  30

Tyr Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Tyr Val Phe Gly Thr Gly Thr Lys Val Thr Val Leu Gly
            100                 105                 110
```

<210> SEQ ID NO 248
<211> LENGTH: 111
<212> TYPE: PRT
<213> ORGANISM: Homo sapiens

<400> SEQUENCE: 248

```
Gln Ser Val Leu Thr Gln Pro Ala Ser Val Ser Gly Ser Pro Gly Gln
  1               5                  10                  15

Ser Ile Thr Ile Ser Cys Thr Gly Thr Ser Ser Asp Phe Gly Asp Tyr
                 20                  25                  30

Asp Tyr Val Ser Trp Tyr Gln Gln His Pro Gly Lys Ala Pro Lys Leu
             35                  40                  45

Met Ile Tyr Asp Val Ser Asp Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Ser Ser Leu Thr Thr Ser
                 85                  90                  95

Ser Thr Leu Val Phe Gly Gly Gly Thr Lys Leu Thr Val Leu Gly
            100                 105                 110
```

<210> SEQ ID NO 249
<211> LENGTH: 108
<212> TYPE: PRT
<213> ORGANISM: Homo sapiens

<400> SEQUENCE: 249

```
Ala Ile Gln Met Thr Gln Ser Pro Ser Ser Leu Ser Ala Ser Val Gly
  1               5                  10                  15

Asp Arg Val Thr Ile Thr Cys Arg Thr Ser Gln Ser Ile Ser Ser Tyr
```

```
            20                  25                  30
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 250
<211> LENGTH: 111
<212> TYPE: PRT
<213> ORGANISM: Homo sapiens

<400> SEQUENCE: 250

Gln Ser Val Leu Thr Gln Pro Pro Ser Val Ser Gly Thr Pro Gly Gln
1               5                   10                  15

Arg Val Thr Ile Phe Cys Ser Gly Gly Ser Asn Asn Ile Gly Arg Ser
            20                  25                  30

Ser Val Tyr Trp Tyr Arg Gln Ala Ala Gly Thr Ala Pro Lys Leu Leu
        35                  40                  45

Ile Tyr Lys Thr Asp Gln Arg Pro Ser Gly Val Pro Asp Arg Phe Ala
    50                  55                  60

Ala Ser Lys Ser Gly Ala Ser Ala Ser Leu Ala Ile Ser Gly Leu Arg
65                  70                  75                  80

Ser Glu Asp Glu Ala Asp Tyr His Cys Ala Thr Trp Asp Asp Ser Leu
                85                  90                  95

Ser Ala Val Val Phe Gly Gly Gly Thr Lys Leu Thr Val Leu Gly
            100                 105                 110

<210> SEQ ID NO 251
<211> LENGTH: 116
<212> TYPE: PRT
<213> ORGANISM: Homo sapiens

<400> SEQUENCE: 251

Gln Ser Ala Leu Thr Gln Pro Ala Leu Thr Gln Pro Ala Ser Val Ser
1               5                   10                  15

Gly Ser Pro Gly Gln Ser Ile Thr Ile Ser Cys Thr Gly Thr Ser Ser
            20                  25                  30

Asp Phe Gly Asp Tyr Asp Tyr Val Ser Trp Tyr Gln Gln His Pro Gly
        35                  40                  45

Lys Ala Pro Lys Leu Met Ile Tyr Asp Val Ser Asp Arg Pro Ser Gly
    50                  55                  60

Val Ser Asn Arg Phe Ser Gly Ser Lys Ser Gly Asn Thr Ala Ser Leu
65                  70                  75                  80

Thr Ile Ser Gly Leu Gln Ala Glu Asp Glu Ala Asp Tyr Phe Cys Ser
                85                  90                  95

Ser Phe Thr Thr Ser Ser Thr Leu Val Phe Gly Gly Gly Thr Lys Leu
            100                 105                 110

Thr Val Leu Gly
        115
```

```
<210> SEQ ID NO 252
<211> LENGTH: 112
<212> TYPE: PRT
<213> ORGANISM: Homo sapiens

<400> SEQUENCE: 252

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Pro Trp Val Phe Gly Gly Gly Thr Lys Leu Thr Val Leu Gly
            100                 105                 110

<210> SEQ ID NO 253
<211> LENGTH: 116
<212> TYPE: PRT
<213> ORGANISM: Homo sapiens

<400> SEQUENCE: 253

Gln Ser Ala Leu Thr Gln Pro Ala Leu Thr Gln Pro Ala Ser Val Ser
1               5                   10                  15

Gly Ser Pro Gly Gln Ser Ile Thr Ile Ser Cys Thr Gly Thr Ser Ser
            20                  25                  30

Asp Phe Gly Asp Tyr Asp Tyr Val Ser Trp Tyr Gln Gln His Pro Gly
        35                  40                  45

Lys Ala Pro Lys Leu Met Ile Tyr Asp Val Ser Asp Arg Pro Ser Gly
    50                  55                  60

Val Ser Asn Arg Phe Ser Gly Ser Lys Ser Gly Asn Thr Ala Ser Leu
65                  70                  75                  80

Thr Ile Ser Gly Leu Gln Ala Glu Asp Glu Ala Asp Tyr Phe Cys Ser
                85                  90                  95

Ser Phe Thr Thr Ser Ser Thr Leu Val Phe Gly Gly Gly Thr Lys Leu
            100                 105                 110

Thr Val Leu Gly
        115

<210> SEQ ID NO 254
<211> LENGTH: 112
<212> TYPE: PRT
<213> ORGANISM: Homo sapiens

<400> SEQUENCE: 254

Asn Phe Met Leu Thr Gln Pro Arg Ser Val Ser Glu Ser Pro Gly Lys
1               5                   10                  15

Thr Val Thr Ile Ser Cys Thr Gly Asn Gly Gly Arg Val Ala Asn Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Ala Arg Phe Ser
    50                  55                  60
```

Gly Ser Ile Asp Ser Ser Asn Ser Ala Ser Leu Thr Ile Ser Gly
65                  70                  75                  80

Leu Lys Thr Asp Asp Glu Ala Asp Tyr Tyr Cys Gln Ser Tyr Asp Ile
                85                  90                  95

Ser Asn Gln Arg Val Phe Gly Gly Gly Thr Lys Leu Thr Val Leu Gly
            100                 105                 110

<210> SEQ ID NO 255
<211> LENGTH: 108
<212> TYPE: PRT
<213> ORGANISM: Homo sapiens

<400> SEQUENCE: 255

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Leu Asn Trp Tyr Gln Gln Lys Pro Gly Glu Ala Pro Ile Leu Ile Ile
        35                  40                  45

Gln Glu Ala Thr Thr Leu Val Pro Gly Ile Pro Pro Arg Phe Ser Gly
50                  55                  60

Ser Gly Phe Gly Thr Asp Phe Thr Leu Thr Ile Asn Ser Met Gln Ser
65                  70                  75                  80

Glu Asp Val Ala Tyr Tyr Phe Cys Leu Gln His Asp Asn Phe Pro Pro
                85                  90                  95

Thr Phe Gly Gln Gly Thr Lys Val Glu Ile Lys Arg
            100                 105

<210> SEQ ID NO 256
<211> LENGTH: 111
<212> TYPE: PRT
<213> ORGANISM: Homo sapiens

<400> SEQUENCE: 256

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asp Tyr Val Ser Trp Tyr Gln Gln Tyr Pro Gly Asn Ala Pro Lys Leu
        35                  40                  45

Met Ile Tyr Asp Val Ser Arg Arg Pro Ser Gly Val Ser His Arg Phe
50                  55                  60

Ser Ala Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Ser Thr Arg Val Phe Gly Gly Gly Thr Lys Val Thr Val Leu Gly
            100                 105                 110

<210> SEQ ID NO 257
<211> LENGTH: 108
<212> TYPE: PRT
<213> ORGANISM: Homo sapiens

<400> SEQUENCE: 257

Asp Ile Gln Leu Ala Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Glu Ile Lys Arg
            100                 105

<210> SEQ ID NO 258
<211> LENGTH: 112
<212> TYPE: PRT
<213> ORGANISM: Homo sapiens

<400> SEQUENCE: 258

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Ser Val Val Phe Gly Gly Gly Thr Lys Leu Thr Val Leu Gly
            100                 105                 110

<210> SEQ ID NO 259
<211> LENGTH: 111
<212> TYPE: PRT
<213> ORGANISM: Homo sapiens

<400> SEQUENCE: 259

Gln Ser Val Leu Thr Gln Pro Ala Ser Val Ser Gly Ser Pro Gly Gln
1               5                   10                  15

Ser Ile Thr Ile Ser Cys Thr Gly Thr Thr Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Asp Val Phe Gly Thr Gly Thr Lys Leu Thr Val Leu Gly
            100                 105                 110

<210> SEQ ID NO 260
<211> LENGTH: 111

```
<212> TYPE: PRT
<213> ORGANISM: Homo sapiens

<400> SEQUENCE: 260

Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Lys Asn
            20                  25                  30

Tyr Val Ser Trp Tyr Gln Gln Phe Pro Gly Thr Ala Pro Lys Leu Leu
            35                  40                  45

Ile Tyr Asp Asn Asn Glu Arg Pro Ser Gly Ile Pro Ala Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Phe Asp Thr Ser Leu
                85                  90                  95

Trp Ala Ala Val Phe Gly Gly Gly Thr Lys Leu Thr Val Leu Gly
            100                 105                 110

<210> SEQ ID NO 261
<211> LENGTH: 111
<212> TYPE: PRT
<213> ORGANISM: Homo sapiens

<400> SEQUENCE: 261

Gln Ser Ala Leu Thr Gln Pro Ala Ser Val Ser Gly Ser Pro Gly Gln
1               5                   10                  15

Ser Ile Thr Leu Ser Cys Thr Gly Thr Ser Ser Asp Val Gly Gly Tyr
            20                  25                  30

Asn Tyr Val Ser Trp Tyr Gln Gln His Pro Gly Asn Gly Pro Lys Leu
            35                  40                  45

Ile Ile Tyr Asp Val Thr Lys Arg Pro Ser Gly Val Ser Asn Arg Phe
        50                  55                  60

Ser Gly Ser Lys Ser Gly Asn Thr Ala Tyr Leu Thr Ile Ser Gly Leu
65                  70                  75                  80

Gln Ala Glu Asp Glu Ala Asp Tyr Tyr Cys Ala Ser Tyr Thr Arg Ser
                85                  90                  95

Thr Thr Leu Val Phe Gly Gly Gly Thr Lys Leu Thr Val Leu Gly
            100                 105                 110

<210> SEQ ID NO 262
<211> LENGTH: 110
<212> TYPE: PRT
<213> ORGANISM: Homo sapiens

<400> SEQUENCE: 262

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Gly Arg
```

```
                    85                  90                  95

Ser Thr Val Phe Gly Gly Gly Thr Lys Leu Thr Val Leu Gly
                100                 105                 110

<210> SEQ ID NO 263
<211> LENGTH: 111
<212> TYPE: PRT
<213> ORGANISM: Homo sapiens

<400> SEQUENCE: 263

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Gly Gly Thr Lys Leu Thr Val Leu Gly
                100                 105                 110

<210> SEQ ID NO 264
<211> LENGTH: 108
<212> TYPE: PRT
<213> ORGANISM: Homo sapiens

<400> SEQUENCE: 264

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
                100                 105

<210> SEQ ID NO 265
<211> LENGTH: 112
<212> TYPE: PRT
<213> ORGANISM: Homo sapiens

<400> SEQUENCE: 265

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45
```

```
Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Leu Thr Val Leu Gly
            100                 105                 110
```

<210> SEQ ID NO 266
<211> LENGTH: 109
<212> TYPE: PRT
<213> ORGANISM: Homo sapiens

<400> SEQUENCE: 266

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly
            100                 105
```

<210> SEQ ID NO 267
<211> LENGTH: 111
<212> TYPE: PRT
<213> ORGANISM: Homo sapiens

<400> SEQUENCE: 267

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Arg Gly Leu Gln
65                  70                  75                  80

Ser Asp Asp Glu Ala Glu Tyr Tyr Cys Ala Ala Trp Asp Asp Ser Leu
                85                  90                  95

Lys Ser Phe Val Phe Gly Lys Gly Thr Lys Val Thr Val Leu Gly
            100                 105                 110
```

<210> SEQ ID NO 268
<211> LENGTH: 108
<212> TYPE: PRT
<213> ORGANISM: Homo sapiens

<400> SEQUENCE: 268

-continued

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 269
<211> LENGTH: 111
<212> TYPE: PRT
<213> ORGANISM: Homo sapiens

<400> SEQUENCE: 269

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 270
<211> LENGTH: 108
<212> TYPE: PRT
<213> ORGANISM: Homo sapiens

<400> SEQUENCE: 270

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Val Arg Asn Tyr
            20                  25                  30

Leu Asn Trp Tyr Gln Gln Lys Pro Gly Lys Ala Pro Asn Leu Leu Ile
        35                  40                  45

Tyr Asp Ala Thr Asn Leu Glu Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asn Leu Pro Leu
                85                  90                  95

Ser Phe Gly Gly Gly Thr Lys Val Glu Ile Lys Arg
            100                 105

<210> SEQ ID NO 271
<211> LENGTH: 111
<212> TYPE: PRT
<213> ORGANISM: Homo sapiens

<400> SEQUENCE: 271

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Phe Thr Ser Ser
                85                  90                  95

Ile Thr Tyr Val Phe Gly Thr Gly Thr Lys Val Thr Val Leu Gly
            100                 105                 110

<210> SEQ ID NO 272
<211> LENGTH: 119
<212> TYPE: PRT
<213> ORGANISM: Homo sapiens

<400> SEQUENCE: 272

Glu Val Gln Leu Val Glu Ser Gly Gly Gly Pro Gly Lys Gly Leu Lys
1               5                   10                  15

Trp Leu Ser Tyr Leu Arg Met Asn Asn Leu Arg Val Glu Asp Leu Val
            20                  25                  30

Lys Pro Gly Gly Ser Leu Lys Leu Ile Ser Asp Arg Ala His Thr Ile
        35                  40                  45

Tyr Asp Thr Ala Val Tyr Tyr Cys Ala Arg Ala Val Ser Cys Ala Ala
    50                  55                  60

Ser Gly Phe Thr Phe Ser Thr His Ser Val Lys Gly Arg Phe Thr Ile
65                  70                  75                  80

Gly Ala Gly Glu Gly Phe Asp Tyr Trp Cys Asp Tyr Tyr Met Gly Trp
                85                  90                  95

Val Arg Gln Ala Ser Arg Asp Asp Ala Lys Ser Ser Leu Tyr Gln Gly
            100                 105                 110

Thr Leu Val Thr Val Ser Ser
        115

<210> SEQ ID NO 273
<211> LENGTH: 124
<212> TYPE: PRT
<213> ORGANISM: Homo sapiens

<400> SEQUENCE: 273

Gln Leu Gln Leu Gln Glu Ser Gly Pro Gly Gln Pro Gly Lys Gly Gly
1               5                   10                  15

Leu Glu Trp Ile Ser Leu Thr Leu Asn Ser Val Thr Ala Ala Val Val
            20                  25                  30

Lys Pro Ser Gly Thr Leu Ser Leu Gly Ser Ile Tyr Asp Thr Gly Thr
        35                  40                  45

Thr Tyr Asp Thr Ala Val Tyr Tyr Cys Ala Ser Met Thr Cys Thr Val

```
                50                  55                  60
Ser Gly Gly Ser Ile Ser Tyr Ser Pro Ser Leu Lys Ser Arg Leu Ile
 65                  70                  75                  80

Gly Gly Leu Arg Ser Ser Ser Asp Ala Arg Ser Asp Gly Tyr Trp
                 85                  90                  95

Gly Trp Val Arg Ile Ser Val Asp Thr Ser Lys Asn Gln Phe His
                100                 105                 110

Thr Trp Gly Pro Gly Thr Met Val Thr Val Ser Ser
                115                 120
```

<210> SEQ ID NO 274
<211> LENGTH: 118
<212> TYPE: PRT
<213> ORGANISM: Homo sapiens

<400> SEQUENCE: 274

```
Gln Val Gln Leu Val Gln Ser Gly Thr Glu Pro Gly Gln Gly Leu Glu
 1               5                  10                  15

Trp Val Gly Arg Met Glu Leu Ile Ser Leu Gly Ser Asp Asp Val Lys
                20                  25                  30

Lys Pro Gly Ser Ser Val Lys Val Ile Ile Pro Met Phe Gly Val Thr
                35                  40                  45

Asp Tyr Thr Ala Val Tyr Phe Cys Ala Arg Glu Ser Ser Cys Gln Ala
 50                  55                  60

Ser Gly Gly Ser Leu Ser Ala Gln Lys Phe Gln Asp Arg Val Thr Ile
 65                  70                  75                  80

Arg Gly Ala Thr Phe Glu Tyr Trp Gly Gln Ser His Gly Val Ser Trp
                 85                  90                  95

Leu Arg Gln Ala Thr Ala Asp Lys Ser Thr Ser Thr Val Tyr Gly Thr
                100                 105                 110

Leu Val Thr Val Ser Ser
                115
```

<210> SEQ ID NO 275
<211> LENGTH: 121
<212> TYPE: PRT
<213> ORGANISM: Homo sapiens

<400> SEQUENCE: 275

```
Glu Val Gln Leu Val Gln Ser Gly Gly Asp Pro Gly Lys Gly Leu Glu
 1               5                  10                  15

Trp Val Ser Ser Leu Gln Met Asn Ser Leu Arg Ala Glu Asp Leu Val
                20                  25                  30

Gln Pro Gly Gly Ser Leu Arg Leu Ile Ser Ser Ser Ser Tyr Ile
                35                  40                  45

Tyr Tyr Thr Ala Val Tyr Tyr Cys Ala Arg Gly Leu Ser Cys Ala Ala
 50                  55                  60

Ser Gly Phe Thr Phe Ser Ala Asp Ser Val Lys Gly Arg Phe Thr Ile
 65                  70                  75                  80

Gly Gly Trp Thr His Asp Ala Phe Asp Ile Ser Tyr Ser Met Asn Trp
                 85                  90                  95

Val Arg Gln Ala Ser Arg Asp Asn Ala Lys Asn Ser Leu Tyr Trp Gly
                100                 105                 110

Gln Gly Thr Thr Val Thr Val Ser Ser
                115                 120
```

```
<210> SEQ ID NO 276
<211> LENGTH: 125
<212> TYPE: PRT
<213> ORGANISM: Homo sapiens

<400> SEQUENCE: 276

Glu Val Gln Leu Val Gln Ser Gly Ala Glu Pro Gly Gln Gly Leu Glu
1               5                   10                  15

Trp Met Gly Trp Met Glu Leu Arg Ser Leu Arg Ser Asp Asp Val Lys
            20                  25                  30

Lys Pro Gly Ala Ser Val Lys Val Ile Ser Val Tyr Asn Gly Asn Thr
        35                  40                  45

Asn Tyr Thr Ala Val Tyr Tyr Cys Ala Arg Asp Tyr Ser Cys Lys Ala
    50                  55                  60

Ser Gly Tyr Thr Phe Asn Ala Gln Lys Leu Gln Gly Arg Val Thr Met
65                  70                  75                  80

Tyr Ser Asp Ser Ser Gly Tyr Trp Asp Asp Asn Tyr Gly Phe Ser Trp
                85                  90                  95

Val Arg Gln Ala Thr Thr Asp Thr Ser Thr Ser Thr Ala Tyr Ala Phe
            100                 105                 110

Asp Ile Trp Gly Gln Gly Thr Met Val Thr Val Ser Ser
            115                 120                 125

<210> SEQ ID NO 277
<211> LENGTH: 125
<212> TYPE: PRT
<213> ORGANISM: Homo sapiens

<400> SEQUENCE: 277

Gln Val Gln Leu Gln Gln Ser Gly Ala Glu Pro Gly Gln Gly Leu Glu
1               5                   10                  15

Trp Met Gly Trp Met Glu Leu Arg Ser Leu Arg Ser Asp Asp Val Lys
            20                  25                  30

Lys Pro Gly Ala Ser Val Arg Val Ile Ser Thr Tyr Asn Gly Asn Thr
        35                  40                  45

Asn Tyr Thr Ala Val Tyr Tyr Cys Ala Arg Asp Tyr Ser Cys Lys Ala
    50                  55                  60

Ser Gly Tyr Ser Phe Gly Ala Gln Lys Leu Gln Gly Arg Val Thr Met
65                  70                  75                  80

Tyr Ser Asp Ser Ser Gly Tyr Trp Asp Asp Asn Asn Gly Ile Thr Trp
                85                  90                  95

Val Arg Gln Ala Thr Thr Asp Thr Ser Thr Ser Thr Ala Tyr Ala Phe
            100                 105                 110

Asp Ile Trp Gly Gln Gly Thr Thr Val Thr Val Ser Ser
            115                 120                 125

<210> SEQ ID NO 278
<211> LENGTH: 121
<212> TYPE: PRT
<213> ORGANISM: Homo sapiens

<400> SEQUENCE: 278

Gln Val Gln Leu Gln Gln Ser Gly Ala Glu Pro Gly Gln Gly Leu Glu
1               5                   10                  15

Trp Met Gly Leu Leu Glu Leu Ser Ser Leu Arg Ser Asp Asp Val Lys
            20                  25                  30

Lys Pro Gly Ala Ser Val Lys Val Ile Asn Pro Gly Gly Gly Ser Thr
        35                  40                  45
```

```
Asn Tyr Thr Ala Val Tyr Tyr Cys Ala Arg Asp Tyr Ser Cys Lys Ala
            50                  55                  60

Ser Gly Tyr Thr Phe Ser Ala Gln Lys Phe Gln Gly Arg Val Thr Met
 65                  70                  75                  80

Gly Thr Ile Asp Ala Arg Arg Phe Asp Phe Arg Tyr Tyr Ile His Trp
                85                  90                  95

Val Arg Arg Ala Thr Arg Asp Thr Ser Thr Asn Thr Val Tyr Trp Gly
            100                 105                 110

Gln Gly Thr Leu Val Thr Val Ser Ser
            115                 120

<210> SEQ ID NO 279
<211> LENGTH: 119
<212> TYPE: PRT
<213> ORGANISM: Homo sapiens

<400> SEQUENCE: 279

Gln Leu Gln Leu Gln Glu Ser Gly Pro Gly Pro Pro Gly Lys Gly
 1               5                  10                  15

Leu Glu Trp Ile Ser Leu Lys Leu Gly Ser Val Thr Ala Ala Leu Val
            20                  25                  30

Lys Pro Ser Glu Thr Leu Ser Leu Gly Ser Ile Tyr Tyr Ser Gly Ser
            35                  40                  45

Thr Tyr Asp Thr Ala Val Tyr Tyr Cys Ala Arg His Thr Cys Thr Val
            50                  55                  60

Ser Gly Gly Ser Ile Ser Tyr Asn Pro Ser Leu Lys Ser Arg Val Thr
 65                  70                  75                  80

Asp Gly Thr Asp Ala Phe Asp Ile Trp Gly Ser Ser Ser Tyr Tyr Trp
                85                  90                  95

Gly Trp Ile Arg Ile Ser Val Asp Thr Ser Lys Asn Gln Phe Gln Gly
            100                 105                 110

Thr Thr Val Thr Val Ser Ser
            115

<210> SEQ ID NO 280
<211> LENGTH: 125
<212> TYPE: PRT
<213> ORGANISM: Homo sapiens

<400> SEQUENCE: 280

Glu Val Gln Leu Val Gln Ser Gly Ala Glu Pro Gly Gln Gly Leu Glu
 1               5                  10                  15

Trp Met Gly Trp Met Glu Leu Arg Ser Leu Arg Ser Asp Asp Val Lys
            20                  25                  30

Lys Pro Gly Ser Ser Val Lys Ile Ile Ser Thr Tyr Asn Ser Glu Thr
            35                  40                  45

Asn Tyr Thr Ala Val Tyr Tyr Cys Ala Arg Asp Tyr Ser Cys Lys Ala
            50                  55                  60

Ser Gly Gly Ala Phe Thr Ala Gln Lys Leu Gln Gly Arg Val Thr Met
 65                  70                  75                  80

Tyr Ser Asp Ser Ser Gly Tyr Trp Asp Asp Asn Phe Gly Ile Ser Trp
                85                  90                  95

Val Arg Gln Ala Thr Thr Asp Thr Ser Thr Ser Thr Ala Tyr Ala Phe
            100                 105                 110

Asp Ile Trp Gly Gln Gly Thr Leu Val Thr Val Ser Ser
            115                 120                 125
```

<210> SEQ ID NO 281
<211> LENGTH: 119
<212> TYPE: PRT
<213> ORGANISM: Homo sapiens

<400> SEQUENCE: 281

Gln Val Gln Leu Gln Gln Ser Gly Pro Gly Gln Ser Pro Ser Arg Gly
1               5                   10                  15

Leu Glu Trp Leu Gln Phe Ser Leu Gln Leu Asn Ser Val Thr Leu Val
            20                  25                  30

Lys Pro Ser Gln Thr Leu Ser Leu Gly Arg Thr Tyr Tyr Arg Ser Lys
        35                  40                  45

Trp Tyr Pro Glu Asp Thr Ala Val Tyr Tyr Cys Ala Thr Cys Ala Ile
    50                  55                  60

Ser Gly Asp Ser Val Ser Asn Asp Tyr Ala Val Ser Val Lys Ser Arg
65                  70                  75                  80

Arg Gly Val Arg Ala Phe Asp Ile Trp Gly Ser Asn Ser Ala Thr Trp
                85                  90                  95

Asn Trp Ile Arg Ile Ile Ile Asn Pro Asp Thr Ser Lys Asn Gln Gly
            100                 105                 110

Thr Thr Val Thr Val Ser Ser
        115

<210> SEQ ID NO 282
<211> LENGTH: 120
<212> TYPE: PRT
<213> ORGANISM: Homo sapiens

<400> SEQUENCE: 282

Gln Val Gln Leu Val Gln Ser Gly Ala Glu Pro Gly Gln Gly Leu Glu
1               5                   10                  15

Trp Met Gly Trp Met Glu Leu Arg Ser Leu Ser Ser Asp Asp Val Lys
            20                  25                  30

Glu Pro Gly Ala Ser Val Lys Val Ile Asn Pro Asn Ser Gly Gly Ala
        35                  40                  45

Met Tyr Thr Ala Val Tyr Tyr Cys Ala Arg Gly Met Ser Cys Lys Ala
    50                  55                  60

Ser Gly Tyr Thr Phe Arg Val Asp Asn Phe Gln Gly Arg Ala Thr Met
65                  70                  75                  80

Ala Asp Leu Ile Asp Val Phe Asp Ile Trp Asn Ser Gly Ile Thr Trp
                85                  90                  95

Val Arg Gln Ala Thr Arg Asp Thr Ser Ile Asn Thr Ala Tyr Gly Gln
            100                 105                 110

Gly Thr Leu Val Thr Val Ser Ser
        115                 120

<210> SEQ ID NO 283
<211> LENGTH: 120
<212> TYPE: PRT
<213> ORGANISM: Homo sapiens

<400> SEQUENCE: 283

Gln Val Gln Leu Val Gln Ser Gly Ala Glu Pro Gly Lys Gly Leu Glu
1               5                   10                  15

Trp Met Gly Ile Leu Gln Trp Ser Ser Leu Lys Ala Ser Asp Val Lys
            20                  25                  30

```
Lys Pro Gly Glu Ser Leu Lys Ile Ile Tyr Pro Gly Asp Ser Asp Thr
        35                  40                  45

Arg Tyr Thr Ala Met Tyr Tyr Cys Ala Arg Leu Ser Ser Cys Lys Gly
 50                  55                  60

Ser Gly Tyr Ser Phe Thr Ser Pro Ser Phe Gln Gly Gln Val Thr Ile
 65                  70                  75                  80

Ser Ser Ser Tyr Asp Ala Phe Asp Ile Trp Ser Tyr Trp Ile Gly Trp
                 85                  90                  95

Val Arg Gln Met Ser Ala Asp Lys Ser Ile Ser Thr Ala Tyr Gly Gln
                100                 105                 110

Gly Thr Met Val Thr Val Ser Ser
        115                 120
```

<210> SEQ ID NO 284
<211> LENGTH: 120
<212> TYPE: PRT
<213> ORGANISM: Homo sapiens

<400> SEQUENCE: 284

```
Glu Val Gln Leu Val Gln Ser Gly Ala Glu Pro Gly Gln Gly Leu Glu
 1               5                  10                  15

Trp Met Gly Trp Met Glu Leu Arg Ser Leu Ser Ser Asp Leu Lys
            20                  25                  30

Lys Pro Gly Ser Ser Val Arg Val Ile Asn Pro Asn Ser Gly Gly Ala
        35                  40                  45

Leu Tyr Thr Ala Val Tyr Tyr Cys Ala Arg Gly Met Ser Cys Lys Thr
 50                  55                  60

Ser Gly Gly Ser Phe Lys Val Asp Asn Phe Gln Gly Arg Ala Thr Met
 65                  70                  75                  80

Ala Asp Leu Ile Asp Val Phe Asp Ile Trp Thr His Gly Ile Ser Trp
                 85                  90                  95

Val Arg Gln Ala Thr Arg Asp Thr Ser Ile Asn Thr Ala Tyr Gly Gln
                100                 105                 110

Gly Thr Met Val Thr Val Ser Ser
        115                 120
```

<210> SEQ ID NO 285
<211> LENGTH: 118
<212> TYPE: PRT
<213> ORGANISM: Homo sapiens

<400> SEQUENCE: 285

```
Glu Val Gln Leu Val Glu Ser Gly Gly Gly Pro Gly Lys Gly Leu Glu
 1               5                  10                  15

Trp Met Gly Phe Asn Leu Ala Ser Val Thr Thr Ala Asp Thr Val Val
            20                  25                  30

Arg Pro Gly Gly Ser Leu Arg Leu Ile Tyr Lys Ser Val Asn Thr Asn
        35                  40                  45

Tyr Ser Ala Ile Tyr Tyr Cys Ala Arg Gly Lys Val Ser Cys Ala Thr
 50                  55                  60

Ser Gly Phe Asn Phe Asp Pro Ser Leu Lys Ser Arg Leu Thr Ile Ser
 65                  70                  75                  80

Glu Thr Ser Val Val Asp Tyr Trp Gly Gln Asn Tyr Gly Leu Ser Trp
                 85                  90                  95

Val Arg Gln Gly Met Asp Thr Ser Lys Asn Gln Phe Leu Gly Thr
                100                 105                 110
```

```
Leu Val Thr Val Ser Ser
            115

<210> SEQ ID NO 286
<211> LENGTH: 121
<212> TYPE: PRT
<213> ORGANISM: Homo sapiens

<400> SEQUENCE: 286

Gln Val Gln Leu Gln Glu Ser Gly Pro Gly Ala Gly Lys Gly Leu Glu
1               5                   10                  15

Trp Met Gly Arg Asn Leu Ser Ser Val Thr Ala Ala Asp Thr Leu Val
            20                  25                  30

Lys Ser Ser Glu Thr Leu Ser Leu Ile Tyr Ser Ser Gly Ser Thr Asn
        35                  40                  45

Tyr Asn Ala Ile Tyr Tyr Cys Ala Arg Ala Ser Trp Thr Cys Thr Val
    50                  55                  60

Ser Gly Gly Ser Met Asn Pro Ala Leu Lys Ser Arg Val Thr Met Ser
65                  70                  75                  80

Ser Gly Thr Tyr Trp Ala Leu Phe Asp Tyr Asn Tyr Tyr Trp Ser Trp
                85                  90                  95

Ile Arg Gln Pro Val Asp Thr Ser Lys Asn Gln Phe Ser Leu Trp Gly
            100                 105                 110

Gln Gly Thr Leu Val Thr Val Ser Ser
        115                 120

<210> SEQ ID NO 287
<211> LENGTH: 121
<212> TYPE: PRT
<213> ORGANISM: Homo sapiens

<400> SEQUENCE: 287

Glu Val Gln Leu Val Gln Ser Gly Gly Gly Pro Gly Lys Gly Leu Glu
1               5                   10                  15

Trp Val Ser Ser Leu Gln Met Asn Ser Leu Arg Ala Glu Asp Val Val
            20                  25                  30

Gln Pro Gly Gly Pro Leu Arg Leu Ile Ser Ser Ser Ser Tyr Ile
        35                  40                  45

Tyr Tyr Thr Ala Val Tyr Tyr Cys Ala Arg Gly Leu Ser Cys Ala Ala
    50                  55                  60

Ser Gly Phe Thr Phe Ser Ala Asp Ser Val Lys Gly Arg Phe Thr Ile
65                  70                  75                  80

Gly Gly Trp Thr His Asp Ala Phe Asp Ile Ser Tyr Ser Met Asn Trp
                85                  90                  95

Val Arg Gln Ala Ser Arg Asp Asn Ala Lys Asn Ser Leu Tyr Trp Gly
            100                 105                 110

Gln Gly Thr Met Val Thr Val Ser Ser
        115                 120

<210> SEQ ID NO 288
<211> LENGTH: 125
<212> TYPE: PRT
<213> ORGANISM: Homo sapiens

<400> SEQUENCE: 288

Glu Val Gln Leu Val Gln Ser Gly Asn Glu Pro Gly Gln Gly Leu Glu
1               5                   10                  15

Trp Met Gly Trp Met Glu Leu Arg Ser Leu Arg Ser Asp Asp Val Lys
```

```
                20                  25                  30
Arg Pro Gly Ala Ser Val Lys Val Ile Ser Thr Tyr Asn Gly Asn Thr
            35                  40                  45
Asn Tyr Thr Ala Val Tyr Tyr Cys Ala Arg Asp Tyr Ser Cys Lys Ala
        50                  55                  60
Ser Gly His Ser Phe Ser Ala Gln Lys Leu Gln Gly Arg Val Thr Met
65                  70                  75                  80
Tyr Ser Asp Ser Gly Tyr Trp Asp Thr Tyr Gly Phe Ser Trp
                85                  90                  95
Val Arg Gln Ala Thr Thr Asp Thr Ser Thr Thr Ala Tyr Ala Phe
            100                 105                 110
Asp Ile Trp Gly Gln Gly Thr Leu Val Thr Val Ser Ser
        115                 120                 125

<210> SEQ ID NO 289
<211> LENGTH: 121
<212> TYPE: PRT
<213> ORGANISM: Homo sapiens

<400> SEQUENCE: 289

Gln Met Gln Leu Val Gln Ser Gly Gly Asp Pro Gly Lys Gly Leu Glu
1               5                   10                  15
Trp Val Ser Ser Leu Gln Met Asn Ser Leu Arg Ala Glu Asp Leu Val
            20                  25                  30
Gln Pro Gly Gly Ser Leu Arg Leu Ile Ser Ser Ser Ser Tyr Ile
        35                  40                  45
Tyr Tyr Thr Ala Val Tyr Tyr Cys Ala Arg Gly Leu Ser Cys Ala Ala
    50                  55                  60
Ser Gly Phe Thr Phe Ser Ala Asp Ser Val Lys Gly Arg Phe Thr Ile
65                  70                  75                  80
Gly Gly Trp Thr His Asp Ala Phe Asp Ile Ser Tyr Ser Met Asn Trp
                85                  90                  95
Val Arg Gln Ala Ser Arg Asp Asn Ala Lys Asn Ser Leu Tyr Trp Gly
            100                 105                 110
Gln Gly Thr Thr Val Thr Val Ser Ser
        115                 120

<210> SEQ ID NO 290
<211> LENGTH: 121
<212> TYPE: PRT
<213> ORGANISM: Homo sapiens

<400> SEQUENCE: 290

Glu Val Gln Leu Val Gln Ser Gly Gly Asp Pro Gly Lys Gly Leu Glu
1               5                   10                  15
Trp Val Ser Ser Leu Gln Met Asn Ser Leu Arg Ala Glu Asp Leu Val
            20                  25                  30
Gln Pro Gly Gly Ser Leu Arg Leu Ile Ser Ser Ser Ser Tyr Ile
        35                  40                  45
Tyr Tyr Thr Ala Val Tyr Tyr Cys Ala Arg Gly Leu Ser Cys Ala Ala
    50                  55                  60
Ser Gly Phe Thr Phe Ser Ala Asp Ser Val Lys Gly Arg Phe Thr Ile
65                  70                  75                  80
Gly Gly Trp Thr His Asp Ala Phe Asp Ile Ser Tyr Ser Met Asn Trp
                85                  90                  95
Val Arg Gln Ala Ser Arg Asp Asn Ala Lys Asn Ser Leu Tyr Trp Gly
```

Gln Gly Thr Thr Val Thr Val Ser Ser
            115                 120

<210> SEQ ID NO 291
<211> LENGTH: 119
<212> TYPE: PRT
<213> ORGANISM: Homo sapiens

<400> SEQUENCE: 291

Gln Leu Gln Leu Gln Glu Ser Gly Pro Gly Gln Pro Pro Lys Gly
1               5                   10                  15

Leu Glu Trp Ile Ser Leu Lys Leu Gly Ser Val Thr Ala Ala Leu Val
            20                  25                  30

Lys Pro Ser Glu Thr Leu Ser Leu Gly Ser Ile Tyr Tyr Ser Gly Ser
            35                  40                  45

Thr Tyr Asp Thr Ala Val Tyr Tyr Cys Ala Arg His Thr Cys Thr Val
        50                  55                  60

Ser Gly Gly Ser Ile Ser Tyr Asn Pro Ser Leu Lys Ser Arg Val Thr
65                  70                  75                  80

Asp Gly Thr Asp Ala Phe Asp Ile Trp Gly Ser Asn Ser Tyr Tyr Trp
                85                  90                  95

Gly Trp Ile Arg Ile Ser Val Asp Thr Ser Lys Asn Gln Phe Gln Gly
                100                 105                 110

Thr Thr Val Thr Val Ser Ser
            115

<210> SEQ ID NO 292
<211> LENGTH: 121
<212> TYPE: PRT
<213> ORGANISM: Homo sapiens

<400> SEQUENCE: 292

Gln Val Gln Leu Val Gln Ser Gly Gly Asp Pro Gly Lys Gly Leu Glu
1               5                   10                  15

Trp Val Ser Ser Leu Gln Met Asn Ser Leu Arg Ala Glu Asp Leu Val
            20                  25                  30

Gln Pro Gly Gly Ser Leu Arg Leu Ile Ser Ser Ser Ser Tyr Ile
            35                  40                  45

Tyr Tyr Thr Ala Val Tyr Tyr Cys Ala Arg Gly Leu Ser Cys Ala Ala
        50                  55                  60

Ser Gly Phe Thr Phe Ser Ala Asp Ser Val Lys Gly Arg Phe Thr Ile
65                  70                  75                  80

Gly Gly Trp Thr His Asp Ala Phe Asp Ile Ser Tyr Ser Met Asn Trp
                85                  90                  95

Val Arg Gln Ala Ser Arg Asp Asn Ala Lys Asn Ser Leu Tyr Trp Gly
                100                 105                 110

Gln Gly Thr Thr Val Thr Val Ser Ser
            115                 120

<210> SEQ ID NO 293
<211> LENGTH: 121
<212> TYPE: PRT
<213> ORGANISM: Homo sapiens

<400> SEQUENCE: 293

Glu Val Gln Leu Val Gln Ser Gly Gly Asp Pro Gly Lys Gly Leu Glu
1               5                   10                  15

```
Trp Val Ser Ser Leu Gln Met Asn Ser Leu Arg Ala Glu Asp Leu Val
            20                  25                  30

Gln Pro Gly Gly Ser Leu Arg Leu Ile Ser Ser Ser Ser Tyr Ile
        35                  40                  45

Tyr Tyr Thr Ala Val Tyr Tyr Cys Ala Arg Gly Leu Ser Cys Ala Ala
 50                  55                  60

Ser Gly Phe Thr Phe Ser Ala Asp Ser Val Lys Gly Arg Phe Thr Ile
 65                  70                  75                  80

Gly Gly Trp Thr His Asp Ala Phe Asp Ile Ser Tyr Ser Met Asn Trp
             85                  90                  95

Val Arg Gln Ala Ser Arg Asp Asn Ala Lys Asn Ser Leu Tyr Trp Gly
            100                 105                 110

Gln Gly Thr Thr Val Thr Val Ser Ser
            115                 120
```

<210> SEQ ID NO 294
<211> LENGTH: 121
<212> TYPE: PRT
<213> ORGANISM: Homo sapiens

<400> SEQUENCE: 294

```
Glu Val Gln Leu Val Gln Ser Gly Gly Asp Pro Gly Lys Gly Leu Glu
 1               5                  10                  15

Trp Val Ser Ser Leu Gln Met Asn Ser Leu Arg Ala Glu Asp Leu Val
            20                  25                  30

Gln Pro Gly Gly Ser Leu Arg Leu Ile Ser Ser Ser Ser Tyr Ile
        35                  40                  45

Tyr Tyr Thr Ala Val Tyr Tyr Cys Ala Arg Gly Leu Ser Cys Ala Ala
 50                  55                  60

Ser Gly Phe Thr Phe Ser Ala Asp Ser Val Lys Gly Arg Phe Thr Ile
 65                  70                  75                  80

Gly Gly Trp Thr His Asp Ala Phe Asp Ile Ser Tyr Ser Met Asn Trp
             85                  90                  95

Val Arg Gln Ala Ser Arg Asp Asn Ala Lys Asn Ser Leu Tyr Trp Gly
            100                 105                 110

Gln Gly Thr Thr Val Thr Val Ser Ser
            115                 120
```

<210> SEQ ID NO 295
<211> LENGTH: 119
<212> TYPE: PRT
<213> ORGANISM: Homo sapiens

<400> SEQUENCE: 295

```
Glu Val Gln Leu Val Gln Ser Gly Ala Glu Pro Gly Lys Gly Leu Glu
 1               5                  10                  15

Trp Met Gly Ile Leu Gln Trp Ser Ser Leu Lys Ala Ser Asp Val Lys
            20                  25                  30

Lys Pro Gly Glu Ser Leu Lys Ile Ile Tyr Pro Arg Asp Ser Asp Thr
        35                  40                  45

Arg Tyr Thr Ala Met Tyr Tyr Cys Ala Thr Pro Val Ser Cys Lys Gly
 50                  55                  60

Ser Gly Tyr Ser Phe Ser Pro Ser Phe Gln Gly Gln Val Thr Ile
 65                  70                  75                  80

Val Thr Ala Gly Ala Phe Asp Ile Trp Gly Arg Tyr Trp Ile Gly Trp
             85                  90                  95
```

Val Arg Gln Met Ser Ala Asp Lys Ser Ile Ser Thr Ala Tyr Gln Gly
            100                 105                 110

Thr Met Val Thr Val Ser Ser
        115

<210> SEQ ID NO 296
<211> LENGTH: 116
<212> TYPE: PRT
<213> ORGANISM: Homo sapiens

<400> SEQUENCE: 296

Glu Val Gln Leu Val Glu Thr Gly Gly Pro Gly Lys Gly Leu Glu
1               5                   10                  15

Trp Val Ser Ser Leu Gln Met Asp Asn Leu Arg Ala Glu Asp Leu Val
            20                  25                  30

Lys Pro Gly Gly Ser Leu Arg Leu Ile Ser Ser Ser Thr His Ile
        35                  40                  45

Tyr Tyr Thr Ala Val Tyr Tyr Cys Ala Arg Ala Thr Ser Cys Glu Ala
    50                  55                  60

Ser Gly Phe Ser Leu Ser Ala Asp Ser Leu Lys Gly Arg Phe Thr Ile
65                  70                  75                  80

Ile Gly Phe Asp Tyr Trp Gly Gln Gly Thr Ser Tyr Ser Met Asn Trp
            85                  90                  95

Val Arg Gln Ala Ser Arg Asp Asn Ala Lys Asn Ser Leu Phe Leu Val
            100                 105                 110

Thr Val Ser Ser
        115

<210> SEQ ID NO 297
<211> LENGTH: 121
<212> TYPE: PRT
<213> ORGANISM: Homo sapiens

<400> SEQUENCE: 297

Glu Val Gln Leu Val Gln Ser Gly Ala Glu Pro Gly Gln Gly Leu Glu
1               5                   10                  15

Trp Met Gly Trp Met Glu Leu Ser Ser Leu Thr Ser Asp Asp Ser Val
            20                  25                  30

Lys Lys Pro Gly Ala Ser Val Lys Val Met Asn Pro Asn Ser Gly Asn
        35                  40                  45

Ser Val Ser Thr Ala Val Tyr Tyr Cys Ala Arg Asn Ser Ser Cys Lys
    50                  55                  60

Ala Ser Gly Tyr Thr Phe Thr Ala Gln Lys Phe Gln Gly Arg Val Thr
65                  70                  75                  80

Met Glu Trp His Pro Trp Gly Tyr Tyr Asp Tyr Asp Tyr Tyr Ile His
            85                  90                  95

Trp Val Arg Gln Ala Thr Arg Asp Thr Ser Ile Asn Thr Ala Tyr Trp
            100                 105                 110

Gly Gln Gly Thr Leu Val Thr Val Ser
        115                 120

<210> SEQ ID NO 298
<211> LENGTH: 121
<212> TYPE: PRT
<213> ORGANISM: Homo sapiens

<400> SEQUENCE: 298

```
Gln Val Gln Leu Val Gln Ser Gly Ala Glu Pro Gly Gln Gly Leu Glu
1               5                   10                  15

Trp Met Gly Leu Leu Glu Leu Ser Ser Leu Arg Ser Asp Asp Val Lys
            20                  25                  30

Lys Pro Gly Ala Ser Val Lys Val Ile Asn Pro Gly Gly Gly Ser Thr
            35                  40                  45

Asn Tyr Thr Ala Val Tyr Tyr Cys Ala Arg Asp Tyr Ser Cys Lys Ala
    50                  55                  60

Ser Gly Tyr Thr Phe Ser Ala Gln Lys Phe Gln Gly Arg Val Thr Met
65                  70                  75                  80

Gly Thr Ile Asp Ala Arg Arg Phe Asp Phe Arg Tyr Tyr Ile His Trp
                85                  90                  95

Val Arg Gln Ala Thr Arg Asp Thr Ser Thr Asn Thr Val Tyr Trp Gly
                100                 105                 110

Gln Gly Thr Leu Val Thr Val Ser Ser
            115                 120
```

<210> SEQ ID NO 299
<211> LENGTH: 125
<212> TYPE: PRT
<213> ORGANISM: Homo sapiens

<400> SEQUENCE: 299

```
Gln Val Gln Leu Gln Gln Ser Gly Ala Glu Pro Gly Gln Gly Leu Glu
1               5                   10                  15

Trp Met Gly Trp Met Glu Leu Arg Ser Leu Arg Ser Asp Asp Val Lys
            20                  25                  30

Lys Pro Gly Ala Ser Val Lys Val Ile Ser Thr Tyr Asn Gly Asn Thr
            35                  40                  45

Asn Tyr Thr Ala Val Tyr Tyr Cys Ala Arg Asp Tyr Ser Cys Lys Ala
    50                  55                  60

Ser Gly His Thr Phe Ser Ala Gln Lys Leu Gln Gly Arg Val Thr Met
65                  70                  75                  80

Tyr Ser Asp Ser Ser Gly Tyr Trp Asp Asp Asn Tyr Gly Ile Ser Trp
                85                  90                  95

Val Arg Gln Ala Thr Asp Thr Ser Thr Ser Thr Ala Tyr Ala Phe
                100                 105                 110

Asp Ile Trp Gly Gln Gly Thr Val Thr Val Ser Ser
            115                 120                 125
```

<210> SEQ ID NO 300
<211> LENGTH: 121
<212> TYPE: PRT
<213> ORGANISM: Homo sapiens

<400> SEQUENCE: 300

```
Gln Met Gln Leu Val Gln Ser Gly Ala Glu Pro Gly Gln Gly Leu Glu
1               5                   10                  15

Trp Met Gly Leu Leu Glu Leu Ser Ser Leu Arg Ser Asp Asp Val Lys
            20                  25                  30

Lys Pro Gly Ala Ser Val Lys Val Ile Asn Pro Gly Gly Gly Ser Thr
            35                  40                  45

Asn Tyr Thr Ala Val Tyr Tyr Cys Ala Arg Asp Tyr Ser Cys Lys Ala
    50                  55                  60

Ser Gly Tyr Thr Phe Ser Ala Gln Lys Phe Gln Gly Arg Val Thr Met
65                  70                  75                  80
```

-continued

Gly Thr Ile Asp Ala Arg Arg Phe Asp Phe Arg Tyr Tyr Ile His Trp
            85                  90                  95

Val Arg Gln Ala Thr Arg Asp Ser Thr Asn Thr Val Tyr Trp Gly
            100                 105                 110

Gln Gly Thr Leu Val Thr Val Ser Ser
            115                 120

<210> SEQ ID NO 301
<211> LENGTH: 119
<212> TYPE: PRT
<213> ORGANISM: Homo sapiens

<400> SEQUENCE: 301

Glu Ala Gln Leu Val Glu Ser Gly Gly Gly Pro Gly Lys Gly Leu Lys
1               5                   10                  15

Trp Leu Ser Tyr Leu Arg Met Asn Asn Leu Arg Val Glu Asp Leu Val
                20                  25                  30

Lys Pro Gly Gly Ser Leu Arg Leu Ile Ser Asp Arg Ala His Thr Ile
            35                  40                  45

Tyr Asp Thr Ala Val Tyr Tyr Cys Ala Arg Ala Val Ser Cys Ala Ala
        50                  55                  60

Ser Gly Phe Thr Phe Ser Thr Asp Ser Val Lys Gly Arg Phe Thr Ile
65                  70                  75                  80

Gly Ala Gly Glu Gly Phe Asp Tyr Trp Gly Asp Tyr Tyr Met Gly Trp
                85                  90                  95

Val Arg Gln Ala Ser Arg Asp Asp Ala Lys Ser Ser Leu Tyr Gln Gly
            100                 105                 110

Thr Leu Val Thr Val Ser Ser
            115

<210> SEQ ID NO 302
<211> LENGTH: 120
<212> TYPE: PRT
<213> ORGANISM: Homo sapiens

<400> SEQUENCE: 302

Gln Met Gln Leu Val Gln Ser Gly Ala Glu Pro Gly Gln Gly Leu Glu
1               5                   10                  15

Trp Met Gly Ile Met Glu Leu Ser Ser Leu Arg Ser Glu Asp Val Lys
                20                  25                  30

Lys Pro Gly Ala Ser Val Lys Val Ile Asn Pro Ser Gly Gly Ser Thr
            35                  40                  45

Ser Tyr Thr Ala Val Tyr Tyr Cys Ala Arg Gly Gly Ser Cys Lys Ala
        50                  55                  60

Ser Gly Tyr Thr Phe Thr Ala Gln Lys Phe Gln Gly Arg Val Thr Met
65                  70                  75                  80

Tyr Thr Gly Trp Ser Pro Ser Asp Pro Trp Ser Tyr Tyr Met His Trp
                85                  90                  95

Val Arg Gln Ala Thr Arg Asp Thr Ser Thr Val Tyr Gly Gln
            100                 105                 110

Gly Thr Leu Val Thr Val Ser Ser
            115                 120

<210> SEQ ID NO 303
<211> LENGTH: 11
<212> TYPE: PRT
<213> ORGANISM: Homo sapiens

<400> SEQUENCE: 303

Gln Ala Ser Gln Asp Ile Arg Asn Tyr Leu Asn
1               5                   10

<210> SEQ ID NO 304
<211> LENGTH: 7
<212> TYPE: PRT
<213> ORGANISM: Homo sapiens

<400> SEQUENCE: 304

Ala Ala Ser Asn Leu Glu Thr
1               5

<210> SEQ ID NO 305
<211> LENGTH: 9
<212> TYPE: PRT
<213> ORGANISM: Homo sapiens

<400> SEQUENCE: 305

Gln Gln Asp Asp Asn Leu Pro Leu Thr
1               5

<210> SEQ ID NO 306
<211> LENGTH: 11
<212> TYPE: PRT
<213> ORGANISM: Homo sapiens

<400> SEQUENCE: 306

Gly Gly Thr Asn Ile Gly Ser Glu Ser Val His
1               5                   10

<210> SEQ ID NO 307
<211> LENGTH: 7
<212> TYPE: PRT
<213> ORGANISM: Homo sapiens

<400> SEQUENCE: 307

Asp Asp Thr Asp Arg Pro Ser
1               5

<210> SEQ ID NO 308
<211> LENGTH: 11
<212> TYPE: PRT
<213> ORGANISM: Homo sapiens

<400> SEQUENCE: 308

Gln Val Trp Asp Ser Val Ser Asp Arg Tyr Val
1               5                   10

<210> SEQ ID NO 309
<211> LENGTH: 12
<212> TYPE: PRT
<213> ORGANISM: Homo sapiens

<400> SEQUENCE: 309

Arg Ala Ser Gln Ser Val Ser Ser Ser Tyr Leu Ala
1               5                   10

<210> SEQ ID NO 310
<211> LENGTH: 7
<212> TYPE: PRT
<213> ORGANISM: Homo sapiens

<400> SEQUENCE: 310

Gly Ala Ser Ser Arg Ala Thr
1               5

<210> SEQ ID NO 311
<211> LENGTH: 6
<212> TYPE: PRT
<213> ORGANISM: Homo sapiens

<400> SEQUENCE: 311

Gln Gln Tyr Gly Ser Ser
1               5

<210> SEQ ID NO 312
<211> LENGTH: 14
<212> TYPE: PRT
<213> ORGANISM: Homo sapiens

<400> SEQUENCE: 312

Thr Gly Thr Ser Ser Asp Val Gly Gly Tyr Asn Tyr Val Ser
1               5                   10

<210> SEQ ID NO 313
<211> LENGTH: 7
<212> TYPE: PRT
<213> ORGANISM: Homo sapiens

<400> SEQUENCE: 313

Asp Val Ser Asn Arg Pro Ser
1               5

<210> SEQ ID NO 314
<211> LENGTH: 9
<212> TYPE: PRT
<213> ORGANISM: Homo sapiens

<400> SEQUENCE: 314

Ser Ser Tyr Thr Ser Ser Ser Thr Leu
1               5

<210> SEQ ID NO 315
<211> LENGTH: 11
<212> TYPE: PRT
<213> ORGANISM: Homo sapiens

<400> SEQUENCE: 315

Gln Ala Ser Gln Asp Ile Ser Asn Tyr Leu Asn
1               5                   10

<210> SEQ ID NO 316
<211> LENGTH: 7
<212> TYPE: PRT
<213> ORGANISM: Homo sapiens

<400> SEQUENCE: 316

Ala Ala Ser Ser Leu Gln Ser
1               5

<210> SEQ ID NO 317
<211> LENGTH: 9
<212> TYPE: PRT
<213> ORGANISM: Homo sapiens

<400> SEQUENCE: 317

Gln Gln Ser Tyr Ser Thr Pro Phe Thr
1               5

-continued

<210> SEQ ID NO 318
<211> LENGTH: 11
<212> TYPE: PRT
<213> ORGANISM: Homo sapiens

<400> SEQUENCE: 318

Arg Ala Ser Gln Ser Ile Ser Ser Tyr Leu Asn
1               5                   10

<210> SEQ ID NO 319
<211> LENGTH: 7
<212> TYPE: PRT
<213> ORGANISM: Homo sapiens

<400> SEQUENCE: 319

Ala Ala Ser Ser Leu Gln Ser
1               5

<210> SEQ ID NO 320
<211> LENGTH: 10
<212> TYPE: PRT
<213> ORGANISM: Homo sapiens

<400> SEQUENCE: 320

Gln Gln Ser Tyr Ser Thr Pro Pro Trp Thr
1               5                   10

<210> SEQ ID NO 321
<211> LENGTH: 13
<212> TYPE: PRT
<213> ORGANISM: Homo sapiens

<400> SEQUENCE: 321

Pro Gly Ser Ser Ser Asn Ile Gly Ser Asn Tyr Val Tyr
1               5                   10

<210> SEQ ID NO 322
<211> LENGTH: 7
<212> TYPE: PRT
<213> ORGANISM: Homo sapiens

<400> SEQUENCE: 322

Arg Asn Asn Gln Arg Pro Ser
1               5

<210> SEQ ID NO 323
<211> LENGTH: 11
<212> TYPE: PRT
<213> ORGANISM: Homo sapiens

<400> SEQUENCE: 323

Gly Thr Trp Asp Ser Ser Leu Ser Ala Tyr Val
1               5                   10

<210> SEQ ID NO 324
<211> LENGTH: 14
<212> TYPE: PRT
<213> ORGANISM: Homo sapiens

<400> SEQUENCE: 324

Thr Gly Thr Ser Ser Asp Phe Gly Asp Tyr Asp Tyr Val Ser
1               5                   10

```
<210> SEQ ID NO 325
<211> LENGTH: 7
<212> TYPE: PRT
<213> ORGANISM: Homo sapiens

<400> SEQUENCE: 325

Asp Val Ser Asp Arg Pro Ser
1               5

<210> SEQ ID NO 326
<211> LENGTH: 10
<212> TYPE: PRT
<213> ORGANISM: Homo sapiens

<400> SEQUENCE: 326

Ser Ser Leu Thr Thr Ser Ser Thr Leu Val
1               5                   10

<210> SEQ ID NO 327
<211> LENGTH: 11
<212> TYPE: PRT
<213> ORGANISM: Homo sapiens

<400> SEQUENCE: 327

Arg Thr Ser Gln Ser Ile Ser Ser Tyr Leu Asn
1               5                   10

<210> SEQ ID NO 328
<211> LENGTH: 7
<212> TYPE: PRT
<213> ORGANISM: Homo sapiens

<400> SEQUENCE: 328

Ala Ala Ser Ser Leu Gln Ser
1               5

<210> SEQ ID NO 329
<211> LENGTH: 9
<212> TYPE: PRT
<213> ORGANISM: Homo sapiens

<400> SEQUENCE: 329

Gln Gln Ser Tyr Ser Thr Pro Phe Thr
1               5

<210> SEQ ID NO 330
<211> LENGTH: 13
<212> TYPE: PRT
<213> ORGANISM: Homo sapiens

<400> SEQUENCE: 330

Ser Gly Gly Ser Asn Asn Ile Gly Arg Ser Ser Val Tyr
1               5                   10

<210> SEQ ID NO 331
<211> LENGTH: 7
<212> TYPE: PRT
<213> ORGANISM: Homo sapiens

<400> SEQUENCE: 331

Lys Thr Asp Gln Arg Pro Ser
1               5

<210> SEQ ID NO 332
<211> LENGTH: 11
```

```
<212> TYPE: PRT
<213> ORGANISM: Homo sapiens

<400> SEQUENCE: 332

Ala Thr Trp Asp Asp Ser Leu Ser Ala Val Val
1               5                   10

<210> SEQ ID NO 333
<211> LENGTH: 14
<212> TYPE: PRT
<213> ORGANISM: Homo sapiens

<400> SEQUENCE: 333

Thr Gly Thr Ser Ser Asp Phe Gly Asp Tyr Asp Tyr Val Ser
1               5                   10

<210> SEQ ID NO 334
<211> LENGTH: 7
<212> TYPE: PRT
<213> ORGANISM: Homo sapiens

<400> SEQUENCE: 334

Asp Val Ser Asp Arg Pro Ser
1               5

<210> SEQ ID NO 335
<211> LENGTH: 10
<212> TYPE: PRT
<213> ORGANISM: Homo sapiens

<400> SEQUENCE: 335

Ser Ser Phe Thr Thr Ser Ser Thr Leu Val
1               5                   10

<210> SEQ ID NO 336
<211> LENGTH: 14
<212> TYPE: PRT
<213> ORGANISM: Homo sapiens

<400> SEQUENCE: 336

Thr Gly Thr Ser Ser Asp Val Gly Gly Tyr Asn Tyr Val Ser
1               5                   10

<210> SEQ ID NO 337
<211> LENGTH: 7
<212> TYPE: PRT
<213> ORGANISM: Homo sapiens

<400> SEQUENCE: 337

Asp Val Ser Asn Arg Pro Ser
1               5

<210> SEQ ID NO 338
<211> LENGTH: 11
<212> TYPE: PRT
<213> ORGANISM: Homo sapiens

<400> SEQUENCE: 338

Ser Ser Tyr Thr Ser Ser Ser Ile Pro Trp Val
1               5                   10

<210> SEQ ID NO 339
<211> LENGTH: 14
<212> TYPE: PRT
<213> ORGANISM: Homo sapiens
```

```
<400> SEQUENCE: 339

Thr Gly Thr Ser Ser Asp Phe Gly Asp Tyr Asp Tyr Val Ser
1               5                   10

<210> SEQ ID NO 340
<211> LENGTH: 7
<212> TYPE: PRT
<213> ORGANISM: Homo sapiens

<400> SEQUENCE: 340

Asp Val Ser Asp Arg Pro Ser
1               5

<210> SEQ ID NO 341
<211> LENGTH: 10
<212> TYPE: PRT
<213> ORGANISM: Homo sapiens

<400> SEQUENCE: 341

Ser Ser Phe Thr Thr Ser Ser Thr Leu Val
1               5                   10

<210> SEQ ID NO 342
<211> LENGTH: 13
<212> TYPE: PRT
<213> ORGANISM: Homo sapiens

<400> SEQUENCE: 342

Thr Gly Asn Gly Gly Arg Val Ala Asn Asn Tyr Val Gln
1               5                   10

<210> SEQ ID NO 343
<211> LENGTH: 7
<212> TYPE: PRT
<213> ORGANISM: Homo sapiens

<400> SEQUENCE: 343

Glu Asp Asn Gln Arg Pro Ser
1               5

<210> SEQ ID NO 344
<211> LENGTH: 10
<212> TYPE: PRT
<213> ORGANISM: Homo sapiens

<400> SEQUENCE: 344

Gln Ser Tyr Asp Ile Ser Asn Gln Arg Val
1               5                   10

<210> SEQ ID NO 345
<211> LENGTH: 11
<212> TYPE: PRT
<213> ORGANISM: Homo sapiens

<400> SEQUENCE: 345

Lys Ala Ser Gln Asp Ile Asp Asp Asp Leu Asn
1               5                   10

<210> SEQ ID NO 346
<211> LENGTH: 7
<212> TYPE: PRT
<213> ORGANISM: Homo sapiens

<400> SEQUENCE: 346
```

Glu Ala Thr Thr Leu Val Pro
1               5

<210> SEQ ID NO 347
<211> LENGTH: 9
<212> TYPE: PRT
<213> ORGANISM: Homo sapiens

<400> SEQUENCE: 347

Leu Gln His Asp Asn Phe Pro Pro Thr
1               5

<210> SEQ ID NO 348
<211> LENGTH: 14
<212> TYPE: PRT
<213> ORGANISM: Homo sapiens

<400> SEQUENCE: 348

Thr Gly Thr Ser Arg Asp Val Gly Gly Tyr Asp Tyr Val Ser
1               5                   10

<210> SEQ ID NO 349
<211> LENGTH: 7
<212> TYPE: PRT
<213> ORGANISM: Homo sapiens

<400> SEQUENCE: 349

Asp Val Ser Arg Arg Pro Ser
1               5

<210> SEQ ID NO 350
<211> LENGTH: 10
<212> TYPE: PRT
<213> ORGANISM: Homo sapiens

<400> SEQUENCE: 350

Ser Ser Tyr Thr Ser Ser Ser Thr Arg Val
1               5                   10

<210> SEQ ID NO 351
<211> LENGTH: 11
<212> TYPE: PRT
<213> ORGANISM: Homo sapiens

<400> SEQUENCE: 351

Arg Ala Ser Gln Ser Ile Ser Asn Tyr Leu Asn
1               5                   10

<210> SEQ ID NO 352
<211> LENGTH: 7
<212> TYPE: PRT
<213> ORGANISM: Homo sapiens

<400> SEQUENCE: 352

Ala Ala Ser Ser Leu Gln Ser
1               5

<210> SEQ ID NO 353
<211> LENGTH: 9
<212> TYPE: PRT
<213> ORGANISM: Homo sapiens

<400> SEQUENCE: 353

Gln Gln Ser Tyr Ser Thr Pro Phe Thr

<210> SEQ ID NO 354
<211> LENGTH: 14
<212> TYPE: PRT
<213> ORGANISM: Homo sapiens

<400> SEQUENCE: 354

Thr Gly Thr Ser Ser Asp Val Gly Gly Tyr Asn Tyr Val Ser
1               5                   10

<210> SEQ ID NO 355
<211> LENGTH: 7
<212> TYPE: PRT
<213> ORGANISM: Homo sapiens

<400> SEQUENCE: 355

Asp Val Ser Lys Arg Pro Ser
1               5

<210> SEQ ID NO 356
<211> LENGTH: 11
<212> TYPE: PRT
<213> ORGANISM: Homo sapiens

<400> SEQUENCE: 356

Ser Ser Tyr Thr Ser Ser Thr Ser Val Val
1               5                   10

<210> SEQ ID NO 357
<211> LENGTH: 14
<212> TYPE: PRT
<213> ORGANISM: Homo sapiens

<400> SEQUENCE: 357

Thr Gly Thr Thr Ser Asp Val Gly Gly Tyr Asn Tyr Val Ser
1               5                   10

<210> SEQ ID NO 358
<211> LENGTH: 7
<212> TYPE: PRT
<213> ORGANISM: Homo sapiens

<400> SEQUENCE: 358

Asp Val Ser Lys Arg Pro Ser
1               5

<210> SEQ ID NO 359
<211> LENGTH: 10
<212> TYPE: PRT
<213> ORGANISM: Homo sapiens

<400> SEQUENCE: 359

Ser Ser Tyr Thr Ser Ser Ser Thr Asp Val
1               5                   10

<210> SEQ ID NO 360
<211> LENGTH: 13
<212> TYPE: PRT
<213> ORGANISM: Homo sapiens

<400> SEQUENCE: 360

Ser Gly Ser Ser Ser Asn Ile Gly Lys Asn Tyr Val Ser
1               5                   10

<210> SEQ ID NO 361
<211> LENGTH: 7
<212> TYPE: PRT
<213> ORGANISM: Homo sapiens

<400> SEQUENCE: 361

Asp Asn Asn Glu Arg Pro Ser
1               5

<210> SEQ ID NO 362
<211> LENGTH: 11
<212> TYPE: PRT
<213> ORGANISM: Homo sapiens

<400> SEQUENCE: 362

Ala Thr Phe Asp Thr Ser Leu Trp Ala Ala Val
1               5                   10

<210> SEQ ID NO 363
<211> LENGTH: 14
<212> TYPE: PRT
<213> ORGANISM: Homo sapiens

<400> SEQUENCE: 363

Thr Gly Thr Ser Ser Asp Val Gly Gly Tyr Asn Tyr Val Ser
1               5                   10

<210> SEQ ID NO 364
<211> LENGTH: 7
<212> TYPE: PRT
<213> ORGANISM: Homo sapiens

<400> SEQUENCE: 364

Asp Val Thr Lys Arg Pro Ser
1               5

<210> SEQ ID NO 365
<211> LENGTH: 10
<212> TYPE: PRT
<213> ORGANISM: Homo sapiens

<400> SEQUENCE: 365

Ala Ser Tyr Thr Arg Ser Thr Thr Leu Val
1               5                   10

<210> SEQ ID NO 366
<211> LENGTH: 14
<212> TYPE: PRT
<213> ORGANISM: Homo sapiens

<400> SEQUENCE: 366

Thr Gly Thr Ser Ser Asp Val Gly Gly Tyr Asn Tyr Val Ser
1               5                   10

<210> SEQ ID NO 367
<211> LENGTH: 7
<212> TYPE: PRT
<213> ORGANISM: Homo sapiens

<400> SEQUENCE: 367

Asp Val Ser Lys Arg Pro Ser
1               5

<210> SEQ ID NO 368

-continued

<210> SEQ ID NO 368
<211> LENGTH: 9
<212> TYPE: PRT
<213> ORGANISM: Homo sapiens

<400> SEQUENCE: 368

Ser Ser Tyr Thr Gly Arg Ser Thr Val
1               5

<210> SEQ ID NO 369
<211> LENGTH: 14
<212> TYPE: PRT
<213> ORGANISM: Homo sapiens

<400> SEQUENCE: 369

Thr Gly Thr Ser Ser Asp Val Gly Gly Tyr Asn Tyr Val Ser
1               5                   10

<210> SEQ ID NO 370
<211> LENGTH: 7
<212> TYPE: PRT
<213> ORGANISM: Homo sapiens

<400> SEQUENCE: 370

Asp Val Ser Asn Arg Pro Ser
1               5

<210> SEQ ID NO 371
<211> LENGTH: 10
<212> TYPE: PRT
<213> ORGANISM: Homo sapiens

<400> SEQUENCE: 371

Ser Ser Tyr Thr Ser Ser Ser Thr Arg Val
1               5                   10

<210> SEQ ID NO 372
<211> LENGTH: 11
<212> TYPE: PRT
<213> ORGANISM: Homo sapiens

<400> SEQUENCE: 372

Arg Ala Ser Gln Gly Ile Ser Ser Trp Leu Ala
1               5                   10

<210> SEQ ID NO 373
<211> LENGTH: 7
<212> TYPE: PRT
<213> ORGANISM: Homo sapiens

<400> SEQUENCE: 373

Ala Ala Ser Ser Leu Gln Ser
1               5

<210> SEQ ID NO 374
<211> LENGTH: 9
<212> TYPE: PRT
<213> ORGANISM: Homo sapiens

<400> SEQUENCE: 374

Gln Gln Ala Asn Ser Phe Pro Leu Thr
1               5

<210> SEQ ID NO 375
<211> LENGTH: 14
<212> TYPE: PRT

```
<213> ORGANISM: Homo sapiens

<400> SEQUENCE: 375

Thr Gly Ser Ser Ser Asn Ile Gly Ala Gly Tyr Asp Val His
1               5                   10

<210> SEQ ID NO 376
<211> LENGTH: 7
<212> TYPE: PRT
<213> ORGANISM: Homo sapiens

<400> SEQUENCE: 376

Gly Asn Ser Asn Arg Pro Ser
1               5

<210> SEQ ID NO 377
<211> LENGTH: 11
<212> TYPE: PRT
<213> ORGANISM: Homo sapiens

<400> SEQUENCE: 377

Gln Ser Tyr Asp Ser Ser Leu Ser Gly Tyr Val
1               5                   10

<210> SEQ ID NO 378
<211> LENGTH: 11
<212> TYPE: PRT
<213> ORGANISM: Homo sapiens

<400> SEQUENCE: 378

Gln Gly Asp Ser Leu Arg Ser Tyr Tyr Ala Ser
1               5                   10

<210> SEQ ID NO 379
<211> LENGTH: 7
<212> TYPE: PRT
<213> ORGANISM: Homo sapiens

<400> SEQUENCE: 379

Gly Lys Asn Asn Arg Pro Ser
1               5

<210> SEQ ID NO 380
<211> LENGTH: 11
<212> TYPE: PRT
<213> ORGANISM: Homo sapiens

<400> SEQUENCE: 380

Asn Ser Arg Asp Ser Ser Gly Asn His Leu Val
1               5                   10

<210> SEQ ID NO 381
<211> LENGTH: 13
<212> TYPE: PRT
<213> ORGANISM: Homo sapiens

<400> SEQUENCE: 381

Ser Gly Ser Ser Ser Asn Ile Gly Ser Asn Thr Val Asn
1               5                   10

<210> SEQ ID NO 382
<211> LENGTH: 7
<212> TYPE: PRT
<213> ORGANISM: Homo sapiens
```

```
<400> SEQUENCE: 382

Ser Asn Asn Gln Arg Pro Ser
1               5

<210> SEQ ID NO 383
<211> LENGTH: 11
<212> TYPE: PRT
<213> ORGANISM: Homo sapiens

<400> SEQUENCE: 383

Ala Ala Trp Asp Asp Ser Leu Lys Ser Phe Val
1               5                   10

<210> SEQ ID NO 384
<211> LENGTH: 12
<212> TYPE: PRT
<213> ORGANISM: Homo sapiens

<400> SEQUENCE: 384

Arg Ala Ser Gln Asn Ser Ile Ser Ser His Leu Asn
1               5                   10

<210> SEQ ID NO 385
<211> LENGTH: 7
<212> TYPE: PRT
<213> ORGANISM: Homo sapiens

<400> SEQUENCE: 385

Ala Ala Ser Ser Leu Gln Ser
1               5

<210> SEQ ID NO 386
<211> LENGTH: 9
<212> TYPE: PRT
<213> ORGANISM: Homo sapiens

<400> SEQUENCE: 386

Gln Gln Ser Tyr Ser Thr Pro Phe Thr
1               5

<210> SEQ ID NO 387
<211> LENGTH: 12
<212> TYPE: PRT
<213> ORGANISM: Homo sapiens

<400> SEQUENCE: 387

Ser Gly Ser Ser Ser Ile Gly Ser Asn Tyr Val Tyr
1               5                   10

<210> SEQ ID NO 388
<211> LENGTH: 7
<212> TYPE: PRT
<213> ORGANISM: Homo sapiens

<400> SEQUENCE: 388

Arg Asn Asn Gln Arg Pro Ser
1               5

<210> SEQ ID NO 389
<211> LENGTH: 11
<212> TYPE: PRT
<213> ORGANISM: Homo sapiens

<400> SEQUENCE: 389
```

```
Ala Ala Trp Asp Asp Ser Leu Ser Gly Tyr Val
1               5                   10
```

<210> SEQ ID NO 390
<211> LENGTH: 11
<212> TYPE: PRT
<213> ORGANISM: Homo sapiens

<400> SEQUENCE: 390

```
Gln Ala Ser Gln Asp Val Arg Asn Tyr Leu Asn
1               5                   10
```

<210> SEQ ID NO 391
<211> LENGTH: 7
<212> TYPE: PRT
<213> ORGANISM: Homo sapiens

<400> SEQUENCE: 391

```
Asp Ala Thr Asn Leu Glu Ser
1               5
```

<210> SEQ ID NO 392
<211> LENGTH: 9
<212> TYPE: PRT
<213> ORGANISM: Homo sapiens

<400> SEQUENCE: 392

```
Gln Gln Tyr Asp Asn Leu Pro Leu Ser
1               5
```

<210> SEQ ID NO 393
<211> LENGTH: 14
<212> TYPE: PRT
<213> ORGANISM: Homo sapiens

<400> SEQUENCE: 393

```
Thr Gly Thr Ser Ser Asp Val Gly Gly Tyr Asn Tyr Val Ser
1               5                   10
```

<210> SEQ ID NO 394
<211> LENGTH: 7
<212> TYPE: PRT
<213> ORGANISM: Homo sapiens

<400> SEQUENCE: 394

```
Asp Val Ser Lys Arg Pro Ser
1               5
```

<210> SEQ ID NO 395
<211> LENGTH: 10
<212> TYPE: PRT
<213> ORGANISM: Homo sapiens

<400> SEQUENCE: 395

```
Gly Ser Phe Thr Ser Ser Ile Thr Tyr Val
1               5                   10
```

<210> SEQ ID NO 396
<211> LENGTH: 10
<212> TYPE: PRT
<213> ORGANISM: Homo sapiens

<400> SEQUENCE: 396

```
Gly Phe Thr Phe Ser Asp Tyr Tyr Met Ser
1               5                   10
```

```
<210> SEQ ID NO 397
<211> LENGTH: 12
<212> TYPE: PRT
<213> ORGANISM: Homo sapiens

<400> SEQUENCE: 397

Gly Phe Ser Leu Ser Ser Phe Gly Val Ala Val Gly
1               5                   10

<210> SEQ ID NO 398
<211> LENGTH: 12
<212> TYPE: PRT
<213> ORGANISM: Homo sapiens

<400> SEQUENCE: 398

Gly Phe Ser Leu Asn Ser Phe Gly Val Ala Val Gly
1               5                   10

<210> SEQ ID NO 399
<211> LENGTH: 11
<212> TYPE: PRT
<213> ORGANISM: Homo sapiens

<400> SEQUENCE: 399

Gly Gly Ser Ile Ser Ser Ser Asn Trp Trp Ser
1               5                   10

<210> SEQ ID NO 400
<211> LENGTH: 10
<212> TYPE: PRT
<213> ORGANISM: Homo sapiens

<400> SEQUENCE: 400

Gly Phe Thr Phe Ser Asp Tyr Tyr Met Gly
1               5                   10

<210> SEQ ID NO 401
<211> LENGTH: 10
<212> TYPE: PRT
<213> ORGANISM: Homo sapiens

<400> SEQUENCE: 401

Gly Phe Thr Phe Ser Asp Tyr Tyr Met Gly
1               5                   10

<210> SEQ ID NO 402
<211> LENGTH: 17
<212> TYPE: PRT
<213> ORGANISM: Homo sapiens

<400> SEQUENCE: 402

Tyr Ile Ser Asp Arg Ala His Thr Ile Tyr Asp Thr His Ser Val Lys
1               5                   10                  15

Gly

<210> SEQ ID NO 403
<211> LENGTH: 10
<212> TYPE: PRT
<213> ORGANISM: Homo sapiens

<400> SEQUENCE: 403

Ala Val Gly Ala Gly Glu Gly Phe Asp Tyr
1               5                   10
```

```
<210> SEQ ID NO 404
<211> LENGTH: 12
<212> TYPE: PRT
<213> ORGANISM: Homo sapiens

<400> SEQUENCE: 404

Gly Gly Ser Ile Ser Arg Ser Asp Gly Tyr Trp Gly
 1               5                  10

<210> SEQ ID NO 405
<211> LENGTH: 16
<212> TYPE: PRT
<213> ORGANISM: Homo sapiens

<400> SEQUENCE: 405

Ser Ile Tyr Asp Thr Gly Thr Thr Tyr Tyr Ser Pro Ser Leu Lys Ser
 1               5                  10                  15

<210> SEQ ID NO 406
<211> LENGTH: 14
<212> TYPE: PRT
<213> ORGANISM: Homo sapiens

<400> SEQUENCE: 406

Met Gly Gly Leu Arg Ser Ser Ser Ser Asp Ala Phe His Thr
 1               5                  10

<210> SEQ ID NO 407
<211> LENGTH: 10
<212> TYPE: PRT
<213> ORGANISM: Homo sapiens

<400> SEQUENCE: 407

Gly Gly Thr Phe Ser Thr Phe Ala Ile Asn
 1               5                  10

<210> SEQ ID NO 408
<211> LENGTH: 10
<212> TYPE: PRT
<213> ORGANISM: Homo sapiens

<400> SEQUENCE: 408

Gly Tyr Ser Phe Thr Asn Tyr Trp Leu Gly
 1               5                  10

<210> SEQ ID NO 409
<211> LENGTH: 10
<212> TYPE: PRT
<213> ORGANISM: Homo sapiens

<400> SEQUENCE: 409

Gly Gly Ser Leu Ser Ser His Gly Val Ser
 1               5                  10

<210> SEQ ID NO 410
<211> LENGTH: 10
<212> TYPE: PRT
<213> ORGANISM: Homo sapiens

<400> SEQUENCE: 410

Gly Gly Ser Leu Ser Ser His Gly Val Ser
 1               5                  10
```

```
<210> SEQ ID NO 411
<211> LENGTH: 17
<212> TYPE: PRT
<213> ORGANISM: Homo sapiens

<400> SEQUENCE: 411

Arg Ile Ile Pro Met Phe Gly Val Thr Asp Tyr Ala Gln Lys Phe Gln
1               5                   10                  15
Asp

<210> SEQ ID NO 412
<211> LENGTH: 9
<212> TYPE: PRT
<213> ORGANISM: Homo sapiens

<400> SEQUENCE: 412

Glu Ser Arg Gly Ala Thr Phe Glu Tyr
1               5

<210> SEQ ID NO 413
<211> LENGTH: 10
<212> TYPE: PRT
<213> ORGANISM: Homo sapiens

<400> SEQUENCE: 413

Gly Phe Thr Phe Ser Ser Tyr Ser Met Asn
1               5                   10

<210> SEQ ID NO 414
<211> LENGTH: 17
<212> TYPE: PRT
<213> ORGANISM: Homo sapiens

<400> SEQUENCE: 414

Ser Ile Ser Ser Ser Ser Ser Tyr Ile Tyr Tyr Ala Asp Ser Val Lys
1               5                   10                  15
Gly

<210> SEQ ID NO 415
<211> LENGTH: 12
<212> TYPE: PRT
<213> ORGANISM: Homo sapiens

<400> SEQUENCE: 415

Gly Leu Gly Gly Trp Thr His Asp Ala Phe Asp Ile
1               5                   10

<210> SEQ ID NO 416
<211> LENGTH: 10
<212> TYPE: PRT
<213> ORGANISM: Homo sapiens

<400> SEQUENCE: 416

Gly Tyr Thr Phe Asn Asn Tyr Gly Phe Ser
1               5                   10

<210> SEQ ID NO 417
<211> LENGTH: 17
<212> TYPE: PRT
<213> ORGANISM: Homo sapiens

<400> SEQUENCE: 417

Trp Ile Ser Val Tyr Asn Gly Asn Thr Asn Tyr Ala Gln Lys Leu Gln
1               5                   10                  15
```

-continued

Gly

<210> SEQ ID NO 418
<211> LENGTH: 16
<212> TYPE: PRT
<213> ORGANISM: Homo sapiens

<400> SEQUENCE: 418

Asp Tyr Tyr Ser Asp Ser Ser Gly Tyr Trp Asp Asp Ala Phe Asp Ile
1               5                   10                  15

<210> SEQ ID NO 419
<211> LENGTH: 10
<212> TYPE: PRT
<213> ORGANISM: Homo sapiens

<400> SEQUENCE: 419

Gly Tyr Thr Ser Thr Asn Tyr Gly Ile Ser
1               5                   10

<210> SEQ ID NO 420
<211> LENGTH: 10
<212> TYPE: PRT
<213> ORGANISM: Homo sapiens

<400> SEQUENCE: 420

Gly Tyr Ser Phe Gly Asn Asn Gly Ile Thr
1               5                   10

<210> SEQ ID NO 421
<211> LENGTH: 17
<212> TYPE: PRT
<213> ORGANISM: Homo sapiens

<400> SEQUENCE: 421

Trp Ile Ser Thr Tyr Asn Gly Asn Thr Asn Tyr Ala Gln Lys Leu Gln
1               5                   10                  15

Gly

<210> SEQ ID NO 422
<211> LENGTH: 16
<212> TYPE: PRT
<213> ORGANISM: Homo sapiens

<400> SEQUENCE: 422

Asp Tyr Tyr Ser Asp Ser Ser Gly Tyr Trp Asp Asp Ala Phe Asp Ile
1               5                   10                  15

<210> SEQ ID NO 423
<211> LENGTH: 10
<212> TYPE: PRT
<213> ORGANISM: Homo sapiens

<400> SEQUENCE: 423

Gly Tyr Thr Phe Ser Arg Tyr Tyr Ile His
1               5                   10

<210> SEQ ID NO 424
<211> LENGTH: 17
<212> TYPE: PRT
<213> ORGANISM: Homo sapiens

<400> SEQUENCE: 424

Leu Ile Asn Pro Gly Gly Gly Ser Thr Asn Tyr Ala Gln Lys Phe Gln
1               5                   10                  15

Gly

<210> SEQ ID NO 425
<211> LENGTH: 12
<212> TYPE: PRT
<213> ORGANISM: Homo sapiens

<400> SEQUENCE: 425

Asp Tyr Gly Thr Ile Asp Ala Arg Arg Phe Asp Phe
1               5                   10

<210> SEQ ID NO 426
<211> LENGTH: 10
<212> TYPE: PRT
<213> ORGANISM: Homo sapiens

<400> SEQUENCE: 426

Gly Tyr Thr Phe Thr Gly Tyr Tyr Met His
1               5                   10

<210> SEQ ID NO 427
<211> LENGTH: 12
<212> TYPE: PRT
<213> ORGANISM: Homo sapiens

<400> SEQUENCE: 427

Gly Gly Ser Ile Ser Ser Ser Ser Tyr Tyr Trp Gly
1               5                   10

<210> SEQ ID NO 428
<211> LENGTH: 16
<212> TYPE: PRT
<213> ORGANISM: Homo sapiens

<400> SEQUENCE: 428

Ser Ile Tyr Tyr Ser Gly Ser Thr Tyr Tyr Asn Pro Ser Leu Lys Ser
1               5                   10                  15

<210> SEQ ID NO 429
<211> LENGTH: 9
<212> TYPE: PRT
<213> ORGANISM: Homo sapiens

<400> SEQUENCE: 429

His Asp Gly Thr Asp Ala Phe Asp Ile
1               5

<210> SEQ ID NO 430
<211> LENGTH: 10
<212> TYPE: PRT
<213> ORGANISM: Homo sapiens

<400> SEQUENCE: 430

Gly Gly Ala Phe Thr Asn Phe Gly Ile Ser
1               5                   10

<210> SEQ ID NO 431
<211> LENGTH: 17
<212> TYPE: PRT
<213> ORGANISM: Homo sapiens

<400> SEQUENCE: 431

```
Trp Ile Ser Thr Tyr Asn Ser Glu Thr Asn Tyr Ala Gln Lys Leu Gln
1               5                   10                  15

Gly

<210> SEQ ID NO 432
<211> LENGTH: 16
<212> TYPE: PRT
<213> ORGANISM: Homo sapiens

<400> SEQUENCE: 432

Asp Tyr Tyr Ser Asp Ser Ser Gly Tyr Trp Asp Asp Ala Phe Asp Ile
1               5                   10                  15

<210> SEQ ID NO 433
<211> LENGTH: 12
<212> TYPE: PRT
<213> ORGANISM: Homo sapiens

<400> SEQUENCE: 433

Gly Asp Ser Val Ser Ser Asn Ser Ala Thr Trp Asn
1               5                   10

<210> SEQ ID NO 434
<211> LENGTH: 18
<212> TYPE: PRT
<213> ORGANISM: Homo sapiens

<400> SEQUENCE: 434

Arg Thr Tyr Tyr Arg Ser Lys Trp Tyr Asn Asp Tyr Ala Val Ser Val
1               5                   10                  15

Lys Ser

<210> SEQ ID NO 435
<211> LENGTH: 7
<212> TYPE: PRT
<213> ORGANISM: Homo sapiens

<400> SEQUENCE: 435

Gly Val Arg Ala Phe Asp Ile
1               5

<210> SEQ ID NO 436
<211> LENGTH: 10
<212> TYPE: PRT
<213> ORGANISM: Homo sapiens

<400> SEQUENCE: 436

Gly Tyr Thr Phe Arg Asn Ser Gly Ile Thr
1               5                   10

<210> SEQ ID NO 437
<211> LENGTH: 17
<212> TYPE: PRT
<213> ORGANISM: Homo sapiens

<400> SEQUENCE: 437

Trp Ile Asn Pro Asn Ser Gly Gly Ala Met Tyr Val Asp Asn Phe Gln
1               5                   10                  15

Gly

<210> SEQ ID NO 438
<211> LENGTH: 11
<212> TYPE: PRT
```

```
<213> ORGANISM: Homo sapiens

<400> SEQUENCE: 438

Gly Met Ala Asp Leu Ile Asp Val Phe Asp Ile
1               5                   10

<210> SEQ ID NO 439
<211> LENGTH: 10
<212> TYPE: PRT
<213> ORGANISM: Homo sapiens

<400> SEQUENCE: 439

Gly Tyr Ser Phe Thr Ser Tyr Trp Ile Gly
1               5                   10

<210> SEQ ID NO 440
<211> LENGTH: 17
<212> TYPE: PRT
<213> ORGANISM: Homo sapiens

<400> SEQUENCE: 440

Ile Ile Tyr Pro Gly Asp Ser Asp Thr Arg Tyr Ser Pro Ser Phe Gln
1               5                   10                  15

Gly

<210> SEQ ID NO 441
<211> LENGTH: 11
<212> TYPE: PRT
<213> ORGANISM: Homo sapiens

<400> SEQUENCE: 441

Leu Ser Ser Ser Ser Tyr Asp Ala Phe Asp Ile
1               5                   10

<210> SEQ ID NO 442
<211> LENGTH: 10
<212> TYPE: PRT
<213> ORGANISM: Homo sapiens

<400> SEQUENCE: 442

Gly Gly Ser Phe Lys Thr His Gly Ile Ser
1               5                   10

<210> SEQ ID NO 443
<211> LENGTH: 17
<212> TYPE: PRT
<213> ORGANISM: Homo sapiens

<400> SEQUENCE: 443

Trp Ile Asn Pro Asn Ser Gly Gly Ala Leu Tyr Val Asp Asn Phe Gln
1               5                   10                  15

Gly

<210> SEQ ID NO 444
<211> LENGTH: 11
<212> TYPE: PRT
<213> ORGANISM: Homo sapiens

<400> SEQUENCE: 444

Gly Met Ala Asp Leu Ile Asp Val Phe Asp Ile
1               5                   10

<210> SEQ ID NO 445
```

```
<211> LENGTH: 10
<212> TYPE: PRT
<213> ORGANISM: Homo sapiens

<400> SEQUENCE: 445

Gly Phe Asn Phe Asp Asn Tyr Gly Leu Ser
1               5                   10

<210> SEQ ID NO 446
<211> LENGTH: 16
<212> TYPE: PRT
<213> ORGANISM: Homo sapiens

<400> SEQUENCE: 446

Phe Ile Tyr Lys Ser Val Asn Thr Asn Tyr Ser Pro Ser Leu Lys Ser
1               5                   10                  15

<210> SEQ ID NO 447
<211> LENGTH: 10
<212> TYPE: PRT
<213> ORGANISM: Homo sapiens

<400> SEQUENCE: 447

Gly Lys Val Glu Thr Ser Val Val Asp Tyr
1               5                   10

<210> SEQ ID NO 448
<211> LENGTH: 12
<212> TYPE: PRT
<213> ORGANISM: Homo sapiens

<400> SEQUENCE: 448

Gly Phe Ser Leu Ser Thr Arg Gly Val Gly Val Gly
1               5                   10

<210> SEQ ID NO 449
<211> LENGTH: 10
<212> TYPE: PRT
<213> ORGANISM: Homo sapiens

<400> SEQUENCE: 449

Gly Gly Ser Met Asn Asn Tyr Tyr Trp Ser
1               5                   10

<210> SEQ ID NO 450
<211> LENGTH: 16
<212> TYPE: PRT
<213> ORGANISM: Homo sapiens

<400> SEQUENCE: 450

Arg Ile Tyr Ser Ser Gly Ser Thr Asn Tyr Asn Pro Ala Leu Lys Ser
1               5                   10                  15

<210> SEQ ID NO 451
<211> LENGTH: 13
<212> TYPE: PRT
<213> ORGANISM: Homo sapiens

<400> SEQUENCE: 451

Ala Ser Trp Ser Gly Thr Tyr Trp Ala Leu Phe Asp Tyr
1               5                   10

<210> SEQ ID NO 452
<211> LENGTH: 10
<212> TYPE: PRT
```

<213> ORGANISM: Homo sapiens

<400> SEQUENCE: 452

Gly Phe Thr Phe Ser Ser Tyr Ser Met Asn
1               5                   10

<210> SEQ ID NO 453
<211> LENGTH: 17
<212> TYPE: PRT
<213> ORGANISM: Homo sapiens

<400> SEQUENCE: 453

Ser Ile Ser Ser Ser Ser Ser Tyr Ile Tyr Tyr Ala Asp Ser Val Lys
1               5                   10                  15

Gly

<210> SEQ ID NO 454
<211> LENGTH: 12
<212> TYPE: PRT
<213> ORGANISM: Homo sapiens

<400> SEQUENCE: 454

Gly Leu Gly Gly Trp Thr His Asp Ala Phe Asp Ile
1               5                   10

<210> SEQ ID NO 455
<211> LENGTH: 10
<212> TYPE: PRT
<213> ORGANISM: Homo sapiens

<400> SEQUENCE: 455

Gly His Ser Phe Ser Thr Tyr Gly Phe Ser
1               5                   10

<210> SEQ ID NO 456
<211> LENGTH: 17
<212> TYPE: PRT
<213> ORGANISM: Homo sapiens

<400> SEQUENCE: 456

Trp Ile Ser Thr Tyr Asn Gly Asn Thr Asn Tyr Ala Gln Lys Leu Gln
1               5                   10                  15

Gly

<210> SEQ ID NO 457
<211> LENGTH: 16
<212> TYPE: PRT
<213> ORGANISM: Homo sapiens

<400> SEQUENCE: 457

Asp Tyr Tyr Ser Asp Ser Ser Gly Tyr Trp Asp Asp Ala Phe Asp Ile
1               5                   10                  15

<210> SEQ ID NO 458
<211> LENGTH: 10
<212> TYPE: PRT
<213> ORGANISM: Homo sapiens

<400> SEQUENCE: 458

Gly Phe Thr Phe Ser Ser Tyr Ser Met Asn
1               5                   10

<210> SEQ ID NO 459

```
<211> LENGTH: 17
<212> TYPE: PRT
<213> ORGANISM: Homo sapiens

<400> SEQUENCE: 459

Ser Ile Ser Ser Ser Ser Ser Tyr Ile Tyr Tyr Ala Asp Ser Val Lys
1               5                   10                  15

Gly

<210> SEQ ID NO 460
<211> LENGTH: 12
<212> TYPE: PRT
<213> ORGANISM: Homo sapiens

<400> SEQUENCE: 460

Gly Leu Gly Gly Trp Thr His Asp Ala Phe Asp Ile
1               5                   10

<210> SEQ ID NO 461
<211> LENGTH: 10
<212> TYPE: PRT
<213> ORGANISM: Homo sapiens

<400> SEQUENCE: 461

Gly Phe Thr Phe Ser Ser Tyr Ser Met Asn
1               5                   10

<210> SEQ ID NO 462
<211> LENGTH: 17
<212> TYPE: PRT
<213> ORGANISM: Homo sapiens

<400> SEQUENCE: 462

Ser Ile Ser Ser Ser Ser Ser Tyr Ile Tyr Tyr Ala Asp Ser Val Lys
1               5                   10                  15

Gly

<210> SEQ ID NO 463
<211> LENGTH: 12
<212> TYPE: PRT
<213> ORGANISM: Homo sapiens

<400> SEQUENCE: 463

Gly Leu Gly Gly Trp Thr His Asp Ala Phe Asp Ile
1               5                   10

<210> SEQ ID NO 464
<211> LENGTH: 12
<212> TYPE: PRT
<213> ORGANISM: Homo sapiens

<400> SEQUENCE: 464

Gly Gly Ser Ile Ser Ser Asn Ser Tyr Tyr Trp Gly
1               5                   10

<210> SEQ ID NO 465
<211> LENGTH: 16
<212> TYPE: PRT
<213> ORGANISM: Homo sapiens

<400> SEQUENCE: 465

Ser Ile Tyr Tyr Ser Gly Ser Thr Tyr Tyr Asn Pro Ser Leu Lys Ser
1               5                   10                  15
```

```
<210> SEQ ID NO 466
<211> LENGTH: 9
<212> TYPE: PRT
<213> ORGANISM: Homo sapiens

<400> SEQUENCE: 466

His Asp Gly Thr Asp Ala Phe Asp Ile
1               5

<210> SEQ ID NO 467
<211> LENGTH: 10
<212> TYPE: PRT
<213> ORGANISM: Homo sapiens

<400> SEQUENCE: 467

Gly Phe Thr Phe Ser Ser Tyr Ser Met Asn
1               5                   10

<210> SEQ ID NO 468
<211> LENGTH: 10
<212> TYPE: PRT
<213> ORGANISM: Homo sapiens

<400> SEQUENCE: 468

Gly Phe Thr Phe Ser Ser Tyr Ser Met Asn
1               5                   10

<210> SEQ ID NO 469
<211> LENGTH: 17
<212> TYPE: PRT
<213> ORGANISM: Homo sapiens

<400> SEQUENCE: 469

Ser Ile Ser Ser Ser Ser Ser Tyr Ile Tyr Tyr Ala Asp Ser Val Lys
1               5                   10                  15
Gly

<210> SEQ ID NO 470
<211> LENGTH: 12
<212> TYPE: PRT
<213> ORGANISM: Homo sapiens

<400> SEQUENCE: 470

Gly Leu Gly Gly Trp Thr His Asp Ala Phe Asp Ile
1               5                   10

<210> SEQ ID NO 471
<211> LENGTH: 10
<212> TYPE: PRT
<213> ORGANISM: Homo sapiens

<400> SEQUENCE: 471

Gly Phe Thr Phe Ser Ser Tyr Ser Met Asn
1               5                   10

<210> SEQ ID NO 472
<211> LENGTH: 17
<212> TYPE: PRT
<213> ORGANISM: Homo sapiens

<400> SEQUENCE: 472

Ser Ile Ser Ser Ser Ser Ser Tyr Ile Tyr Tyr Ala Asp Ser Val Lys
1               5                   10                  15
```

Gly

<210> SEQ ID NO 473
<211> LENGTH: 12
<212> TYPE: PRT
<213> ORGANISM: Homo sapiens

<400> SEQUENCE: 473

Gly Leu Gly Gly Trp Thr His Asp Ala Phe Asp Ile
1               5                   10

<210> SEQ ID NO 474
<211> LENGTH: 10
<212> TYPE: PRT
<213> ORGANISM: Homo sapiens

<400> SEQUENCE: 474

Gly Phe Thr Phe Gly Thr Tyr Ser Met Asn
1               5                   10

<210> SEQ ID NO 475
<211> LENGTH: 10
<212> TYPE: PRT
<213> ORGANISM: Homo sapiens

<400> SEQUENCE: 475

Gly Phe Thr Phe Ser Ser Tyr Ser Met Asn
1               5                   10

<210> SEQ ID NO 476
<211> LENGTH: 17
<212> TYPE: PRT
<213> ORGANISM: Homo sapiens

<400> SEQUENCE: 476

Ser Ile Ser Ser Ser Ser Ser Tyr Ile Tyr Tyr Ala Asp Ser Val Lys
1               5                   10                  15

Gly

<210> SEQ ID NO 477
<211> LENGTH: 12
<212> TYPE: PRT
<213> ORGANISM: Homo sapiens

<400> SEQUENCE: 477

Gly Leu Gly Gly Trp Thr His Asp Ala Phe Asp Ile
1               5                   10

<210> SEQ ID NO 478
<211> LENGTH: 10
<212> TYPE: PRT
<213> ORGANISM: Homo sapiens

<400> SEQUENCE: 478

Gly Tyr Ser Phe Ser Arg Tyr Trp Ile Gly
1               5                   10

<210> SEQ ID NO 479
<211> LENGTH: 17
<212> TYPE: PRT
<213> ORGANISM: Homo sapiens

<400> SEQUENCE: 479

Ile Ile Tyr Pro Arg Asp Ser Asp Thr Arg Tyr Ser Pro Ser Phe Gln

-continued

```
                1               5                  10                 15

Gly

<210> SEQ ID NO 480
<211> LENGTH: 10
<212> TYPE: PRT
<213> ORGANISM: Homo sapiens

<400> SEQUENCE: 480

Pro Val Val Thr Ala Gly Ala Phe Asp Ile
1               5                  10

<210> SEQ ID NO 481
<211> LENGTH: 10
<212> TYPE: PRT
<213> ORGANISM: Homo sapiens

<400> SEQUENCE: 481

Gly Phe Ser Leu Ser Ser Tyr Ser Met Asn
1               5                  10

<210> SEQ ID NO 482
<211> LENGTH: 17
<212> TYPE: PRT
<213> ORGANISM: Homo sapiens

<400> SEQUENCE: 482

Ser Ile Ser Ser Ser Ser Thr His Ile Tyr Tyr Ala Asp Ser Leu Lys
1               5                  10                 15

Gly

<210> SEQ ID NO 483
<211> LENGTH: 7
<212> TYPE: PRT
<213> ORGANISM: Homo sapiens

<400> SEQUENCE: 483

Ala Thr Ile Gly Phe Asp Tyr
1               5

<210> SEQ ID NO 484
<211> LENGTH: 10
<212> TYPE: PRT
<213> ORGANISM: Homo sapiens

<400> SEQUENCE: 484

Gly Tyr Thr Phe Thr Asp Tyr Tyr Ile His
1               5                  10

<210> SEQ ID NO 485
<211> LENGTH: 17
<212> TYPE: PRT
<213> ORGANISM: Homo sapiens

<400> SEQUENCE: 485

Trp Met Asn Pro Asn Ser Gly Asn Ser Val Ser Ala Gln Lys Phe Gln
1               5                  10                 15

Gly

<210> SEQ ID NO 486
<211> LENGTH: 12
<212> TYPE: PRT
<213> ORGANISM: Homo sapiens
```

<400> SEQUENCE: 486

Asn Ser Glu Trp His Pro Trp Gly Tyr Tyr Asp Tyr
1               5                   10

<210> SEQ ID NO 487
<211> LENGTH: 10
<212> TYPE: PRT
<213> ORGANISM: Homo sapiens

<400> SEQUENCE: 487

Gly Tyr Thr Phe Ser Arg Tyr Tyr Ile His
1               5                   10

<210> SEQ ID NO 488
<211> LENGTH: 17
<212> TYPE: PRT
<213> ORGANISM: Homo sapiens

<400> SEQUENCE: 488

Leu Ile Asn Pro Gly Gly Gly Ser Thr Asn Tyr Ala Gln Lys Phe Gln
1               5                   10                  15

Gly

<210> SEQ ID NO 489
<211> LENGTH: 12
<212> TYPE: PRT
<213> ORGANISM: Homo sapiens

<400> SEQUENCE: 489

Asp Tyr Gly Thr Ile Asp Ala Arg Arg Phe Asp Phe
1               5                   10

<210> SEQ ID NO 490
<211> LENGTH: 10
<212> TYPE: PRT
<213> ORGANISM: Homo sapiens

<400> SEQUENCE: 490

Gly Tyr Thr Phe Ser Arg Tyr Tyr Ile His
1               5                   10

<210> SEQ ID NO 491
<211> LENGTH: 10
<212> TYPE: PRT
<213> ORGANISM: Homo sapiens

<400> SEQUENCE: 491

Gly His Thr Phe Ser Asn Tyr Gly Ile Ser
1               5                   10

<210> SEQ ID NO 492
<211> LENGTH: 17
<212> TYPE: PRT
<213> ORGANISM: Homo sapiens

<400> SEQUENCE: 492

Trp Ile Ser Thr Tyr Asn Gly Asn Thr Asn Tyr Ala Gln Lys Leu Gln
1               5                   10                  15

Gly

<210> SEQ ID NO 493
<211> LENGTH: 16

```
<212> TYPE: PRT
<213> ORGANISM: Homo sapiens

<400> SEQUENCE: 493

Asp Tyr Tyr Ser Asp Ser Ser Gly Tyr Trp Asp Asp Ala Phe Asp Ile
1               5                   10                  15

<210> SEQ ID NO 494
<211> LENGTH: 10
<212> TYPE: PRT
<213> ORGANISM: Homo sapiens

<400> SEQUENCE: 494

Gly Tyr Thr Phe Ser Arg Tyr Tyr Ile His
1               5                   10

<210> SEQ ID NO 495
<211> LENGTH: 17
<212> TYPE: PRT
<213> ORGANISM: Homo sapiens

<400> SEQUENCE: 495

Leu Ile Asn Pro Gly Gly Gly Ser Thr Asn Tyr Ala Gln Lys Phe Gln
1               5                   10                  15

Gly

<210> SEQ ID NO 496
<211> LENGTH: 12
<212> TYPE: PRT
<213> ORGANISM: Homo sapiens

<400> SEQUENCE: 496

Asp Tyr Gly Thr Ile Asp Ala Arg Arg Phe Asp Phe
1               5                   10

<210> SEQ ID NO 497
<211> LENGTH: 10
<212> TYPE: PRT
<213> ORGANISM: Homo sapiens

<400> SEQUENCE: 497

Gly Phe Thr Phe Ser Asp Tyr Tyr Met Gly
1               5                   10

<210> SEQ ID NO 498
<211> LENGTH: 17
<212> TYPE: PRT
<213> ORGANISM: Homo sapiens

<400> SEQUENCE: 498

Tyr Ile Ser Asp Arg Ala His Thr Ile Tyr Asp Thr Asp Ser Val Lys
1               5                   10                  15

Gly

<210> SEQ ID NO 499
<211> LENGTH: 10
<212> TYPE: PRT
<213> ORGANISM: Homo sapiens

<400> SEQUENCE: 499

Ala Val Gly Ala Gly Glu Gly Phe Asp Tyr
1               5                   10
```

```
<210> SEQ ID NO 500
<211> LENGTH: 10
<212> TYPE: PRT
<213> ORGANISM: Homo sapiens

<400> SEQUENCE: 500

Gly Tyr Thr Phe Thr Ser Tyr Tyr Met His
1               5                   10

<210> SEQ ID NO 501
<211> LENGTH: 17
<212> TYPE: PRT
<213> ORGANISM: Homo sapiens

<400> SEQUENCE: 501

Ile Ile Asn Pro Ser Gly Gly Ser Thr Ser Tyr Ala Gln Lys Phe Gln
1               5                   10                  15

Gly

<210> SEQ ID NO 502
<211> LENGTH: 11
<212> TYPE: PRT
<213> ORGANISM: Homo sapiens

<400> SEQUENCE: 502

Gly Gly Tyr Thr Gly Trp Ser Pro Ser Asp Pro
1               5                   10
```